US007109009B2

(12) United States Patent
Wilson et al.

(10) Patent No.: US 7,109,009 B2
(45) Date of Patent: Sep. 19, 2006

(54) **REGULATORY REGION OF THE CYP52A2A GENE FROM *CANDIDA TROPICALIS***

(75) Inventors: C. Ron Wilson, Loveland, OH (US); David L. Craft, Fort Thomas, KY (US); L. Dudley Eirich, Cincinnati, OH (US); Mark Eshoo, Fairfax, CA (US); Krishna M. Madduri, Westfield, IN (US); Cathy A. Cornett, Crescent Springs, KY (US); Alfred A. Brenner, Santa Rosa, CA (US); Maria Tang, Fairfield, CA (US); John C. Loper, Cincinnati, OH (US); Martin Gleeson, San Diego, CA (US)

(73) Assignee: Cognis Corporation, Ambler, PA (US)

( * ) Notice: Subject to any disclaimer, the term of this patent is extended or adjusted under 35 U.S.C. 154(b) by 130 days.

(21) Appl. No.: 10/405,660

(22) Filed: Apr. 2, 2003

(65) Prior Publication Data

US 2003/0186411 A1    Oct. 2, 2003

Related U.S. Application Data

(60) Continuation of application No. 09/976,800, filed on Oct. 12, 2001, now abandoned, which is a division of application No. 09/302,620, filed on Apr. 30, 1999, now Pat. No. 6,331,420.

(60) Provisional application No. 60/123,555, filed on Mar. 10, 1999, provisional application No. 60/103,099, filed on Oct. 5, 1998, provisional application No. 60/083,798, filed on May 1, 1998.

(51) Int. Cl.
*C12N 9/02* (2006.01)
*C12N 1/20* (2006.01)
*C12N 15/00* (2006.01)
*C12Q 1/00* (2006.01)
*C12Q 1/68* (2006.01)
*C07H 21/02* (2006.01)
*C07H 21/04* (2006.01)
*C12P 21/04* (2006.01)

(52) U.S. Cl. .............................. 435/189; 435/4; 435/6; 435/252.3; 435/320.1; 435/440; 435/69.1; 435/71.1; 536/23.1; 536/23.2; 536/23.7

(58) Field of Classification Search ............... 536/24.1, 536/24.2, 24.33, 23.2, 23.7, 23.1; 435/189, 435/252.3, 320.1, 69.1, 71.1, 440, 6, 4
See application file for complete search history.

(56) References Cited

U.S. PATENT DOCUMENTS 5,254,466 A    10/1993    Picataggio et al.

(Continued)

FOREIGN PATENT DOCUMENTS

WO    WO 91/147781    10/1991

OTHER PUBLICATIONS

Sutter et al., NADPH-Cytochrome P450 reductase (EC 1.6.2.4) (CPR), Swissport Sequence Data Base, Oct. 1, 1994, Ac P37201.

(Continued)

*Primary Examiner*—P. Achutamurthy
*Assistant Examiner*—Yong D. Pak
(74) *Attorney, Agent, or Firm*—John F. Daniels

(57) ABSTRACT

Novel genes have been isolated which encode cytochrome P450 and NADPH reductase enzymes of the ω-hydroxylase complex of *C. tropicalis* 20336. Vectors including these genes, transfected host cells and transformed host cells are provided. Methods of producing of cytochrome P450 and NADPH reductase enzymes are also provided which involve transforming a host cell with a gene encoding these enzymes and culturing the cells. Methods of increasing the production of a dicarboxylic acid and methods of increasing production of the aforementioned enzymes are also provided which involve increasing in the host cell the number of genes encoding these enzymes. A method for discriminating members of a gene family by quantifying the expression of genes is also provided.

5 Claims, 89 Drawing Sheets

U.S. PATENT DOCUMENTS

| | | |
|---|---|---|
| 5,620,878 A | 4/1997 | Picataggio et al. |
| 5,648,247 A | 7/1997 | Picataggio et al. |
| 6,331,420 B1 | 12/2001 | Wilson et al. |

OTHER PUBLICATIONS

Sutter et al., C. tropicalis NADPH-cytochrome P450 reductase gene, complete cds. EMBL Sequence Database, Jul. 21, 1990, Heidelberg DE Ac M35199.

Nelson, D. R. 1996. P450 Superfamily; Update on New sequences, gene mapping, accession numbers, and nomenclature. Pharmacogenetics. 6(1):1-42.

Garfinkel, D. 1958. Studies on pig liver microsomes. I. Enzymatic and pigment composition of different microsomal fractions. Arch. Biochem. Biophys. 77:493-509.

Klaassen, C. D., M. O. Amdur, and J. Doull. 1986. Toxicology, 3rd ed. Macmillan, New York.

Omura, T., and R. Sato. 1964. The carbon-monoxide-binding pigment of liver microsomes. I. Evidence of its hemoprotein nature. J. Biol. Chem. 239:2370-2378.

Goeptar, A. R., Heleen Scheerens and Nico P.E. Vermeulen. 1995. Oxygen and Xenobiotic Reductase Activities of Cytochrome P450. Critical Reviews in Toxicology. 25(1):25-65.

Taniguchi, H., Y. Imai. and R. Sato. 1984. Role of electron transfer system in microsomal drug monooxygenase reaction catalyzed by cytochrome P450. Arch. Biochem. Biophys. 232:585-596.

Potter, D. W., and D. J. Reed. 1983. Involvement of FMN and phenobarbital cytochrome P450 in stimulating a one-electron reductive denitrosation of 1-(2-chloroethyl)-3-(cyclohexyl)-1-nitrosourea catalyzed by NADPH-cytochrome P450 reductase J. Biol. Chem. 258:6906-6911.

Vermilion, J. L., and M. J. Coon. 1978. Identification of the high and low potential flavins of liver microsomal NADPH-cytochrome P450 reductase. J. Biol. Chem. 253:8812-8819.

Guengerich, F. P., and M. V. Martin. 1980. Purification of cytochrome P-450, NADPH-cytochrome P-450 reductase and epoxide hydratase from a single preparation of rat liver microsomes. Arch. Biochem. Biophys. 205:365-379.

Ortiz de Montellano, P. R 1986. Cytochrome P450; Structure, Mechanism and Biochemistry. Plenum Press, New York (Table of Contents).

Kuthen, H., and V. Ulrich. 1982. Oxidase and oxygenase function of the microsomal cytochrome P450 monooxygenase system. Eur. J. Biochem. 126:583-588.

Poulos, T. L., and R. Raag. 1992. Cytochrome P450 crystallography, oxygen activation and electron transfer. FASEB J. 6:674-679.

Mukhopadhyay, C. K. a. I. B. C. 1994. NADPH initiated cytochrome P450-mediated free metal ion independent oxidative damage of microsomal proteins. Journal of Biological Chemistry. 269(18):13390-13397.

Ross, A. D., Varghese. G., Oporto. B., Carmichael, F.J., and Isreal Y. 1995. Effects of propylthiouracil treatment on NADPH-cytochrome P450 reductase levels. oxygen consumption and hydroxyl radical formation in liver microsomes from rats fed ethanol or acetone chronically. Biochemical Pharmacology. 49(7):979-989.

Yamazaki, S., Nakano, N., Imai, Y., Ueng, Y.F., Guengerich, F.P., and T. Shimada. 1996. Roles of cytochrome b5 in the oxidation of testosterone and nifedipine by recombinant cytochrome P450 3A4 and by human liver microsomes. Archives of Biochemistry and Biophysics. 325(2):174-182.

Gotoh, O., Tagashira, Y., Iizuka, T., and Y. Fuji-kuriyama. 1983. Structural characteristics of Cytochrome P450. Possible location of the heme-binding cysteine in determined amino acid sequences. J. Biochem. 93(807-817).

Morohashi, K., Sogawa,K., Omura, T., and Y. Fuji-kuriyama. 1987. Gene structure of human cytochrome P450 (SCC), cholestrol desmolase. J. Biochem. 101:879-887.

Kalb, V. and. J. Loper. 1988. Proteins from eight eukaryotic cytochrome P-450 families share a segmented region of sequence similarity. PNAS. 85:7221-7225.

Kaiser, C., S. Michaelis, and A. Mitchell, 1994. Methods in Yeast Genetics. Cold Spring Harbor Laboratory Press, USA (Title page).

Sambrook, J., E. Fritsch, and T. Maniatis. 1989. Molecular Cloning: A Laboratory Manual. 2nd Ed. Cold Spring Harbor Laboratory Press, USA (Title page).

Boeke, J. D., LaCroute. F., and G.R. Fink. A positive selection for mutants lacking orotidine-5'-phosphate decarboxylase activity in yeast:5-fluro-orotic acid resistance. Mol. Gen. Genet. (1984) 197:345-346.

Picataggio, S., Deanda, K., and J. Mielenz. Determination of *Candida tropicalis* Acyl Coenzyme A Oxidase Isozyme Function by Sequential Gene Disruption. 1991. Mol. and Cell. Biol. 11:4333-4339.

Rohrer, T.L. and S.K. Picataggio. Targeted integrative transformation of *Candida tropicalis* by electroporation. Appl. Microbiol. Biotechnol. 1992. 36:650-654.

Picataggio, S., Rohrer, T., Deanda, K., Lanning, D., Reynolds, R., Mielenz, J. and L.D. Eirich. Metabolic engineering of *Candida tropicalis* for the production of long-chain dicarboxylic acids. 1992. Bio/Technology 10:894-898.

Sutter, T.R., Sangard, D. and J.C. Loper. 1990. Isolation and characterization of the alkane-inducible NADPH-cytochrome P-450 oxidoreductase gene from *Candida tropicalis*. J. Biol. Chem. 265:16428-16436.

Kargel, E., Menzel, R., Honeck, H., Vogel, F., Bohmer, A. and W. Schhunck. 1996. *Candida maltosa* NADPH-cytochrome P450 reductase: cloning of a full-length cDNA, heterologous expression in *Saccharomyces cerevisiae* and function of the N-terminus region of membrane anchoring and proliferation of the endiplasmic reticulum. Yeast. 12:333-348.

Ohkuma, M., Muraoka, S., Tanimoto, T., Fuji. M., Ohta. A. and Takagi, M. 1995. CYP52 (cytochrome P450alk) multigene family in *Candida maltosa*: identification and characterization of eight members. DNA and Cell Biology. 14:163-173.

Seghezzi, W., Meili. C., Ruffiner. R., Kuenzi. R., Sanglard. D. and A. Fiechter. 1992. Identification and characterization of additional members of the cytochrome P450 multigene family CYP52 of *Candida tropicalis*. DNA and Cell Biology. 11.767-780.

Sutter et al., Isolation and Characterization of the Alkane-inducible NADPH-Cytochrome P-450 Oxidoreductase Gene for *Candida tropicalis*, The Journal of Biological Chemistry, vol. 265, Sep. 25, 1990, pp. 16428-16436.

Ohkuma et al., C. Maltosa ALK2-A and ALK3-A Genes for n-alkane inducible cytochrome P-450, EMBL Sequence Database Mar. 14, 1995, Heidelberg DE Ac X55881.

Ohkuma et al., Cytochrome P450 52D1, Swissprot Sequence Data Base, Dec. 15, 1998, Ac Q12585.

Ohkuma, et al., CYP52 (Cytochrome P450alk) Multigene Family in *Candida maltosa*: Identification and Characterization of Eight Members, DNA and Cell Biology, Vol. 14, 1995, pp. 163-175.

Kobayashi et al., Quantiative Analysis of Human Multidrug Resistance 1 (MDR1) Gene Expression by Nonisotopic Competitive Reverse Transcriptase Polymerase Chain Reaction Assay, Journal of Clinical Laboratory Analysis, vol. 11, 1997, pp. 258-266.

Mattes et al., Quantitative reverse transcriptase/PCR assay for the measurement of induction in cultured hepatocytes, Chemico-Biological Interactions, vol. 107, Nov. 6, 1997, pp. 47-61.

Helfrich, et al., A quantitative reverse transcriptase polymerase chain reaction-based assay to detect carcinoma cells in peripheral blood, British Journal of Cancer, vol. 76, No. 1, Jul. 1997, pp. 29-35.

Seghezzi et al., C. tropicalis CYP52A6 gene encoding cytochrome P450alk3, EMBL Sequence Database, Jun. 27, 1992. Heidelberg DE, AC Z13010.

Seghezzi et al., Cytochrome P450 52A6, Swissprot Sequence Data Base, Apr. 1, 1993, Heidelberg DE, Ac P30608.

Seghezzi et al., Identification and Characterization of Additional Members of the Cytochrome P450 Multigene Family CYP52 of *Candida tropicalis*, DNA and Cell Biol., vol. 11, 1992, pp. 767-780.

Seghezzi et al., *Candida tropicalis* cytochrome P450alk2 and cytochrome P450alk1 genes, EMBL Sequence Database, Jul. 10, 1991. Heidelberg DE, Ac. M63258.

Seghezzi et al., Cytochrome P450 52A2, Swissprot Sequence Data Base, Apr. 1, 1993, Ac P30607.

Seghezzi et al., Characterization of a second alkane-inducible cytochrome P450-encoding gene, CYP52A2, from *Candida tropicalis*, Gene, vol. 106, 1991, pp. 51-60.

Sanglard et al., *Candida tropicalis* alkane-inducible cytochrome P450 gene, EMBL Sequence Database, Nov. 23, 1989, Heidelberg DE, Ac M24894.

Sanglard et al., Cytochrome P450 52A1, SwissProt Sequence Data Base, Jul. 1, 1989, AC P10615.

Sanglard et al., Characterization of the alkane-inducible cytochrome P450 (P450alk) gene from the yeast *Candida tropicalis*: identification of a new P450 gene family. Gene. vol. 76, No. 1, 1989, pp. 121-136.

Seghezzi et al., C tropicalis CYP52A8 gene encoding cytochrome P450alk5, EMBL Sequence Database, Jun. 27, 1992, Heidelberg DE. Ac Z13012.

Seghezzi et al., Cytochrome P450 52A8, Swissprot Sequence Data Base, Apr. 1, 1993, Ac P30610.

Seghezzi et al., C. tropicalis CYP52A7 gene encoding cytochrome P450alk4, EMBL Sequence Database, Jun. 27, 1992, Heidelberg DE, Ac Z13011.

Seghezzi et al., Cytochrome P450 52A7, Swissprot Sequence Database, Apr. 1, 1993, Ac P30609.

QC-RT-PCR primers for the 5' coding sequence of
Candida tropicalis 20336 P450CYP52A5A

```
5' ATGATTGAACAACTCCTAGAATATTGGTAT GTCGTTGTGCCAGTGTTGTACATCATCAAA CAACTCCTTGCATACACAAAGACTCGCGTC 3' 90
3' TACTAACTTGTTGAGGATCTTATAACCATA CAGCAACACGGTCACAACATGTAGTAGTTT GTTGAGGAACGTATGTGTTTCTGAGCGCAG 5'

5' TTGATGAAAAAGTTGGGTGCTGCTCCAGTC ACAAACAAGTTGTACGACAACGCTTTCGGT ATCGTCAATGGATGGAAGGCTCTCCAGTTC 3' 180
3' AACTACTTTTTCAACCCACGACGAGGTCAG TGTTTGTTCAACATGCTGTTGCGAAAGCCA TAGCAGTTACCTACCTTCCGAGAGTCAAG 5'

5' AAGA AGAGGGCAGGGCTCAAGAG ACAAC GATTACAAGTTTGACCACTCCAAGAACCCA AGCGTGGGCACCTACGTCAGTATTCTTTTC 3' 270
3' TTCT TCTCCCGTCCCGAGTTCTC TGTTG CTAATGTTCAAACTGGTGAGGTTCTTGGGT TCGCACCCGTGGATGCAGTCATAAGAAAAG 5'
        Forward Primer 7581-97F 5' GGCACCAGGATCGTCGTGACCAAAGATCCA GAGAATATCAAAGCTATTTTGGCAACCCAG TTTGGTGATTTTCTTTGGGCAAGAGCAC 3' 360
3' CCGTGGTCCTAGCAGCACTGGTTTCTAGGT CTCTTATAGTTTCGATAAAACGTTGGGTC AAACCACTAAAAGAAACCCGTTCTCCGTG 5'

5' ACTCTTTTTAAGCCTTTGTTAGGTGATGGG ATCTTCACATTGGACGGGCGAAGGCTGAAG CACAGCAGAGCCATGTTGAGACCACAGTTT 3' 450
3' TGAGAAAAATTCGGAAACAATC ACTACCC TAGAAGTGTAACCTG CCGCTTCCGACCTTC GTGTCGTCTCGGTACAACTCTGGTGTCAAA 5'
                       Reverse Primer 7581-97M 5' GCCAGAGAACAAGTTGCTCATGTGACGTCG TTGGAACCACACTTCCAGTTGTTGAAGAAG CATATTCTTAAGCACAAGGGTGAATACTTT 3' 540
3' CGGTCTCTTGTTCAACGAGTACACTGCAGC AACCTTGGTGTGAAGGTCAACAACTTCTTC GTATAAGAATTCGTGTTCCCACTTATGAAA 5'
```

FIG. 3

CYP Gene
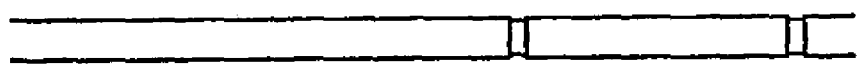
Helix I      HR2
CPR Gene
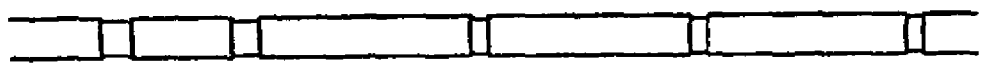
FMN-binding region    FAD-binding region    NADPH-binding
FIG. 4

C. tropicalis 20336 CPR Allele DNA Alignment of DS Sequence

```
CPRA    1                                                              CATCA      5
CPRB    1   TATATGATATATGATATATCTTCCTGTGTAATTATTATTCGTATTACTACATTTTTT            70
                                                                 *

CPRA    6   AGATCATCTATGGGGATAATTA-----CGACAGCAACATTGCAGAAAGAGCCGTTGGTCTCACAATCGAAAGA    70
CPRB   71   TCTTTATTATGAAGAAAAGGAGAGTATCCGACGAGGAGGAGTTCGTAAGTTGAGTTAGAATAGGCTGTTGTGCATACGGGGA   140
               ** * *****   **       * **    ** ** ** *  ** *  **  **  * *****

CPRA   71   GCCTATG-GCGTTGCCGTCGTGAGGCAAATGACAGCAC--CAACAATAACGATGGTCCCAGTGAAGAGC   137
CPRB  141   GCAGAGGAGTATCCGACGAGGAGGAGTTCGTAAATTTCATCTATGCTGTTGCGTCCTGTACTGTAC   210
             *  *   * ***  * ***   *  **  * ***      ** *  ** ** * *** **  **  **

CPRA  138   CTTCAGAACAGTCCATTGTTGACGCT--TAAGGCACGGATAATTACGTGGGCAAAGGAACGCGGAATTA   205
CPRB  211   TGTAAATCTTAGATTTCCTAGAGGTTGTGTTCTAGCAAATAAAGTGTTTCAAGATACAATTTTACAGGCAAG   280
             *  *    *      **           ** *  *    **  *  *** *       **    *

CPRA  206   GTTATGGGGGATCAAA--AGCGGAAGATTTGTGTTGCTTGTGGGTTTTTCCTTTATTTTCATATGAT   273
CPRB  281   GGTAAAGGATCAACTGATTAGCGGAAGATTGGTGTGCCTGTGCCTGTGGGGTTCTT---TTATTTTCATATGAT   347
              *     ** ** *  **  ****************** *** *  *** ** *  *  ****************

CPRA  274   TTCTTTGCGCAAGTAACATGTGCCAATTAGTTTGTGATTAGCGTGCC-CCACAATTGGCATCGTGGACG   342
CPRB  348   TTCTTTGCGCAGTAACATGTGCCAATCTAGTTTATGATTAGCGTACCTCCACAATTGGCATCTTGGACG   417
            ***********  ************   ****** ********* ** * **************** ******

CPRA  343   GGCCGTGTTTTGTCATACCCCAAGTCTTAACTAGTCCACAGTCTCGACGGTGTCTCGACGATGTCTTCTT   412
CPRB  418   GGCGTGTTTTGTCTTACCCCAAGCCTTAGTTCCACAGTCTCGACGTCTCGACGGTCTCGCCGATGTCTTCTC   487
            ***  ******** ********* ***  **   ****************  *******  ************
```

FIG. 13A-1

```
CPRA  413  CCACCCCTCCCATGAATCATTCAAAGTTGTTGGGGATCTCCACCAAGGGCACCGGAGTTAATGCTTATG  482
CPRB  488  CCACCCCTCGCAGGAATCATTCGAAGTTGTTGGGGATCTCC----------GCAGTTTATGTTCATG  548
           ********  ** ******** ************************          * **** ** * ***

CPRA  483  TTTCTCCCACTTTGGTTGTGTGATTGGGTAGTCTAGTGAGTTGGAGATTTCTTTTTTTCGCAGGTGTCTC  552
CPRB  549  TCTTTCCCACTTTGGTTGTGTGATTGGGTAGCGTAGTGAGTTGGTGTGATTTCTTTTTT-CGCAGGTGTCTC  617
           * * *************************** * ********** *  ************* ***************

CPRA  553  CGATATCGAAATTTGATGAATATAGAGAGAAGCCAGATCAGCACAGTAGACATGCCTTTGTAGTTAGAGAT  622
CPRB  618  CGATATCGAAGTTTGATGAATATTGATGAATATAG----GAGCCAGATCAGCATGGTATATGCCTTTGTAGATAGAGAT  683
           ********** ************ *  ***  *    ***************  ** ***************** ********

CPRA  623  GTTGAACAGCAACTAGTTGAATTACACGCCACCACTTGACACAGCCAAGTGCAGTGAGCTGTAAACGATGCAG  692
CPRB  684  GTTGAACAACAACTAGCTGAATTACACTGAATTACACACCACCGCT----------AAACGATGCGC  730
           ********* ****** *********   ** ********** *****          ********* *

CPRA  693  CCAGAGTGTCACCACCAACTGACGTTGGGTGGAGTTGTTGTTGTTGTTGTTG--------TTGTTGGCAGGGCCATATTGCTAA  762
CPRB  731  ACAGGGTGTCACCGCCAACTGACGTTGGGTGGAGTTG----------TTGTTGGCAGGGCCATATTGCTAA  791
            *** ******** ****************** *****           *********************

CPRA  763  ACGAAGAGACAAGTAGCACACAAAAACCCAAGCTTAAGAACAAAATAAAAAAAATTCATACGACAATTCCAAAG  832
CPRB  792  ACGAAGAAGAAGTAGCACACAAAAACCCAAGGTTAAGAACAA---TTAAAAAATTCATACGACAATTCCACAG  858
           *******   ********************* *********   * ******************** **

CPRA  833  CCATTGATTTACATAAT--CAACAG-TAAGACAGAAAAACTTTCAACATTCAAAGTTCCCTTTTCCT  899
CPRB  859  CCATTTACATAATCAACAGCGACAAATGAGACAGAAAAAACTTTCAACATTTCAAAGTTCCCTTTTCCT  928
           *****  * *   * *  *     *****************************************
```

FIG. 13A-2

```
CPRA  900  ATTACTTCTTTTTTTCTTCTTCCTT------CTTTCCTTCTGTTTTCTTACTTTATCAGTCTTTTA  962
CPRB  929  ATTACTTCTTTTTCTTTCTTCCTTCCTTCCTTCATTCCTTCCTTCTGCTTTTATTACTTACCAGTCTTTTG  998
           ********* ***** ** ***  *** ** *****  ****** ****** ********

CPRA  963  CTTGTTTTTGCAATTCCTCAATCCTCACTCCTCCTCCTACTCCTCACCATGGCTTTAGACAAGTTAGATTTGTAT  1032
CPRB  999  CTTGTTTTTGCAATTCCTCAATCCTCATCCTCAGCCT------CACCATGGCTTTAGACAAGTTAGATTTGTAT  1059
           *************************  ****   ***      ***************************
```

FIG. 13A-3

```
CPRA  1033  GTCATCATAAACATTGGTGGTCGCTGCTGTAGCCGCTGTAGCCGCCTATTTGCTAAGAACCAGTTCCTTGATCAGCCCCAGG  1102
CPRB  1060  GTCATCATAAACATTGGTGGTCGCTGCTGTGGCCGCTGTGGCCGCCTATTTGCTAAGAACCAGTTCCTTGATCAGCCCCAGG  1129
            ********************************  *************  **********************************

CPRA  1103  ACACCGGGTTCCTCAACACGGACAGCGGAAGCAACTCCAGAGACGTCTTGCTGACATTGAAGAAGAATAA  1172
CPRB  1130  ACACCGGGTTCCTCAACACGGACAGCGGAAGCAACTCCAGAGACGTCTTGCTGACATTGAAGAAGAATAA  1199
            ****** **************************************************************

CPRA  1173  TAAAAACACGTTGTTGTTGTTTGGGTCCCAGACGGGTACGGCAGAAGATTACGCCAACAAATTGTCCAGA  1242
CPRB  1200  TAAAAACACGTTGTTGTTGTTTGGGTCCCAGACCGGGTACGGCAGAAGATTACGCCAACAAATTGTCAAGA  1269
            ********************************  * ******************************* ***

CPRA  1243  GAATTGCACTCCAGATTTGGCTTGAAAAACGATGGTTGCAGATTTCGCTGATTACGATTGGGATAACTTCG  1312
CPRB  1270  GAATTGCACTCCAGATTTGGCTTGAAAAACCATGGTTGCAGATTTCGCTGATTACGATTGGGATAACTTCG  1339
            ******************************  *************************************

CPRA  1313  GAGATATCACCGAAGACATCTTGGTGTTTTTCATTGTTGCCACCTATGGTGAGGGTGAACCTACCGATAA  1382
CPRB  1340  GAGATATCACCGAAGACATCTTGGTGTGTTTTTCATCGTTGCCACCTATGGTGAGGGTGAACCTACCGACAA  1409
            ***************************  *****  *****************************   **

CPRA  1383  TGCCGACGAGTTCCACACCTGGTTGACTGAAGAAGCTGACACTTTGAGTACCTTGAAATACACCGTGTTC  1452
CPRB  1410  TGCCGACGAGTTCCACACCTGGTTGACTGAAGAAGCTGACACTTTGAGTACTTTGAGATATACCGTGTTC  1479
            *************************************************** ****** *********

CPRA  1453  GGGTTGGGTAACTCCACGTACGAGTTCTTCAATGCCATTGGTAGAAAGTTTGACAGATTGTTGAGCGAGA  1522
CPRB  1480  GGGTTGGGTAACTCCACCTACGAGTTCTTCAATGCTATTGGTAGAAAAGTTTGACAGATTGTTGAGTGAGA  1549
            *****************  ***************  ***********  ****************** ****
```

FIG. 13B-1

```
CPRA  1523  AAGGTGGTGACAGGTTTGCTGAATACGCTGAAGGTGATGACGGTACTGGCACCTTGGACGAAGATTTCAT  1592
CPRB  1550  AAGGTGGTGACAGATTGCTGAATATGCTGAAGGTGACGACGGCACTGGCACCTTGGACGAAGATTTCAT  1619
            ***************** *********** ***** ***** ********************************

CPRA  1593  GGCCTGGAAGGACAATGTCTTTGACGCCTTGAAGAATTGAACTTTGAAGAAAAGGAATTGAAGTAC     1662
CPRB  1620  GGCCTGGAAGGATAATGTCTTTGACGCCTTGAAGAATTGAACTTTGAAGAAAAGGAATTGAAGTAC     1689
            ************ ******************************************************

CPRA  1663  GAACCAAACGTGAAATTGACTGAGAGAGACGACTTGTCTGCTGCTGACTCCCAAGTTTCCTTGGGTGAGC  1732
CPRB  1690  GAACCAAACGTGAAATTGACTGAGAGAGAGACGACTTGTCTGCCGCTGACTCCCAAGTTTCCTTGGGTGAGC  1759
            ***************************** *********** ****************************

CPRA  1733  CAAACAAGAAGTACATCAACTCCGAGGGCATCGACTTGACCAAGGGTCCATTCGACCACACACCCATA   1802
CPRB  1760  CAAACAAGAAGTACATCAACTCCGAGGGCATCGACTTGACCAAGGGTCCATTCGACCACACACCCATA   1829
            ********************************************************************

CPRA  1803  CTTGGCCAGAATCACCGAGAGACGAGAGTTGTTCAGCTCCAAGGACAGAAAGACACTGTATCCACGTTGAATTT  1872
CPRB  1830  CTTGGCCAGGATCACCGAGAGACGAGAGTTGTTCAGCTCCAAGGACAGAAAGACACTGTATTCACGTTGAATTT  1899
            ********* *************************************************** *************

CPRA  1873  GACATTTCTGAATCGAACTTGAAATACACCACCGGTGACCATCTAGCTACTCGGCCATCCAACTCCGACG  1942
CPRB  1900  GACATTTCTGAATCGAACTTGAAATACACCACCGGTGACCATCTGGCCATCTGGCCATCCAACTCCGACG  1969
            ******************************************** *** ************************

CPRA  1943  AAAACATTAAGCAATTTGCCAAGTGTTTCGGATTGGAAGATAAACTCGACACTGTTATTGAATTGAAGGC  2012
CPRB  1970  AAAACATCAAGCAATTTGCCAAGTGTTTCGGATTGGAAGATAAACTCGACACTGTTATTGAATTGAAGGC  2038
            ******* *****************************************************************
```

FIG. 13B-2

```
CPRA  2013  GTTGGACTCCACTTACACCATCCCATTCCCAACCCCAATTACTTACGGTGCTGTCATTAGACACCATTTA  2082
CPRB  2040  ATTGGACTCCACTTACACCATTCCATTCCCAACTCCAATTACTTACGGTGCTGTCATTAGACACCATTTA  2109
            *****************  ******* *******************************************

CPRA  2083  GAAATCTCCGGTCCAGTCTCGAGACAATTCTTTTTGTCAATTGCTGGGTTTGCTCCTGATGAAGAAACAA  2152
CPRB  2110  GAAATCTCCGGTCCAGTCTCGAGACAATTCTTTTTGTCTTTTGCTGGGTTTGCTCCTGATGAAGAAACAA  2179
            **************************************  *****************************

CPRA  2153  AGAAGGCTTTTACCAGACTTGGTGGTGACAAGCAAGAATTCGCCGCCAAGGTCACCCGCAGAAAGTTCAA  2222
CPRB  2180  AGAAGACTTTCACCAGACTTGGTGGTGACAAACAAGAATTCGCCACCAAGGTTACCCGCAGAAAGTTCAA  2249
            ***** **** ******************** ************ ****** *****************
```

FIG. 13B-3

```
CPRA   2223  CATTGCCGATGCCTTGTTATATTCCTCCAACAACGCTCCATGGTCCGATGTTCCTTTGAATTCCTTATT  2292
CPRB   2250  CATTGCCGATGCCTTGTTATATTCCTCCAACACTCCATGGTCCGATGTTCCTTTGAGTTCCTTATT   2319
             **********************************  ****************** **********

CPRA   2293  GAAAACGTTCCACACTTGACTCCACGTTACTACTCCATTTCGTCTTCGTCATTGAGTGAAAAGCAACTCA  2362
CPRB   2320  GAAAACATCCACACTTGACTCCACGTTACTACTCCATTTCTTCTTCGTTGAGTGAAAAACAACTCA  2389
             ******  * * ****************************  * ***** ******** ********

CPRA   2363  TCAACGTTACTGCAGTTGTTGAAGCCGAAGAAGAAGCTGATGGCAGACCAGTCACTGGTGTTGTCACCAA  2432
CPRB   2390  TCAATGTTACTGCAGTCGTTGAGGCCGAAGAAGAAGCCGATGGCAGACCAGTCACTGGTGTTGTTACCAA  2459
             **** *********** ***** **************  ******************** * *****

CPRA   2433  CTTGTGTTGAAGAACGTTGAAATTGTGCAAAACAAGACTTGTCCACTACGATTTGAGC  2502
CPRB   2460  CTTGTGTTGAAGAACATTGAAATTGCGCAAAACAAGACTTGTCCACTTGTCACTACGATTTGAGC  2529
             ****  * ******* ********  *************** **************

CPRA   2503  GGCCCAAGAGGCAAGTTCAACAAGTTCAAGTGCCAGTGCATGTGAGAAGATCCAACTTAAGTTGCCAA  2572
CPRB   2530  GGCCCAAGAGGCAAGTTCAACAAGTTCAAGTGCCAGTGCACGTGAGAAGATCCAACTTAAGTTGCCAA  2599
             ****************************************  **********************

CPRA   2573  AGAACTCCACCACCCCAGTTATCTTGATTGGTCCAGGTACTGGTGTTGCCCCATTGAGAGGTTTGTCAG  2642
CPRB   2600  AGAACTCCACCACCCCAGTTATCTTGATTGGTCCAGGTACTGGTGTTGCCCCATTGAGAGAGTTTCGTTAG  2669
             ***********************************************************  **  **

CPRA   2643  AGAAAGAGTTCAACAAGTCAAGAATGGTGTCAATGTTGGCAAGACTTTGTTGTTTATGGTTGCAGAAAC  2712
CPRB   2670  AGAAAGAGTTCAACAAGTCAAGAATGGTGTCAATGTTGGCAAGACTTTGTTGTTTTATGGTTGCAGAAAC  2739
             ****************************************************** *************
```

FIG. 13C-1

```
CPRA  2713  TCCAACGAGGACTTTTGTACAAGCAAGAATGGGCCGAGTACGCTTCTGTTTTGGGTGAAAACTTTGAGA  2782
CPRB  2740  TCCAACGAGGACTTTTGTACAAGCAAGAATGGGCCGAGTACGCTTCTGTTTTGGGTGAAAACTTTGAGA  2809
            *****************************************************************

CPRA  2783  TGTTCAATGCCTTCTCCAGACAAGACCCATCCAAGAGAAGTTTACGTCCAGGATAAGATTTAGAAAACAG  2852
CPRB  2810  TGTTCAATGCCTTCTCCAGACAAGACCCATCCAAGAGAAGTTTACGTCCAGGATAAGATTTAGAAAACAG  2879
            ******************************************************************

CPRA  2853  CCAACTTGTGCACGAGTTGTTGACTGAAGGTGCCATTATCTACGTCTGTGGTGATGCCAGTAGAATGGCT  2922
CPRB  2880  CCAACTTGTGCACGAGTTGTTGACTGAAGGTGCCATTATCTACGTCTGTGGTGACGCCAGTAGAATGGCC  2949
            ****************************************************  ************

CPRA  2923  AGAGACGTGCAGACCACAATTTCCAAGATTGTTGCTAAAAGCAGAGAAATTAGTGAAGACAAGGCTGCTG  2992
CPRB  2950  AGAGACGTCCAGACCACAATTTCCAAGATTGTTGCCAAAAGCAGAGAAATCAGTGAAGACAAGGCCGCTG  3019
            ********  *************************  *************  *************  ****

CPRA  2993  AATTGGTCAAGTCCTGGAAGGTCCAAAATAGATACCAAGAAGATGTTTGGTAGACTCAAACGAATCTCTC  3062
CPRB  3020  AATTGGTCAAGTCCTGGAAGGTCCAAAATAGATACCAAGAAGATGTTTGGTAGACTCAAACGAATCTCTC  3089
            ******************************************************************

CPRA  3063  TTTCTCCCAACGCCATTTATGAATCTTTATTCTCATTGAAGCTTTACATATGTTCTACACTTTATTTTTT  3132
CPRB  3090  TTTCTCCCAACGCCATTTATGAA---TATTCTCATTGAAGTTTTACATATGTTCTATATTCATTTTTT  3155
            **********************   *************** *************** ** ********

CPRA  3133  TTTTTTTTTTATTATTATTATTACGAAACATAGGTCAACTATATATATACTTGATTAAATGTTATAGAAAACAA  3202
CPRB  3156  TTT------ATTATTACGAAACATAGGTCAACTATATATATACTTGATTAAATGTTATAGAAAACAA  3215
            ***      ***********************************************************
```

FIG. 13C-2

```
CPRA   3203  TAACTATTATTATCTACTCGTCCTACTTCTCTTTGGCATTGACATCAACATTACCGTTCCCATTACCGTTGCCGTT  3272
CPRB   3216  TAATTATTATTATCTACTCGTCCTACTTCTCTTTGGCATTGGCATTGGCATTGCCGTTGCCGTTGCCGTT        3285
             *** ************************************ *** **** *** ******************

CPRA   3273  GGCAATGCCGGGATATTTAGTACAGTATCTCCAATCCGGATTTGAGCTATTGTAGATCAGCTGCAAGTCA        3342
CPRB   3286  GGTAATGCCGGGATATTTAGTACAGTATCTCCAATCCGGATTTGAGCTATTGTAAATCAGCTGCAAGTCA        3355
             ** ************************************************** ***************

CPRA   3343  TTCTCCACCTTCAACCAGTACTTATACTTCATCTTTGACTTCAAGTCCAAGTCATAAATATTACAAGTTA        3214
CPRB   3356  TTCTCCACCTTCAACCAGTACTTATACTTCATCTTTGACTTCAAGTCCAAGTCATAAATATTACAAGTTA        3425
             ******************************************************************
```

FIG. 13C-3

```
CPRA  3413  GCAAGAACTTCTGGCCATCCACGATATAGACGTTATTCACGTTATTATGCGACGTATGGATGTGGTTATC  3482
CPRB  3426  GCAAGAACTTCTGGCCATCCACAATATAGACGTTATTCACGTTATTATGCGACGTATGGATATGGTTATC  3495
            ************************ ******************************** * *********

CPRA  3483  CTTATTGAACTTCTCAAACTTCAAAACAACCCCACGTCCCGCAAGTCATTATCAACGACAAGTTCTGG    3552
CPRB  3496  CTTATTGAACTTCTCAAACTTCAAAACAACCCCACGTCCCGCAAGTCATTATCAACGACAAGTTCTGA    3565
            ***************************************************************** *

CPRA  3553  CTCACGTCGTCGGAGCTCGTCAAGTTCCTCGTTGTTCAAATAGATCTTCTGTTATTGATCTTCTGGTACTTTCTCA  3622
CPRB  3566  CTCACGTCGTCGGAGCTCGTCAAGTTCCTCGTTGTTCAAATAGATCTTCTGTTATTGATCTTCTGGTACTTTCTCA  3635
            ***************************************************************************

CPRA  3623  ATTGCTGGAACACATTGTCCTCGTTGTTCAAATAGATCTTGAACAACTTTTCAACGGGATCAACTTCTC  3692
CPRB  3636  ACTGCTGGAACACATTGTCCTCGTTGTTCAAATAGATCTTGAACAACTTTTCAAGGGAATCAACTTTTC  3705
            * ******************************************** ***  *****  ****** **

CPRA  3693  AATCTGGGCCAAGATCTCCGCCGGGATCTTCAGAAACAAGTCCTGCAACCCCTGGTCGATGGTCTCCGGG  3762
CPRB  3706  GATCTGGGCCAAGATTCCGCCGGGATCTTCAGAAACAAGTCCTGCAACCCCTGGTCGATGGTCTCGGGG  3775
             ************** ****************************************** ** * ***

CPRA  3763  TACAACAAGTCCAAGGGGCAGAAGTGTCTAGGCACGTGTTCAACTGGTTCAACGAACATGTTCGACAGT  3832
CPRB  3776  TACAACAAGTCTAAGGGGCAGAAGTGTCTAGGCACGTGTTCAACTGGTTCAAGGAACATGTTCGACAGT  3845
            *********** ************************************** ****************

CPRA  3833  AGTTCGAGTTATAGTTATCGTACAACCATTTGGTTTGATTTCGAAAATGACGGAGCTGATGCCATCATT  3902
CPRB  3846  AGTTCGAGTTATAGTTATCGTACAACCACTTTGGCTTGATTTCGAAAATGACGGAGCTGATCCATCATT  3915
            **************************** ***** ************************* ******

FIG. 13D-1
```

```
CPRA  3903  CTCCTGGTTCCTCTCATAGTACAACTGGCACTTCTTCGAGAGGCTCAATTCCTCGTAGTTCCCGTCCAAG  3972
CPRB  3916  CTCCTGGTTCCTTCATAGTACAACTGGCATTCTTCGAGAGACTCAACTCCTCGTAGTTCCCGTCCAAG    3985
            ****************  ********************** *****   ******************

CPRA  3973  ATATTCGGCAACAAGAGCCCGTACCGGCTCACGGAGCATCAAGTCGTGGCCCTGGTTGTTCAACTTGTTGA  4042
CPRB  3986  ATATTCGGCAACAAGAGCCCGTAGCCGCTCACGGAGCATCAAGTCGTGGCCCTGGTTGTTCAACTTGTTGA  4055
            ********************** * ******************************************

CPRA  4043  TGAAGTCCGAGGTCAAGACAATCAACTGGATGTCGATGATCTGGTGCGGGAACAAGTTCTTGCATTTTAG  4112
CPRB  4056  TGAAGTCCGATGTCAAGACAATCAACTGGATGTCGATGATCTGGTGCGGGAAACAAGTTCTTGCACTTTAG  4125
            ********** ***************************************** ************ *****

CPRA  4113  CTCGATGAAGTCGTACAACTCACACGTCGAGATATACTCCTGTTCCTCCTTCAAGAGCCGGATCCGCAAG  4182
CPRB  4126  CTCGATGAAGTCGTACAACT                                                    4125
            ********************

CPRA  4183  AGCTTGTGCTTCAAGTAGTCGTTG  4206
CPRB  4146                            4145
```

FIG. 13D-2

```
CPRA    MALDKLDLYVIITLVVAVAAYFAKNQFLDQPQDTGFLNTDSGSNSRDVLLTLKKNNKNTL    60
CPRB    MALDKLDLYVIITLVVAVAAYFAKNQFLDQPQDTGFLNTDSGSNSRDVLLTLKKNNKNTL    60

CPRA    LLFGSQTGTAEDYANKLSRELHSRFGLKTMVADFADYDWDNFGDITEDILVFFIVATYGE   120
CPRB    LLFGSQTGTAEDYANKLSRELHSRFGLKTMVADFADYDWDNFGDITEDILVFFIVATYGE   120
                            *

CPRA    GEPTDNADEFHTWLTEEADTLSTLKYTVFGLGNSTYEFFNAIGRKFDRLLSEKGGDRFAE   180
CPRB    GEPTDNADEFHTWLTEEADTLSTLRYTVFGLGNSTYEFFNAIGRKFDRLLSEKGGDRFAE   180

CPRA    YAEGDDGTGTLDEDFMAWKDNVFDALKNDLNFEEKELKYEPNVKLTERDDLSAADSQVSL   240
CPRB    YAEGDDGTGTLDEDFMAWKDNVFDALKNDLNFEEKELKYEPNVKLTERDDLSAADSQVSL   240
                                      *

CPRA    GEPNKKYINSEGIDLTKGPFDHTHPYLARITETRELFSSKDRHCIHVEFDISESNLKYTT   300
CPRB    GEPNKKYINSEGIDLTKGPFDHTHPYLARITETRELFSSKERHCIHVEFDISESNLKYTT   300

CPRA    GDHLAIWPSNSDENIKQFAKCFGLEDKLDTVIELKALDSTYTIPFPTPITYGAVIRHHLE   360
CPRB    GDHLAIWPSNSDENIKQFAKCFGLEDKLDTVIELKALDSTYTIPFPTPITYGAVIRHHLE   360
                                            *

CPRA    ISGPVSRQFFLSIAGFAPDEETKKAFTRLGGDKQEFAAKVTRRKFNIADALLYSSNNAPW   420
CPRB    ISGPVSRQFFLSIAGFAPDEETKKTFTRLGGDKQEFATKVTRRKFNIADALLYSSNNTPW   420
                                **

CPRA    SDVPFEFLIENVPHLTPRYYSISSSSLSEKQLINVTAVVEAEEEADGRPVTGVVTNLLKN   480
CPRB    SDVPFEFLIENIQHLTPRYYSISSSSLSEKQLINVTAVVEAEEEADGRPVTGVVTNLLKN   480
```

FIG. 14A

```
CPRA  *      *  VEIVQNKTGEKPLVHYDLSGPRGKFNKFKLPVHVRRSNFKLPKNSTTPVILIGPGTGVAP  540
CPRB             IEIAQNKTGEKPLVHYDLSGPRGKFNKFKLPVHVRRSNFKLPKNSTTPVILIGPGTGVAP  540

CPRA             LRGFVRERVQQVKNGVNVGKTLLFYGCRNSNEDFLYKQEWAEYASVLGENFEMFNAFSRQ  600
CPRB             LRGFVRERVQQVKNGVNVGKTLLFYGCRNSNEDFLYKQEWAEYASVLGENFEMFNAFSRQ  600

CPRA             DPSKKVYVQDKILENSQLVHELLTEGAIIYVCGDASRMARDVQTTISKIVAKSREISEDK  660
CPRB             DPSKKVYVQDKILENSQLVHELLTEGAIIYVCGDASRMARDVQTTISKIVAKSREISEDK  660

CPRA             AAELVKSWKVQNRYQEDVW  680
CPRB             AAELVKSWKVQNRYQEDVW  680
```

FIG. 14B

C. tropicalis 20336 CYP52 DNA Alignment of DS Sequence

```
CYP52A1A    1                                                                              0
CYP52A2A    1   GACCTGTGACGCTTCCGGTGTCTTGCCACCAGTCTCCAAGTTGACCGACGCCCAAGTCATGTACCACTTT       70
CYP52A2B    1                                                                              0
CYP52A3A    1                                                        GACATCATAAT          11
CYP52A3B    1                                                                              0
CYP52A5A    1                                                                              0
CYP52A5B    1                                                     TTACAATCATGG            12
CYP52A8A    1                                                                              0
CYP52A8B    1                                                                              0
CYP52D4A    1                                                                              0

CYP52A1A    1                     CATATGCGCTAATCTTCTTTTTCTTTTATCACAGGAGAAACTATCCCACCCCACTTC    59
CYP52A2A   71   ATTTCCGGTTACACTTCCAAGATGGCTGGTGGTACTGGTGAAGAAGGTGTCACGGAACCACAAGCTACTTCTCCG     140
CYP52A2B    1                                                                              0
CYP52A3A   12   GACCCGGTTATTTCGCCCTCAGGTTGCTTATTTGAGCCGTAAAGTGCAGTAGAAACTTTGCCTTGGGTTC        81
CYP52A3B    1                                                                              0
CYP52A5A    1                                                                 TGGAGTC      7
CYP52A5B   13   AGCTCGCTAGGAACCCAGATGTCTCGGGAGAAGCTCCGCGAAGAGGTCAACACGAACTTTGGCATGGAGTC       82
CYP52A8A    1                                                                              0
CYP52A8B    1                                                                              0
CYP52D4A    1                                                                              0
```

FIG. 15A-1

| | | | |
|---|---|---|---|
| CYP52A1A | 60 | GAAACACAATGACAACTCCTGCGTAACTTGCAAATTCTTGTCTGACTAATTGAAAACTCCGGACGAGTCA | 129 |
| CYP52A2A | 141 | CTTGTTTCGGTCAACCATTCTTGGTGTTGCACCCAATGAAGTACGCTCAACAATTGTCTGACAAGATCTC | 210 |
| CYP52A2B | 1 | GCTCAACAATGTCTGACAAGATCTC | 26 |
| CYP52A3A | 82 | AAACTCTAGTATAATGGTGATAACTGGTTGCACTCTTGCCATAGGCATGAAAAATAGGCCGTTATAGTACT | 151 |
| CYP52A3B | 1 | | 0 |
| CYP52A5A | 8 | GCCAGACTTGCTCACTTTTGACTCCCCTTCGAAACTCAAAGTACGTTCAGGCGGTGCTCAACGAAACGCTC | 77 |
| CYP52A5B | 83 | GCCAGACTTGCTCACTTTTGACTCTCTCTTAGAAGCTCAAAGTACGTTCAGGCGGTGCTCAACGAAACGCTT | 152 |
| CYP52A8A | 1 | | 0 |
| CYP52A8B | 1 | AAAACCGATACAAGAAGAAGACAGTCAA | 28 |
| CYP52D4A | 1 | | 0 |
| | | | |
| CYP52A1A | 130 | GACCTCCAGTCAAACGGACAGACAAACACTTGGTGCGATGTTCATACCTACAGACATGTCAACGGG | 199 |
| CYP52A2A | 211 | GCAACACAAGGCTAACGCCCTGGTTGTTGAACACGGTTGAACACTGGTTGGGTTGGTTCTGCTAGAGGTGGTAAG | 280 |
| CYP52A2B | 27 | GCAACACAAGGCTAACGCCCTGGTTGTTGAACACTGGTTGGGTTGGTTCTGCTGCTAGAGGTGGTAAG | 96 |
| CYP52A3A | 152 | ATATTTAATAAGCGTAGGAGTATAGGATGCATATGACCGGTTTTCTATATTTTTAAGATAATCTCTAGT | 221 |
| CYP52A3B | 1 | CCTGCAGA | 8 |
| CYP52A5A | 78 | CGTATCTACCCGGGGTACCACGAAACATGAAGACAG--CTACGTGCAACACGACGTTGCCACGCGGAGG | 145 |
| CYP52A5B | 153 | CGTATCTACCCGGGGGGTACCACGAAACATGAAGACAG--CTACGTGCAACACGACGTTGCCGCGTGGAGG | 220 |
| CYP52A8A | 1 | | 0 |
| CYP52A8B | 29 | CAAGAACGTTAATGTCAACCAGGCGCCAAGAAGACGG--TTTGGCGGACTTGGAAGAATGTGGCATTTGC | 96 |
| CYP52D4A | 1 | | 0 |

FIG. 15A-2

| | | | |
|---|---|---|---|
| CYP52A1A | 200 | TGTTAGACGACGGTTCTTGCAAAGAC-AGGTGTTGGCATCTCGTACGATGGCAACTGCAGGAGGTGTCG | 268 |
| CYP52A2A | 281 | AGATGCTCATTGAAGTACACCAGAGCCATTTTGGACGCTATCCACTCTGGTGATTGTCCAAGGTTGAAT | 350 |
| CYP52A2B | 97 | AGATGTTCATTGAAGTACACCAGAGCCATTTTGGACGCTATCCACTCTGGTGAATTGTCCAAGGTTGAAT | 166 |
| CYP52A3A | 222 | AAATTTGTATTCTCAGTAGGATTCATCAAATTCGCAACCAATTCTGGCGAAAAATGATTCTTTTAC | 291 |
| CYP52A3B | 9 | ATTCGCGGCCCGGTCGACAGAGTAGCAGTTATGCAAGCAGTAGTCTGATTGTGGTTTTGCAACCTGTTTGCAC | 78 |
| CYP52A5A | 146 | AGGCA-AAGACGGCAAGGAACCTATCT-TGGTGCAGAAGGACAGTCCGTTGGGTTGATTACTATTGCCA | 213 |
| CYP52A5B | 221 | AGGCA-AAGACGGTAAGGAACCTATTT-TGGTGCAGAAGGGCCAGTCCGTTGGGTTGATTACTATTGCCA | 288 |
| CYP52A8A | 1 | | 0 |
| CYP52A8B | 97 | CCATG-ATGTTTATGTTCTGGAGAGGT-TTTTCAAGGAATCGTCATCCTCCGCCACCACAAGAACCACCA | 164 |
| CYP52D4A | 1 | | 0 |

FIG. 15A-3

| | | | |
|---|---|---|---|
| CYP52A1A | 269 | ACTTCTCCTTTAGGCAATAGAAAAAGACTAAGAGAACAGCGTTTTACAGGTTGCATTGGTTAATGTAGT | 338 |
| CYP52A2A | 351 | ACGAAACTTTCCCAGTCTTCAACTTGAATGTCCCAACCTCCTGTCCAGTGTCCCAAGTGTCCCAAGTGAAATCTTGAA | 420 |
| CYP52A2B | 167 | ACGAGACTTTCCCAGTCTTCAACTTGAATGTCCCAACCTCCTGCCCAGTGTCCCAAGTGTCCCAAGTGAAATCTTGAA | 236 |
| CYP52A3A | 292 | GTCAAAAGCTGA-ATAGTGCAGTTAAAGCACCTAAAATCACATATACAGCCTCTAGATACGACAGAGAA | 360 |
| CYP52A3B | 79 | GACAAATGATCG-ACAGT-CGATT--ACGTAATCCATATATTTAGAGGGTAATAAAAAATAAATGGCA | 144 |
| CYP52A5A | 214 | CGCAGACGGACCCAGAGTATTTGGGCCGACGCTGGTGAGTTTAAGCCGGAGATGGTTTGATTCA-- | 281 |
| CYP52A5B | 289 | CGCAGACGGACCCAGAGTATTTTGGGCCAGATGCTGGTGAGTTGAGTTCAAACCGGAGATGGTTTGATTCA-- | 356 |
| CYP52A8A | 1 | | 0 |
| CYP52A8B | 165 | GTTAACGAGAGATCCATATTCACAACCCACCCGCAAGGTGACAATGCTCAACACAACAGCAACAACAACA- | 232 |
| CYP52D4A | 1 | | 0 |
| | | | |
| CYP52A1A | 339 | ATTTTTAGTCCCAGCATTCTGTGGGTTGCTCTGGGTTTCTAGAATAGGAAATCACAGGAGAATGCAAA | 408 |
| CYP52A2A | 421 | CCCAACCAAGGCCTGGACCGG--AAGGTGTTGACTCCTTCAACAAGGAAATCAAGTCTTTGGCTGGTAAGT | 489 |
| CYP52A2B | 237 | CCCAACCAAGGCCTGGACCG--AAGGTGTTGACTCCTTCAACAAGGAAATCAAGTCTTTGGCTGGTAAGT | 304 |
| CYP52A3A | 361 | GCTCTTATGATCTGAAGAAGCATTAGAATAGCT---ACTATGAGCCACTATTGGTGTATATTAGGGA | 427 |
| CYP52A3B | 145 | GCC----AGAATTTCAAACATTTGCAAACAATGCAAAAGATGAGAAACTCCAACAGAAAAATAAAAAA | 210 |
| CYP52A5A | 282 | AGCATGAAGAACTTGGGTGTAAATACTTGCCGTTCAATGCTGGGACTTGCTTGGGCAGCAGT | 351 |
| CYP52A5B | 357 | AGCATGAAGAACTTGGGGTGTAAGTACTTGCCGTTCAATGCTGGGCCCCGGACTTGTTTGGGCAGCAGT | 426 |
| CYP52A8A | 1 | | 0 |
| CYP52A8B | 233 | ACCCCCACAAGAACAGTGGAATAATGCCAGTCAA-CAAAGAGTGGTGACAGACGAGGGAGAAAACGCAAG | 301 |
| CYP52D4A | 1 | | 0 |

FIG. 15B-1

```
CYP52A1A  409  TTCAGATGGAAGAACAAAGAGATAAAAACAAAAAAAACTGAGTTTTGCACCAATAGAATGTTTG----  474
CYP52A2A  490  TTGCTGAAAAC--TTCAAGACCTATGCTGACCAAGCTACCGCTGA--AGTGAGCTGCAGGTCCAGAAG  555
CYP52A2B  305  TTGCTGAAAAC--TTCAAGACCTATGCTGACCAAGCTACCGCTGA--AGTTAGAGCTGCAGGTCCAGAAG  370
CYP52A3A  428  TTGGTGCAATTAAGTACGTACTAATAAACAGAAGAAAATACTTAACCAATTTCTGGTGTATACTTAGTGG  497
CYP52A3B  211  ACTCCGCAGC--ACTCCGAACCAACAAAACAATGGGGGCCAG--AATTATTGAC---TATT-------  267
CYP52A5A  352  ACACTTTGATTGAAGCGAGCTACTTGCTAGTCCAGTTCCGGTTGGCCCAGACCTAC-CGGGCAATAGATTTG----  416
CYP52A5B  427  ACACTTTGAAGCGAGCTAGCTATTTGCTAGTCCAGTTGGCCAGACCTAC-CGGGTAATCGATTTG----  491
CYP52A8A    1                                                                             0
CYP52A8B  302  CAACAGTGGTTCTGATGCAAGATCAGTCACACCGCTTCATCAGGAAAAGC-AGGAGCTCCCACCAC----  366
CYP52D4A    1                         GATGTGGTGCTTGATTTCTGAGACACATCCTTGTGAGGTGCCATGAATCTGTACCTG-  58

CYP52A1A  475  -ATGATATCATCCACTCGCTAAACGAATCATGTGGGTGATCTTCTCTCTTAGTTTTGGTCTATCATAAAAC  543
CYP52A2A  556  CTTAAAGATATTTATTCACTATTAGTTTGCCTATTTGCCTATTTCTCATTACCCATC-ATCATTCAACACTAT  624
CYP52A2B  371  CTTAAAGATATTATTCACTATTAGTTTGCCTATTTGCCTATTTCTCATCCATC-ATCATTCAACAATAT  439
CYP52A3A  498  -TGAGGGACCTTTTCTGAACATTCGGGTCAAACTTTTTTTTGGAGTGCGACATGCGATTTTCGTTTGTGT  556
CYP52A3B  268  ----GTGACTTTTTTTATTTTATTTTCCGTTAA--CTTTCATTGCAGTGAAGTGT--GTTACACGGGGTGGT  329
CYP52A5A  417  -CAGCCAGGATCGGCGGCGTACC-CACCAAGAAAGAAGTCGTTGATCAACATGAGTGCTGCCGACGGTGTT  484
CYP52A5B  492  -CTGCCAGGTCGGCGTACC--CACCAAGAAGAAGAAGTCGTTGATCAATATGAGTGCTGCCGATGGGGTGGT  559
CYP52A8A    1                                                                              0
CYP52A8B  367  -CATATGCCCATCACGAGCAACACCAGCAGTTAGTGTATAGTAGTCTGTAGTAAGTCAATGCAATGTA      435
CYP52A4A   59  -TCTGTAAGCACAGGAACTGCTTCAACACCTTATTGCATATTCGTCTATTGCAAGCGTGTGCTGCAAC      127
```

FIG. 15B-2

| | | | |
|---|---|---|---|
| CYP52A1A | 544 | ACATGAAAGTGAAATCCAAA-TACACTACACTCCGGGTATTGTCCTTCGTTTACAGATGTCTCATTGTC | 612 |
| CYP52A2A | 625 | ATATAAAGTTACTTCGGA---------TATCATTGTAATCGTGCGTGTCGCAATTGGATGATTGGAA | 683 |
| CYP52A2B | 440 | ATATAAAGTTATTTCGGAAC-TCATA---TATCATTGTAATCGTGCGTGTTGCAATTGGGTAATTGAAA | 505 |
| CYP52A3A | 567 | AATAATAGTGAACCTTTGTG-TAATAAATCTTCATGCAAGACTTGCATAATTCGAGCTTGGAGTTCACG | 635 |
| CYP52A3B | 330 | GATGGTGTTGGTTTCTACAA-TGCAAGGGCACAGTTGAAGGTTTCCACATAACGT-TGCACCATATCAAC | 397 |
| CYP52A5A | 485 | TGT--AAAGCTTTATAAGGA-TGTAACGGTAGATAGTTGTGTAGGAGGAGCGGAGATAAATTAGAT | 551 |
| CYP52A5B | 560 | TGT--AAAGTTTCACAAGGA-TCTAGATGGATATGTA-AGGTGTGTAGGAGGAGCGGAGATAAATTAGAT | 625 |
| CYP52A8A | 1 | | 0 |
| CYP52A8B | 436 | CCA--ATAAGACTATCCCTT-CTTACAACCAAGTTTCTGCCGCCTGTCTGGCA-ACAGATGCTGGCC | 501 |
| CYP52D4A | 128 | GATATCTGCCAAGGTATATAGCAGAACGTGCTGATGGTTCCTCCGGTCATATTCTGTTGGTAGTTCTGCA | 197 |

FIG. 15B-3

```
CYP52A1A  613  TTACTTTGAGGTCATAGAGGAGTTGCCTGTGAGAGATCACAGAGATTATCACACTCACATTATCGTAGTT  682
CYP52A2A  684  CTGGCTTGAAACGGATTCATGCACGAAGCGGAGA-TAAAAGATTACGT---AATTTATCTCCTGAGACA  749
CYP52A2B  506  CTGTAGTTGGAACGGATTCATGCACGATGCGGAGA-TAACACG--------AGATTATCTCCTAAGACA  565
CYP52A3A  636  C--CAATTTGACCTCGTTCATGTGATAAAGAAAAGCCAAAAGGTAATT---AGCAGACGC---AATGGG  697
CYP52A3B  398  T--CAATTTATCCTCATTCATGTGATAAAGAAGAGCCAAAAGGTAATT---GGCAGACCCCCAAGGGG  462
CYP52A5A  552  TTGATTTTG---TGTAAGGTTTTGGATGTCAACCTACTCCGCACTTCATGCA-GTGTGTGTGACACAAGG  617
CYP52A5B  626  TTGATTTTG---TGTAAGGTTTAGCACGTCAAGTCACTCCGCACTTTGT-----GTGTAGGAGCACA---  685
CYP52A8A    1                                                                              0
CYP52A8B  502  GACACACTT---TCAACTGAGTTTGGTCTAGAATTCTTGCACATGCACGACA-AGGAAACTCTTACAAAG  567
CYP52D4A  198  GGTAAATTTGGATGTCAGGTAGTGGAGGGAGGTTTGTATCGGTTGTGTT-TTCTTCTCCTCCTCTCTG  266

CYP52A1A  683  TCCTATCTCATGCTCTGTGTCTCTCGGTTGGTTCATGAGTTTGGATT--GTTGTACATTAAAGGAATCGCT  750
CYP52A2A  750  ATTTTAGCCGTGTTCACACGCCCTTCTTTGTT-CTGAGCCGAAGAT--AAATAATTAGACTTCCACAGCT  816
CYP52A2B  566  ATTTTGGCCTCATTCACACGCCCTTCTT-----CTGAGCTAAGGAT--AAATAATTAGACTTCACAAGTT  628
CYP52A3A  698  AACATGGAGTGGAAAGCACGCAATGGAAGCACGCCC-AGGACGAGTAATTAGTCCACTACATCTGGGGT  766
CYP52A3B  463  AACACGGAGTAGAAAGCACGCAATGGAAACACGCCC-ATGACAGTGCCATTTAGCCCACACACATCTAGTATT  531
CYP52A5A  618  GTGTACTACGTGTGCGTGCCCTGTGCGCCAAGAGACA---GCCCAAGGGGG--TGGTAGTGT-GTGTTGGCGGAA  681
CYP52A5B  686  ---TACTCCGTCTGCGCCTGTGCCAAGACG--GCCCAGGGG-------TAGTGT-GTGGTGTGGAA  741
CYP52A8A    1         GAATTCTTTGGATCTAATTCCAGCTGATC---TTGCTAATCCT--TATCAACGTAGTTGTGATCATT   62
CYP52A8B  568  --ACAACACTGTGCTCTGATGCCACTTGATC---TTGCTAAGCCT--TATCAACGTAATTGAGATCATT  630
CYP52D4A  267  ATTCAACCTCCACGTCCTCCTTCGGTTCTGTGTCTGTGAGTC--GTACTGTTGGATTAAGTCCATC  334
```

FIG. 15C-1

```
CYP52A1A   751 TCTTTCCTGATTGGGCAAGTGCACAAACTACA-ACCTGCAAAACAG----CACTCCGCTTGTCACAGGTT  820
CYP52A2A   817 CATTCTAATTCCGT---CACGCGAATATTGAA--------------------GGGGGTACATGTGCCGCTGAA-  869
CYP52A2B   629 CATTAAAATATCCGT---CACGCGAAAACTGCAACAATAAGGAAGGGGGGGGGTAGACGTAGCCGATGAA-  694
CYP52A3A   767 ----TTTTTTTTGTGCGCAAGTACACACACTGGACT-TTAGTTTTTGCCCCATAAAGTTAACAATCTAA-  830
CYP52A3B   532 CTTTTTTTTTTTTGTGCGCAGTGCACACACTGGACT-TTAGTTATTGCCCCATAAAGTTAACAATCTCA-  599
CYP52A5A   682 GTGCATGTGACACA---ACGCGTGGGTTCTGGCCAATGGTGGACTAAGTGCAGGTAAGCAGCGACCTGAA  748
CYP52A5B   742 GTGCATGTGACACA---ATACCCTGTTCTGGCCAATTGGGGATTTAGTGTAGGTAAGCTGCGACCTGAA  808
CYP52A8A    63 GTTTGTCTGAATTAT--ACACACCAGTGGAAGAATATGGTCTAATTTGCACGTCCCACTGCCATTGTG--  128
CYP52A8B   631 GTTTGTCTGAATTAT--ACACACCAGTGGAAGAATCTGGTCTAATCTGCACGCCTCATGGCATTGTG--  696
CYP52D4A   335 GCATGTGTGAAAAAGTAGCGCTTATTTAGACAACCAGTTCGTTGGGCGGTATCAGAAATAGTCTGTT  404

CYP52A1A   821 TCTTTCCTGATTGGGCAAGTGCACAAACTACA-ACCTGCAAAACAG----CACTCCGCTTGTCACAGGTT  885
CYP52A2A   870 -TGTGGGGG--CAGTAAACGCAGTCTCTC--------------CTCTCCCAGGAATAGTGCAACGG  918
CYP52ACB   695 -TGTGGGGTGCCAGTAAACGCAGTCTCTCTCCGCCCCCCCCCCCTCAGGAATAGTACAACGG  763
CYP52A3A   831 -CCTTTGGC-TCTCCAACTCTCTCCGCCCCCAAATATTCGTTTTT-ACACCCTCAAGCTAGCGACAGCAC  897
CYP52A3B   600 -CCTTTGGC-TCTCCCAGTGTCTCCGCCTCCAGATGCTCGTTTT--ACACCCTCGAGCTAACGACAACAC  665
CYP52A5A   749 ACATTCCTCAACGCTTAAGACACTGGTGG-TAGAGATGCGGACCAGG-----CTATTCTTGTCGT-GCTA  811
CYP52A5B   809 ACACGCTTCAACGCTTGAGACACTGGTGGGTAGACATGGGCCAGGA--GGCTATTCTTGTCGT-GCTA  875
CYP52A8A   129 -TGTTT-----GTGGGGGGGGGGGGGTGCACACATTTTAGTGCCA----TTCTTTGTTGATTAC-CCCT  187
CYP52A8B   697 -TGTTTT--GGGGGGGGGGGGGGGGGGTGCACACATTTTAGTGCACAATGTTTGTTGCTGGTTCC-CCCT  762
CYP52D4A   405 GTGCACGACCATGAGTATGCAACTTGACGAGAACGTCGTTAGGA-----ATCCACAGAATGATAGCAGGAA  469
```

FIG. 15C-2

```
CYP52A1A  886  GTCTCCTCTCAACCAACAAAAAATAAGATTAAACTTTCTTTGCTCATGATCAATCGGAGTTATCTCTG
CYP52A2A  919  AGGAAGGATAACGGATAGAAAAGCGAATGCGAGGAAAAT--TTTGAACGCGCAAGAAAAGCAATATCCGG   955
CYP52A2B  764  GGGAAGGATAACGGATAGCAAGTGGAAGTGGAGGAAAAT--TTTGAATGCGCAAGGAAAGCAATATCCGG   986
CYP52A3A  898  AACACCCATTAGAGGAATGGGGCAAAGTTAAACACTTTTGGCTTCAATGATTCCTATTCGCTACATT     831
CYP52A3B  666  AACACCCATGAGGGGAATGGG-CAAAGTTAAACACTTTTGGTTTCAATGATTCCTATTGCTACT-----   967
CYP52A5A  812  CCCGGCGCATGGA-AAATCAACTGCGGGAAGAA--TAAATTATCCGTAGAATCCACAGAGCG------G  729
CYP52A5B  876  CCCG-TGCACGGA-AAATCGATTGAGGGAAGAA--CAAATTATCCGTGAAATCCACAGAGCG------G  872
CYP52A8A  188  CCCCCTATCAT---TCATTCCCACAGGATTAG--TTTTTTCCTCACTGGAATTCGCTGTCC-------  935
CYP52A8B  763  CCCCCCCTCCCCCTATCATGCCCACAGGATTAG--TTTTTCCTCACTGGAATTCGCTGTCC-------  244
CYP52D4A  470  GCTTACTACGTGAGAGATTCTGCTTAGAGGATG--TTCTCTCTTCTTGTTGATTCCATTAGGTGGTATCAT  822
                                                                                      537
```

FIG. 15C-3

| | | |
|---|---|---|
| CYP52A1A | 956 | A--AAGAGTTGCCTTTGTGTAATGTGTCCCAAA-CTCAAACTGCAAAACTAACCACAGAATGAT------ | 1016 |
| CYP52A2A | 987 | GCTACCAGGTTTTGAGCCAGGGAACACACTCCTATTTCTGTCTCAATGACTGAACATAGAAAAA------ | 1050 |
| CYP52A2B | 832 | GCTATCAGGTTTTGAGCCAGGCAGGGACACACTCCT-CTTCTGCACAAAAACTTAACGTAGACAAAAAAAAA | 900 |
| CYP52A3A | 968 | CTTCTCTGTTGTGTGCTTTGAATTGCACCATGCACCATGTGAAATAAACGACAATTATATATACCTTTTCATC--- | 1034 |
| CYP52A3B | 730 | ---CTCTGTTTGTGTTTGATTTGCACCATGCACCATGTGAAATAAACGACAATTATATATACCTTTTCGTC--- | 793 |
| CYP52A5A | 873 | A--TAAATTTGCCCACCTCCATCATCAACCACG-CCGCCACTAACTACATCACTCCCTATTTT---- | 933 |
| CYP52A5B | 936 | A--TAAATTTGTCACATTGCTGCGTTGCCCAC-----------CCACAGCATTCTC---- | 978 |
| CYP52A8A | 245 | ----ACCTGTCAACCCCCCCCCCCC--CCACTGCC--CTACCCTGCCCTGC----- | 293 |
| CYP52A8B | 823 | ----ACCTGTCAACCCCTCAC-------------TGCCCTGCCCTGC------ | 853 |
| CYP52D4A | 538 | CTCCGGTGGTGACAACTTGACACAAGCAGTTCCGAGAACCACCCACAATCACCATTCCAGC------ | 601 |
| | | * | |
| CYP52A1A | 1017 | TTCCCTCACAATTATATAAACTCACCCACATTTCCACAGACCGTAATTTCATGTCTCTAC-TTTCTCTTTT | 1085 |
| CYP52A2A | 1051 | -----CACCAAGACGCAATGCAAATGAAACGCACATGGACATTTAGACCTCCCACATGTGATAGTTGTCTTAAC | 1115 |
| CYP52A2B | 901 | AACTCCACCAAGACACACATGCAATGAATCGCACATGGACATGGACATTTAGACCTCCCACATGTGAAAGCTTCTCTGGCG | 970 |
| CYP52A3A | 1035 | CCTCCTCCTATATCTCTTTTGCTAC-ATTTGTTTTGTCTTTGCCATTTGTCTTTTGCTTTTGCACTCTCTCCCACTCCC | 1103 |
| CYP52A3B | 794 | TGTCCTCCAATGCTCTCTTTTGCTCTTTTGTCTTTTGCCATTGTCTTTGCTTTCCTTAGCCACAGATACACACCACT-GCAAACAGCA | 863 |
| CYP52A5A | 934 | CTCTCTCTCTCTCTTGTCTTTGTCTTACTCCGTTCTCCGCTCCGTTCTTCCTTATCCGACGCTATAAAAAGCCCTGGCGTCCGGCGTACGGCCAAGTTTT | 1002 |
| CYP52A5B | 979 | TTTTCTCTCTCTCTCTTTGTCTTTGTCTTACTCCGCTCCGTCTGTGTCTTCCTTATCCGACGCTATAAAAAGCCCTGGCGTCCGGCGTACGGCCAAGTTTT | 1048 |
| CYP52A8A | 294 | CCTGCACGTCCTGTGTTTGTGCTGTGTGGCACTCCACGCTATAAAAGCCCTGGCGTCCGGCGTACGGCCAAGTTTT | 363 |
| CYP52A8B | 854 | CCTGCACGCCCCTGTGTTTGTGCTGTGTGGCACTCCACGCTATAAAAGCCCTGGCGTACGGCCAAGTTTT | 923 |
| CYP52D4A | 602 | TATCACTTCTACAGTCAACCTACGATGTATCCATCACCATCTAGTTTCTTGGCAATCGTTTATTTGTT | 671 |

FIG. 15D-I

```
CYP52A1A 1086  GCTCTCTTCTTTACTTAGTCAGGTTTGATAACTTCCTCTTTTTATTACCTATCTATTATTATTATTATTC  1155
CYP52A2A 1116  AGA------AAAGTATAATAAGAACCATGCCGTCCCTTTCTTCGCCGCTTCAACTTTTTTTTTA        1179
CYP52A2B  971  AAAGCAAAAAAAGTATAATAAGGACCCATGCCTTCCCTCCTTCAACTTTTCTTTTTCT              1040
CYP52A3A 1104  ACAA---------------------AGAAAAAAAACTACACTATGTCGTCTCTCCATCGTTT          1146
CYP52A3B  864  ACAATCAGTGCAGCAACACACAGAGAAGAAGAAAATAAAAACCTACACTATGTCGTCTTCTCCATCGTTT   933
CYP52A5A 1003  GCA--ACAATTATAAAGATACGCC-----AGGCCCACCTTCTCTTTTTCTTCACTTTTTGACTGC-A     1064
CYP52A5B 1049  ACG--CTAGCCCAGCTGTCTTTCT-----TTTTCTTCACTTTTTTTGGTGTGTTGGTTGCAAGGTTT---CCAC-C  1110
CYP52A8A  364  TCCACCCAGCCAAAAAACAGTCTAAAAATTGGTTGATCCTTTTGGTTGCAAGGTTT---CCAC-C        429
CYP52A8B  924  TCCTCACAGCCAAAAAA---------AATTTGGCTGATCCTTTTGGGCTGCAAGGTTTTTCACCAC-C     982
CYP52D4A  672  ATGGGTCAACATCCAATACAACTCCACCAA--TGAAGAAGAAACGGAAAGCAGAATACCAGAATGACA     739

CYP52A1A 1156  ATTTATACCAACCAACC--AACCATGGCCACACGACCACACAAGAAATCATCGATTCTGTACTTCCGTACTTGACCAA  1223
CYP52A2A 1180  TCTT------ACACACATCAACACACACCTCACGACCA-TGACTGTACACGATTATCGCCACATACTTCACCAA     1236
CYP52A2B 1041  TTGTCTATCAACACACACACCTCACGACCA-TGACTGCACAGGATATTATCGCCACATACATCACCAA           1109
CYP52A3A 1147  GCCC------AAGAGGTTCTCGCTACCACTAGTCCTTACATCGAGTACTTTCTTGACA-ACTACACCAG          1208
CYP52A3B  934  GCTC------AGGAGGTTCTCGCTACCACTAGTCCTTACATCGAGTACTTTCTTGACA-ACTACACCAG           995
CYP52A5A 1065  ACTTTCTACAATCCACCACAGCCACCACCACCACAGCCGCTATGATTGAACAACTCCTAGAATATT----         1127
CYP52A5B 1111  ACTTTCTACAACC------ACCACCACCACCACCACCATGATTGAACAAATCCTAGAATATT--------         1166
CYP52A8A  430  ACCACTTCCACCA--CCTCAACTATTCGAACAA--AAGATGCTCGATCAGATCTTACATTACT-------          488
CYP52A8B  983  ACCACCACCACCA--CCTCAACTATTCAAACAA--AGGATGCTCGACCAGATCTTCCATTACT-------         1041
CYP52D4A  740  GTGTG----AGTTCCTGACCATTGCTAATCTA-TGGCTATATCTAGTTTGCTATCGTGGATG--------          797
```

FIG. 15D-2

```
CYP52A1A  1224  ATGGTACACTGTGATTACTGCAGCAGTATTAGTCTTCTTCCTTATCTCCACAAACATCAAGAACTACGTCAAG  1293
CYP52A2A  1237  ATGGTACGTGATAGTAGTACCACTCGCCTTTGATTGCTTATAGAGTCCTGACTACTTCTATGGCAGATACTTG  1306
CYP52A2B  1110  ATGGTACGTGATAGTAGTACCACTCGCTTTGATTGCTTATAGGGTCCTCGACTACTTTACGGCAGATACTTG  1179
CYP52A3A  1209  ATGGTACTACTTCATACCTTTGGTGCTCTTCTTTCGTTGAACTTTATAAGTTTGCTCCACACAAGGTACTTG  1278
CYP52A3B   996  ATGGTACTACTTCATCCTCTTTGGTGCTGCTCTTCTTCGTTGAACTTCATCAGCTTGCTCCACACAAAGTACTTG  1065
CYP52A5A  1128  --GGTATGTCGTTGTGCCAGTGTTGTACATCAAACAACTCCTTGCATACACAAAGACTCCTACAGCAAGACTCCGCGTCTTG  1195
CYP52A5B  1167  --GGTATATTGTTGTGCCTGTGTTGTACATCAAACAACTCATTATCAACAATTATCAACCAGATCGTGGCTCATGTCGTGCTCAGGACTCCGCGTCTTG  1234
CYP52A8A   489  --GGTACATTGTCTTGCCATTGTCTTGCCATTATCAACCAGATCGTGGCTCATGTCGTGCTCAGGACTCCGCGTCTTG  556
CYP52A8B  1042  --GGTACATTGTCTTGCCATTGTCTTGGTCATTATCATTATCAAGCAGATCAGCAGATCGTGGCTCATGCCTCAGGACCAATTATTTG  1109
CYP52D4A   798  -TGATCTGTGTCGTCTTCATTTGCGTTTATTCGGGTAT-GAATATTGTTATACTAAATACTTG  865
                  *  * *        *                         *                                       *
```

FIG. I5D-3

```
CYP52A1A  1294  GCAAAGAAATTGAAATGTGTCGATCCACCATACTTGAAGGATGCCCGTCTCACTGTATTCTGTCTTTGA  1363
CYP52A2A  1307  ATGTACAAGCTTGGTGCTAAACCATTTTCCAGAAACAGACAGACGGCTGTTTCGGATTCAAAGCTCCGC  1376
CYP52A2B  1180  ATGTACAAGCTTGGTGCTAAACCGTTTTTCCAGAAACAAACAGACGGTTATTTCGGATTCAAAGCTCCAC  1249
CYP52A3A  1279  GAACGCAGGTTCCACGCCAAGCCACTCGGTAACTTGTCAGGGACCCTACTCCTACGTTGGTATCGCTACTCCGT  1348
CYP52A3B  1066  GAACGCAGGTTCCACGCCAAGCCGCTCGGTAACGTCGTGTTGGATCGTCACAAGCGCTTTGGTATCGCTACTCCGT  1135
CYP52A5A  1196  ATGAAAAAGTTGGGTGCTGCTCCAGTCACAACAAGTGTACGACAAACCAGTGTACGACAACGTTTTCGGTATCGTCAATGGAT  1265
CYP52A5B  1235  ATGAAACAGTTGGGTGCTGCTCCAATCACAACACACCAGTCCACACGTGACGGGGTGGTTGGCTTCAAATTCGGCC  1304
CYP52A8A   557  ATGAAGAAATTGGGCGCTAAGCCATTCACACACTGTCCACACATGTCACACTAGACGGGGTGGTTGGCTTCAAATTTGGCC   626
CYP52A8B  1110  ATGAAGAAGTTGGGCGCTAAGCCATTCACACATCACACATGTCACACTAGACGGGTGGTTCTTTGGGTTCCGCTTACCTT  1179
CYP52D4A   866  ATGCACACAAACATGGCGCTCGCTCCAGAGAATCGAGAAATCGAGAAATGTGATCAACGATGGGGTTCTTTGGGTTCCGCTTACCTT   935
                                      *                                   *      **
                                                                                 *

CYP52A1A  1364  TCGCCGCCATCAAGGCCAAGAACGACGGTAG-ATTGGCTAACTTTGCC------GATGAAGTTTT----  1421
CYP52A2A  1377  TTGAATTGTTGAAGAAGAAGAGAGTGACGGTAC-CCTCATAGACTTCACA------CTCCAGCGTATC---C  1436
CYP52A2B  1250  TTGAATTGTTAAAAAGAAGAGAGTGACGGTAC-CCTCATAGACTTCACT------CTCGAGCGTATC---C  1309
CYP52A3A  1349  TGCTTTTGATCTACTTGAAGTCGAAAGGTAC-GGTCATGAAGTTTGCTTGGGCCTCTGAACAACAAGT  1417
CYP52A3B  1136  TGATCTTGATCTACTTAAAGTCGAAAGGTAC-AGTCATGAAGTTTGCCTGGAGCTTCTGGAACAACAAGT  1204
CYP52A5A  1266  GGAAGGCTCTCCCAGTTCAAGAGGGCAGGCTCAAGAGTACAACG------ATTACAAGTTTG----  1325
CYP52A5B  1305  GGAAGGCTCTCCCAGTTCAAGAGGGCAGAGCTCAAGAGTACAACG------ATCACAAGTTTG----  1364
CYP52A8A   627  GTGAATTCCTCAAAGCAAAAGTGCTGGGAG-ACTGGTTGATTAATC------ATCTCCCGTTT----   684
CYP52A8B  1180  GTGAATTCCTCAAAGCTAAAAGTGCTGGGAG-GCAGGTTGATTAATC------ATCTCCCGTTT----  1237
CYP52D4A   936  TGCTACTCATGCGAGCCAGCAATGAGGGCCG-ACTTATCGAGTTCAGT------GTCAAGAGATTCGAGT   998
                          *                *                    **
                *

FIG. 15E-1
```

```
CYP52A1A 1422 ----CGACGAGTACCCAAACCACACCTTCTACTTGTCTGTTGCCGGTGCTCTTTGAAGATTGTCATGACTGT      1487
CYP52A2A 1437 ACGATCTCGATCGTCCCGATATCCAGATATCCCAACTTTCACATTCCCGGTCTCTTTCCATCAACCTTGTCAATACCCT  1506
CYP52A2B 1310 AAGCGCTCAATCGTCCAGATATCCCAACTTTTACATTCCAATCTTTTCCATCAACCTTATCAGCACCCT            1379
CYP52A3A 1418 ACATCGTCAGAGACCCAAAGTACAAGACAACTGGGCTCAGGATTGTTGGCCTCCCATTGATTGAAACCAT           1487
CYP52A3B 1205 ACATTGTCAAAGACCCAAAGTACAAGACAACTGGGCTCAGGATTGTCGCGCCTCCCATTGATTGAAACCAT          1274
CYP52A5A 1326 ACCACTCCAAGAACCCAAGCGTGGGCACCACCTACGTCAGTATTCTTTCTTTGCACCAGGATCGTCGTGACCAA       1395
CYP52A5B 1365 ACAGCTCCAAGAACCCAAGCGTCGGCACCACCTATGTCAGTATTCTTTCTTTGGCACCAAGATTGTCGTGACCAA      1434
CYP52A8A  685 ------CCACGA------TAATGAGGACACTTTCTCCAGTACTTTTGGCAACCATGGTGTTCACCAG               744
CYP52A8B 1238 ------CCACGA------TAATGAGGACACTTTCTCCAGTACTTTTGGCAACCATGGTGTTCACCAG             1297
CYP52D4A  999 -CGGCGCCACAT--CCACAGAACAAGACAATTGTCAACCGGGCATTGAGCGTTCCTGTGATACTCACCAA          1065
                            *                      *  *       *           **

CYP52A1A 1488 TGACCCAGAAAACATCAAGGCTGTCTCTTCCTGGCCACCCAATTCACTGACTTCTCTCCTTGGGTACCAGACACGCC   1557
CYP52A2A 1507 TGAGCCGGAGAACATCAAGGCCATCTTGGCCACTCGGCCACTCAGTTCAACGATTTCTCCTTGGGTACCAGACACTCG  1576
CYP52A2B 1380 TGAGCCGGAGAACATCAAGGCTCAAGGCTATCTTGGCCACTCAGTTCAACGATTTCTCCTTGGCCACCAGACACTCG   1449
CYP52A3A 1488 GGAGCCAGAGAACATCAAGGCTCAAGGCTGTGTTTTGCTACTCAGTTCAGTTCAATGATTTCTCTTGGAACCAGACACGAT 1557
CYP52A3B 1275 AGACCCAGAGAACATCAAAGCTGTCTGGCTACTCAGTTTGGCAACCAGTTTGGCAGTTTCTTGGGAACTAGACACGAT   1344
CYP52A5A 1396 AGATCCAGAGAACATCAAAGCTATCAAAGCTATTTTGGCAACCAGTTTGGTGATTTTCTTTGGCAAGAGGCACACT    1465
CYP52A5B 1435 GGATCCAGAGAATATCAAAGCTATCAAAGCTATTTTGGCAACCAGTTTGGCGATTTTCTTTGGGCAAGAGAGACACGCT  1504
CYP52A8A  745 GGACCCCGAGAATATCAAGGCGCTTTTGGCGCTTTTTGGCAACCAGTTTGGTGATTTTTCATTGGGCAGCAGGGTCAAG   814
CYP52A8B 1298 GGACCCAGAGAATATCAAGGCGCTTTTGGCGCTTTTTGGCAACCAGTTTGGTGATTTTTCATTGGGAAGCAGGGTCAAA  1367
CYP52D4A 1066 GGACCCAGTGAATATCAAAGCGATGCTATCGACCAGTTGATGACTTTCCCTTGGGTTGAGACTACAC            1135
              *** ***  * ** * *****  *  *    *  * **   **  * ** **  *****    **
```

FIG. 15E-2

```
CYP52A1A  1558  CACTTTGCTCCTTTGTTGGGTGACGGTATCTTCACCTTGGACGGAGAAGGTTGGAAGCACTCCAGAGCTA  1627
CYP52A2A  1577  CACTTTGCTCCTTTGTTGGGTGACGGTATCTTCACCTTGGACGGAGAAGGTTGGAAGCACTCCAGAGCTA  1646
CYP52A2B  1450  CACTTTGCTCCTTTGTTGGGCGATGGTATCTTTACGTTGGATGGCCCGGCTGGAAGCACAGCAGATCTA  1519
CYP52A3A  1558  TTCTTGTACTCCTTGTTGGGTGACGGTATTTTCACCTTGGACGGTGCTGGCTGGAAGCACAGAGATCTA  1627
CYP52A3B  1345  TTCTTGTACTCCTTGTTGGGCGATGGTATTTTTACCTTGGACGGTGCTGGCTGGAAACATAGTAGAACTA  1414
CYP52A5A  1466  CTTTTTAAGCCTTTGTTAGTGATGGGATCTTCACATTGGACGGCGAAGGCTGGAAGCACACAGTAGAACTA  1535
CYP52A5B  1505  CTTTTTAAACCTTTGTTAGTGATGGGATCTTCACCTTGGACGGCGAAGGCTGGAAGCTGGAAGCACATAGCAGATCCA  1574
CYP52A8A   815  TTCTTCAAACCATTATTGGGTACGGTATCTTCACATTGGACGCCGAAGCTGGAAGCACACAGCAGAGCCA   884
CYP52A8B  1368  TTCTTCAAACCATTGTTGGGTATCGTATCTTCACCTTGGACGGCGAAGCTGGAAGCACACAGCAGAGCCA  1437
CYP52D4A  1136  CAGTTTGCGCCGTTGTTGGGGAAAGGCATCTTTACTTTGGACGCCCAGAGTGGAAGTGGAAGCAGAGCCGATCTA  1205
                   ** *         *  ** * *** * **  ** **  ** **   *  ** **  *     **
```

FIG. 15E-3

```
CYP52A1A 1628  TGTTGAGACCACAGTTTGCTAGAGACCAGAGATTGGACACGTTAAAGCCTTGGAACCACACATCCAAATCAT  1697
CYP52A2A 1647  TGTTGAGACCACAGTTTGCCAGAGAACAGAGATTCCCACGTCAAGTTGTTGGAGCCACACGTTCAGTTGTT  1716
CYP52A2B 1520  TGTTGAGACCACAGTTTGCCAGAGAACAGAGATTCCCACGTCAAGTTGTTGGAGCCACACATGCAGGTGTT  1589
CYP52A3A 1628  TGTTGAGACCACAGTTTGCTAGAGAACAGAGATTCCCACGTCAAGTTGTTGGAGCCACACGTTCAGTTGTT  1697
CYP52A3B 1415  TGTTGAGACCACAGTTTGCTAGAGAACAGAGGTTTCCCACGTCAAGTTGTTGGAACCACACGTTCAGTGTT  1484
CYP52A5A 1536  TGTTGAGACCACAGTTTGCCAGAGAACAGAGTTGCTCATGTGACGTCATGTGACGTCGTTGGAACCACACTTCCAGTTGTT  1605
CYP52A5B 1575  TGTTAAGACCACAGTTTGCCAGAGAACAAGAGTTGCTCATGTGACGTCATGTGACGTCGTTGGAACCACACTTCCAGTTGTT  1644
CYP52A8A 885   TGTTGAGACCACAGTTTGCCAGAGAACAAGAGTTGCTCATGTGACGTCAGTGACGTCGTTGGAACCACATTCCAGTTGTT   954
CYP52A8B 1438  TGTTGAGACCACAGTTTGCCAGAGAACAAGAGCAAGTTGCTCATGTGACGTGACGTCGTTGGAACCACATTCCAGTTGTT  1507
CYP52D4A 1206  TGTTGCGTCCGCAATTGCCAAAGATCGGGTTCTCATATCCTGGATCTAGAACCGCATTTGTGTTGCT               1275
                **** * * * ****** * *** *  ** ** ** * *  ** ** **** *

CYP52A1A 1698  GGCTAAGCAGATCAAGTTGAACCAGGGAAAAGACTTTGATATCCAAGAATTGTCTTTAGATTTACCGTC   1767
CYP52A2A 1717  CTTCAAACACGTCAGAAAGGCACAGGGCAAGACTTTTGACATCCAGGAATGTTTTCAGATTGACCGTC   1786
CYP52A2B 1590  CTTCAAGCACGTCAGAAAGGCACAGGGCAAGACTTTTGACATCCAAGAATTGTTCAGATTGACCGTC   1659
CYP52A3A 1698  CTTCAAGCACGTCAGAAAGCACACCGCGGTCAAACGTTCGACATCCAAGAATTGTCTTCAGGTTGACCGTC  1767
CYP52A3B 1485  CTTCAAGCACGTCAGAAAACACCGCGCGCGGTCAAGGGGTCAGATTCAAGATTCTGAATACTTGTCTTCAGATTGACCGTC  1554
CYP52A5A 1606  GAAGAAGCATATATTCTTAAGCACAAGACAAGGGTGAATACTTTGATATCCAGGAATTGTTCTTTAGATTTACCGTT  1675
CYP52A5B 1645  GAAGAAGCATATCCTTAAACACAAGACAAGGGTGAGTACTTTGATATCCAGGAATTGTCTTTTAGATTTACCGTC  1714
CYP52A8A 955   GAAGAAGCATATTCTTAAGCACAAGACAAGGGTGAATACTTTGATATCCAGGAATTGTTCTTTAGATTTACCGTC  1024
CYP52A8B 1508  GAAGAAGCATATTCTTAAGCACAAGACAAGGGTGAATACTTTGATATCCAGGAATTGTCTTTAGATTTACCGTT  1577
CYP52D4A 1276  TCGGAAGCACATTGATGGCCACATTCGACATTCGACATCCAGGAGACTACTTCGACATCCAGGAGCTCAGCTCTACTTCCGGTTCCGATG  1345
                ***   *         **            **     ** ****    * **   ** ****  *** **  *     *

FIG. 15F-1
```

```
CYP52A1A 1768 GACACCGCTACTGAGTTCTTGTTTGGTGAATCCGTTCACTCCTTGTACGATGAAAAATTGGGCATCCCAA 1837
CYP52A2A 1787 GACTCCGCCACCGAGTTTTGTTTGGTGAATCCGTTGAGTTCCTTGAGAGATGAATCTATCGGCATGTCCA 1856
CYP52A2B 1660 GACTCCGCCACCGAGTTTTGTTTGGTGAATCCGTTGAGTCCTTGAGAGATGAATCTATTGGGATGTCCA 1729
CYP52A3A 1768 GACTCCGCCACCGAGTTCTTGTTTGGTGAGTCTGCTGAGATCCTTGAGGGACGAATCTATTGGACCC 1837
CYP52A3B 1555 GACTCCGCCACCGAGTTCTTGTTTGGTGAGTCTGCTGAGATCCTTGAGGGACGAATCTATTGGTTGACCC 1624
CYP52A5A 1676 GATTCGGCCACCGAGTTCTTATTTGGTGAGTCCGTGCACTCCTTAAAGGACGAATCTATTGGTATCAACC 1745
CYP52A5B 1715 GACTCGGCCACCGAGTTCTTATTTGGTGAGTCCGTGCACTCCTTAAAGGACGAAACTATCGGTATCAACC 1784
CYP52A8A 1025 GACTCGGCCACGGAGTTCTTATTTGGTGAGTCCGTGCACTCCTTAAGGACGAGGAAATTGGCTACGACA 1094
CYP52A8B 1578 GATTCAGCGACGAGTTCTTATTTGGTGAGTCCGTGCACTCCTTAAGGACGAGGAAATTGGCTACGATA 1647
CYP52D4A 1346 GATGTGGCGACGGGGTTTTTGTTTGTTGGCCGAGTCTGTGGGGTCGTTGAAAGACGAAGATGCGAGG---- 1408
              *      *   ** * *    ** *  **  ** *****   **         **     *

CYP52A1A 1838 CTCCAAACGAAA---TCCCAGGAAGAGAAAACTTTGCCGCTGCTTTCAACGTTTCCAACACTACTTGGC 1904
CYP52A2A 1857 TCAATGCGCTTGACTTGACTTGACGGCAAGGCTGGCTTTGCTTTGATGCTTTAACTATTCGCAGAATTATTTGGC 1926
CYP52A2B 1730 TCAATGCACTTGACTTGACGGCAAGGCTGGCTTTGCTCTGATGCTTTTAACTACTCGCAGAACTATTTGGC 1799
CYP52A3A 1838 CAACCACCAAGGATTTCGATGGCAGAAGAGAGATTTCGCTGACGTTTCAACTATTCGCAGACTTACCAGGC 1907
CYP52A3B 1625 CAACCACCAAGGATTTCGAAGGCAGGAGAGATTTCGCTGACGTTTCAACTATTCGCAGACTTACCAGGC 1694
CYP52A5A 1746 AAGACGGATAGATAGATTTGCTGGTGGTAGAAAGGACTTTGCTGAGTCGTCGTTCAACAAAGCCCAGGAATACTTGGC 1815
CYP52A5B 1785 AAGACGATATAGATTTGCTGGTGGTAGAAAGAAGGACTTTGCTGAGTCGTCGTTCAACAAGCCCAGGAGTACTTGGC 1854
CYP52A8A 1095 CGAAAGACATGT---CTGAAGAAAGACGCAGATTTGCCGACGCGTTCAACAAGTCGCAAGTCGCAAGTCTACGTGGC 1161
CYP52A8B 1648 CGAAGGACATGG---CTGAAGAAAGACGCAAATTTGCCGACGCGTTCAACAAGTCGCAAGTCGCAAGTCTATTTGTC 1714
CYP52D4A 1409 ---------------TTCCTGGAAGCATTCAATGAGTCGCAGAAGTATTTGGC 1445
                                 **  ** * **    **  *   **
```

FIG. 15F-2

```
CYP52A1A 1905  CACCAGAAGTTACTCCCAGACTTTTTACTTTTTGACCAACCCTAAGGAATTCAGAGACTGTAACGCCAAG   1974
CYP52A2A 1927  TTCGAGAGCGGTTATGCAACAATTGTACTGGGTGTTGAACGGGAAAAAGTTTAAGGAGTGCAACGCTAAA   1996
CYP52A2B 1800  TTCGAGAGCGGTTATGCAACAATTGTACTGGGTGTTGAACGGGAAAAAGTTTAAGGAGTGCAACGCTAAA   1869
CYP52A3A 1908  CTACAGATTTTTGTTGCAACAAATGTACTGGATCTTGAATGGCTCGGAATTCAGAAAGTCGATTGCTGTC   1977
CYP52A3B 1695  CTACAGATTTTTGTTGCAACAAATGTACTGGATTTGAATGGCGCGGAATTCAGAAAGTCGATTGCCATC   1964
CYP52A5A 1816  TATTAGAACCTGGTGCAGACGTTCTACTGGTTGGTCAACAACAAGGAGTTAGAGACTGTACCAAGCTG    1885
CYP52A5B 1855  TATTAGAATTTGGTGCAGACCTTCTACTGGTTGATCAACAACAAGGAGTTAGAGACTGTACCAAGCTG    1924
CYP52A8A 1162  CACCAGAGTTGCTTTACAGAACTTGTACTGGTCAACAACAACAAGAGTTCAAGGAGTGCAATGACATT    1231
CYP52A8B 1715  CACCAGAGTTGCTTTACAGACATTGTACTGGTCAACAACAACAAGAGTTCAAGGAGTGCAACGACATT    1784
CYP52D4A 1447  AACTAGGGCAACGTTGCACGAGTTGTACTTTCTTTGTGACGGGTTTAGGTTTCGCCAGTACAACAAGGTT   1516
                **                  *           * ****         **     *      * *    ***      **
```

FIG. 15F-3

```
CYP52A1A  1975  GTCCACCACTTGGCCAAGTACTTTGTCAACAAGGCCTTGAACTTTACTCCTGAAGAACTCGAAGAGAAAT  2044
CYP52A2A  1997  GTGCACAAGTTTGCTGACTACTACGTCAACAAGGCCTTGGACTTGACGCCTGAACAATTGGAAAAGGAGG  2066
CYP52A2B  1870  GTGCACAAGTTTGCTGACTATTACGTCAGCAAGGCTTTGGACTTGACACCTGAACAATTGGAAAAGCAGG  1939
CYP52A3A  1978  GTGCACAAGTTTGCTGACCACTACTATGTGCAAAAGGCTTTGGAGTTGACCGACGATGACTTGCAGAAACAAG  2047
CYP52A3B  1765  GTGCACAAGTTTGCTGACCACTACTATGTGCAAAAGGCTTTGGAGTTGACCGACGATGACTTGCAGAAACAAG  1834
CYP52A5A  1886  GTGCACAAGTTCACCAACTACTATGTTCAGAAAGCTTTGGATGCTAGCCCAGAAGAGCTTGAAAAGCAAA  1955
CYP52A5B  1925  GTGCACAAGTTACCAACTACTATGTTCAGAAAGCTTTGGATGCTACCCCAGAGGAACTTGAAAAGCAAG  1994
CYP52A8A  1232  GTCCACAAGTTTACCAACTACTATGTTCAGAAAGCCTTGGATGCTACCCCAGAGGAACTTGAAAAGCAAG  1301
CYP52A8B  1785  GTCCACAAGTTCACCAACTACTATGTTCAGAAAGCCTTGGATGCTACCCCAGAGGAACTTGAAAAACAAG  1854
CYP52D4A  1517  GTGCGAAAGTTCTGCAGCCAGTGTGTCCACAAGGCGTTAGATGTTGCACCGGAAGACACC------A      1577
                 **  *  **  *  *     **         **   **  **       *  **

CYP52A1A  2045  CCAAGTCCGGTTACGTTTCTCTTGTACGAATTGGTTAAGCAAACCAGAGATCCAAAGGTCTTGCAAGATCA  2114
CYP52A2A  2067  ATGGTT------ATGTGTTTTGTACGAGTTGGTAAGCAAACAACCAGAGACAAGACAAGTGTTGAGAGACCA  2130
CYP52A2B  1940  ATGGTT------ATGTGTTCTTGTACGAGTTGGTCAGCAAGCAACCAGAGACAAGCAAGTGTTGAGAGACCA  2003
CYP52A3A  2048  ACGGCT------ATGTGTTCTTGTACGAGTTGGTCAGCAAGCAGCCAGACCCCAAAGGTCTTGAGAGACCA  2111
CYP52A3B  1835  ACGGCT------ATGTGTTCTTGTACGAGTTGGCTAAGCAAGCAAACCAGACCCCAAAGGTCTTGAGAGACCA  1898
CYP52A5A  1956  GTGGGT------ATGTGTTCTTGTACGAGTTGGCTGAGCTTGTCAAGCAGAACAAGAGACCCCAATGTGTTGCGTGACCA  2019
CYP52A5B  1995  GCGGGT------ATGTGTTCTTGTACGAGTTGGCTTGTCAAGCTTGTCAAGCAGAGAGAGACCCCAAGGTGTTGCGTGACCA  2058
CYP52A8A  1302  GCGGGT------ATGTGTTCTTGTATGAGTTGGCTATGAGCTTGTCAAGCAGCAGAGAGAAAGAGAAAGAGAAAGACCCAATGTTGCGTGACCA  1365
CYP52A8B  1855  GCGGGT------ATGTGTTCTTGTACGAGTTGGCTTGTCAAGCAGCAGAAAGAGCGAGACCCCAATGTTGCGTGACCA  1918
CYP52D4A  1578  GCGAGT------ACGTGTTTCTCCGCGAGTTGGTCAAACACACTCGAGATCCCGAGTTCCGTTGTTTTTACAAGACCA  1641
                          *    ** **   * *** *   *  **       * * *** **     ** **
```

FIG. 15G-I

```
CYP52A1A 2115  ATTGTTGAACATTATGGTTGCCGAAGAGACACCACTGCCGGTTTGTGTCCTTTGTTTGAATTG  2184
CYP52A2A 2131  ATTGTTGAACATCATGGTTGCTGCCGGTTGCCGGTTAGAGACACCACCACCGCCGGTTTTGTTGTTCTTTGAATTG  2200
CYP52A2B 2004  GTTGTTGAACATCATGGTTGCCGGTTGCCGGTAGAGACACCACCGCCGGTTTGTGTTGTTTCTTTGAATTG  2073
CYP52A3A 2112  GTTATTGAACATTTGGTTGCCGGTTGCCGGTAGAGACACGACCACCGCCGGTTTGTTGTTGTCATTTGTTCTACGAGTTG  2181
CYP52A3B 1899  GTTGTTGAACATTTGGTTGCCGGTTGCCGGTAGAGACACAACCACCGCCGGTTTGTTGTTGTCGTTTGTGTTCTACGAGTTG  1968
CYP52A5A 2020  GTCTTTGAACATCTTGTTGGCCGGCCGGAAGAGAGACCACCACTGCTGGGTTTGTTGTTGTCGTTTGCTTTGAGTTG  2089
CYP52A5B 2059  GTCTTTGAACATCTTGTTGGCAGGAGGAGAGAGACCACCACTGCTGGGTTTGTGTTGTCCTTGCTCTTGAGTTG  2128
CYP52A8A 1366  GTCTTTGAACATCTTGTTGGCAGGAGGAGAGACACCACCACTGCTGGGTTTGTGTTGTTGCTCTTTGCTGTGTTGAGTTG  1435
CYP52A8B 1919  GTCTTTGAACACTTGTTGGCTGCCGAAGGGACTGGAAGGACTGGAAGGAACGCGACCACCACCGCGTCGTTATATCGTTGCAACATTGAGCTA  1998
CYP52D4A 1642  AGCGTTGAACGTCTTGCTGCTGGACGCGACGACCACCGCGTCGTTATATCGTTGCAACATTGAGCTA  1711
                                   *      *  ** ** * **       *  **   **  ** **** **  **

CYP52A1A 2185  GCTAGACACCCAGAGATGTGGTCCAAGTTGAGAGAAGAGAAATCGAAGTTAACTTTGGTGTTGGTGAAGACT  2254
CYP52A2A 2201  GCCAGAGAAACCCAGAGAAGTTACCAACAAGTTGAGGACAAGTTGAGGACTCGGTTGGACTCGGTGAGAATG  2270
CYP52A2B 2074  GCCAGAGAAACCCAGAGAAGTTGACCAACAAGTTGAGAGAATCGAGGAGAATCGAAGTTGGTCTTGGTGAGAATG  2143
CYP52A3A 2182  TCAAGAAAACCCTGAGGGTGTTTGCTAAGTTGAGAGTTGAAGTTGAGAGTTGAAGTTGGACTTGGACTTGGACTCGGCGAAGAAG  2251
CYP52A3B 1969  TCGAGAAAACCCAGAGATCTGGGCCAAGTGTTGCCAAGTGTTGAGAGTGAAGTTGAGAAACAGATTTGGACTCGGCGAAGAGG  2038
CYP52A5A 2090  GCCAGACACCCACACACATCGGGCCAAGTTGAGAGTTGAGAGAGGTGGAAAACAGATTGAACAACAGTTGGTCTTGGAGAAGACT  2159
CYP52A5B 2129  GCCAGAAAACCCACACACATCGGGCCAAGTCTGGGCCAAGTTGAGAGTTGAGAGAGTGGAAATTGAACAACAGTTGGTCTTGGAGAAGACT  2198
CYP52A8A 1436  GCCAGAAAACCCACACACATCGGGCCAAGTTGAGAGTTGAGAGAGTGGAAATTGAACAGAAATTGAACAGCAGTTTGGTCTTGGAGAAGACT  1505
CYP52A8B 1989  GCCAGGAACCCACACACATCGGGCCAAGTCTGGGCCAAGTTGAGAGAAGAATTGAATCACACTTTGGGCTTGGAGGACT  2058
CYP52D4A 1712  GCCCGGAATGACCACATGTGGAGGAAGCTACGAGAGGAGGTT------ATCCTGA---CGATGGACCG  1771
                 *            * *   *    *  * * ***  *  ****  **          *          *
```

FIG. 15G-2

```
CYP52A1A  2255  CCCGCGTTGAAGAAATTACCTTCGAAGCCTTGAAGAGATGTGAATACTTGAAGGCTATCCTTAACGAAAC  2324
CYP52A2A  2271  CTAGTGTTGAAGACATTCCTTGAGTCGTTGAAGTCCTGTGAATACTTGAAGGCTGTTCTCAACGAAAC    2340
CYP52A2B  2144  CTCGTGTTGAAGACATTCCTTGAGTCGTTGAAGTCATGTGAATACTTGAAGGCTGTTCTCAACGAAAC   2213
CYP52A3A  2252  CTCGTGTTGAAGAGATCTCGTTTGAGTCCTTGAAGTCTTGTGAGTACTTGAAGGCTGTCATCAATGAAAC 2321
CYP52A3B  2039  CTCGTGTTGAAGAGATCTCTTTTGAGTCCTTGAAGTCCTGTGAGTACTTGAAGGCTGTCATCAATGAAGC 2108
CYP52A5A  2160  CTCGTGTTGAAGAGATTACCTTTGAGAGCTTGAAGTCTTGAGAGATGTGAGTACTTGAAAGCGTTCCTTAATGAAAC 2229
CYP52A5B  2199  CTCGTGTTGAAGAGATTACCTTTGAGAGCTTGAAGTCTTGAGAGATGTGAGTACTTGAAAGCGTTCCTTAACGAAAC 2268
CYP52A8A  1506  CTCGTGTTGAAGAGATTACCTTTGAGAGCTTGAAGTCTTGAGAGATGTGAGTACTTGAAAGGCCGTGTTGAACGAAAC 1575
CYP52A8B  2059  CTCGTGTTGAAGAGATTACCTTTGAGAGCTTGAAGTCTTGAGAGATGTGAGTACTTGAAAGCCGTGTTGAACGAAAC  2128
CYP52D4A  1772  TCCAG--TGATGAAATAACCGTGGCCGGGTTGAAGAGTTGCCGTTACCTCAAAGCAATCCTAAACGAAAC 1839
                       * ** *  *       **       *    ** *        *  * *    *  ***  *  ** **** *
```

FIG. 15G-3

```
CYP52A1A  2325  CTTGCGTATGTACCCATCTGTTCCTGTCAACTTTAGAACCGCCACCAGAGACACCACTTTGCCAAGAGT  2394
CYP52A2A  2341  CTTGAGATTGTACCCATCCGTCCGTGCCGTGCCACCAGAATTTCAGAGTTGCCACCAGAACAACTACCCTCCAAGAGGT  2410
CYP52A2B  2214  TTTGAGATTGTACCCATCCGTGCCGTGCCACACAGAATTTCAGAGTTGCCACCAGAAAACACTACCCTTCCAAGGGGA  2283
CYP52A3A  2322  CTTGAGATTGTACCCATCCGGTTCCACACAGAATTTCAGAGTTGCCACCAGAGTTGCTACCAGAAACACTACCCTCCAAGAGGT  2391
CYP52A3B  2109  CTTGAGATTGTACCCATCGTTCCACACAGAATTTCAGAGTTGCCACCAGAGTTGCCACCAGAAACACTACCCTTCCAAGAGGC  2178
CYP52A5A  2230  CTTGCGTATTTACCCAAGTGTCCCAAGAAACTTCAGAATCGCCACCAGAGAACTTCAGAACACGACAGCCAAGGGC  2299
CYP52A5B  2269  CTTGCGTGTTTACCCAAGTGTCCCAAGAAACTTCAGAAATCGCCACCAGAGAACTCAGAACATTGCCAAGGGT  2338
CYP52A8A  1576  TTTGAGATTACACCCAAGTGTCCCAAGAAACGCAAGATTTGCGATTAAAGACACGACTTTACCAAGAGGC  1645
CYP52A8B  2129  GTTGAGATTACACCCAAGTGTCCCAAGAAACGCAAGATTTGCGATTAAAGACACGACTTTACCAAGAGGC  2198
CYP52D4A  1840  TCTTCGACTATACCAAGTGTGCCTAGAACGCGAGATTTGCTACGAGGAATACGACGCTTCCTCGTGGC  1909
                  *    * *   * *****   *  *    **    **     *       ***        *  *    **

CYP52A1A  2395  GGTGGTGCTAACGGTACCGACCCAATCTACATTCCTAAAGGCTCCACTGTTGCTTACGTTGTCTACAAGA  2464
CYP52A2A  2411  GGTGGTAAGGACGGGTTGTCTCCTGTTCCTGTTTGGTGAGAAAAGGGTCAGACCGTTATTTACGGTCTACGCGCAG  2480
CYP52A2B  2284  GGTGGTAAGGACGGGTTGTCTCCTGTTCCTGTTTGGTCAGAAAAGGGTCAAACCGTTATGTACGGTCTACGCTG  2353
CYP52A3A  2392  GGTGGTGAAGATGGATGACGGATGCTCGCCAATTGTCGTCAAGTTGTCATGTACACTGTTATTGCTA  2461
CYP52A3B  2179  GGTGGTAAAGACGGATGCTCGCCAATTGTCTGCCAATTGTCTGTCAAGTTGTCATGTACACTGTCATTGGTA  2248
CYP52A5A  2300  GGTGGTTCAGACGGTACCTCGCCAATCTTGATCCAAAAGGGAGAAGTTGTCGTATGGTCGTATGGTCATTCAACTCTA  2369
CYP52A5B  2339  GGTGGTTCCAGACGGTACCCAGCCAATCTTGATCCAAAAGGGAGGATGAGGTGGTGCAGTACTCCATCTCGGCAA  2408
CYP52A8A  1646  GGTGGCCCCAACGGCAAGGATCCTATCTTGATCAGGAAGAAGGATGAGGTGGTGCAGTACTCCATCTCGGCAA  1715
CYP52A8B  2199  GGTGGCCCCAACGGCAAGGATCCTATCTTGATCAGGAAGAAATGAGGTGGTGCAATACTCCATCTCGGCAA  2268
CYP52D4A  1910  GGAGGTCCAGATGGATCGTTTCCGATTTTGATAAGAAAAGGGCCAGCCAGTGGGTATTTCATTGTGCTA  1979
                   *        **    *   *      * *      **  **            **        *

FIG. 15H-I
```

```
CYP52A1A  2465  CCCACCGTTTGGAAGAATACTACGGTAAGGACGCTAACGACTTCAGACCAGAAAGATGGTTTGAACCATC  2534
CYP52A2A  2481  CCCACAGAAACCCAGCTGTTTACGGTAAGGACGCTCTTGAGTTTAGACCAGAGAGATGGTTTGAGCCAGA  2550
CYP52A2B  2354  CCCACAGAAACCCAGCTGTCTACGGTAAGGACGCCCCTGAGTTTAGACCAGAGAGGTGGTTTGAGCCAGA  2423
CYP52A3A  2462  CCCACAGAGACCCAAGTATCTACGGTGCCGACGCTGAGCGTCTTCAGACCAGAAAGATGGTTTGAACCAGA  2531
CYP52A3B  2249  CCCACAGAGACCCAAGTATCTACGGTGCCGACGCCGACGTCTTCAGACCAGAAAGATGGTTCGAGCCAGA  2318
CYP52A5A  2370  CTCATTTGGACCCTGTCTATTACGGCCCTGATGCTGCTGAGTTCAGACCAGAGAGAGATGGTTTGAGCCATC  2439
CYP52A5B  2409  CCCACTTAGATCCTGTCTATTATTACGGCCCTGATGCTGCTGAGTTCAGACCAGAGAGAGATGGTTTGAGCCATC  2478
CYP52A8A  1716  CTCAGACAAATCCTGCTTATTATGGCGCCGATGCTGCTGATTTTAGACCGGAAAGATGGTTTGAACCATC  1785
CYP52A8B  2269  CTCAGACAAATCCTGCTTATTATGGCGCCGATGCTGCTGATTTTAGACCGGAAAGATGGTTTGAGCCATC  2338
CYP52D4A  1980  CACACTTGAATGAGAAGGTATATGGAATGATAGCCATGTGTTTCGACCGAGAGATGGGCTGCGTTAGA  2049
                 *  *                 **         *     *    * ****  ** *  *****

CYP52A1A  2535  TACTAAGAAGTTGGGCTGGCTTATGTTCCATTCAACGGTGGTCCAAGAGTCTGCTTGGGTCAACAATTC  2604
CYP52A2A  2551  GACAAAGAAGCTTGGCTGGCTGGGCCTTCCTCCCATTCAACGGTGGTCCAAGAATCTGTTGGGACAGCAGTTT  2620
CYP52A2B  2424  GACAAAGAAGCTTGGCTGGCTGGGCCTTCCATTCAACGGTGGTCCAAGAATCTGTTGCTTGGGACAGCAGTTT  2493
CYP52A3A  2532  AACTAGAAAGTTGGGCTGGCTGGGCATACGTTCCATTCAATGGTGGTCCAAGAATCTGTTGGGTCAACAGTTT  2601
CYP52A3B  2319  AACTAGAAAGTTGGGCTGGCTGGGCATATGTTCCATTGCCATTCAATGGTGGTCCAAGAATCTGTTTGGGTCAGCAGTTT  2388
CYP52A5A  2440  AACCAAAGAAGCTCGGCTGGCTTACTTGCCATTCCATTGCCATTGCCAACGGTGGTCCAAGAATCTGTTTGGGTCAGCAGTTT  2509
CYP52A5B  2479  AACCAGAGAAGCTCGGCTGGCTGGACTTGCCATTGCCATTGCCAACGGTGGGCCACGAATCTGTTTGGGTCAGCAGTTT  2548
CYP52A8A  1786  AACTAGAAACTTGGGATGGCTTTCTTGCCATTGCTACTTGCCATTGCCAACGGTGGTCCAAGAATCTGTTGGGACAACAGTTT  1855
CYP52A8B  2339  AACTAGAAACTTGGGATGGCTTACTTGCGTATCTTCCATTGCCATTGCCAACGGTGGTCCAAGAATCTGTTGGGACAACAGTTT  2408
CYP52D4A  2050  GGGCAAGAGTTTGGGCTGGCTGGTCGTATCTTCCATTCAACGGCGGCCCTTGGTCAGAAGCTGCCTTGGTCAGCAGTTT  2119
                                         ***                   *        *             **
```

FIG. 15H-2

```
CYP52A1A 2605  GCCTTGACTGAAGCTTCTTATGTGATCACTAGATTGGCCCAGATGTTTGAAACTGTCTCATCTGATCCAG  2674
CYP52A2A 2621  GCCTTGACAGAGAAGCTTCGTATGTCACTGTCACTGTCAGGAGTTGCACACTTGTCTATGGACCCAG     2690
CYP52A2B 2494  GCCTTGACAGAGAAGCTTCGTATGTCACTGTCACTGTCAGATTGCTCCAAGAGTTGGACACTTGTCTATGGACCCCA  2563
CYP52A3A 2602  GCCTTGACCGAAGCTTCATACGTCACTGTCACTGTCAGATTGCTCCAGAGTTGCACACTTGTCTATGGACCCAG     2671
CYP52A3B 2389  GCCTTGACTGAAGCTTCATACGTCACTGTCACTGTCAGATTGCTCCAAGAGTTGGAAACTTGTCCCTGGATCCAA    2458
CYP52A5A 2510  GCCTTGACGGAAGCTGGCTATGTTGGTTAGTGTTAGATTGGTCAAGAGTTCTCCCACGTTAGGCTGGACCCAG      2579
CYP52A5B 2549  GCCTTGACCGAAGCTGGTTACGTTTGGTCAGTTACGTTTGGTTAGACTTGTTCAGGAGTTCCAAATTGTCACAAGACCCAG  2618
CYP52A8A 1856  GCTTTGACTGAAGCCGGTTACGTTTTGGTCAGTTACGTTTGGTTAGACTTGTTCAGGAGTTCAGGAATTCCCTAGCTTGTCACAGGACCCCG  1925
CYP52A8B 2409  GCTTTGACCGAAGCCGGTTACGTTTGGTTAGACTTGTTCAGGAATTCCCTAGCTTGTCACAGGACCCCG           2478
CYP52D4A 2120  GCAATCCTTGAAGCTTCGTATGTTTTGGCTCGATTGACACAGTGCTACACGACGACGATACAGCTTAG--AA       2186
               * *  * ****   *****    * ** * **  *   * **    *   *     *   *
```

FIG. 15H-3

```
CYP52A1A  2675  GTCTCGAATACCCTCCACCAAAGTGTATTCACTTGACCATGAGTCACAACGATGGTGTCTTTGTCAAGAT  2744
CYP52A2A  2691  ACACCGAATATCCACCTAGGAAAGAAAATGTCGCATTGACCATGTCCCTTTCGACGGTGCCAACATTGAGAT  2760
CYP52A2B  2564  ACACCGAATATCCACCTAGGAAAGAAAATGTCGCATTGACCATGTCCCTTTCGACGGTGCCAACATTGAGAT  2633
CYP52A3A  2672  ACACCGAATATCCACCACCAAAATTGCAGAACACCTTGACCTTGTCGCTCTTGATGGTGCTGATGTTAGAAT  2741
CYP52A3B  2459  ACGCTGAGTACCCACCACCAAAATTGCAGAACACCTTGACCTTGTCACTCTTGATGGTGCTGACGTTAGAAT  2528
CYP52A5A  2580  ACGAGGTGTACCCGCCAAAGAGGTTGACCAACTTGACCATGTGTTGCAGGATGGTGCTATTGTCAAGTT  2649
CYP52A5B  2619  ATGAAGTGTATCCACCAAAGAGGTTGACCAACTTGACCATGTGTTGCAGGATGGTGCTATTGTCAAGTT  2688
CYP52A8A  1926  AAACCAAGTACCCACCACCTAGATTGGCACACTTGACGATGTGCTTGTTGACGGTGCACACGTCAAGAT  1995
CYP52A8B  2479  AAACTGAGTACCCACCACCTAGATTGGCACACTTGACGATGTGTCTTGTTGACGGGCATACGTCAAGAT  2548
CYP52D4A  2187  CTACCGAGTACCCACCACCAAAGAAACTCGTTCATCTCACGATGAGTCTTCAACGGGGTACATCCGAAC  2256
                                      *     *  *            *    *           * **        *

CYP52A1A  2745  GTAA-AGTAGTCGATGCTGGGTATTCGATTACATGT--GTATAGGAAGATTTGGTTTTTTATTCGTTCT  2811
CYP52A2A  2761  GTATTAGAGGGTCATGTGTTATTT-GATTGTTTA-----GTTGTAATTACTGATTAGGTTAATTCATG  2824
CYP52A2B  2634  GTATTAGAGGATCATGTGTTATTTTGATGGTTTAGTCTGTTAGCTATTGTGTATAGCTTGTATTAATTCACG  2703
CYP52A3A  2742  GTACTAAGGTTGCTTTTCCTTGCTAATTTTCTTGCTAGTGTTATAGCTTGTGTATTAAATTGAATCGGCAATTG  2811
CYP52A3B  2529  GTTCTAAGGTTGCTTGCTTATTCCTTGCTAGTGTTATT---TATAGTTGTGTATTAAATTAAATTGAATCGGCGATTG  2595
CYP52A5A  2650  TGACTAGCGGCGTGGCGTGAATGCGTTTGATTTTGTA---GTTTCTGTTTGCAGTAATGAGATAACTATTCA  2716
CYP52A5B  2689  TGACTAGTA-CGTA-TGAGTGCGTTTGATTTTGTA---GTTTCTGTTTGCAGTAATGAGATAACTATTCA  2753
CYP52A8A  1996  GTCATAGGTTTCCC---CATACAAGTAGTTCAGTA---ATTATACACTGTTTTTACTTTCTCCTTCATACC  2059
CYP52A8B  2549  GCAATAGGTTT-----------------------------TGGTTTGACTTGTTTCCATA--  2580
CYP52D4A  2257  TAGAACTTGATTATGTGTTTATGTGTTAATCGGGGCAAAGCACTGCAAGTCATTGATGTTTGTGGAAGCCC  2326

FIG. 15I-I
```

```
CYP52A1A 2812  TTTTTTAATTTTTGTTAAATTAG-TTTAGAGATTCATTAATACATAGATGGGTGCTATTCCGAAACT         2880
CYP52A2A 2825  GATTGTTATTTATTGATAGGGGTT-------------TGCGCGTGTTGCATTCACTTGGATCGTTCCAGGTTG    2885
CYP52A2B 2704  GATTGTTATTTATTGATAGGGGGTGCGTGTGTGTGTGTGTGTTGCATTCACATGGATCGTCGTTCCAGGTTG      2773
CYP52A3A 2812  ATTTTCTGATACCAATAACCGTA-------------GTGCGATTTGACCAAAACCGTTCAAAGTTTTTGTCTC   2873
CYP52A3B 2596  ATTTTTCTGGTACTAATAACTGTA------------GTGGGTTTTGACCAAAACCGTTCAAACTTTTTTTTT    2657
CYP52A5A 2717  GATAAGGCGAGTGGATGGATGTACGTTT--TGTAAGAGTTT--CCT-TACAACCTTGTGTGGG-TGTGTGAGGTT 2781
CYP52A5B 2754  GATAAGGCGGGTGGATGTACGTTT--TGTAAGAGTTT--CCT-TACAACCCTGGTGGG--TGTGTGAGGTT      2817
CYP52A8A 2060  AAATGGACAAAAGTTTAAGCATG-CCTAACAACGTGACCG-GACAATTGTCGCACTAGTATGTAACA          2127
CYP52A8B 2581  ------------------------------------------------------------TGCAAGT         2587
CYP52D4A 2327  AGCATTGGTGTTCCGGAGCATCAATAACCAATGTCTTGAAGGGTTGATTTTCTTGACCTTCTTCCT           2396

CYP52A1A 2881  TTACTTCTATCC--CCTGTATCCCCTATTATCCCTCAGTCACATGATTGCTGTAATTGTCGTGCAGGA         2948
CYP52A2A 2886  ATGTTTCCTTCCATCCT--GTCGAGTCAAAAGGAGTTTGTTTTGTAACTCCGGACGATGTTTAAATAG        2953
CYP52A2B 2774  TTGTTCCTTCCATCCT--GTTGAGTCAAAAGGAGTTTGTTTTGTAACTCCGGACGATGCTTAGATAG         2841
CYP52A3A 2874  TCGTTGACG--------------TGCTCGCTCATCAGCACTGTTGAAGACGAAAGA-GAAAATTTTTGTA      2930
CYP52A3B 2658  TTTTCTTCCCCCTACCTTCGTTGCTCGCTCATCAGCACACTTTG-CAGCTCTCCGTATACACTGTTGAAAAAGAAAAAGAAAATTTTTGTA 2727
CYP52A5A 2782  GAGGTTGCATCTT-GGGAGAGATTACACCTTTG-CAGCTCTCCGTATACACTGTTTACTCTTTGTAACCTC     2849
CYP52A5B 2818  G----CATCTTAG-GGAGAGATAGCACCTTTG-CAGCTCTCCGTATACACAGTTTTACTCTTTGTAACCTA     2881
CYP52A8A 2128  ATTGTAAAAATAG-TGTACACTAATTGTGGTGGCCGGAGATAAATTACAGTTTGGTTTGTAAACTC          2196
CYP52A8B 2588  AGTTCAGTAAT---TACACACTAATTGTGGTGGCCGGCGGATAAATTACCGTTTGGTTTGTGTAAAAAT       2654
CYP52D4A 2397  GAGCTTCTTTCCG--TCAAACTTGTACAGAATGGCCATCATTCAGGAACAACCA-CGTACGACGGCCGG       2463
                                                                       *
```

FIG. 15I-2

```
CYP52A1A 2949  CACAAACTCCCTAACGGACTTAAACCATAAACAAGCTCAGAACCATAAGCCGACATCACTCCTTCTCTC  3018
CYP52A2A 2954  AAGGTCGATCTCCATGTGATTGTTTGACTGTTACTGTTGTGATTATGTAATCTGCG------GACGTTATA  3016
CYP52A2B 2842  AAGGTCGATCTCCATGTGATTGTTT-GACTGCTACTCTGATTATGTAATCTGTAAAGCCTAGACGTTATG  2910
CYP52A3A 2931  AACAACACTGTCCAAATTTACCCAACGTGAACCATTATG--CAAATGAGCGGCC------CTTTCAA   2989
CYP52A3B 2728  AACAACATTGCCCAAACTTACCCAACGTGAACCATTATAACCAAATGAGCGGCG------CTTTCAA   2788
CYP52A5A 2850  TATCAATCATGTGGGGGGGGGTTCATTGTTTGGC-CATGGTGGTGCATGTTAAATCCGCC-AACTACC  2917
CYP52A5B 2882  TGCCAATCATGTGG------GGATTCATTGTTTGCC-CATGGTGGTGCATGCAAAATCCCCCAACTACC  2944
CYP52A8A 2197  GCGGATATCTCTGGC------AGTTTCTTCTTCCGC-AGCAGCTTTGCCACGGGTTTGCTCTGGGGCCAA  2260
CYP52A8B 2655  TCGGACATCTCTGGT------GGTTCCCTTCTCCGC-AGCAGCTTTGCCACGGGTTTGCTCTGCGGCCAA  2718
CYP52D4A 2464  TACCGCATCTGGAGTA---TCTCGCCGTCGTTCAAGTAG---CACGAAAACAGCAACGACGTCACCATCTG  2528
```

FIG. 15I-3

```
CYP52A1A  3019  TCTTCTCCAACCAATAGCATGGACAGACCCCACCCTCCTATCCGAATCGAAGACCCTTATTGACTCCATAC  3088
CYP52A2A  3017  CAAGCATGTGATTGTGTGGTTTT------GCAGCCT-TTTGCACGACAAATGATCGTCAGACGATTACGTAA  3079
CYP52A2B  2911  CAAGCATGTGATTGTGTGGTTTT-------GCAACCTGTTTGCACGACACAAATGATCGACAGTCGATTACGTAA  2975
CYP52A3A  2990  CTGGTCGCTGGAAGCATTCGGG-----GATATCTACAACGCCCTTAAGTTTGAAACAGACATTGATTTAG  3054
CYP52A3B  2789  CTGGTCACTGGAGGCATTCGGG-----GATATCTACACACCCTTAAGTTTGAGGAAGACATTGATTTAG  2853
CYP52A5A  2918  CAATCTCACATGAAACTCAAGCACACTAAAAAAAAAAGATGTTGGGGAAACTT-TGGTTTCCCTTC  2986
CYP52A5B  2945  CAATCTCACATGAAACTCAAGCACACTAGAAAAAAA--GATGTTGCGTGGGTTCTT-TTGATG------  3005
CYP52A8A  2261  CAAATTCAAAAGGGGG---------AGAAACTTAACACCCCTTATCTCCACTC-TAGGTTGTAGCT  2318
CYP52A8B  2719  CAAATTCGAAAGGGGGGGGGGGGGGGAGAAAGTTAACACCCCCTGTTCC--CACCG-TAGGCTGTAGCT  2785
CYP52D4A  2529  CTTCCCAATCTTGACACCC-------ACAGATACCCCTGCGGCTTCATGGATCAAAAACGTCGGCAACC  2590

CYP52A1A  3089  CCACCTGGAAGCCCCTCAAGCCACACGTCATCCAGCCACCCACCATCACCACATCCCTCTACTCGACAAC  3158
CYP52A2A  3080  TCTTTGTTA-----GAGGGTAAAAAAACAAAATGGCAGCCAGAATTCAAACATTCTGCAAACAATG  3144
CYP52A2B  2976  TCCATATTAT-TTAGAGGGTAATAAAAATAAA-TGGCAGCCAGAATTCAAACATTTGCAAACAATG  3043
CYP52A3A  3055  ACACCATAGA-TTTCAGCGGCATCCAAGAATGACC-----TTGCCCACATTTGACGCCCAACACCACTG  3119
CYP52A3B  2854  ACACCATAGA-TTTCAGCGGCATCAAGAATGACC-----TTGTCCACATTTGACAACCCAACACCACTG  2918
CYP52A5A  2987  TTAGTAATT--AAACACTCTCACTCTCCACTCTCCAGAACGTTCTCACTGACTTTGATGATTACGTTGGGCTGC  3054
CYP52A5B  3006  TTGGGGAAA---ACTTTCGTTTCCTTTCTCAGTAATTAAACGTTTTGTCTAGACTTTGATGATTACGTTGGGCTGC  3073
CYP52A8A  2319  CTTGTGGGG--ATGCAATTGTCGTACGTTTTTATGTTTGCCCAGACTTGATGATTACGTTGGATTTC  2386
CYP52A8B  2786  CTTGTGGGGGATGTAATTGTCGTACGTTTC-ATGTTGGCCCAGACTTGATGATTACGTAGGCTTTC  2854
CYP52D4A  2591  CCGCGTATATGTCCATGTAATTCTCCATGGCCACCT--CCATCAACACACACTGATGGAGCGACTGACGGTG  2658
                                                                   *
```

FIG. 15J-1

```
CYP52A1A 3159  GTCCAAAGACGGCGAGTTCTGGTGTGCCCGGAAATCAGCGCCATCCGGCCACATACAAGCAGCCGTTGATT  3228
CYP52A2A 3145  CAAAAATGGGAAACTC--CAACAGACAAAA-AAAAAAACTCCGCAGCACTCCGAACCCACAGAACAATG    3211
CYP52A2B 3044  CAAAAGATGAGAAACTC--CAACAGAGAAAATAAAAAAACTCCGCAGCACTCCGAACCACAAAACAATG    3111
CYP52A3A 3120  GAAGAATCACGCCAGA----AACTAGGCGATGGATCCAAGCCTGTGACCTTGCCCAATGGAGACGAAGTG   3185
CYP52A3B 2919  GAAGAATCGCGCCAGA----AACTAGGCGATGGATCCAAGCCTGTGGCCTTGCCCAATGGAGACGAAGTG   2984
CYP52A5A 3055  AGACAACCAGAAAAAAAGAACAAAATCCAGATAGAAAAACAAAGGGCT-GGACAACCATAAAT-AAAC    3122
CYP52A5B 3074  AGACAACCAGAAAAAA-----CAAAATCCAGATAGAAGAAGAAAGGGCT-GGACAACCATAAAT-AAAC   3135
CYP52A8A 2387  TTATGTCTGAGGCGTG-----CTTGAAAGAAGTGTCAAAATGTGACAGGCG-ACGCTATTGGACAT-GAAC   2450
CYP52A8B 2855  TTATGTCTAAGGCGTG-----CTTGACACAAGTGTCAAAAGGTGACAGGCG-ACGTTATTGGACAT-GAAC   2918
CYP52D4A 2659  CCACCACTGCCCTCGG--------TTGAGTCAAGGCAGTATGATGCCGGATCCAGTCCAATGGGAACC     2722

CYP52A1A 3229  GCGTGCATACTCGGCGGAGCCCACAATGGGAGCCACGCATTCGGACCATGAAGCAAAGTACATTCACGAGA  3298
CYP52A2A 3212  GGG----CGCCAGAATTATTGACTATTGTGACTTTTA---------CGCTAACGCTCATTGCAGTG      3266
CYP52A2B 3112  GGGG---GCGCCAGAATTATTGACTATTGTGACTTTTTT---ATTTTTCCGTTAACTTTCATTGCAGTG   3177
CYP52A3A 3186  GAGTTGAACCAAGCGTTCCTAGAAGTTACCACACATTATTGTCGAATGAGTTGACTTGACCAATTGAACG  3255
CYP52A3B 2985  GAGTTGAACCAAGCGTTCCTAGAAGTTACCACACATTATTGTCGAACGAGTTGACCAATTGAACG       3054
CYP52A5A 3123  AATCTAGGGTCTACTCCATCTTCCACTGTTTCTTCTTCTTCAGACTTAGCT-AACAAACAACTCACTTCA  3191
CYP52A5B 3136  AACCTAGGGTCCACTCCATCCATCTTTCACT---TCTTCTTCTTCAGACTTATCT-AACAAACGACTCACTTCA 3201
CYP52A8A 2451  GCGAAAGGGTTATTGCATCAATACGAG--GGGCTGACTCTAGTCTAGG---ATGGCAGTCCTAGGTTGC  2515
CYP52A8B 2919  GCAAAAGGGTAATTGCATCGATACGAG--GGGTTGCCTCTGGTCTAAG---AAGGACCCCCAGGTTGC   2983
CYP52D4A 2723  TCT-----GCACGGTGTCGCTGCAGTTTTTGAGGCGTATTCGA---------TCCATGATCGTTCTTTGG  2779
```

FIG. 15J-2

```
CYP52A1A 3299  TCACGGGTGTGTTTCAG-TGTCGCAGATTGAGAAGTTCGACGATGGAAGTACGATCTCGTTGCGGATT  3367
CYP52A2A 3267  TAGTGCGTCTTACACGG-------GGTATTGCTTTCTACAATGCAAGGGCA-CAGTTGAAGGTTTGCACC  3328
CYP52A2B 3178  AAGTGTGTTACACGGGGTGGTTGGTGATGGTGTTGGTTTCTACAATGCAAGGGCA-CAGTTGAAGGTTTCCACA  3246
CYP52A3A 3256  CGGCAGAGTTGTTATACTA-CGCTGGCGACATATCCTACAAGAAGGCACATCAATCGCAGACAGTGCCA  3324
CYP52A3B 3055  CGGCCGAGTTGTTATACTA-CGCCGGGCGACATATCCTACAAGAAGGGCACATCAATTGCCGACAGTGCCA  3123
CYP52A5A 3192  CCATGGATTACGCAGGCATCACGCCGTGCCTCCATCAGAGG-CGAGGCCTTGAAGAAACTCG--CAGAATT  3258
CYP52A5B 3202  CCATGGATTACGCAGGTATCACGCCGTGGGTCCATCAGAGG-CGAAGCCTTGAAGAAAACTCG--CCGAGTT  3268
CYP52A8A 2516  AAACATGTTGCACCA-TATCCCTCCTGGAGTTGGTCGAC--CTCGCCTACGCC-ACCCTCA--GCGATCG  2579
CYP52A8B 2984  AAACATGTTGCACTG-CATCCCACTCAGAGTTGGTCGAC--CACGCCTACGCTTACCCTCA--GCGATCG  3048
CYP52D4A 2780  TGCTGTAGTATAACGAGCT--CTTGGTGTCCTTGAAATGAACAGGTTGGATGTGTTGTTGAGTTTGTCT  2847
```

FIG. 15J-3

```
CYP52A1A  3368  ACGACTTCGGTGGGTTGTTGTTATCTAAACGAAGATTCTATGAGACGCAGCATGTGTTTCGGTTCGAGGATTG  3437
CYP52A2A  3329  TAACGTTGCCCCGTGTCAACTCAACTCAATTTGAC-------G--AGTAACTTCCTAAGCTCGAATTATGC   3385
CYP52A2B  3247  TAACGTTGCACCATATCAATTTGAGAGCAAACTAC--------CTCATTCATGTGATAAAAGAAGAGCCAAA  3305
CYP52A3A  3325  GATTGTCTTATTATTTGAGAGCAAACTAC---------------ATCTTGAACATACTTGGGTATTTGAT    3379
CYP52A3B  3124  GATTGTCTTACTATTTGAGAGCCATCCAGT---------------ATCTTGAACATACTTGGGTACTTTAT   3178
CYP52A5A  3259  G-ACCATCCAGAACCAGCCATCCAGT-------TGAAAGAAATCAACACCGGCATCCAGAAGGACGACTT    3321
CYP52A5B  3269  G-ACCATCCAGAACCAGCCATCCAGT-------TGAAAGAAATCAACACCGGCATCCAGAAGGACGACTT    3331
CYP52A8A  2580  GCACTTTCCGTTGTTGCTCAATATTTCTC---------CTTCCCATTGTTCCAGGGTTA--TC          2629
CYP52A8B  3049  GCACTTTCCGTTGTTGCTCAATATTTCTCT--------CCCCCTGCTTCCCCCATTGTTCCAGGATTA--TC 3110
CYP52D4A  2848  GCGTGCTTGGTTTGCAAGTCTTCGATCG----------------AGCGTAGTGAGTAGACAGTTGGCGGG   2901

CYP52A1A  3438  TGCGTACGTCATGAGTGTGCCTTTTGATGGACCCAAGGAGGAAGGTTACGTGGTTGGGACGTTACGTACAGATCC  3507
CYP52A2A  3386  AGCT-CGTGCGTCAACCTATGTGCAGAGGGGAACAGGAAAGAAAATCCAAAAA-ATCGAAA-ATGCGACTTTCGAT  3451
CYP52A2B  3306  AGGT-AAT-TGGCAGACGGATTGGATTTGATAGTCACGGAACACGGAGTAGAAAGC--AATGGAAACACGCCATGACAGT  3371
CYP52A3A  3380  TTCG-AAGCAGCGATTGGATTTGATAGTGATAGTCACGGACACGGCGT--TGTTTGATAGTAGTATATTTGAAAAGT  3446
CYP52A3B  3179  TTCG-AAGCAGCGATTGGATTTGATAGTGATAGTCACGGACACGGCGT--TGTTTGATATATTTGAAAAGT   3245
CYP52A5A  3322  TGCC-AAGTTGTTGTCTGCCACCCCGAAATCCCACCAAGCACA--AGTTGAACGGCAACCACGAATT-       3387
CYP52A5B  3332  TGCC-AAGTTGTTGTCTTCCACCCCGAAATCCACACACCAAGCACA--AGTTGAATGGCAACCACGAATT-      3397
CYP52A8A  2630  AACA-ACGTTGCCGGCCCTCC----------CCCAAATTA-------CAAGAAAATAAATT-           2674
CYP52A8B  3111  AACA-ACGTTGCCGGTCTCTCTCTCTCCCCCCCCCCCAGTTAT-----GTACAAGAAAATTAAATT-      3171
CYP52D4A  2902  GGTGGTGCTCGGGCTTTATTCTGTGTTGTGTTCCTTCTTAGT--CTTGGAATGACGCTGTTATCGAC       2969
```

FIG. 15K-1

| | | | |
|---|---|---|---|
| CYP52A1A | 3508 | ATTGAAAGGTTGAGCTGGGTAAAGACGGGGACGTGGA-GTGGACCATGG---CGACGACGTCGGATCCT | 3573 |
| CYP52A2A | 3452 | TTTGAATAAACCAAAAGAAAAATGTCGCACTTTTTC-----TCGCTCTCGCTCTCTCGACCCAAATCA | 3516 |
| CYP52A2B | 3372 | GCCATTAGCCCACA---ACACATCTAGTATTCTTTT-----TTTTTTGTGCGCAGTGCACACCTGG | 3433 |
| CYP52A3A | 3447 | TTTGAAAAGATCTAC----AAGTTGATAAGCGTGTTGA-----ACGATATGATTGACAAGCAAAAGGTGA | 3507 |
| CYP52A3B | 3246 | TTTGAAAAGATCTAC----AAGTTGATAAGCGCGTTGA-----ACGATATGATTGACAAGCAAAAGGTGA | 3306 |
| CYP52A5A | 3388 | GTCTGAGGTCGCCATTGCCAAAAGGAGTACGAGGTGTTGATTGCCTTGAGCGACGCCACAAAAGACCCA | 3457 |
| CYP52A5B | 3398 | GTCCGAAGTCGCCATTGCCAAAAGGAGTACGAGGTGTTGATTGCCTTGAGCGACGCCACGAAAGAACCA | 3467 |
| CYP52A8A | 2675 | GTCGCACGGCACCGATCTGTCAAAGATACAGATAA------ACCTTAAATCTGCAAAAACAAGACCCC | 2736 |
| CYP52A8B | 3172 | GTCGCACGGCACCGATACGTCAAAGATACAGAGAA--------ACCTTAA----------TCC | 3216 |
| CYP52D4A | 2970 | GGTTCGTAGTATAAGTAGCGCCAATATGAGAATGTATA-----TCCGCATCACCCAAGACTCTTCAGCCT | 3034 |
| | | | |
| CYP52A1A | 3574 | GGTGGGTTTATCCCGCA-ATGGATAACTCGATTGAGCA-TCCCTGGAGCAATGCAAAAGATGTGCCTAG | 3641 |
| CYP52A2A | 3517 | CAACAAATCCTCGCGGCAGTCGCCAGTATTCGACGAAAC--CACAACAAATAAAAACAAATTCTACACCACT | 3584 |
| CYP52A2B | 3434 | ACTTTAGTTATTGCCC-CATAAAGTTAACAATCT--CACCTTTGGCTCTCCCAGTGTCTCCGCTCCAGA | 3500 |
| CYP52A3A | 3508 | CAAGCGACACAGTCTAGACATCAATTG--CATCAACTACTCGAGAGGTCAACTATTCTCCGCA | 3575 |
| CYP52A3B | 3307 | CAAGCGACACAGTCTAGACATCAATTG--CATCAACTACTCGAGGGGTCAACTATTCTCCGCA | 3374 |
| CYP52A5A | 3458 | ATCAAAGTGACCTCCCAGATCAAGATCTTGATTGACAAGTTCAAGGTGTACTTGT---TTGAGTTGCCTG | 3524 |
| CYP52A5B | 3468 | ATCAAAGTCACCTCCCAGATCAAGATCTTGATTGACAAGTTCAAGGTGTACTTGT---TTGAGTTGCCCG | 3534 |
| CYP52A8A | 2737 | TCCCCATAGCCTAGAAGCACCAGCAAGATGATGGAGCAACTCCTCCAGTACTGGTACATCGCACTCTCTG | 2806 |
| CYP52A8B | 3217 | CTCCCATAGCCTAGAAGCCTAGAAGATTGAGCAACTCCTCCAGTACTGGTACATTGCACTCCCTG | 3286 |
| CYP52D4A | 3035 | GTTACAACGACTGAGGCTGTTGGCCGTGTTGGCCGTGTGACCAATTGGTTTCTTTGGTGACCTAGATTGGTCCCGCAGG | 3104 |

```
CYP52A1A  3642  TG----TATTAAACTACATACAGAAATAAAAACGTGTCTTGATTCATTGGTTT---GGTTCTTGTTGGTT  3705
CYP52A2A  3585  T-----CTTTTCTTCACCAGTCAACAAAAACAACAAATTATACACCATTCAACGATTTTGCTCTTAT  3650
CYP52A2B  3501  TG----CTCGTTTTACACCCTGAGCTAACGACAACAACACCCATGAGGGAATGGCAAAGTT------  3562
CYP52A3A  3576  CA----CGAACTTTTGGG-ACTGGTTTTGTTGTTTGGATTGGTCGACATCTATTCAACCAGTTGGCACATTA  3641
CYP52A3B  3375  CA----CGAACTTTTGGG-ACTGGTTTGTTGTTTGGATTGGTTGACAACTATTTCAACCAGTTGGCTCATTA  3440
CYP52A5A  3525  AC----CAGAAGTTCTCCTACTCCTACTCCGTCTCCAACTCGTCAACATCCGCCCCC-TGGACCTTGCTCGGGG  3590
CYP52A5B  3535  AC----CAGAAGTTCTCCTACTCCTACTCCGTCTCCAACTCGTCCAACATTGCCCCC-TGGACCTTGCTCGGTG  3600
CYP52A8A  2807  TA----TGGTTCATCCTTCGCTACTTGGCTTCCCACGCCGTCTACTTG-CGCCACAAGCTCGGCG  2872
CYP52A8B  3287  TA----TGGTTCATTCTCCGCTACGTGGCTTCCCACGACGCACGAACCATCACTACTTG-CGCCACAAGCTCGGCG  3352
CYP52D4A  3105  GAAAGCAAGGGCTGCTAGGGGGCATACCAAACAAGTCGTAATCAGTATCTATGGTGCTACCATGTG  3174
```

FIG. 15K-3

| | | |
|---|---|---|
| CYP52A1A | 3706 | CCGAGCCAATATATTCACATCATCTCCTAAATTCTCCAAGAATCCCAACGTAGCGTAGTCCAGCACGCCCT 3775 |
| CYP52A2A | 3651 | AAATGCTATATAATGGTTTAATTCAACTCAGGTATGTTTAT-TTTACTGTTTTCAGCTCAAGTATGT--T 3717 |
| CYP52A2B | 3563 | AAACACTTTGGTTTCAATGATTCCTATTGCTACTCTCTTGTTTTGTGTTTTGATTGCACCATGT--G 3630 |
| CYP52A3A | 3642 | GACAACTACAAGAAGTATTGGCATTGATACTGAAGAACATCAGCGATGAAGAACATCTTGATCATAC--A 3709 |
| CYP52A3B | 3441 | GACAACTACAAGAAGAAGTATTGGCATTGATACTGAAGAACATCAGTGAAGAAGATATCTTGATCGTAC--G 3508 |
| CYP52A5A | 3591 | AGAAGTTGACCACGGGCTTGATCAACTTGGCCTTCCAGAACAACAAGCAGCACTTGGACGAGGTCATT-G 3659 |
| CYP52A5B | 3601 | AGAAGTTGACCACGGCTTGATCAACTTGGCGTTCCAGAACAACAAGCAGCACTTGGACGAAGTCATC-G 3669 |
| CYP52A8A | 2873 | CGGCGCCATTCACGCACACACCCAGTACGACGACGGCTGGTATGGTTCAAGTTGGGCGGAGTTTCTCAA--G 2940 |
| CYP52A8B | 3353 | CGGCGCCGTTCACGCACGCACACCCAGTACGACGACGGATGGTATGGTTCAAGTTGGGCGGAGTTTCTCAA--G 3420 |
| CYP52D4A | 3175 | TGTGGTTGGGGGGAAATTCCCGCATTTTGTGTAACGAAAGTTCTAGAAAGTTCTGTGGTTCTGAG-A 3243 |
| | | |
| CYP52A1A | 3776 | CTGAGATCTTATTTAATATCGACTTCTCAACCACCGGTGTGGAATC--CCGTTCAGACCATTGTTACCTGTA 3843 |
| CYP52A2A | 3718 | CAAATACTAACTACTTTTGATGTTGTCGTTTCTAGAATCAAAACACCCCAACACGCCGAGCTT 3787 |
| CYP52A2B | 3631 | AAATAAACGACAATTATATATACCTTT---TCGTCTGTCCTC----CAATGTCT-CTTTTGCTGCCATT 3692 |
| CYP52A3A | 3710 | CTTCCTCCCATCGACACTACAATTGTTAAGCTGGTGTTGGACAA-GAAAGACGACGCTGCAGTTGAACA 3778 |
| CYP52A3B | 3509 | CTTCCTCCCATCGACACTACAATTGTTAAGCTGGTGTTGGATAA-GAAAGAGACGCCACTGTTGACCA 3557 |
| CYP52A5A | 3660 | ACATCTTCAACGAGTTCATCGACAAGTTCTTTGGCAACACGGAG--CCGCAATTGAC-----CAACTTCT 3722 |
| CYP52A5B | 3670 | ACATCTTCAACGAGTTCATCGACAAGTTCTTTGGCAACACAGAG--CCGCAATTGAC------CAACTTCT 3732 |
| CYP52A8A | 2941 | GCGAAGAAGATCGGGGCGGCAGAGGCAGACTTGGTGCATGCCGCGTT-CCGTGGCGG------CATGGACA 3001 |
| CYP52A8B | 3421 | GCGAAGAAGATTGGAAGGCAGAGGCAGACTTGGTGCATGCGCGGTT-CCGTGGAGGGGG----CATGGATA 3484 |
| CYP52D4A | 3244 | ATCTGCTGGAACCATCCACCCGCATTCCGTTGCCAAAGTGGGAA-GAGCAATCAACCACCCTGCTTTG 3312 |

FIG. 15L-1

```
CYP52A1A  3844  GTGTGTTGCTCTCTTGTGTTCTTGATGACAATGATGTATTTGTCACGATACCTGAAATAATAAACATCCAGT  3913
CYP52A2A  3788  GTCGAATAGACGGTTGTTTTGTTTACTCATTAGATGGTCCCAGATTACTTTCAAGCCAAAGTCTCT-CGAGTT  3856
CYP52A2B  3693  TTGCTTTTTTGCTTTTTGCTTTTTGCACT---CTCTCCCACTCCACAATCAGTGCAGCAACACA-CAA      3755
CYP52A3A  3779  GTTCTACAAGTACATCACTTCAACAGT--GTCACGAGACTACAACATCCAACATCGGCTCCACAGCCAAAG  3846
CYP52A3B  3578  GTTCTACAAGTACATCACCTCAACAGT--GTCGCAAGACTACAACTCCAACATCGGAGCCACAGCCAAAG   3645
CYP52A5A  3723  TGACCTTGTGCGGTGTGTTGGACGGGTTGATTGACCATGCC-AACTTCTTGAGCGTGTCCTCGCGGACCT   3791
CYP52A5B  3733  TGACCTTGTCCGGTGTGTTGGACGGGTTGATTGACCATGCC-AACTTCTTGAGCTTGCCTGTCCTCCAGGACCT  3801
CYP52A8A  3002  CCTTCTCGAGCTACACTTTCGGCATCCATCCATATCATCCTTACC-CGGGACCCGGAGAACATCAAGCCGTCT  3070
CYP52A8B  3485  CTTTCTCGAGCTATACTTTCGGCATCCATCCATATCATTCTTACT-CGGGACCCGGAGAACATCAAGGCGGTCT  3553
CYP52D4A  3313  CCCAATCAGCCATTCCCCTGGGAATATAAATTCAAC                                     3348

CYP52A1A  3914  CATTGAGCTTATTACTCGTGAACTTATGAAAGAACTCATTCAAGCCGTTCCCAAAAACCCAGAATTGAA   3983
CYP52A2A  3857  TTGTTTGCTGTTCCCCAATTCCTAACTATGAAGGTTTTATAAGGTCAAAGACCCCAAGGCATAGTT     3926
CYP52A2B  3756                                                                           3755
CYP52A3A  3847  ATGATATCGATTTGTCCAAAACCAAACTCAGTGGCTTTGAGGTGTTGACGAGTT                 3900
CYP52A3B  3646  ATGATATCGATTTGTCCAAGCC                                                 3663
CYP52A5A  3792  TCAAGATCTTCTTGAACTTGGACTCGTATGTGGAC                                    3826
CYP52A5B  3802  TCAAGATCTTCTTGAACTTGGACTCGTTGTGGACAACTCGGACTTCTTGAACGACGTGGAGAACTACTC 3871
CYP52A8A  3071  TGGCGACGCAGTTCGATGACTTCTCGCTCGGTGGCAGGATCAGGTTCTTGAAGCCGTTGTTGGGGTATGG  3140
CYP52A8B  3554  TGGCGACGCAGTTCGATGACTTTTCG                                             3579
CYP52D4A  3349                                                                          3348
```

FIG. 15L-2

| | | | |
|---|---|---|---|
| CYP52A1A | 3984 | GATCTTGCTCAACTGGTCATGCAAGTAGTAGATCGCCATGATCTGATACTTTACCAAGCTATCCTCTCCA | 4053 |
| CYP52A2A | 3927 | TTTTTGGTTCCTTCTTGTCGTG | 3948 |
| CYP52A2B | 3756 | | 3755 |
| CYP52A3A | 3901 | | 3900 |
| CYP52A3B | 3669 | | 3668 |
| CYP52A5A | 3827 | | 3826 |
| CYP52A5B | 3872 | CGACTTTTTGTACGACGAGCCGAACGAGTACCAGAACTT | 3910 |
| CYP52A8A | 3141 | GATATTCACGTT | 3152 |
| CYP52A8B | 3580 | | 3579 |
| CYP52D4A | 3349 | | 3348 |

FIG. 15L-3

| | | | |
|---|---|---|---|
| CYP52A1A | 4054 | AGTTCTCCCACGTACGGCAAGTACGGCAACGAGCTCTGGAAGCTTTGTTGTTTGGGGTCATA | 4115 |
| CYP52A2A | 3949 | | 3948 |
| CYP52A2B | 3756 | | 3755 |
| CYP52A3A | 3901 | | 3900 |
| CYP52A3B | 3669 | | 3668 |
| CYP52A5A | 3827 | | 3826 |
| CYP52A5B | 3911 | | 3910 |
| CYP52A8A | 3153 | | 3152 |
| CYP52A8B | 3580 | | 3579 |
| CYP52D4A | 3349 | | 3348 |

FIG. 15M

```
CYP52A1A    1                                          MATQEIIDSVLPYL-------TKWYTVITAAVLVFLISTNIKNYV    38
CYP52A2A    1                                          MTVHDIIATY----------FTKWYVIVPLALIAYRVLDYFYGRY    35
CYP52A2B    1                                          MTAQDIIATY----------ITKWYVIVPLALIAYRVLDYFYGRY    35
CYP52A3A    1                              MSSSPSFAQEVLATTSPYIEYFLDNYTRWYYFIPLVLLSLNFISLLHTRY    50
CYP52A3B    1                              MSSSPSFAQEVLATTSPYIEYFLDNYTRWYYFIPLVLLSLNFISLLHTKY    50
CYP52A5A    1                                          MIEQLLEY------WYVVVPVLYIIKQLLAYTKTRV              30
CYP52A5B    1                                          MIEQILEY------WYIVPVLYIIKQLIAYSKTRV               30
CYP52A8A    1                                          MLDQILHY------WYIVLPLLAIINQIVAHVRTNY              30
CYP52A8B    1                                          MLDQIFHY------WYIVLPLLVIIKQIVAHARTNY              30
CYP52D4A    1                                          MAISSLLSWD----VICVVFICVCVYFGYEYCYTKY              32

CYP52A1A   39  KAKKLKCVDPPYLKDAGLTGILSLIAAIKAKNDGRLANFAD---EVFDEY    85
CYP52A2A   36  LMYKLGAKPFFQKQTDGCFGFKAPLELLKKSDGTLIDFTL---QRIHDL    82
CYP52A2B   36  LMYKLGAKPFFQKQTDGYFGFKAPLELLKKSDGTLIDFTL---ERIQAL    82
CYP52A3A   51  LERRFHAKPLGNFVRDPTFGIATPLLIYLKSKGTVMKFAWGLWNNKYIV   100
CYP52A3B   51  LERRFHAKPLGNVVLDPTFGIATPLILIYLKSKGTVMKFAWSFWNNKYIV   100
CYP52A5A   31  LMKKLGAAPVTNKLYDNAFGIVNGWKALQFKKEGRAQEYND---YKFDHS    77
CYP52A5B   31  LMKQLGAAPITNQLYDNVFGIVNGWKALQFKKEGRAQEYND---HKFDSS    77
CYP52A8A   31  LMKKLGAKPFTHVQRDGWLGFKFGREFLKAKSAGRLVDLII---SRFHDN    77
CYP52A8B   31  LMKKLGAKPFTHVQLDGWFGFKFGREFLKAKSAGRQVDLII---SRFHDN    77
CYP52D4A   33  LMHKHGAREIENVINDGFFGFRLPLLLMRASNEGRLIEFSV---KRFESA    79
                                                *                                 *
```

FIG. 16A-1

```
CYP52A1A    86   PN--HTFYLSVAGALKIVMTVDPENIKAVLATQFTDFSLGTRHAHFAPLL    133
CYP52A2A    83   DRPDIPTFTFPVFSINLVNTLEPENIKAILATQFNDFSLGTRHSHFAPLL    132
CYP52A2B    83   NRPDIPTFTFPIFSINLISTLEPENIKAILATQFNDFSLGTRHSHFAPLL    132
CYP52A3A   101   RDPKYKTTGLRIVGLPLIETMDPENIKAVLATQFNDFSLGTRHDFLYSLL    150
CYP52A3B   101   KDPKYKTTGLRIVGLPLIETIDPENIKAVLATQFNDFSLGTRHDFLYSLL    150
CYP52A5A    78   KNPSVGTYVSILFGTRIVVTKDPENIKAILATQFGDFSLGKRHTLFKPLL    127
CYP52A5B    78   KNPSVGTYVSILFGTKIVVTKDPENIKAILATQFGDFSLGKRHALFKPLL    127
CYP52A8A    78   ED----TFSSYAFGNHVVFTRDPENIKALLATQFGDFSLGSRVKFFKPLL    123
CYP52A8B    78   ED----TFSSYAFGNHVVFTRDPENIKALLATQFGDFSLGSRVKFFKPLL    123
CYP52D4A    80   PHPQNKTLVNRALSVPVILTKDPVNIKAMLSTQFDDFSLGLRLHQFAPLL    129
                    .  *  ***.*.*  ****  ****   *****   **

CYP52A1A   134   GDGIFTLDGEGWKHSRAMLRPQFARDQIGHVKALEPHIQIMAKQIKLNQG    183
CYP52A2A   133   GDGIFTLDGAGWKHSRSMLRPQFAREQISHVKLLEPHVQVFFKHVRKAQG    182
CYP52A2B   133   GDGIFTLDGAGWKHSRSMLRPQFAREQISHVKLLEPHMQVFFKHVRKAQG    182
CYP52A3A   151   GDGIFTLDGAGWKHSRTMLRPQFAREQVSHVKLLEPHVQVFFKHVRKHRG    200
CYP52A3B   151   GDGIFTLDGAGWKHSRTMLRPQFAREQVSHVKLLEPHVQVFFKHVRKHRG    200
CYP52A5A   128   GDGIFTLDGEGWKHSRAMLRPQFAREQFAREQVAHVTSLEPHFQLLKKHILKHKG    177
CYP52A5B   128   GDGIFTLDGEGWKHSRAMLRPQFAREQVAHVTSLEPHFQLLKKHILKHKG    177
CYP52A8A   124   GYGIFTLDAEGWKHSRAMLRPQFAREQVAHVTSLEPHFQLLKKHILKHKG    173
CYP52A8B   124   GYGIFTLDGEGWKHSRAMLRPQFAREQVAHVTSLEPHFQLLKKHILKHKG    173
CYP52D4A   130   GKGIFTLDGPEWKQSRSMLRPQFAKDRVSHILDLEPHFVLLRKHIDGHNG    179
                 * ******   **  ** ******    *  *   ****    *
```

FIG. 16A-2

| | | | |
|---|---|---|---|
| CYP52A1A | 184 | KTFDIQELFFRFTVDTATEFLFGESVHSLYDEKLGIPTP-NEIPGRENFA | 232 |
| CYP52A2A | 183 | KTFDIQELFFFRLTVDSATEFLFGESVESLRDESIGMSINALDFDGKAGFA | 232 |
| CYP52A2B | 183 | KTFDIQELFFFRLTVDSATEFLFGESVESLRDESIGMSINALDFDGKAGFA | 232 |
| CYP52A3A | 201 | QTFDIQELFFFRLTVDSATEFLFGESAESLRDESIGLTPTKDFDGRRDFA | 250 |
| CYP52A3B | 201 | QTFDIQELFFFRLTVDSATEFLFGESAESLRDDSVGLTPTTKDFEGRGDFA | 250 |
| CYP52A5A | 178 | EYFDIQELFFFRLTVDSATEFLFGESVHSLKDESIGINQDDIDFAGRKDFA | 227 |
| CYP52A5B | 178 | EYFDIQELFFFRLTVDSATEFLFGESVHSLKDETIGINQDDIDFAGRKDFA | 227 |
| CYP52A8A | 174 | EYFDIQELFFFRFTVDSATEFLFGESVHSLKDEEIGYDTKDMSEERRR-FA | 222 |
| CYP52A8B | 174 | EYFDIQELFFFRFTVDSATEFLFGESVHSLRDEEIGYDTKDMAEERRK-FA | 222 |
| CYP52D4A | 180 | DYFDIQELYFRFSMDVATGFLFGESVGSLKDE------D------ARFL | 216 |
| | | ****** ** .* .** .****** ** . * | |

| | | | |
|---|---|---|---|
| CYP52A1A | 233 | AAFNVSQHYLATRSYSQTFYFLTNPKEFRDCNAKVHHLAKYFVNKALNFT | 282 |
| CYP52A2A | 233 | DAFNYSQNYLASRAVMQQLYWVLNGKKFKECNAKVHKFADYVNKALDLT | 282 |
| CYP52A2B | 233 | DAFNYSQNYLASRAVMQQLYWVLNGKKFKECNAKVHKFADYVVSKALDLT | 282 |
| CYP52A3A | 251 | DAFNYSQTYQAYRFLLQQMYWILNGSEFRKSIAVVHKFADHYVQKALELT | 300 |
| CYP52A3B | 251 | DAFNYSQTYQAYRFLLQQMYWILNGAEFRKSIAIVHKFADHYVQKALELT | 300 |
| CYP52A5A | 228 | ESFNKAQEYLAIRTLVQTFYWLVNNKEFRDCTKLVHKFTNYYVQKALDAS | 277 |
| CYP52A5B | 228 | ESFNKAQEYLSIRILVQTFYWLINNKEFRDCTKLVHKFTNYYVQKALDAT | 277 |
| CYP52A8A | 223 | DAFNKSQVVYATRVALQNLYWLVNNKEFKECNDIVHKFTNYYVQKALDAT | 272 |
| CYP52A8B | 223 | DAFNKSQVVLSTRVALQTLYWLVNNKEFTNYYVQKALDAT | 272 |
| CYP52D4A | 217 | EAFNESQKYLATRATLHELYFLCDGFRFRQYNKVVRKFCSQCVHKALDVA | 266 |
| | | .** * *** . *. . * . * | |

FIG. 16B-1

| | | | |
|---|---|---|---|
| CYP52A1A | 283 | PEELEEKSKSGYVFLYELVKQTRDPKVLQDQLLNIMVAGRDTTAGLLSFA | 332 |
| CYP52A2A | 283 | PEQLE-K-QDGYVFLYEIVKQTRDKQVLRDQLLNIMVAGRDTTAGLLSFV | 330 |
| CYP52A2B | 283 | PEQLE-K-QDGYVFLYELVKQTRDRQVLRDQLLNIMVAGRDTTAGLLSFV | 330 |
| CYP52A3A | 301 | DDDLQ-K-QDGYVFLYELAKQTRDPKVLRDQLLNILVAGRDTTAGLLSFV | 348 |
| CYP52A3B | 301 | DDDLQ-K-QDGYVFLYELAKQTRDPKVLRDQLLNILVAGRDTTAGLLSFV | 348 |
| CYP52A5A | 278 | PEELE-K-QSGYVFLYELVKQTRDPNVLRDQSLNILLAGRDTTAGLLSFA | 325 |
| CYP52A5B | 278 | PEELE-K-QGGYVFLYELVKQTRDPKVLRDQSLNILLAGRDTTAGLLSFA | 325 |
| CYP52A8A | 273 | PEELE-K-QGGYVFLYELVKQTRDPKVLRDQSLNILLAGRDTTAGLLSFA | 320 |
| CYP52A8B | 273 | PEELE-K-QGGYVFLYELAKQTKDPNVLRDQQALNVLLAGRDTTAGLLSFA | 320 |
| CYP52D4A | 267 | PEDTS-----EYVFLRELVKHTRDPVVLQDQALNVLLAGRDTTASLLSFA | 311 |
| | | *** * ****.. .**** ** | |

| | | | |
|---|---|---|---|
| CYP52A1A | 333 | LFELARHPEMWSKLREEIEVNFGVGEDSRVEEITFEALKRCEYLKAILNE | 382 |
| CYP52A2A | 331 | FFELARNPEVTNKLREEIEDKFGLGENASVEDISFESLKSCEYLKAVLNE | 380 |
| CYP52A2B | 331 | FFELARNPEVTNKLREEIEDKFGLGENARVEDISFESLKSCEYLKAVLNE | 380 |
| CYP52A3A | 349 | FYELSRNPEVFAKLREEVENRFGLGEEARVEEISFESLKSCEYLKAVINE | 398 |
| CYP52A3B | 349 | FYELSRNPEVFAKLREEVENRFGLGEEARVEEISFESLKSCEYLKAVINE | 398 |
| CYP52A5A | 326 | VFELARHPEIWAKLREEIEQQFGLGEDSRVEEITFESLKRCEYLKAFLNE | 375 |
| CYP52A5B | 326 | VFELARNPHIWAKLREEIEQQFGLGEDSRVEEITFESLKRCEYLKAFLNE | 375 |
| CYP52A8A | 321 | VFELARNPHIWAKLREEIEQQFGLGEDSRVEEITFESLKRCEYLKAVLNE | 370 |
| CYP52A8B | 321 | VFELARNPHIWAKLREESHFGLGEDSRVEEITFESLKRCEYLKAVLNE | 370 |
| CYP52D4A | 312 | TFELARNDHMWRKLREEVILTMGPSSD----EITVAGLKSCRYLKAILNE | 357 |
| | | .** .* ***** * * ** ****.* | |

FIG. 16B-2

```
CYP52A1A   383  TLRMYPSVPVNFRTATRDTTLPRGGGANGTDPIYIPKGSTVAYVVYKTHR           432
CYP52A2A   381  TLRLYPSVPQNFRVATKNTTLPRGGGKDGLSPVLVRKGQTVIYGVYAAHR           430
CYP52A2B   381  TLRLYPSVPQNFRVATKNTTLPRGGGKDGLSPVLVRKGQTVMYGVYAAHR           430
CYP52A3A   399  TLRLYPSVPHNFRVATRNTTLPRGGGEDGYSPIVVKKGQVVMYTVIATHR           448
CYP52A3B   399  ALRLYPSVPHNFRVATRNTTLPRGGGKDGCSPIVVKKGQVVMYTVIGTHR           448
CYP52A5A   376  TLRIYPSVPRNFRIATKNTTLPRGGGSDGTSPILIQKGEAVSYGINSTHL           425
CYP52A5B   376  TLRIYPSVPRNFRIATKNTTLPRGGGPDGTQPILIQKGEGVSYGINSTHL           425
CYP52A8A   371  TLRLHPSVPRNARFAIKDTTLPRGGGPNGKDPILIRKDEVVQYSISATQT           420
CYP52A8B   371  TLRLHPSVPRNARFAIKDTTLPRGGGPNGKDPILIRKNEVVQYSISATQT           420
CYP52D4A   358  TLRLYPSVPRNARFATRNTTLPRGGGPDGSFPILIRKGQPVGYFICATHL           407
                 *   ****   **      ******   *           *     *  .

CYP52A1A   433  LEEYYGKDANDFRPERWFEPSTKKLGWAYVPFNGGPRVCLGQQFALTEAS           482
CYP52A2A   431  NPAVYGKDALEFRPERWFEPETKKLGWAFLPFNGGPRICLGQQFALTEAS           480
CYP52A2B   431  NPAVYGKDALEFRPERWFEPETKKLGWAFLPFNGGPRICLGQQFALTEAS           480
CYP52A3A   449  DPSIYGADADVFRPERWFEPETRKLGWAYVPFNGGPRICLGQQFALTEAS           498
CYP52A3B   449  DPSIYGADADVFRPERWFEPETRKLGWAYVPFNGGPRICLGQQFALTEAS           498
CYP52A5A   426  DPVYYGPDAAEFRPERWFEPSTKKLGWAYLPFNGGPRICLGQQFALTEAG           475
CYP52A5B   426  DPVYYGPDAAEFRPERWFEPSTRKLGWAYLPFNGGPRICLGQQFALTEAG           475
CYP52A8A   421  NPAYYGADAADFRPERWFEPSTRNLGWAFLPFNGGPRICLGQQFALTEAG           470
CYP52A8B   421  NPAYYGADAADFRPERWFEPSTRNLGWAYLPFNGGPRICLGQQFALTEAG           470
CYP52D4A   408  NEKVYGNDSHVFRPERWAALEGKSLGWSYLPFNGGPRSCLGQQFALEAS            457
                 *  ** **   *****    *** ****   * ****     ** . **
```

FIG. 16C-1

| | | | |
|---|---|---|---|
| CYP52A1A | 483 | YVITRLAQMFETVSSDPGLEYPPPKCIHLTMSHNDGVFVKM | 523 |
| CYP52A2A | 481 | YVTVRLLQEFAHLSMDPDTEYPPKKMSHLTMSLFDGANIEMY | 522 |
| CYP52A2B | 481 | YVTVRLLQEFGHLSMDPNTEYPPRKMSHLTMSLFDGANIEMY | 522 |
| CYP52A3A | 499 | YVTVRLLQEFAHLSMDPDTEYPPKLQNTLTLSLFDGADVRMY | 540 |
| CYP52A3B | 499 | YVTVRLLQEFGNLSLDPNAEYPPKLQNTLTLSLFDGADVRMF | 540 |
| CYP52A5A | 476 | YVLVRLLQEFSHVRLDPDEVYPPKRLTNLTMCLQDGAIVKFD | 517 |
| CYP52A5B | 476 | YVLVRLVQEFSHIRLDPDEVYPPKRLTNLTMCLQDGAIVKFD | 517 |
| CYP52A8A | 471 | YVLVRLVQEFPNLSQDPETKYPPPRLAHLTMCLFDGAHVKMS | 512 |
| CYP52A8B | 471 | YVLVRLVQEFPSLSQDPETEYPPPRLAHLTMCLFDGAYVKMQ | 512 |
| CYP52D4A | 458 | YVLARLTQCYTTIQLR-TTEYPPKKLVHLTMSLLNGVYIRTRT | 499 |
| | | ** * *** . * ** .. * | |

FIG. 16C-2

Sequence Range: 1 to 1712

```
         10         20         30         40         50         60         70         80
GGTACCGAGC TCACGAGTTT TGGGATTTTC GAGTTTGGAT TGTTTCCTTT GTTGATTGAA TTGACGAAAC CAGAGAGTTTT 90        100        110        120        130        140        150        160
CAAGACAGAT AAGATTGGGT TTATCAAAAC GCAGTTTGAA ATATTCCAGT TGGTTTCCAA GATATCTTGA AGAAGATTGA 170        180        190        200        210        220        230        240
CGATTTGAAA TTTGAAGAAG TGGAGAAGAT CTGGTTTGGA TTGTTGGAGA ATTTCAAGAA TCTCAAGATT TACTCTAACG 250        260        270        280        290        300        310        320
ACGGGTACAA CGAGAATTGT ATTGAATTGA TCAAGAACAT GATCTTGGTG TTACAGAACA TCAAGTTCTT GGACCAGACT 330        340        350        360        370        380        390        400
GAGAATGCCA CAGATATACA AGGCGTCATG TGATAAAATG GATGAGATTT ATCCCACAAT TGAAGAAAGA GTTTATGGAA 410        420        430        440        450        460        470        480
AGTGGTCAAC CAGAAGCTAA ACAGGAAGAA GCAAACGAAG AGGTGAAACA AGAAGAAGAA GGTAAATAAG TATTTTGTAT 490        500        510        520        530        540        550        560
TATATAACAA ACAAAGTAAG GAATACAGAT TTATACAATA AATTGCCATA CTAGTCACGT GAGATATCTC ATCCATTCCC 570        580        590        600        610        620        630        640
CAACTCCCAA GAAAAAAAAA AAGTGAAAAA AAAAATCAAA CCCAAAGATC AACCTCCCCA TCATCATCGT CATCAAACCC
```

FIG. 23A

```
        650         660         670         680         690         700         710         720
CCAGCTCAAT TCGCAATGGT TAGCACAAAA ACATACACAG AAAGGGCATC AGCACACCCC TCCAAGGTTG CCCAACGTTT
           M  V  S  I  K  T  Y  T  E  R  A  S  A  H  P  S  K  V  A  Q  R  L>

730         740         750         760         770         780         790         800
ATTCCGCTTA ATGGAGTCCA AAAGACCAA CCTCTGCGCC TCGATCGACG TGACCACAAC CGCCGAGTTC CTTTCGCTCA
 F  R  L  M  E  S  K  K  T  N  L  C  A  S  I  D  V  T  T  T  A  E  F  L  S  L>

810         820         830         840         850         860         870         880
TCGACAAGCT CGGTCCCCAC ATCTGTCTCG TGAAGACGCA CATCGATATC ATCTTCAGACT TCAGCTACGA GGGCACGATT
 I  D  K  L  G  P  H  I  C  L  V  K  T  H  I  D  I  I  S  D  F  S  Y  E  G  T  I>

890         900         910         920         930         940         950         960
GAGCCGTTGC TTGTGCTTGC AGAGCGCCAC GGGTTCTTGA TATTCGAGGA CAGGAAGTTT GCTGATATCG GAAACACCGT
 E  P  L  L  V  L  A  E  R  H  G  F  L  I  F  E  D  R  K  F  A  D  I  G  N  T  V>

970         980         990        1000        1010        1020        1030        1040
GATGTTGCAG TACACCTCGG GGGTATACCG GATCGCGGCG TGGAGTGACA TCACGAACGC GCACGGAGTG ACTGGGAAGG
 M  L  Q  Y  T  S  G  V  Y  R  I  A  A  W  S  D  I  T  N  A  H  G  V  T  G  K>

1050        1060        1070        1080        1090        1100        1110        1120
GCCGTCGTTGA AGGGTTGAAA CGCGGGTGCGG AGGGGGTAGA AAAGGAAAGG GGCCGTGTTGA TGTTGGCGGA GTTGTCGAGT
 G  V  V  E  G  L  K  R  G  A  E  G  V  E  K  E  R  G  V  L  M  L  A  E  L  S>

1130        1140        1150        1160        1170        1180        1190        1200
AAAGGCTCGT TGGCGCATGG TGAATATACC CGTGAGACGA TCGAGATTGC GAAGAGTGAT CGGGAGTTCG TGATTGGGTT
 K  G  S  L  A  H  G  E  Y  T  R  E  T  I  E  I  A  K  S  D  R  E  F  V  I  G  F>
```

FIG. 23B

```
         1210       1220       1230       1240       1250       1260       1270       1280
CATCGCGCAG CGGGACATGG GGGGTAGAGA AGAAGGGTTT GATTGGATCA TCATGACGCC TGGTGTGGGG TTGGATGATA
 I  A  Q   R  D  M   G  G  R  E   E  G  F   D  W  I   I  M  T  P   G  V  G   L  D  D>

1290       1300       1310       1320       1330       1340       1350       1360
AAGGCGATGC GTTGGGCCAG CAGTATAGGA CTGTTGATGA GGTGGTTCTG ACTGGTACCG ATGTGATTAT TGTCGGGAGA
 K  G  D  A   L  G  Q   Q  Y  R   T  V  D  E   V  V  L   T  G  T   D  V  I  I   V  G  R>

1370       1380       1390       1400       1410       1420       1430       1440
GGGTTGTTTG GAAAAGGAAG AGACCCTGAG GTGGAGGGAA AGAGATACAG GGATGCTGGA TGGAAGGCAT ACTTGAAGAG
 G  L  F   G  K  G  R   D  P  E   V  E  G   K  R  Y  R   D  A  G   W  K  A   Y  L  K  R>

1450       1460       1470       1480       1490       1500       1510       1520
AACTGGTCAG TTAGAATAAA TATTGTAATA AATAGGTCTA CTAAGCTTCT AGGACGTCAT TGTAGTCTTC
 T  G  Q   L  E  *>

1530       1540       1550       1560       1570       1580       1590       1600
GAAGTTGTCT GCTAGTTTAG TTCTCATGAT TTCGAAAACC AATAACGCAA TGGATGTAGC AGGGATGGTG GTTAGTGCGT 1610       1620       1630       1640       1650       1660       1670       1680
TCCTGACAAA CCCAGAGTAC GCCGCCCTCAA ATTCGCCCTT TGCTTCATCC GCATCACTTG CTTGAAGGTA 1690       1700       1710
TCCACGTACG AGTTGTAATA CACCTTGAAG AA
```

FIG. 23C ns and fatty
REGULATORY REGION OF THE CYP52A2A GENE FROM *CANDIDA TROPICALIS*

CROSS REFERENCE TO RELATED APPLICATIONS

The present application is a continuation of U.S. application Ser. No. 09/976,800, filed Oct. 12, 2001, now abandoned, which is a divisional application of U.S. Ser. No. 09/302,620, filed Apr. 30, 1999, now U.S. Pat. No. 6,331,420, issued Dec. 18, 2001, which claims priority to U.S. Provisional Application Ser. No. 60/123,555, filed Mar. 10, 1999, U.S. Provisional Application Ser. No. 60/103,099, filed Oct. 5, 1998, and U.S. Provisional Application Ser. No. 60/083,798, filed May 1, 1998.

BACKGROUND

1. Field of the Invention

The present invention relates to novel genes which encode enzymes of the ω-hydroxylase complex in yeast *Candida tropicalis* strains. In particular, the invention relates to novel genes encoding the cytochrome P450 and NADPH reductase enzymes of the ω-hydroxylase complex in yeast *Candida tropicalis*, and to a method of quantitating the expression of genes.

2. Description of the Related Art

Aliphatic dioic acids are versatile chemical intermediates useful as raw materials for the preparation of perfumes, polymers, adhesives and macrolid antibiotics. While several chemical routes to the synthesis of long-chain alpha, ω-dicarboxylic acids are available, the synthesis is not easy and most methods result in mixtures containing shorter chain lengths. As a result, extensive purification steps are necessary. While it is known that long-chain dioic acids can also be produced by microbial transformation of alkanes, fatty acids or esters thereof, chemical synthesis has remained the most commercially viable route, due to limitations with the current biological approaches.

Several strains of yeast are known to excrete alpha, ω-dicarboxylic acids as a byproduct when cultured on alkanes or fatty acids as the carbon source. In particular, yeast belonging to the Genus *Candida*, such as *C. albicans*, *C. cloacae*, *C. guillermondii*, *C. intermedia*, *C. lipolytica*, *C. maltosa*, *C. parapsilosis* and *C. zeylenoides* are known to produce such dicarboxylic acids (*Agr. Biol. Chem.* 35: 2033–2042 (1971)). Also, various strains of *C. tropicalis* are known to produce dicarboxylic acids ranging in chain lengths from $C_{11}$ through $C_{18}$ (Okino et al., B M Lawrence, B D Mookherjee and B J Willis (eds), in *Flavors and Fragrances: A World Perspective*. Proceedings of the 10th International Conference of Essential Oils, Flavors and Fragrances, Elsevier Science Publishers B V Amsterdam (1988)), and are the basis of several patents as reviewed by Bühler and Schindler, in *Aliphatic Hydrocarbons in Biotechnology*, H. J. Rehm and G. Reed (eds), Vol. 169, Verlag Chemie, Weinheim (1984).

Studies of the biochemical processes by which yeasts metabolize alkanes and fatty acids have revealed three types of oxidation reactions: α-oxidation of alkanes to alcohols, ω-oxidation of fatty acids to alpha, ω-dicarboxylic acids and the degradative, β-oxidation of fatty acids to $CO_2$ and water. The first two types of oxidations are catalyzed by microsomal enzymes while the last type takes place in the peroxisomes. In *C. tropicalis*, the first step in the ω-oxidation pathway is catalyzed by a membrane-bound enzyme complex (ω-hydroxylase complex) including a cytochrome P450 monooxygenase and a NADPH cytochrome reductase. This hydroxylase complex is responsible for the primary oxidation of the terminal methyl group in alkanes and fatty acids (Gilewicz et al., *Can. J. Microbiol.* 25:201 (1979)). The genes which encode the cytochrome P450 and NADPH reductase components of the complex have previously been identified as P450ALK and P450RED respectively, and have also been cloned and sequenced (Sanglard et al., *Gene* 76:121–136 (1989)). P450ALK has also been designated P450ALK1. More recently, ALK genes have been designated by the symbol CYP and RED genes have been designated by the symbol CPR. See, erg., Nelson, *Pharmacogenetics* 6(1):1–42 (1996), which is incorporated herein by reference. See also Ohkuma et al., *DNA and Cell Biology* 14:163–173 (1995), Seghezzi et al., *DNA and Cell Biology*, 11:767–780 (1992) and Kargel et al., *Yeast* 12:333–348 (1996), each incorporated herein by reference. For example, P450ALK is also designated CYP52 according to the nomenclature of Nelson, *supra*. Fatty acids are ultimately formed from alklanes after two additional oxidation steps, catalyzed by alcohol oxidase (Kemp et al., *Appl. Microbiol. and Biotechnol.* 28: 370–374 (1988)) and aldehyde dehydrogenase. The fatty acids can be further oxidized through the same or similar pathway to the corresponding dicarboxylic acid. The ω-oxidation of fatty acids proceeds via the ω-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of ω-oxidation are activated to their CoA-esters at equal rates and are substrates for both mitochondrial and peroxisomal β-oxidation (*J. Biochem.*, 102:225–234 (1987)). In yeast, β-oxidation takes place solely in the peroxisomes (*Agr. Biol. Chem.* 49:1821–1828 (1985)).

It has recently been determined that certain eukaryotes, e.g., certain yeast, do not adhere, in some respects, to the "universal" genetic code which provides that particular codons (triplets of nucleic acids) code for specific amino acids. Indeed, the genetic code is "universal" because it is virtually the same in all living organisms. Certain *Candida sp.* are now known to translate the CTG codon (which, according to the "universal" code designates leucine) as serine. See, e.g., Ueda et al., *Biochemie* (1994) 76, 1217–1222, where *C. tropicalis*, *C. cylindracea*, *C. guilliermodii* and *C. lusitaniae* are shown to adhere to the "non-universal" code faith respect to the CTG codon. Accordingly, nucleic acid sequences may code for one amino acid sequence in "universal" code organisms and a variant of that amino acid sequence in "non-universal" code organisms depending on the number of CTG codons present in the nucleic acid coding sequence. The difference may become evident when, in the course of genetic engineering, nucleic acid encoding a protein is transferred from a "non-universal" code organism to a "universal" code organism or vice versa. Obviously, there will be a different amino acid sequence depending on which organism is used to express the protein.

The production of dicarboxylic acids by fermentation of unsaturated $C_{14}$–$C_{16}$ monocarboxylic acids using a strain of the species *C. tropicalis* is disclosed in U.S. Pat. No. 4,474,882. The unsaturated dicarboxylic acids correspond to the starting materials in the number and position of the double bonds. Similar processes in which other special microorganisms are used are described in U.S. Pat. Nos.

3,975,234 and 4,339,536, in British Patent Specification 1,405,026 and in German Patent Publications 21 64 626, 28 53 847, 29 37 292, 29 51 177, and 21 40 133.

Cytochromes P450 (P450s) are terminal monooxidases of a multicomponent enzyme system as described above. They comprise a superfamily of proteins which exist widely in nature having been isolated from a variety of organisms as described e.g., in Nelson, supra. These organisms include various mammals, fish, invertebrates, plants, mollusk, crustaceans, lower eukaryotes and bacteria (Nelson, supra). First discovered in rodent liver microsomes as a carbon-monoxide binding pigment as described, e.g., in Garfinkel, *Arch. Biochem. Biophys.* 77:493–509 (1958), which is incorporated herein by reference, P450s were later named based on their absorption at 450 nm in a reduced-CO coupled difference spectrum as described, e.g., in Omura et al., *J. Biol. Chem.* 239:2370–2378 (1964), which is incorporated herein by reference.

P450s catalyze the metabolism of a variety of endogenous and exogenous compounds (Nelson, supra). Endogenous compounds include steroids, prostanoids, eicosanoids, fat-soluble vitamins, fatty acids, mammalian alkaloids, leukotrines, biogenic amines and phytolexins (Nelson, supra). P450 metabolism involves such reactions as epoxidation, hydroxylation, deakylation, N-hydroxylation, sulfoxidation, desulfuration and reductive dehalogenation. These reactions generally make the compound more water soluble, which is conducive for excretion, and more electrophilic. These electrophilic products can have detrimental effects if they react with DNA or other cellular constituents. However, they can react through conjugation with low molecular weight hydrophilic substances resulting in glucoronidation, sulfation, acetylation, amino acid conjugation or glutathione conjugation typically leading to inactivation and elimination as described, e.g., in Klaassen et al., *Toxicology*, 3rd ed, Macmillan, N.Y., 1986, incorporated herein by reference.

P450s are heme thiolate proteins consisting of a heme moiety bound to a single polypeptide chain of 45,000 to 55,000 Da. The iron of the heme prosthetic group is located at the center of a protoporphyrin ring. Four ligands of the heme iron can be attributed to the porphyrin ring. The fifth ligand is a thiolate anion from a cysteinyl residue of the polypeptide. The sixth ligand is probably a hydroxyl group from an amino acid residue, or a moiety with a similar field strength such as a water molecule as described, e.g., in Goeptar et al., *Critical Reviews in Toxicology* 25(1):25–65 (1995), incorporated herein by reference.

Monooxygenation reactions catalyzed by cytochromes P450 in a eukaryotic membrane-bound system require the transfer of electrons from NADPH to P450 via NADPH-cytochrome P450 reductase (CPR) as described, e.g., in Taniguchi et al., *Arch. Biochem. Biophys.* 232:585 (1984), incorporated herein by reference. CPR genes are now also referred to as NCP genes. See, e.g., Debacker et al., *Antimicrobial Agents and Chemotherapy*, 45:1660 (2001). CPR is a flavoprotein of approximately 78,000 Da containing 1 mol of flavin adenine dinucleotide (FAD) and 1 mol of flavin mononucleotide (FMN) per mole of enzyme as described, e.g., in Potter et al., *J. Biol. Chem.* 258:6906 (1983), incorporated herein by reference. The FAD moiety of CPR is the site of electron entry into the enzyme, whereas FMN is the electron-donating site to P450 as described, e.g., in Vermilion et al., *J. Biol. Chem.* 253:8812 (1978), incorporated herein by reference. The overall reaction is as follows:

$$H^- + RH + NADPH + O_2 \rightarrow ROH + NADP^+ + H_2O$$

Binding of a substrate to the catalytic site of P450 apparently results in a conformational change initiating electron transfer from CPR to P450. Subsequent to the transfer of the first electron, $O_2$ binds to the $Fe_2^+$-P450 substrate complex to form $Fe_3^+$-P450-substrate complex. This complex is then reduced by a second electron from CPR, or, in some cases, NADH via cytochrome b5 and NADH-cytochrome b5 reductase as described, e.g., in Guengerich et al., *Arch. Biochem. Biophys.* 205:365 (1980), incorporated herein by reference. One atom of this reactive oxygen is introduced into the substrate, while the other is reduced to water. The oxygenated substrate then dissociates, regenerating the oxidized form of the cytochrome P450 as described, e.g., in Klassen, Amdur and Doull, *Casarett and Doull's Toxicology*, Macmillan, N.Y. (1986), incorporated herein by reference.

The P450 reaction cycle can be short-circuited in such a way that $O_2$ is reduced to $O_2^-$ and/or $H_2O_2$ instead of being utilized for substrate oxygenation. This side reaction is often referred to as the "uncoupling" of cytochrome P450 as described, e.g., in Kuthen et al., *Eur. J. Biochem.* 126:583 (1982) and Poulos et al., *FASEBJ.* 6:674 (1992), both of which are incorporated herein by reference. The formation of these oxygen radicals may lead to oxidative cell damage as described, e.g., in Mukhopadhay, *J. Biol. Chem.* 269(18): 13390–13397 (1994) and Ross et al., *Biochem. Pharm.* 49(7):979–989 (1995), both of which are incorporated herein by reference. It has been proposed that cytochrome b5's effect on P450 binding to the CPR results in a more stable complex which is less likely to become "uncoupled" as described, e.g., in Yamazaki et al., *Arch. Biochem. Biophys.* 325(2):174–182 (1996), incorporated herein by reference.

P450 families are assigned based upon protein sequence comparisons. Notwithstanding a certain amount of heterogeneity, a practical classification of P450s into families can be obtained based on deduced amino acid sequence similarity. P450s with amino acid sequence similarity of between about 40–80% are considered to be in the same family, with sequences of about >55% belonging to the same subfamily. Those with sequence similarity of about <40% are generally listed as members of different P450 gene families (Nelson, supra). A value of about >97% is taken to indicate allelic variants of the same gene, unless proven otherwise based on catalytic activity, sequence divergence in non-translated regions of the gene sequence, or chromosomal mapping.

The most highly conserved region is the HR2 consensus containing the invariant cysteine residue near the carboxyl terminus which is required for heme binding as described, e.g., in Gotoh et al. *J. Biochem.* 93:807–817 (1983) and Motohashi et al., *J. Biochem.* 101:879–997 (1987), both of which are incorporated herein by reference. Additional consensus regions, including the central region of helix I and the transmembrane region, have also been identified, as described, e.g, in Goeptar et al., supra and Kalb et al., *PNAS.* 85:7221–7225 (1988), incorporated herein by reference, although the HR2 cysteine is the only invariant amino acid among P450s.

Short chain ($\leq C12$) aliphatic dicarboxylic acids (diacids) are important industrial intermediates in the manufacture of diesters and polymers, and find application as thermoplastics, plasticizing agents, lubricants, hydraulic fluids, agricultural chemicals, pharmaceuticals, dyes, surfactants, and adhesives. The high price and limited availability of short chain diacids are due to constraints imposed by the existing chemical synthesis.

Long-chain diacids (aliphatic α, ω-dicarboxylic acids with carbon numbers of 12 or greater, hereafter also referred to as diacids) (HOOC—$(CH_2)_n$—COOH) are a versatile family of chemicals with demonstrated and potential utility in a variety of chemical products including plastics, adhesives, and fragrances. Unfortunately, the full market potential of diacids has not been realized because chemical processes produce only a limited range of these materials at a relatively high price. In addition, chemical processes for the production of diacids have a number of limitations and disadvantages. All the chemical processes are restricted to the production of diacids of specific carbon chain lengths. For example, the dodecanedioic acid process starts with butadiene. The resulting product diacids are limited to multiples of four-carbon lengths and, in practice, only dodecanedioic acid is made. The dodecanedioic process is based on nonrenewable petrochemical feedstocks. The multireaction conversion process produces unwanted byproducts, which result in yield losses, $NO_x$ pollution and heavy metal wastes.

Long-chain diacids offer potential advantages over shorter chain diacids, but their high selling price and limited commercial availability prevent widespread growth in many of these applications. Biocatalysis offers an innovative way to overcome these limitations with a process that produces a wide range of diacid products from renewable feedstocks. However, there is no commercially viable bioprocess to produce long chain diacids from renewable resources.

SUMMARY OF THE INVENTION

An isolated nucleic acid is provided which encodes a CPRA protein having the amino acid sequence set forth in SEQ ID NO: 83 or SEQ ID NO: 117. An isolated nucleic acid is also provided which includes a coding region defined by nucleotides 1006–3042 as set forth in SEQ ID NO: 81. An isolated protein is provided which includes an amino acid sequence as set forth in SEQ ID NO: 83 or SEQ ID NO: 117. A vector is provided which includes a nucleotide sequence encoding CPRA protein including an amino acid sequence as set forth in SEQ ID NO: 83 or SEQ ID NO: 117. A host cell is provided which is transfected or transformed with the nucleic acid encoding CPRA protein having an amino acid sequence as set forth in SEQ ID NO: 83 or SEQ ID NO: 117. A method of producing a CPRA protein including an amino acid sequence as set forth in SEQ ID NO: 83 or SEQ ID NO: 117 is also provided which includes a) transforming a suitable host cell with a DNA sequence that encodes the protein having the amino acid sequence as set forth in SEQ ID NO: 83 or SEQ ID NO: 117; and b) culturing the cell under conditions favoring the expression of the protein.

An isolated nucleic acid is provided which encodes a CPRB protein having the amino acid sequence set forth in SEQ ID NO: 84 or SEQ ID NO: 118. An isolated nucleic acid is provided which includes a coding region defined by nucleotides 1033–3069 as set forth in SEQ ID NO: 82. An isolated protein is provided which includes an amino acid sequence as set forth in SEQ ID NO: 84 or SEQ ID NO: 118. A vector is provided which includes a nucleotide sequence encoding CPRB protein including an amino acid sequence as set forth in SEQ ID NO: 84 or SEQ ID NO: 118. A host cell is provided which is transfected or transformed with the nucleic acid encoding CPRB protein having an amino acid sequence as set forth in SEQ ID NO: 84 or SEQ ID NO: 118. A method of producing a CPRB protein including an amino acid sequence as set forth in SEQ ID NO: 84 or SEQ ID NO: 118 is provided which includes a) transforming a suitable host cell with a DNA sequence that encodes the protein having the amino acid sequence as set forth in SEQ ID NO: 84 or SEQ ID NO: 118; and b) culturing the cell under conditions favoring the expression of the protein.

An isolated nucleic acid is provided which encodes a CYP52A13A protein having the amino acid sequence set forth in SEQ ID NO: 95 or SEQ ID NO: 110. An isolated nucleic acid is provided which includes a coding region defined by nucleotides 1177–2748 as set forth in SEQ ID NO: 85. An isolated protein is provided which includes an amino acid sequence as set forth in SEQ ID NO: 95 or SEQ ID NO: 110. A vector is provided which includes a nucleotide sequence encoding CYP52A1A protein including an amino acid sequence as set forth in SEQ ID NO: 95 or SEQ ID NO: 110. A host cell is provided which is transfected or transformed with the nucleic acid encoding CYP52A1A protein having an amino acid sequence as set forth in SEQ ID NO: 95 or SEQ ID NO: 110. A method of producing a CYP52A1A protein including an amino acid sequence as set forth in SEQ ID NO: 95 or SEQ ID NO: 110 is provided which includes a) transforming a suitable host cell with a DNA sequence that encodes the protein having the amino acid sequence as set forth in SEQ ID NO: 95 or SEQ ID NO: 110; and b) culturing the cell under conditions favoring the expression of the protein.

An isolated nucleic acid encoding a CYP52A2A protein is provided which has the amino acid sequence set forth in SEQ ID NO: 96. An isolated nucleic acid is provided which includes a coding region defined by nucleotides 1199–2767 as set forth in SEQ ID NO: 86. An isolated protein is provided which includes an amino acid sequence as set forth in SEQ ID NO: 96. A vector is provided which includes a nucleotide sequence encoding CYP52A2A protein including an amino acid sequence as set forth in SEQ ID NO: 96. A host cell is provided which is transfected or transformed with the nucleic acid encoding CYP52A2A protein having an amino acid sequence as set forth in SEQ ID NO: 96. A method of producing a CYP52A2A protein including an amino acid sequence as set forth in SEQ ID NO: 96 is provided which includes a) transforming a suitable host cell with a DNA sequence that encodes the protein having the amino acid sequence as set forth in SEQ ID NO: 96; and b) culturing the cell under conditions favoring the expression of the protein.

An isolated nucleic acid encoding a CYP52A2B protein is provided which has the amino acid sequence set forth in SEQ ID NO: 97. An isolated nucleic acid is provided which includes a coding region defined by nucleotides 1072–2640 as set forth in SEQ ID NO: 87. An isolated protein is provided which includes an amino acid sequence as set forth in SEQ ID NO: 97. A vector is provided which includes a nucleotide sequence encoding CYP52A2B protein including an amino acid sequence as set forth in SEQ ID NO: 97. A host cell is provided which is transfected or transformed with the nucleic acid encoding CYP52A2B protein having an amino acid sequence as set forth in SEQ ID NO: 97. A method of producing a CYP52A2B protein including an amino acid sequence as set forth in SEQ ID NO: 97 is provided which includes a) transforming a suitable host cell with a DNA sequence that encodes the protein having the amino acid sequence as set forth in SEQ ID NO: 97; and b) culturing the cell under conditions favoring the expression of the protein.

An isolated nucleic acid encoding a CYP52A3A protein is provided which has the amino acid sequence set forth in SEQ ID NO: 98. An isolated nucleic acid is provided which includes a coding region defined by nucleotides 1126–2748 as set forth in SEQ ID NO: 88. An isolated protein is provided which includes an amino acid sequence as set forth in SEQ ID NO: 98. A vector is provided which includes a nucleotide sequence encoding CYP52A3A protein including an amino acid sequence as set forth in SEQ ID NO: 98. A host cell is provided which is transfected or transformed with the nucleic acid encoding CYP52A3A protein having art amino acid sequence as set forth in SEQ ID NO: 98. A method of producing a CYP52A3A protein including an amino acid sequence as set forth in SEQ ID NO: 98 is provided which includes a) transforming a suitable host cell with a DNA sequence that encodes the protein having the amino acid sequence as set forth in SEQ ID NO: 98; and b) culturing the cell under conditions favoring the expression of the protein.

An isolated nucleic acid encoding a CYP52A3B protein is provided having the amino acid sequence as set forth in SEQ ID NO: 99 or SEQ ID NO: 111. An isolated nucleic acid is provided which includes a coding region defined by nucleotides 913–2535 as set forth in SEQ ID NO: 89. An isolated protein is provided which includes an amino acid sequence as set forth in SEQ ID NO: 99 or SEQ ID NO: 111. A vector is provided which includes a nucleotide sequence encoding CYP52A3B protein including an amino acid sequence as set forth in SEQ ID NO: 99 or SEQ ID NO: 111. A host cell is provided which is transfected or transformed with the nucleic acid encoding CYP52A3B protein having an amino acid sequence as set forth in SEQ ID NO: 99 or SEQ ID NO: 111. A method of producing a CYP52A3B protein including an amino acid sequence as set forth in SEQ ID NO: 99 or SEQ ID NO: 111 is provided which includes a) transforming a suitable host cell with a DNA sequence that encodes the protein having the amino acid sequence as set forth in SEQ ID NO: 99 or SEQ ID NO: 111; and b) culturing the cell under conditions favoring the expression of the protein.

An isolated nucleic acid encoding a CYP52A5A protein is provided having the amino acid sequence set forth in SEQ ID NO: 100 or SEQ ID NO: 112. An isolated nucleic acid is provided which includes a coding region defined by nucleotides 1103–2656 as set forth in SEQ ID NO: 90. An isolated protein is provided which includes an amino acid sequence as set forth in SEQ ID NO: 100 or SEQ ID NO: 112. A vector is provided which includes a nucleotide sequence encoding CYP52A5A protein including an amino acid sequence as set forth in SEQ ID NO: 100 or SEQ ID NO: 112. A host cell is provided which is transfected or transformed with the nucleic acid encoding CYP52A5A protein having an amino acid sequence as set forth in SEQ ID NO: 100 or SEQ ID NO: 112. A method of producing a CYP52A5A protein including an amino acid sequence as set forth in SEQ ID NO: 100 or SEQ ID NO: 112 is provided which includes a) transforming a suitable host cell with a DNA sequence that encodes the protein having the amino acid sequence as set forth in SEQ ID NO: 100 or SEQ ID NO: 112; and b) culturing the cell under conditions favoring the expression of the protein.

An isolated nucleic acid encoding a CYP52A5B protein is provided having the amino acid sequence as set forth in SEQ ID NO: 101 or SEQ ID NO: 113. An isolated nucleic acid is provided which includes a coding region defined by nucleotides 1142–2695 as set forth in SEQ ID NO: 91. An isolated protein is provided which includes an amino acid sequence as set forth in SEQ ID NO: 101 or SEQ ID NO: 113. A vector is provided which includes a nucleotide sequence encoding CYP52A5B protein including the amino acid sequence as set forth in SEQ ID NO: 101 or SEQ ID NO: 113. A host cell is provided which is transfected or transformed with the nucleic acid encoding CYP52A5B protein having the amino acid sequence as set forth in SEQ ID NO: 101 or SEQ ID NO: 113. A method of producing a CYP52A5B protein including an amino acid sequence as set forth in SEQ ID NO: 101 or SEQ ID NO: 113 is provided which includes a) transforming a suitable host cell with a DNA sequence that encodes the protein having the amino acid sequence as set forth in SEQ ID NO: 101 or SEQ ID NO: 113; and b) culturing the cell under conditions favoring the expression of the protein.

An isolated nucleic acid encoding a CYP52A8A protein is provided having the amino acid sequence set forth in SEQ ID NO: 102 or SEQ ID NO: 114. An isolated nucleic acid is provided which includes a coding region defined by nucleotides 464–2002 as set forth in SEQ ID NO: 92. An isolated protein is provided which includes an amino acid sequence as set forth in SEQ ID NO: 102 or SEQ ID NO: 114. A vector is provided which includes a nucleotide sequence encoding CYP52A8A protein including an amino acid sequence as set forth in SEQ ID NO: 102 or SEQ ID NO: 114. A host cell is provided which is transfected or transformed with the nucleic acid encoding CYP52A8A protein having an amino acid sequence as set forth in SEQ ID NO: 102 or SEQ ID NO: 114. A method of producing a CYP52A8A protein including an amino acid sequence as set forth in SEQ ID NO: 102 or SEQ ID NO: 114 is provided which includes a) transforming a suitable host cell with a DNA sequence that encodes the protein having the amino acid sequence as set forth in SEQ ID NO: 102 or SEQ ID NO: 114; and b) culturing the cell under conditions favoring the expression of the protein.

An isolated nucleic acid encoding a CYP52A8B protein is provided having the amino acid sequence set forth in SEQ ID NO: 103 or SEQ ID NO: 115. An isolated nucleic acid is provided which includes a coding region defined by nucleotides 1017–2555 as set forth in SEQ ID NO: 93. An isolated protein is provided which includes an amino acid sequence as set forth in SEQ ID NO: 103 or SEQ ID NO: 115. A vector is provided which includes a nucleotide sequence encoding CYP52A8B protein including an amino acid sequence as set forth in SEQ ID NO: 103 or SEQ ID NO: 115. A host cell is provided which is transfected or transformed with the nucleic acid encoding CYP52A8B protein having an amino acid sequence as set forth in SEQ ID NO: 103 or SEQ ID NO: 115. A method of producing a CYP52A8B protein including an amino acid sequence as set forth in SEQ ID NO: 103 or SEQ ID NO: 115 is provided which includes a) transforming a suitable host cell with a DNA sequence that encodes the protein having the amino acid sequence as set forth in SEQ ID NO: 103 or SEQ ID NO: 115; and b) culturing the cell under conditions favoring the expression of the protein.

An isolated nucleic acid encoding a CYP52D4A protein is provided having the amino acid sequence set forth in SEQ ID NO: 104 or SEQ ID NO: 116. An isolated nucleic acid is provided including a coding region defined by nucleotides 767–2266 as set forth in SEQ ID NO: 94. An isolated protein is provided which includes an amino acid sequence as set forth in SEQ ID NO: 104 or SEQ ID NO: 116. A vector is provided which includes a nucleotide sequence encoding CYP52D4A protein including an amino acid sequence as set forth in SEQ ID NO: 104 or SEQ ID NO: 116. A host cell is provided which is transfected or transformed with the nucleic acid encoding CYP52D4A protein having an amino acid sequence as set forth in SEQ ID NO: 104 or SEQ ID NO: 116. A method of producing a CYP52D4A protein including an amino acid sequence as set forth in SEQ ID NO: 104 or SEQ ID NO: 116 is provided which includes a) transforming a suitable host cell with a DNA sequence that encodes the protein having the amino acid sequence as set forth in SEQ ID NO: 104 or SEQ ID NO: 116; and b) culturing the cell under conditions favoring the expression of the protein.

A method for discriminating members of a gene family by quantifying the amount of target mRNA in a sample is provided which includes a) providing an organism containing a target gene; b) culturing the organism with an organic substrate which causes upregulation in the activity of the target gene; c) obtaining a sample of total RNA from the organism at a first point in time; d) combining at least a portion of the sample of the total RNA with a known amount of competitor RNA to form an RNA mixture, wherein the competitor RNA is substantially similar to the target mRNA but has a lesser number of nucleotides compared to the target mRNA; e) adding reverse transcriptase to the RNA mixture in a quantity sufficient to form corresponding target DNA and competitor DNA; (f) conducting a polymerase chain reaction in the presence of at least one primer specific for at least one substantially non-homologous region of the target DNA within the gene family, the primer also specific for the competitor DNA; g) repeating steps (c–f) using increasing amounts of the competitor RNA while maintaining a substantially constant amount of target RNA; h) determining the point at which the amount of target DNA is substantially equal to the amount of competitor DNA; i) quantifying the results by comparing the ratio of the concentration of unknown target to the known concentration of competitor; and j) obtaining a sample of total RNA from the organism at another point in time and repeating steps (d–i).

A method for increasing production of a dicarboxylic acid is provided which includes a) providing a host cell having a naturally occurring number of CPRA genes; b) increasing, in the host cell, the number of CPRA genes which encode a CPRA protein having the amino acid sequence as set forth in SEQ ID NO: 83 or SEQ ID NO: 117; c) culturing the host cell in media containing an organic substrate which upregulates the CPRA gene, to effect increased production of dicarboxylic acid.

A method for increasing the production of a CPRA protein having an amino acid sequence as set forth in SEQ ID NO: 83 or SEQ ID NO: 117 is provided which includes a) transforming a host cell having a naturally occurring amount of CPRA protein with an increased copy number of a CPRA gene that encodes the CPRA protein having the amino acid sequence as set forth in SEQ ID NO: 83 or SEQ ID NO: 117; and b) culturing the cell and thereby increasing expression of the protein compared with that of a host cell containing a naturally occurring copy number of the CPRA gene.

A method for increasing production of a dicarboxylic acid is provided which includes a) providing a host cell having a naturally occurring number of CPRB genes; b) increasing, in the host cell, the number of CPRB genes which encode a CPRB protein having the amino acid sequence as set forth in SEQ ID NO: 84 or SEQ ID NO: 118; c) culturing the host cell in media containing an organic substrate which upregulates the CPRB gene, to effect increased production of dicarboxylic acid.

A method for increasing the production of a CPRB protein having an amino acid sequence as set forth in SEQ ID NO: 84 or SEQ ID NO: 118 is provided which includes a) transforming a host cell having a naturally occurring amount of CPRB protein with an increased copy number of a CPRB gene that encodes the CPRB protein having the amino acid sequence as set forth in SEQ ID NO: 84 or SEQ ID NO: 118; and b) culturing the cell and thereby increasing expression of the protein compared with that of a host cell containing a naturally occurring copy number of the CPRB gene.

A method for increasing production of a dicarboxylic acid is provided which includes a) providing a host cell having a naturally occurring number of CYP52A1A genes; b) increasing, in the host cell, the number of CYP52A1A genes which encode a CYP52A1A protein having the amino acid sequence as set forth in SEQ ID NO: 95 or SEQ ID NO: 110; c) culturing the host cell in media containing an organic substrate which upregulates the CYPS2A1A gene, to effect increased production of dicarboxylic acid.

A method for increasing the production of a CYP52A1A protein having an amino acid sequence as set forth in SEQ ID NO: 95 or SEQ ID NO: 110 is provided which includes a) transforming a host cell having a naturally occurring amount of CYP52A1A protein with an increased copy number of a CYP52A1A gene that encodes the CYP52A1A protein having the amino acid sequence as set forth in SEQ ID NO: 95 or SEQ ID NO: 110; and b) culturing the cell and thereby increasing expression of the protein compared with that of a host cell containing a naturally occurring copy number of the CYP52A1A gene.

A method for increasing production of a dicarboxylic acid is provided which includes a) providing a host cell having a naturally occurring number of CYP52A2A genes; b) increasing, in the host cell, the number of CYP52A2A genes which encode a CYP52A2A protein having the amino acid sequence as set forth in SEQ ID NO: 96; c) culturing the host cell in media containing an organic substrate which upregulates the CYP52A2A gene, to effect increased production of dicarboxylic acid.

A method for increasing the production of a CYP52A2A protein having an amino acid sequence as set forth in SEQ ID NO: 96 is provided which includes a) transforming a host cell having a naturally occurring amount of CYP52A2A protein with an increased copy number of a CYP52A2A gene that encodes the CYP52A2A protein having the amino acid sequence as set forth in SEQ ID NO: 96; and b) culturing the cell and thereby increasing expression of the protein compared with that of a host cell containing a naturally occurring copy number of the CYP52A2A gene.

A method for increasing production of a dicarboxylic acid is provided which includes a) providing a host cell having a naturally occurring number of CYP52A2B genes; b) increasing, in the host cell, the number of CYP52A2B genes which encode a CYP52A2B protein having the amino acid sequence as set forth in SEQ ID NO: 97; c) culturing the host cell in media containing an organic substrate which upregulates the CYP52A2B gene, to effect increased production of dicarboxylic acid.

A method for increasing the production of a CYP52A2B protein having an amino acid sequence as set forth in SEQ ID NO: 97 is provided which includes a) transforming a host cell having a naturally occurring amount of CYP52A2B protein with an increased copy number of a CYPS2A2B gene that encodes the CYP52A2B protein having the amino acid sequence as set forth in SEQ ID NO: 97; and b) culturing the cell and thereby increasing expression of the protein compared with that of a host cell containing a naturally occurring copy number of the CYP52A2B gene.

A method for increasing production of a dicarboxylic acid is provided which includes a) providing a host cell having a naturally occurring number of CYP52A3A genes; b) increasing, in the host cell, the number of CYP52A3A genes which encode a CYP52A3A protein having the amino acid sequence as set forth in SEQ ID NO: 98; c) culturing the host cell in media containing an organic substrate which upregulates CYP52A3A gene, to effect increased production of dicarboxylic acid.

A method for increasing the production of a CYP52A3A protein having an amino acid sequence as set forth in SEQ ID NO: 98 is provided which includes a) transforming a host cell having a naturally occurring amount of CYP52A3A protein with an increased copy number of a CYP52A3A gene that encodes the CYP52A3A protein having the amino acid sequence as set forth in SEQ ID NO: 98; and b) culturing the cell and thereby increasing expression of the protein compared with that of a host cell containing a naturally occurring copy number of the CYP52A3A gene.

A method for increasing production of a dicarboxylic acid is provided which includes a) providing a host cell having a naturally occurring number of CYP52A3B genes; b) increasing, in the host cell, the number of CYP52A3B genes which encode a CYP52A3B protein having the amino acid sequence as set forth in SEQ ID NO: 99 or SEQ ID NO: 111; c) culturing the host cell in media containing an organic substrate which upregulates the CYP52A3B gene, to effect increased production of dicarboxylic acid.

A method for increasing the production of a CYP52A3B protein having an amino acid sequence as set forth in SEQ ID NO: 99 or SEQ ID NO: 111 is provided which includes a) transforming a host cell having a naturally occurring amount of CYP52A3B protein with an increased copy number of a CYP52A3B gene that encodes the CYP52A3B protein having the amino acid sequence as set forth in SEQ ID NO: 99 or SEQ ID NO: 111; and b) culturing the cell and thereby increasing expression of the protein compared with that of a host cell containing a naturally occurring copy number of the CYP52A3B gene.

A method for increasing production of a dicarboxylic acid is provided which includes a) providing a host cell having a naturally occurring number of CYP52A5A genes; b) increasing, in the host cell, the number of CYP52A5A genes which encode a CYP52A5A protein having the amino acid sequence as set forth in SEQ ID NO: 100 or SEQ ID NO: 112; c) culturing the host cell in media containing an organic substrate which upregulates the CYP52A5A gene, to effect increased production of dicarboxylic acid.

A method for increasing the production of a CYP52A5A protein having an amino acid sequence as set forth in SEQ ID NO: 100 or SEQ ID NO: 112 is provided which includes a) transforming a host cell having a naturally occurring amount of CYP52A5A protein with an increased copy number of a CYP52A5A gene that encodes the CYP52A5A protein having the amino acid sequence as set forth in SEQ ID NO: 100 or SEQ ID NO: 112; and b) culturing the cell and thereby increasing expression of the protein compared with that of a host cell containing a naturally occurring copy number of the CYP52A5A gene.

A method for increasing production of a dicarboxylic acid is provided which includes a) providing a host cell having a naturally occurring number of CYP52A5B genes; b) increasing, in the host cell, the number of CYP52A5B genes which encode a CYP52A5B protein having the amino acid sequence as set forth in SEQ ID NO: 101 or SEQ ID NO: 113; c) culturing the host cell in media containing an organic substrate which upregulates the CYP52A5B gene, to effect increased production of dicarboxylic acid.

A method for increasing the production of a CYP52A5B protein having an amino acid sequence as set forth in SEQ ID NO: 101 or SEQ ID NO: 113 is provided which includes a) transforming a host cell having a naturally occurring amount of CYP52A5B protein with an increased copy number of a CYP52A5B gene that encodes the CYP52A5B protein having the amino acid sequence as set forth in SEQ ID NO: 101 or SEQ ID NO: 113; and b) culturing the cell and thereby increasing expression of the protein compared with that of a host cell containing a naturally occurring copy number of the CYP52A5B gene.

A method for increasing production of a dicarboxylic acid is provided which includes a) providing a host cell having a naturally occurring number of CYP52A8A genes; b) increasing, in the host cell, the number of CYP52A8A genes which encode a CYP52A8A protein having the amino acid sequence as set forth in SEQ ID NO: 102 or SEQ ID NO: 114; c) culturing the host cell in media containing an organic substrate which upregulates the CYP52A8A gene, to effect increased production of dicarboxylic acid.

A method for increasing the production of a CYP52A8A protein having an amino acid sequence as set forth in SEQ ID NO: 102 or SEQ ID NO: 114 is provided which includes a) transforming a host cell having a naturally occurring amount of CYP52A8A protein with an increased copy number of a CYP52A8A gene that encodes the CYP52A8A protein having the amino acid sequence as set forth in SEQ ID NO: 102 or SEQ ID NO: 114; and b) culturing the cell and thereby increasing expression of the protein compared with that of a host cell containing a naturally occurring copy number of the CYP52A8A gene.

A method for increasing production of a dicarboxylic acid is provided which includes a) providing a host cell having a naturally occurring number of CYP52A8B genes; b) increasing, in the host cell, the number of CYP52A8B genes which encode a CYP52A8B protein having the amino acid sequence as set forth in SEQ ID NO: 103 or SEQ ID NO: 115; c) culturing the host cell in media containing an organic substrate which upregulates the CYP52A8B gene, to effect increased production of dicarboxylic acid.

A method for increasing the production of a CYP52A8B protein having an amino acid sequence as set forth in SEQ ID NO: 103 or SEQ ID NO: 115 is provided which includes a) transforming a host cell having a naturally occurring amount of CYP52A8B protein with an increased copy number of a CYP52A8B gene that encodes the CYP52A8B protein having the amino acid sequence as set forth in SEQ ID NO: 103 or SEQ ID NO: 115; and b) culturing the cell and thereby increasing expression of the protein compared with that of a host cell containing a naturally occurring copy number of the CYP52A8B gene.

A method for increasing production of a dicarboxylic acid is provided which includes a) providing a host cell having a naturally occurring number of CYP52D4A genes; b) increasing, in the host cell, the number of CYP52D4A genes which encode a CYP52D4A protein having the amino acid sequence as set forth in SEQ ID NO: 104 or SEQ ID NO: 116; c), culturing the host cell in media containing an organic substrate which upregulates the CYP52D4A gene, to effect increased production of dicarboxylic acid.

A method for increasing the production of a CYP52D4A protein having an amino acid sequence as set forth in SEQ ID NO: 104 or SEQ ID NO: 116 is provided which includes a) transforming a host cell having a naturally occurring amount of CYP52D4A protein with an increased copy number of a CYP52D4A gene that encodes the CYP52D4A protein having the amino acid sequence as set forth in SEQ ID NO: 104 or SEQ ID NO: 116; and b) culturing the cell and thereby increasing expression of the protein compared with that of a host cell containing a naturally occurring copy number of the CYP52D4A gene.

BRIEF DESCRIPTION OF THE DRAWINGS

FIG. 3 is a double stranded DNA sequence of a portion of the 5 prime coding region of the CYP52A5A gene (SEQ ID NO: 36), the non-coding or antisense sequence (SEQ ID NO: 108), primer 7581-97F (SEQ ID NO: 47) and primer 7581-97M (SEQ ID NO: 48).

FIG. 4 is a diagrammatic representation of highly conserved regions of CYP and CPR gene protein sequences. Helix I represents the putative substrate binding site and HR2 represents the heme binding region. The FMN, FAD and NADPH binding regions are indicated below the CPR gene.

FIGS. 13A–13D show the complete DNA sequences including regulatory and coding regions for the CPRA gene (SEQ ID NO: 81) and CPRB gene (SEQ ID NO: 82) from C. tropicalis ATCC 20336. FIGS. 13A–13D show regulatory and coding region alignment of these sequences. Asterisks indicate conserved nucleotides. The start codons are underlined and the last amino acid coding codons immediately before the stop codon are underlined.

FIG. 14 shows the amino acid sequence of the CPRA (SEQ ID NO: 83) and CPRB (SEQ ID NO: 84) proteins from C. tropicalis ATCC 20336 and alignment of these amino acid sequences. Asterisks indicate residues which are not conserved.

FIGS. 15A–15M show the complete DNA sequences including regulatory and coding regions for the following genes from C. tropicalis ATCC 20366: CYP52A1A (SEQ ID NO: 85), CYP52A2A (SEQ ID NO: 86), CYP52A2B (SEQ ID NO: 87), CYP52A3A (SEQ ID NO: 88), CYP52A3B (SEQ ID NO: 89), CYP52A5A (SEQ ID NO. 90), CYP52A5B (SEQ ID NO: 91), CYP52A8A (SEQ ID NO: 92), CYP52A8B (SEQ ID NO: 93), and CYP52D4A (SEQ ID NO: 94). FIGS. 15A–15M show regulatory and coding region alignment of these sequences. Asterisks indicate conserved nucleotides. The start codons are underlined and the last amino acid coding codons immediately before the stop codon are underlined.

FIGS. 16A–16C show the amino acid sequences encoding the CYP52A1A (SEQ ID NO: 95), CYP52A2A (SEQ ID NO: 96), CYP52A2B (SEQ ID NO: 97), CYP52A3A (SEQ ID NO: 98), CYP52A3B (SEQ ID NO: 99), CYP52A5A (SEQ ID NO: 100), CYP52A5B (SEQ ID NO: 101), CYP52A8A (SEQ ID NO: 102), CYP52A8B (SEQ ID NO: 103) and CYP52D4A (SEQ ID NO. 104) proteins from C. tropicalis ATCC 20336. Asterisks indicate identical residues and dots indicate conserved residues.

FIG. 23 is the complete DNA sequence (SEQ ID NO: 105) encoding URA3A from C. tropicalis ATCC 20336 and the amino acid sequence of the encoded protein (SEQ ID NO: 106).

DESCRIPTION OF THE PREFERRED EMBODIMENTS

Figure 1:
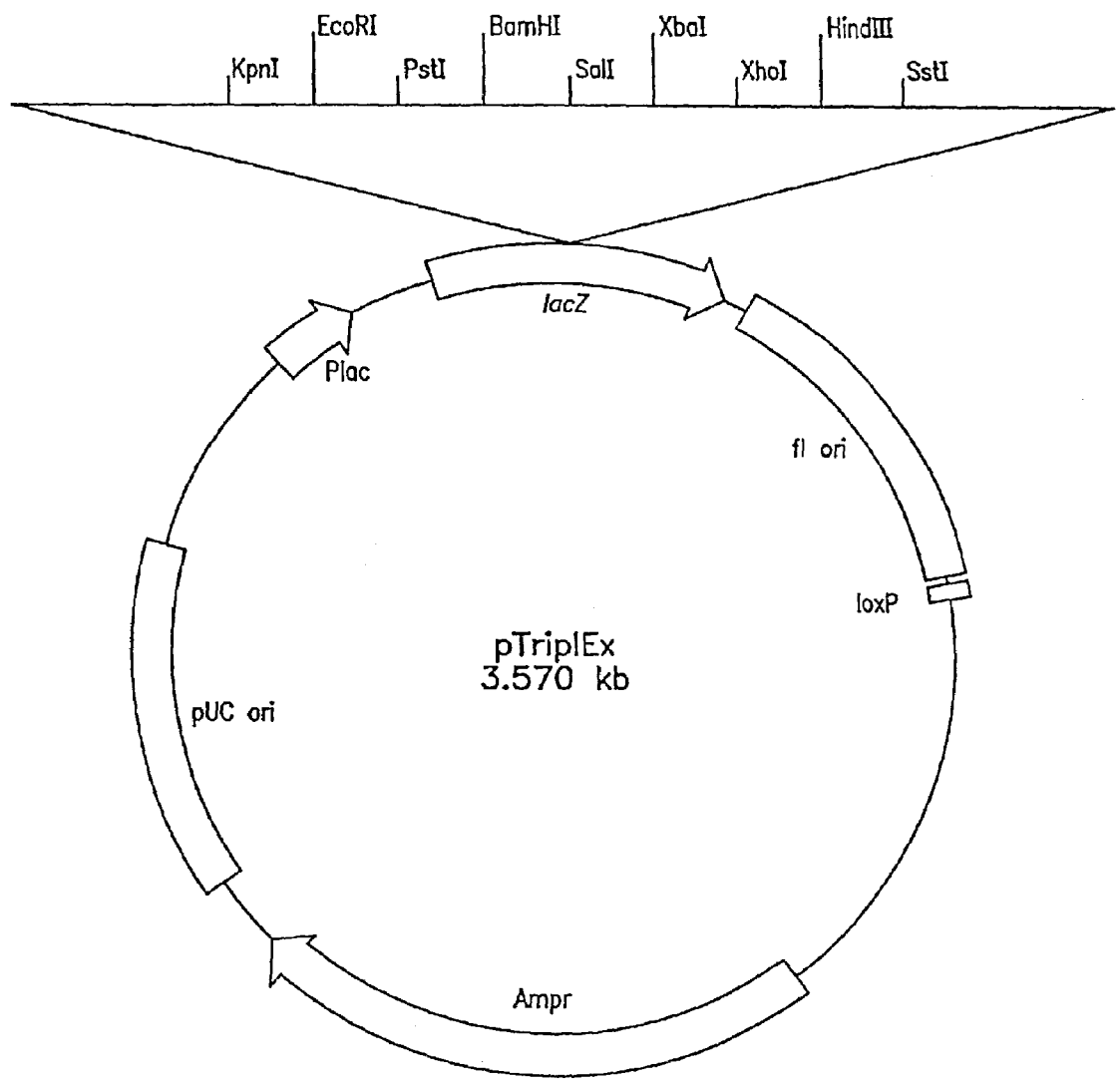
FIG. 1 is a schematic representation of cloning vector pTriplEx from Clontech™ Laboratories, Inc. Selected restriction sites within the multiple cloning site are shown.

Diacid productivity is improved according to the present invention by selectively increasing enzymes which are known to be important to the oxidation of organic substrates such as fatty acids composing the desired feed. According to the present invention, ten CYP genes and two CPR genes of C. tropicalis have been identified and characterized that relate to participation in the ω-hydroxylase complex catalyzing the first step in the ω-oxidation pathway. In addition, a novel quantitative competitive reverse transcription polymerase chain reaction (QC-RT-PCR) assay is used to measure gene expression in the fermentor under conditions of induction by one or more organic substrates as defined herein. Based upon QC-RT-PCR results, three CYP genes, CYP52A1, CYP52A2 and CYP52A5, have been identified as being of greater importance for the ω-oxidation of long chain fatty acids. Amplification of the CPB gene copy number improves productivity. The QC-RT-PCR assay indicates that both CYP and CPR genes appear to be under tight regulatory control.

In accordance with the present invention, a method for discriminating members of a gene family by quantifying the amount of target mRNA in a sample is provided which includes a) providing an organism containing a target gene; b) culturing the organism with an organic substrate which causes upregulation in the activity of the target gene; c) obtaining a sample of total RNA from the organism at a first point in time; d) combining at least a portion of the sample of the total RNA with a known amount of competitor RNA to form an RNA mixture, wherein the competitor RNA is substantially similar to the target mRNA but has a lesser number of nucleotides compared to the target mRNA; e) adding reverse transcriptase to the RNA mixture in a quantity sufficient to form corresponding target DNA and competitor DNA; (f) conducting a polymerase chain reaction in the presence of at least one primer specific for at least one substantially non-homologous region of the target DNA within the gene family, the primer also specific for the competitor DNA; g) repeating steps (c–f) using increasing amounts of the competitor RNA while maintaining a substantially constant amount of target RNA; h) determining the point at which the amount of target DNA is substantially equal to the amount of competitor DNA; i) quantifying the results by comparing the ratio of the concentration of unknown target to the known concentration of competitor; and j) obtaining a sample of total RNA from the organism at another point in time and repeating steps (d–i).

In addition, modification of existing promoters and/or the isolation of alternative promoters provides increased expression of CYP and CPR genes. Strong promoters are obtained from at least four sources: random or specific modifications of the CYP52A2 promoter, CYP52A5 promoter, CYP52A1 promoter, the selection of a strong promoter from available Candida β-oxidation genes such as POX4 and POX5, or screening to select another suitable Candida promoter.

Promoter strength can be directly measured using QT-RT-PCR to measure CYP and CPR gene expression in Candida cells isolated from fermentors. Enzymatic assays and antibodies specific for CYP and CPR proteins are used to verify that increased promoter strength is reflected by increased synthesis of the corresponding enzymes. Once a suitable promoter is identified, it is fused to the selected CYP and CPR genes and introduced into *Candida* for construction of a new improved production strain. It is contemplated that the coding region of the CYP and CPR genes can be fused to suitable promoters or other regulatory sequences which are well known to those skilled in the art.

In accordance with the present invention, studies on *C. tropicalis* ATCC 20336 have identified six unique CYP genes and four potential alleles. QC-RT-PCR analyses of cells isolated during the course of the fermentation bioconversions indicate that at least three of the CYP genes are induced by fatty acids and at least two of the CYP genes are induced by alkanes. See FIG. 34. Two of the CYP genes are highly induced indicating participation in the ω-hydroxylase complex which catalyzes the rate limiting step in the oxidation of fatty acids to the corresponding diacids.

The biochemical characterizations of each P450 enzyme herein is used to tailor the *C. tropicalis* host for optimal diacid productivity and is used to select P450 enzymes to be amplified based upon the fatty acid content of the feedstream. CYP gene(s) encoding P450 enzymes that have a low specific activity for the fatty acid or alkane substrate of choice are targeted for inactivation, thereby reducing the physiological load on the cell.

Since it has been demonstrated that CPR can be limiting in yeast systems, the removal of non-essential P450s from the system can free electrons that are being used by non-essential P450s and make them available to the P450s important for diacid productivity. Moreover, the removal of non-essential P450s can make available other necessary but potentially limiting components of the P450 system (i.e., available membrane space, heme and/or NADPH).

Diacid productivity is thus improved by selective integration, amplification, and over expression of CYP and CPR genes in the *C. tropicalis* production host It should be understood that host cells into which one or more copies of desired CYP and/or CPR genes have been introduced can be made to include such genes by any technique known to those skilled in the art. For example, suitable host cells include procaryotes such as *Bacillus sp., Pseudomous sp., Actinomycetes sp., Eschericia sp., Mycobacterium sp.*, and eukaryotes such as yeast, algae, insect cells, plant cells and and filamentous fungi. Suitable host cells are preferably yeast cells such as *Yarrowia, Bebaromyces, Saccharomyces, Schizosaccharomyces*, and *Pichia* and more preferably those of the *Candida* genus. Preferred species of *Candida* are *tropicalis, maltosa, apicola, paratropicalis, albicans, cloacae, guillermondii, intermedia, lipolytica, parapsilosis* and *zeylenoides*. Certain preferred stains of *Candida tropicalis* are listed in U.S. Pat. No. 5,254,466, incorporated herein by reference.

Vectors such as plasmids, phagemids, phages or cosmids can be used to transform or transfect suitable host cells. Host cells may also be transformed by introducing into a cell a linear DNA vector(s) containing the desired gene sequence. Such linear DNA may be advantageous when it is desirable to avoid introduction of non-native (foreign) DNA into the cell. For example, DNA consisting of a desired target gene(s) flanked by DNA sequences which are native to the cell can be introduced into the cell by electroporation, lithium acetate transformation, spheroplasting and the like. Flanking DNA sequences can include selectable markers and/or other tools for genetic engineering.

It should be understood that, depending on whether a transformed organism utilizes the universal genetic code or the non-universal genetic code known, e.g., in connection with *C. tropicalis*, slight differences can be manifest in the amino acid sequences of protein-products. Thus, nucleotide sequences containing a CTG codon produce proteins containing a CTG encoded leucine in prokaryotes such as *E. coli* and a CTG encoded serine in non-universal coding eukaryotes such as *C. tropicalis*. For example, the CYP52A1A gene contains one CTG codon starting at position 1354 which is translated as a leucine in *E. coli* and a serine in *C. tropicalis*, leading to two versions of the CYP52A1A protein (SEQ. ID. NO: 95 and SEQ. ID. NO: 110); the CYP52A3B gene contains one CTG codon starting at position 2449 which is translated as a leucine in *E. coli* and a serine in *C. tropicalis*, leading to two versions of the CYP52A3B protein (SEQ. ID. NO: 99 and SEQ. ID NO: 111); the CYP52A5A gene contains two CTG codons starting, respectively, at positions 1883 and 2570, which are translated as leucine in *E. coli* and serine in *C. tropicalis*, leading to two versions of the CYP52A5A protein (SEQ. ID. NO: 100 and SEQ. ID. NO: 112); the CYP52A5B gene contains two CTG codons starting, respectively, at positions 1922 and 2609, which are translated as leucine in *E. coli* and serine in *C. tropicalis*, leading to two versions of the CYP52A5B protein (SEQ. ID. NO: 101 and SEQ. ID. NO: 113); the CYP52A8A gene contains one CTG codon starting at position 659, which is translated as a leucine in *E. coli* and a serine in *C. tropicalis*, leading to two versions of the CYP52A8B protein (SEQ. ID. NO: 103 and SEQ. ID. NO: 115); the CYP52D4A gene contains three CTG codons starting, respectively, at positions 1247, 1412 and 1757, which are translated as leucine in *E. coli* and as serine in *C. tropicalis*, leading to two versions of the CYP5234A protein (SEQ. ID. NO: 104 and SEQ. ID. NO: 116); the CPRA (NCP1A) gene contains one CTG codon starting at position 1153 which is translated as a leucine in *E. coli* and as a serine in *C tropicalis*, leading to two versions of the CPRA (NCP1A) protein (SEQ. ID. NO: 83 and SEQ. ID. NO: 117); the CPRG (NCP1B) gene contains one CTG codon starting at position 1180 which is translated as a leucine in *E. coli* and as a serine in *C. tropicalis*, leading to two versions of the CPRB (NCP1B) protein (SEQ. ID. NO: 84 and SEQ. ID. NO: 118).

A suitable organic substrate herein can be any organic compound that is biooxidizable to a mono or polycarboxylic acid. Such a compound can be any saturated or unsaturated aliphatic compound or any carbocyclic or heterocyclic aromatic compound having at least one terminal methyl group, a terminal carboxyl group and/or a terminal functional group which is oxidizable to a carboxyl group by biooxidation. A terminal functional group Which is a derivative of a carboxyl group may be present in the substrate molecule and may be converted to a carboxyl group by a reaction other than biooxidation. For example, if the terminal group is an ester that neither the wild-type *C. tropicalis* nor the genetic modifications described herein will allow hydrolysis of the ester functionality to a carboxyl group, then a lipase can be added during the fermentation step to liberate free fatty acids. Suitable organic substrates include, but are not limited to, saturated fatty acids, unsaturated fatty acids, alkanes, alkenes, alkynes and combinations thereof.

Alkanes are a type of saturated organic substrate which are useful herein. The alkanes can be linear or cyclic, branched or straight chain, substituted or unsubstituted. Particularly preferred alkanes are those having from about 4 to about 25 carbon atoms, examples of which include but are not limited to butane, hexane, octane, nonane, dodecane, tridecane, tetradecane, octadecane and the like.

Examples of unsaturated organic substrates which can be used herein include but are not limited to internal olefins such as 2-pentene, 2-hexene, 3-hexene, 9-octadecene and the like; unsaturated carboxylic acids such as 2-hexenoic acid and esters thereof, oleic acid and esters thereof including triglyceryl esters having a relatively high oleic acid content, erucic acid and esters thereof including triglyceryl esters having a relatively high erucic acid content, ricinoleic acid and esters thereof including triglyceryl esters having a relatively high ricinoleic acid content, linoleic acid and esters thereof including triglyceryl esters having a relatively high linoleic acid content; unsaturated alcohols such as 3-hexen-1-ol, 9-octadecen-1-ol and the like; unsaturated aldehydes such as 3-hexen-1-al, 9-octadecen-1-ol and the like. In addition to the above an organic substrate which can be used herein include alicyclic compounds having at least one internal carbon-carbon double bond and at least one terminal methyl group, a terminal carboxyl group and/or a terminal functional group which is oxidizable to a carboxyl group by biooxidation. Examples of such compounds include but are not limited to 3,6-dimethyl, 1,4-cyclohexadiene; 3-methylcyclohexene; 3-methyl-1,4-cyclohexadiene and the like.

Examples of the aromatic compounds that can be used herein include but are not limited to arenes such as o-, m-, p-xylene; o-, m-, p-methyl benzoic acid; dimethyl pyridine, and the like. The organic substrate can also contain other functional groups that are biooxidizable to carboxyl groups such as an aldehyde or alcohol group. The organic substrate can also contain other functional groups that are not biooxidizable to carboxyl groups and do not interfere with the biooxidation such as halogens, ethers, and the like.

Examples of saturated fatty acids which may be applied to cells incorporating the present CYP and CPR genes include caproic, enanthic, caprylic, pelargonic, capric, undecylic, lauric, myristic, pentadecanoic, palmitic, margaric, stearic, arachidic, behenic acids and combinations thereof. Examples of unsaturated fatty acids which may be applied to cells incorporating the present CYP and CPR genes include palmitoleic, oleic, erucic, linoleic, linolenic acids and combinations thereof. Alkanes and fractions of alkanes may be applied which include chain links from C12 to C24 in any combination. An example of a preferred fatty acid mixtures are Emersol® 267 and Tallow, both commercially available from Henkel Chemicals Group, Cincinnati, Ohio. The typical fatty acid composition of Emersol® 267 and Tallow is as follows:

|  | TALLOW | E267 |
|---|---|---|
| C14:0 | 3.5% | 2.4% |
| C14:1 | 1.0% | 0.7% |
| C15:0 | 0.5% | — |
| C16:0 | 25.5% | 4.6% |
| C16:1 | 4.0% | 5.7% |
| C17:0 | 2.5% | — |
| C17:1 | — | 5.7% |
| C18:0 | 19.5% | 1.0% |
| C18:1 | 41.0% | 69.9% |
| C18:2 | 2.5% | 8.8% |
| C18:3 | — | 0.3% |

-continued

|  | TALLOW | E267 |
|---|---|---|
| C20:0 | 0.5% | — |
| C20:1 | — | 0.9% |

The following examples are meant to illustrate but not to limit the invention. All relevant microbial strains and plasmids are described in Table 1 and Table 2, respectively.

TABLE 1

List of *Escherichia coli* and *Candida tropicalis* strains

| | GENOTYPE | SOURCE |
|---|---|---|
| *E. Coli* STRAIN | | |
| XL1Blue-MRF | endA1, gyrA96; hsdR17, lac, recA1, relA1, supE44, thi-1, [F' lac'Z M15, proAB, Tn10] | Stratagene, La Jolla, CA |
| BM25.8 | SupE44, thi (lac-proAB) [F' traD36, proAB', lac'Z M15] λimm434 (kan")P1 (cam") hsdR tu-Mu-) | Clontech, Palo Alto, CA |
| XLOLR | (mcrA)183 (mcrCB-hsdSMR-mrr)173 endA1 thi-1 recA1 gyr96 relA1 lac [F'proAB lacl'Z M15Tn10 (Tet') Su (nonsuppressing λ'(lambda resistant) | Stratagene, La Jolla, CA |
| *C. tropicalis* STRAIN | | |
| ATCC20336 | Wild-type | American Type Culture Collection, Rockville, MD |
| ATCC750 | Wild-type | American Type Culture Collection, Rockville, MD |
| ATCC20962 | ura3A/ura3B, pox4A::ura3A/pox4B::ura3A, pox5::ur3A/pox5::URA3A | Henkel |
| H5343 ura- | ura3A/ura3B, pox4A::ura3A/pox4B::ura3A, pox5::ura3A/pox5::URA3A, ura3- | Henkel |
| HDC1 | ura3A/ura3B, pox4A::ura3A/pox4B::ura3A, pox5::ura3A/pox5::URA3A, ura3::URA3A-CYP52A2A | Henkel |
| HDC5 | ura3A/ura3B, pox4A::ura3A/pox4B::ura3A, pox5::ura3A/pox5::URA3A, ura3::URA3A-CYP52A3A | Henkel |
| HDC10 | ura3A/ura3B, pox4A::ura3A/pox4B::ura3A, pox5:ura3A/pox5::URA3A, ura3::URA3A-CPRB | Henkel |
| HDC15 | ura3A/ura3B, pox4A::ura3A/pox4B::ura3A, pox5::ura3A/pox5::URA3A, ura3::URA3A-CYP52A5A | Henkel |
| HDC20 | ura3A/ura3B, pox4A::ura3A/pox4B::ura3A, pox5::ura3A/pox5::URA3A, ura3::URA3A-CYP52A2A + CPR B (CYP and CPR have opposite 5' to 3' orientation with respect to each other) | Henkel |
| HDC23 | ura2A/ura3B, pox4A::ura3A/pox4B::ura3A, pox5::ura3A/pox5::URA3A, ura3::URA3A-CYP52A2A + CPR B (CYP and CPR have same 5' to 3' orientation with respect to each other) | Henkel |

TABLE 2

List of plasmids isolated from genomic libraries and constructed for use in gene integrations.

| Plasmid | Base vector | Insert | Insert Size | Plasmid size | Description |
|---|---|---|---|---|---|
| pURAin | pNEB193 | URA3A | 1706 bp | 4399 bp | pNEB193 with the URA3A gene inserted in the AscI-PmeI site, generating a PacI site |
| pURA 2in | pURAin | CYP52A2A | 2230 bp | 6629 bp | pURAin containing a PCR CYP52A2A allele containing PacI restriction sites |
| pURA REDB in | pURAin | CPRB | 3266 bp | 7665 bp | pURAin containing a PCR CPRB allele containing PacI restriction sites |
| pHKM1 | pTriplEx | Truncated CPRA gene | Approx. 3.8 kb | Approx. 7.4 kb | A truncated CPRA gene. obtained by first screening library. containing the 5' untranslated region and 1.2 kb open reading frame |
| pHKM4 | PTriplEx | Truncated CPRA gene | Approx. 5 kb | Approx. 8.6 kb | A truncated CPRA gene obtained by screening second library containing the 3' untranslated region end sequence |
| pHKM9 | pBC-CMV | CPRB gene | Approx. 5.3 kb | Approx. 9.8 kb | CPRB allele isolated from the third library |
| pHKM11 | pBC-CMV | CYP52A1A | Approx. 5 kb | Approx. 9.5 kb | CYP52A1A isolated from the third library |
| pHKM12 | pBC-CMV | CYP52A8A | Approx. 7.5 kb | Approx. 12 kb | CYP52A8A isolated from the third library |
| pHKM13 | pBC-CMV | CYP52D4A | Approx. 7.3 kb | Approx. 11.8 kb | CYP52D4A isolated from the third library |
| pHKM14 | pBC-CMV | CYP52A2B | Approx. 6 kb | Approx. 10.5 kb | CYP52A2B isolated from the third library |
| pHKM15 | pBC-CMV | CYP52A8B | Approx. 6.6 kb | Approx. 11.1 kb | CYP52A8B isolated from the third library |
| pPAL3 | pTriplEx | CYP52A5A | 4.4 kb | Approx. 8.1 kb | CYP52A5A isolated from the 1st library |
| pPA5 | pTriplEx | GYP52A5B | 4.1 kb | Approx. 7.8 kb | CYP52A5B isolated from the 2nd library |
| pPA15 | pTriplEx | CYP52A2A | 6.0 kb | Approx. 9.7 kb | CYP52A2A isolated from the 2nd library |
| pPA57 | pTriplEx | CYP52A3A | 5.5 kb | Approx. 9.2 kb | CYP52A3A isolated from the 2nd library |
| pPA62 | pTriplEx | CYP52A3B | 6.0 kb | Approx. 9.7 kb | CYP52A3B isolated from the 2nd library |

EXAMPLE 1

Purification of Genomic DNA from *Candida tropicalis* ATCC 20336

A. Construction of Genomic Libraries 50 ml of YEPD broth (see Table 9) was inoculated with a single colony of *C. tropicalis* 20336 from YEPD agar plate and grown overnight at 30° C. 5 ml of the overnight culture was inoculated into 100 ml of fresh YEPD broth and incubated at 30° C. for 4 to 5 hr with shaking. Cells were harvested by centrifugation, washed twice with sterile distilled water and resuspended in 4 ml of spheroplasting buffer (1 M Sorbitol, 50 mM EDTA, 14 mM mercaptoethanol) and incubated for 30 min at 37° C. with gentle shaking. 0.5 ml of 2 mg/ml zymolyase (ICN Pharmaceuticals, Inc., Irvine, Calif.) was added and incubated at 37° C. with gentle shaking for 30 to 60 min. Spheroplast formation was monitored by SDS lysis. Spheroplasts were harvested by brief centrifugation (4,000 rpm, 3 min) and were washed once with the spheroplast buffer without mercaptoethanol. Harvested spheroplasts were then suspended in 4 ml of lysis buffer (0.2 M Tris/pH 8.0, 50 mM EDTA, 1% SDS) containing 100 μg/ml RNase (Qiagen Inc., Chatsworth, Calif.) and incubated at 37° C. for 30 to 60 min.

Proteins were denatured and extracted twice with an equal volume of chloroform/isoamyl alcohol (24:1) by gently mixing the two phases by hand inversions. The two phases were separated by centrifugation at 10,000 rpm for 10 min and the aqueous phase containing the high-molecular weight DNA was recovered. To the aqueous layer NaCl was added to a final concentration of 0.2 M and the DNA was precipitated by adding 2 vol of ethanol. Precipitated DNA was spooled with a clean glass rod and resuspended in TE buffer (10 mM Tris/pH 8.0, 1 mM EDTA) and allowed to dissolve overnight at 4° C. To the dissolved DNA, RNase free of any DNase activity (Qiagen Inc., Chatsworth, Calif.) was added to a final concentration of 50 μg/ml and incubated at 37° C. for 30 min. Then protease (Qiagen Inc., Chatsworth, Calif.) was added to a final concentration of 100 μg/ml and incubated at 55 to 60° C. for 30 min. The solution was extracted once with an equal volume of phenol/chloroform/isoamyl alcohol (25:24:1) and once with equal volume of chloroform/isoamyl alcohol (24:1). To the aqueous phase 0.1 vol of 3 M sodium acetate and 2 volumes of ice cold ethanol (200 proof) were added and the high molecular weight DNA was spooled with a glass rod and dissolved in 1 to 2 ml of TE buffer.

B. Genomic DNA Preparation for PCR Amplification of CYP and CPR Genes

Five 5 ml of YPD medium was inoculated with a single colony and grown at 30° C. overnight. The culture was centrifuged for 5 min at 1200×g. The supernatant was removed by aspiration and 0.5 ml of a sorbitol solution (0.9 M sorbitol, 0.1 M Tris-Cl pH 8.0, 0.1 M EDTA) was added to the pellet. The pellet was resuspended by vortexing and 1 µl of 2-mercaptoethanol and 50 µl of a 10 µg/ml zymolyase solution were added to the mixture. The tube was incubated at 37° C. for 1 hr on a rotary shaker (200 rpm). The tube was then centrifuged for 5 min at 1200×g and the supernatant was removed by aspiration. The protoplast pellet was resuspended in 0.5 ml 1×TE (10 mM Tris-Cl pH 8.0, 1 mM EDTA) and transferred to a 1.5 ml microcentrifuge tube. The protoplasts were lysed by the addition of 50 µl 10% SDS followed by incubation at 65° C. for 20 min. Next, 200 µl of 5M potassium acetate was added and after mixing, the tube was incubated on ice for at least 30 min. Cellular debris was removed by centrifugation at 13,000×g for 5 min. The supernatant was carefully removed and transferred to a new microfuge tube. The DNA was precipitated by die addition of 1 ml 100% (200 proof) ethanol followed by centrifugation for 5 min at 13,000×g. The DNA pellet was washed with 1 ml 70% ethanol followed by centrifugation for 5 min at 13,000×g. After partially drying the DNA under a vacuum, it was resuspended in 200 µl of 1×TE. The DNA concentration was determined by ratio of the absorbance at 260 nm/280 nm ($A_{260,280}$).

EXAMPLE 2

Construction of *Candida tropicalis* 20336 Genomic Libraries

Three genomic libraries of *C. tropicalis* were constructed, two at Clontech Laboratories, Inc., (Palo Alto, Calif.) and one at Henkel Corporation (Cincinnati, Ohio).

A. Clontech Libraries

The first Clontech library was made as follows: Genomic DNA was prepared from *C. tropicalis* 20336 as described above, partially digested with EcoRI and size fractionated by gel electrophoresis to eliminate fragments smaller than 0.6 kb. Following size fractionation, several ligations of the EcoRI genomic DNA fragments and lambda (λ) TriplEx™ vector (FIG. 1) arms with EcoRI sticky ends were packaged into λ phage heads under conditions designed to obtain one million independent clones. The second genomic library was constructed as follows: Genomic DNA was digested partially with Sau3A1 and size fractionated by gel electrophoresis. The DNA fragments were blunt ended using standard protocols as described, e.g., in Sambrook et al, *Molecular Cloning: A Laboratory Manual,* 2ed. Cold Spring Harbor Press, USA (1989), incorporated herein by reference. The strategy was to fill in the Sau3A1 overhangs with Klenow polymerase (Life Technologies, Grand Island, N.Y.) followed by digestion with S1 nuclease (Life Technologies, Grand Island, N.Y.). After S1 nuclease digestion the fragments were end filled one more time with Klenow polymerase to obtain the final blunt-ended DNA fragments. EcoRI linkers were ligated to these blunt-ended DNA fragments followed by ligation into the λTriplEx vector. The resultant library contained approximately 2×10⁶ independent clones with an average insert size of 4.5 kb.

B. Henkel Library

Figure 2A:
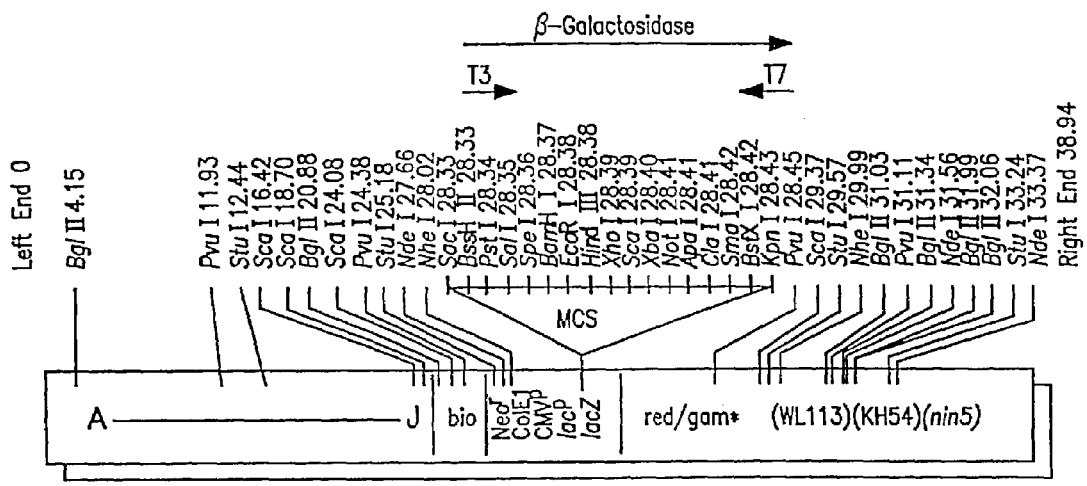
FIG. 2A is a map of the ZAP Express™ vector.
Figure 2B:
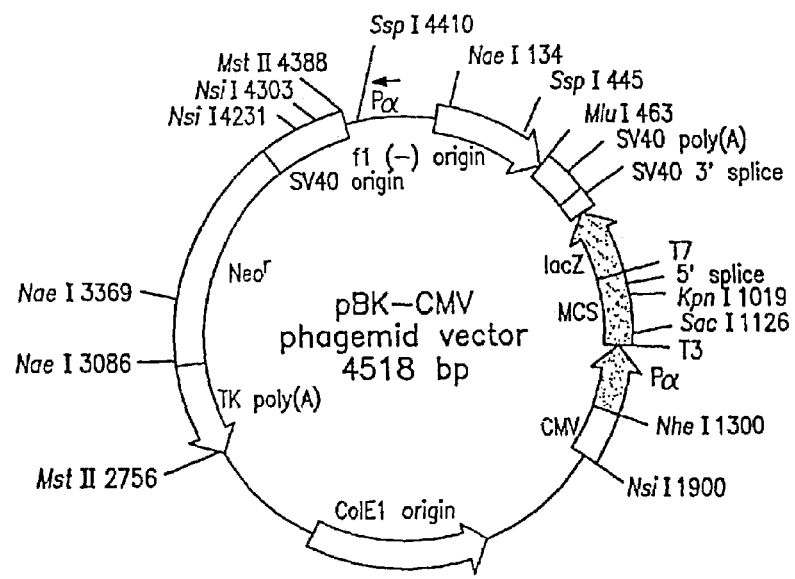
FIG. 2B is a schematic representation of cloning phagemid vector pBK-CMV.

The third genomic library was constructed at Henkel Corporation using λZAP Express™ vector (Stratagene, La Jolla, Calif.) (FIG. 2). Genomic DNA was partially digested with Sau3A1 and fragments in the range of 6 to 12 kb were purified from an agarose gel after electrophoresis of the digested DNA. These DNA fragments were then ligated to BamHI digested λZAP Express™ vector arms according to manufacturers protocols. Three ligations were set up to obtain approximately 9.8×10⁵ independent clones. All three libraries were pooled and amplified according to manufacturer instructions to obtain high-titre (>10⁹ plaque forming units/ml) stock for long-term storage. The titre of packaged phage library was ascertained after infection of *E. coli* XL1Blue-MRF' cells. *E. coli* XL1Blue-MRF' were grown overnight in either in LB medium or NZCYM (Table 9) containing 10 mM $MgSO_4$ and 0.2% maltose at 37° C. or 30° C., respectively with shaking. Cells were then centrifuged and resuspended in 0.5 to 1 volume of 10 mM $MgSO_4$. 200 µl of this *E. coli* culture was mixed with several dilutions of packaged phage library and incubated at 37° C. for 15 min. To this mixture 2.5 ml of LB top agarose or NZCYM top agarose (maintained at 60° C. ) (see Table 9) was added and plated on LB agar or NCZYM agar (see Table 9) present in 82 mm petri dishes. Phage were allowed to propagate overnight at 37° C. to obtain discrete plaques and the phage titre was determined.

EXAMPLE 3

Screening of Genomic Libraries

Both λTriplEx™ and λZAP Express™ vectors are phagemid vectors that can be propagated either as phage or plasmid DNA (after conversion of phage to plasmid). Therefore, the genomic libraries constructed in these vectors can be screened either by plaque hybridization (screening of lambda form of library) or by colony hybridization (screening plasmid form of library after phage to plasmid conversion). Both vectors are capable of expressing the cloned genes and the main difference is the mechanism of excision of plasmid from the phage DNA. The cloning site in λTriplEx™ is located within a plasmid which is present in the phage and is flanked by loxP site (FIG. 1). When λTriplEx™ is introduced into *E. coli* strain BM25.8 (supplied by Clontech), the Cre recombinase present in BM25.8 promotes the excision and circularization of plasmid pTriplEx from the phage λTriplEx™ at the loxP sites. The mechanism of excision of plasmid pBK-CMV from phage λZAP Express™ is different. It requires the assistance of a helper phage such as ExAssist™ (Stratagene) and an *E. coli* strain such as XLOR (Stratagene). Both pTriplEx and pBK-CMV can replicate autonomously in *E. coli.*

A. Screening Genomic Libraries (Plasmid Form)

1) Colony Lifts

A single colony of *E. coli* BM25.8 was inoculated into 5 ml of LB containing 50 µg/ml kanamycin, 10 mM $MgSO_4$ and 0.1% maltose and grown overnight at 31° C., 250 rpm. To 200 µl of this overnight culture (~4×10⁸ cells) 1 µl of phage library (2–5×10⁶ plaque forming units) and 150 µl LB broth were added and incubated at 31° C. for 30 min after which 400 µl of LB broth was added and incubated at 31° C., 225 rpm for 1 h. This bacterial culture was diluted and plated on LB agar containing 50 μg/ml ampicillin (Sigma Chemical Company, St. Louis, Mo.) and kanamycin (Sigma Chemical Company) to obtain 500 to 600 colonies/plate. The plates were incubated at 37° C. for 6 to 7 hrs until the colonies became visible. The plates were then stored at 4° C. for 1.5 h before placing a Colony/Plaque Screen™ Hybridization Transfer Membrane disc (DuPont NEN Research Products, Boston, Mass.) on the plate in contact with bacterial colonies. The transfer of colonies to the membrane was allowed to proceed for 3 to 5 min. The membrane was then lifted and placed on a fresh LB agar (see Table 9) plate containing 200 μg/ml of chloramphenicol with the side exposed to the bacterial colonies facing up. The plates containing the membranes were then incubated at 37° C. overnight in order to allow full development of the bacterial colonies. The LB agar plates from which colonies were initially lifted were incubated at 37° C. overnight and stored at 4° C. for future use. The following morning the membranes containing bacterial colonies were lifted and placed on two sheets of Whatman 3M (Whatman, Hillsboro, Oreg.) paper saturated with 0.5 N NaOH and left at room temperature (RT) for 3 to 6 min to lyse the cells. Additional treatment of membranes was as described in the protocol provided by NEN Research Products.

2) DNA Hybridizations

Membranes were dried overnight before hybridizing to oligonucleotide probes prepared using a non-radioactive ECL™ 3'-oligolabelling and detection system from Amersham Life Sciences (Arlington Heights, Ill.). DNA labeling, prehybridization and hybridizations were performed according to manufacturer's protocols. After hybridization, membranes were washed twice at room temperature in 5×SSC, 0.1% SDS (in a volume equivalent to 2 ml/cm² of membrane) for 5 min each followed by two washes at 50° C. in 1×SSC, 0.1% SDS (in a volume equivalent to 2 ml/cm² of membrane) for 15 min each. The hybridization signal was then generated and detected with Hyperfilm ECL™ (Amersham) according to manufacturer's protocols. Membranes were aligned to plates containing bacterial colonies from which colony lifts were performed and colonies corresponding to positive signals on X-ray were then isolated and propagated in LB broth. Plasmid DNA's were isolated from these cultures and analyzed by restriction enzyme digestions and by DNA sequencing.

B. Screening Genomic Libraries (Plaque Form)

1) λ Library Plating

E. coli XL1Blue-MRF' cells were grown overnight in LB medium (25 ml) containing 10 mM $MgSO_4$ and 0.2% maltose at 37° C., 250 rpm. Cells were then centrifuged (2,200×g for 10 min) and resuspended in 0.5 volumes of 10 mM $MgSO_4$. 500 μl of this E. coli culture was mixed with a phage suspension containing 25,000 amplified lambda phage particles and incubated at 37° C. for 15 min. To this mixture 6.5 ml of NZCYM top agarose (maintained at 60° C.) (see Chart) was added and plated on 80–100 ml NCZYM agar (see Chart) present in a 150 mm petridish. Phage were allowed to propagate overnight at 37° C. to obtain discrete plaques. After overnight growth plates were stored in a refrigerator for 1–2 hr before plaque lifts were performed.

2) Plaque Lift and DNA Hybridizations

Magna Lift™ nylon membranes (Micron Separations, Inc., Westborough, Mass.) were placed on the agar surface in complete contact with λ plaques and transfer of plaques to nylon membranes was allowed to proceed for 5 min at RT. After plaque transfer the membrane was placed on 2 sheets of Whatman 3M™ (Whatman, Hillsboro, Oreg.) filter paper saturated with a 0.5 N NaOH, 1.0 M NaCl solution and left for 10 min at RT to denature DNA. Excess denaturing solution was removed by blotting briefly on dry Whatman 3M paper. Membranes were then transferred to 2 sheets of Whatman 3M™ paper saturated with 0.5 M Tris-HCl (pH 8.0), 1.5 M NaCl and left for 5 min to neutralize. Membranes were then briefly washed in 200–500 ml of 2×SSC, dried by air and baked for 30–40 min at 86° C. The membranes were then probed with labelled DNA.

Membranes were prewashed with a 200–500 ml solution of 5×SSC, 0.5% SDS, 1 mM EDTA (pH 8.0) for 1–2 hr at 42° C. with shaking (60 rpm) to get rid of bacterial debris from the membranes. The membranes were prehybridized for 1–2 hr at 42° C. with (in a volume equivalent to 0.125–0.25 ml/cm² of membrane) ECL Gold™ buffer (Amersham) containing 0.5 M NaCl and 5% blocking reagent. DNA fragments that were used as probes were purified from agarose gel using a QIAEX II™ gel extraction kit (Qiagen Inc., Chatsworth, Calif.) according to manufacturers protocol and labeled using an Amersham ECL™ direct nucleic acid labeling kit (Amersham). Labeled DNA (5–10 ng/ml hybridization solution) was added to the prehybridized membranes and the hybridization was allowed to proceed overnight. The following day membranes were washed with shaking (60 rpm) twice at 42° C. for 20 min each time in (in a volume equivalent to 2 ml/cm² of membrane) a buffer containing either 0.1 (high stringency) or 0.5 (low stringency) ×SSC, 0.4% SDS and 360 g/l urea. This was followed by two 5 min washes at room temperature in (in a volume equivalent to 2 ml/cm² of membrane) 2×SSC. Hybridization signals were generated using the ECL™ nucleic acid detection reagent and detected using Hyperfilm ECL™ (Amersham).

Agar plugs which contained plaques corresponding to positive signals on the X-ray film were taken from the master plates using the broad-end of Pasteur pipet. Plaques were selected by aligning the plates with the x-ray film. At this stage, multiple plaques were generally taken. Phage particles were eluted from the agar plugs by soaking in 1 ml SM buffer (Sambrook et al., supra) overnight. The phage eluate was then diluted and plated with freshly grown E. coli XL1Blue-MRF' cells to obtain 100–500 plaques per 85 mm NCZYM agar plate. Plaques were transferred to Magna Lift nylon membranes as before and probed again using the same probe. Single well-isolated plaques corresponding to signals on X-ray film were picked by removing agar plugs and eluting the phage by soaking overnight in 0.5 ml SM buffer.

C. Conversion of λ Clones to Plasmid Form

The lambda clones isolated were converted to plasmid form for further analysis. Conversion from the plaque to the plasmid form was accomplished by infecting the plaques into E. coli strain BM25.8. The E. coli strain was grown overnight at 31° C., 250 rpm in LB broth containing 10 mM $MgSO_4$ and 0.2% maltose until the $OD_{600}$ reached 1.1–1.4. Ten milliliters of the overnight culture was removed and mixed with 100 μl of 1 M $MgCl_2$. A 200 μl volume of cells was removed, mixed with 150 μl of eluted phage suspension and incubated at 31° C. for 30 min. LB broth (400 μl) was added to the tube and incubation was continued at 31° C. for 1 hr with shaking, 250 rpm. 1–10 μl of the infected cell suspension was plated on LB agar containing 100 μg/ml ampicillin (Sigma, St. Louis, Mo.). Well-isolated colonies were picked and grown overnight in 5 ml LB broth containing 100 μg/ml ampicillin at 37° C., 250 rpm. Plasmid DNA was isolated from these cultures and analyzed. To convert the λZAP Express™ vector to plasmid form E. coli strains XL1Blue-MRF' and XLOR were used. The conversion was performed according to the manufacturer's (Stratagene) protocols for single-plaque excision.

EXAMPLE 4

Transformation of C. tropicalis H5343 ura⁻

A. Transformation of C. tropicalis H5343 by Electroporation 5 ml of YEPD was inoculated with C. topicalis H5343 ura⁻ from a frozen stock and incubated overnight on a New Brunswick shaker at 30° C. and 170 rpm. The next day, 10 µl of the overnight culture was inoculated into 100 ml YEPD and growth was continued at 30° C., 170 rpm. The following day the cells were harvested at an $OD_{600}$ of 1.0 and the cell pellet was washed one time with sterile ice-cold water. The cells were resuspended in ice-cold sterile 35% Polyethylene glycol (4,000 MW) to a density of $5 \times 10^3$ cells/ml. A 0.1 ml volume of cells were utilized for each electroporation. The following electroporation protocol was followed: 1.0 µg of transforming DNA was added to 0.1 ml cells, along with 5 µg denatured, sheared calf thymus DNA and the mixture was allowed to incubate on ice for 15 min. The cell solution was then transferred to an ice-cold 0.2 cm electroporation cuvette, tapped to make sure the solution was on the bottom of the cuvette and electroporated. The cells were electroporated using an Invitrogen electroporator (Carlsbad, Calif.) at 450 Volts, 200 Ohms and 250 µF. Following electroporation, 0.9 ml SOS media (1M Sorbitol, 30% YEPD, 10 mM $CaCl_2$) was added to the suspension. The resulting culture was grown for 1 hr at 30° C., 170 rpm. Following the incubation, the cells were pelleted by centrifugation at 1500×g for 5 min. The electroporated cells were resuspended in 0.2 ml of 1M sorbitol and plated on synthetic complete media minus uracil (SC-uracil) (Nelson, supra). In some cases the electroporated cells were plated directly onto SC-uracil. Growth of transformants was monitored for 5 days. After three days, several transformants were picked and transferred to SC-uracil plates for genomic DNA preparation and screening.

B. Transformation of C. tropicalis Using Lithium Acetate

The following protocol was used to transform C. tropicalis in accordance with the procedures described in *Current Protocols in Molecular Biology*, Supplement 5, 13.7.1 (1989), incorporated herein by reference.

5 ml of YEPD was inoculated with C. tropicalis H5343 ura⁻ from a frozen stock and incubated overnight on a New Brunswick shaker at 30° C. and 170 rpm. The next day, 10 µl of the overnight culture was inoculated into 50 ml YEPD and growth was continued at 30° C., 170 rpm. The following day the cells were harvested at an $OD_{600}$ of 1.0. The culture was transferred to a 50 ml polypropylene tube and centrifuged at 1000×g for 10 min. The cell pellet was resuspended in 10 ml sterile TE (10 mM Tris-Cl and 1 mM EDTA, pH 8.0). The cells were again centrifuged at 1000×g for 10 min and the cell pellet was resuspended in 10 ml of a sterile lithium acetate solution [LiAc (0.1 M lithium acetate, 10 mM Tris-Cl, pH 8.0, 1 mM EDTA)]. Following centrifugation at 1000×g for 10 min., the pellet was resuspended in 0.5 ml LiAc. This solution was incubated for one hour at 30° C. while shaking gently at 50 rpm. A 0.1 ml aliquot of this suspension was incubated with 5 µg of transforming DNA at 30° C. with no shaking for 30 min. A 0.7 ml PEG solution (40% wt/vol polyethylene glycol 3340, 0.1 M lithium acetate, 10 mM Tris-Cl, pH 8.0, 1 mM EDTA) was added and incubated at 30° C. for 45 min. The tubes were then placed at 42° C. for 5 min. A 0.2 ml aliquot was plated on synthetic complete media minus uracil (SC-uracil) (Kaiser et al. *Methods in Yeast Genetics*, Cold Spring Harbor Laboratory Press, USA, 1994, incorporated herein by reference). Growth of transformants was monitored for 5 days. After three days, several transformants were picked and transferred to SC-Uracil plates for genomic DNA preparation and screening.

EXAMPLE 5

Plasmid DNA Isolation

Plasmid DNA were isolated from *E. coli* cultures using Qiagen plasmid isolation kit (Qiagen Inc., Chatsworth, Calif.) according to manufacturer's instructions.

EXAMPLE 6

DNA Sequencing and Analysis

DNA sequencing was performed at Sequetech Corporation (Mountain View, Calif.) using Applied Biosystems automated sequencer (Perkin Elmer, Foster City, Calif.). DNA sequences were analyzed with MacVector and GeneWorks software packages (Oxford Molecular Group, Campbell, Calif.).

EXAMPLE 7

PCR Protocols

PCR amplification was carried out in a Perkin Elmer Thermocycler using the AmpliTaqGold enzyme (Perkin Elmer Cetus, Foster City, Calif.) kit according to manufacturer's specifications. Following successful amplification, in some cases, the products were digested with the appropriate enzymes and gel purified using QiaexII (Qiagen, Chatsworth, Calif.) as per manufacturer instructions. In specific cases the Ultma Taq polymerase (Perkin Elmer Cetus, Foster City, Calif.) or the Expand Hi-Fi Taq polymerase (Boehringer Mannheim, Indianapolis, Ind.) were used per manufacturer's recommendations or as defined in Table 3.

TABLE 3

PCR amplification conditions used with different primer combinations.

| PRIMER COMBINATION | Taq | TEMPLATE DENATURING CONDITION | ANNEALING TEMP/TIME | EXTENSION TEMP/TIME | CYCLE Number |
|---|---|---|---|---|---|
| 3674-41-1/41-2/41-4 + 3674-41-4 | Ampli-Taq Gold | 94 C./30 sec | 55 C./30 sec | 72 C./1 min | 30 |
| URA Primer 1a | Ampli-Taq | 95 C./1 min | 70 C./1 min | 72 C./2 min | 35 |

TABLE 3-continued

PCR amplification conditions used with different primer combinations.

| PRIMER COMBINATION | Taq | TEMPLATE DENATURING CONDITION | ANNEALING TEMP/TIME | EXTENSION TEMP/TIME | CYCLE Number |
|---|---|---|---|---|---|
| URA Primer 1b | Gold | | | | |
| URA Primer 2a | Ampli-Taq | 95 C./1 min | 70 C./1 min | 72 C./2 min | 35 |
| URA Primer 2b | Gold | | | | |
| CYP2A#1 | Ampli-Taq | 95 C./1 min | 70 C./1 min | 72 C./2 min | 35 |
| CYP2A#2 | Gold | | | | |
| CYP3A#1 | Ultma Taq | 95 C./1 min | 70 C./1 min | 72 C./1 min | 30 |
| CYP3A#2 | | | | | |
| CPR B#1 | Expand | 94 C./15 sec | 50 C./30 sec | 68 C./3 min | 10 |
| CPR B#2 | Hi-Fi Taq | 94 C./15 sec | 50 C./30 sec | 68 C./3 min +20 sec/cycle | 15 |
| CYP5A#1 | Expand | 94 C./15 sec | 50 C./30 sec | 68 C./3 min | 10 |
| CYR5A#2 | Hi-Fi Taq | 94 C./15 sec | 50 C./30 sec | 68 C./3 min +20 sec/cycle | 15 |

Table 4 below contains a list of primers (SEQ ID NOS: 1–35) used for PCR amplification to construct gene integration vectors or to generate probes for gene detection and isolation.

TABLE 4

Primer table for PCR amplification to construct gene integration vectors, to generate probes for gene isolation and detection and to obtain DNA sequence of constructs. (A-deoxyadenosine triphosphate [dATP], G-deoxyguanosine triphosphate [dCTP], C-deoxycytosine triphosphate [dCTP], T-deoxythymidine triphosphate [dTTP], Y-dCTP or dTTP, R-dATP or dGTP, W-dATP or dTTP, M-dATP or dCTP, N-dATP or dCTP or dGTP or dTTP).

| Target gene(s) | Patent Primer Name | Lab Primer Name | Sequence (5' to 3') | PCR Product Size |
|---|---|---|---|---|
| CYP52A2A | CYP2A#1 | 3659-72M | CCTTAATTAAATGCACGAAGCGGAGATAAAAG (SEQ ID NO: 1) | 2230 bp |
| | CYP2A#2 | 3659-72N | CCTTAATTAAGCATAAGCTTGCTCGAGTCT (SEQ ID NO: 2) | |
| CYP52A3A | CYP3A#1 | 3659-72O | CCTTAATTAAACGCAATGGGAACATGGAGTG (SEQ ID NO: 3) | 2154 bp |
| | CYP3A#2 | 3659-72P | CCTTAATTAATCGCACTACGGTTATTGGTATCAG (SEQ ID NO: 4) | |
| CYPS2A5A | CYP5A#1 | 3659-72K | CCTTAATTAATCAAAGTACGTTCAGGCGG (SEQ ID NO: 5) | 3298 bp |
| | CYP5A#2 | 3659-72L | CCTTAATTAAGGCAGACAACAACTTGGCAAAGTC (SEQ ID NO: 6) | |
| CPRB | CPRB#1 | 3698-20A | CCTTAATTAAGAGGTCGTTGGTTGAGTTTTC (SEQ ID NO: 7) | 3266 bp |
| | CPRB#2 | 3698-20B | CCTTAATTAATTGATAATGACGTTGGGGG (SEQ ID NO: 8) | |
| URA3A | URA Primer 1a | 3698-7C | AGGCGCGCCGGAGTCCAAAAAGACCAACCTCTG (SEQ ID NO: 9) | 956 bp |
| | URA Primer 1b | 3698-7D | CCTTAATTAATACGTGGATACCTTCAAGCAAGTG (SEQ ID NO: 10) | |
| URA3A | URA Primer 2a | 3698-7A | CCTTAATTAAGCTCACGAGTTTTGGGATTTTCGAG (SEQ ID NO: 11) | 750 bp |
| | URA Primer 2b | 3698-7B | GGGTTTAAACCGCAGAGGTTGGTCTTTTTGGACTC (SEQ ID NO: 12) | |
| | | | GGGTTTAAAC-Pme I restriction site (SEQ ID NO: 13) | |
| | | | AGGCGCGCG-AscI resriction site (SEQ ID NO: 14) | |
| | | | CCTTAATTAA-PacI restriction site (SEQ ID NO: 15) | |

TABLE 4-continued

Primer table for PCR amplification to construct gene integration vectors, to generate probes for gene isolation and detection and to obtain DNA sequence of constructs. (A-deoxyadenosine triphosphate [dATP], G-deoxyguanosine triphosphate [dCTP], C-deoxycytosine triphosphate [dCTP], T-deoxythymidine triphosphate [dTTP], Y-dCTP or dTTP, R-dATP or dGTP, W-dATP or dTTP, M-dATP or dCTP, N-dATP or dCTP or dGTP or dTTP).

| Target gene(s) | Patent Primer Name | Lab Primer Name | Sequence (5' to 3') | PCR Product Size |
|---|---|---|---|---|
| CPR | FMN1 | 3674-41-1 | TGYCAAACWGGTACWGCWGAA (SEQ ID NO: 16) | |
| CPR | FMN2 | 8674-41-2 | GGTTTGGGTAAYTCWACTTAT (SEQ ID NO: 17) | |
| CPR | FAD | 3674-41-3 | CGTTATTAYTCYATTTCTTC (SEQ ID NO: 18) | |
| CPR | NADPH | 8674-41-4 | GCMACACCRGTACCTGGACC (SEQ ID NO: 19) | |
| CPR | PRK1.F3 | PRKL.F3 | ATCCCAATCGTAATCAGC (SEQ ID NO: 20) | |
| CPR | PRK1.F5 | PRK1.F5 | ACTTGTCTTCGTTTAGCA (SEQ ID NO: 21) | |
| CPR | PRK4.R20 | PRK4.R20 | CTACGTCTGTGGTGATGC (SEQ ID NO: 22) | |
| CYP | UCup1 | UCup1 | CGNGAYACNACNGCNGG (SEQ ID NO: 23) | |
| CYP | UCup2 | UCup2 | AGRGAYACNACNGCNGG (SEQ ID NO: 24) | |
| CYP | UCdown1 | UCdown1 | AGNGCRAAYTGYTGNCC (SEQ ID NO: 25) | |
| CYP | UCdown2 | UCdowu2 | YAANGCRAAYTGYTGNCC (SEQ ID NO: 26) | |
| CYP | HemeB1 | HemeB1 | ATTCAACGGTGGTCCAAGAATCTGTTTGG (SEQ ID NO: 27) | |
| CYP | 2, 3, 5P | 2, 3, 5P | GAGCTATGTTGAGACCACAGTTTGC (SEQ ID NO: 28) | |
| CYP | 2, 3, 5M | 2, 3, 5M | CTTCAGTTAAAGCAAATTGTTTGGCC (SEQ ID NO: 29) | |
| pTriplEx vector | Triplex5' | Triplex5' | CTCGGGAAGCGCGCCATTGTGTTGG (SEQ ID NO: 30) | |
| pTriplEx vector | Triplex3' | Triplex3' | TAATACGACTCACTATAGGGCGAATTGGC (SEQ ID NO: 31) | |
| CYP | Cyp52a | Cyp52a | TGRYTCAAACCATCTYTGTGG (SEQ ID NO: 32) | |
| CYP | Cyp52b | Cyp52b | GGACCGGCGTTAAAGGG (SEQ ID NO: 33) | |
| CYP | Cyp52c | Cyp52c | CATAGTCGWATYATGCTTAGACC (SEQ ID NO: 34) | |
| CYP | Cyp52d | Cyp52d | GGACCACCATTGAATGG (SEQ ID NO: 35) | |

EXAMPLE 8

Yeast Colony PCR Procedure for Confirmation of Gene Integration into the Genome of C. tropicalis Single yeast colonies were removed from the surface of transformation plates, suspended in 50 µl of spheroplasting buffer (50mM KCl, 10 mM Tris-HCl, pH 8.3, 1.0 mg/ml Zymolyase, 5% glycerol) and incubated at 37° C. for 30 min. Following incubation, the solution was heated for 10 min at 95° C. to lyse the cells. Five µl of this solution was used as a template in PCR. Expand Hi-Fi Taq polymerase (Boehringer Mannheim, Indianapolis, Ind.) was used in PCR coupled with a gene-specific primer (gene to be integrated) and a URA3 primer. If integration did occur, amplification would yield a PCR product of predicted size confirming the presence of an integrated gene.

EXAMPLE 9

Fermentation Method for Gene Induction Studies

A fermentor was charged with a semi-synthetic growth medium having the composition 75 g/l glucose (anhydrous), 6.7 g/l Yeast Nitrogen Base (Difco Laboratories), 3 g/l yeast extract, 3 g/l ammonium sulfate, 2 g/l monopotassium phosphate, 0.5 g/l sodium chloride. Components were made as concentrated solutions for autoclaving then added to the fermentor upon cooling: final pH approximately 5.2. This charge was inoculated with 5–10% of an overnight culture of C. tropicalis ATCC 20962 prepared in YM medium (Difco Laboratories) as described in the methods of Examples 17 and 20 of U.S. Pat. No. 5,254,466, which is incorporated herein by reference. C. tropicalis ATCC 20962 is a POX 4 and POX 5 disrupted C. tropicalis ATCC 20336. Air and agitation were supplied to maintain the dissolved oxygen at greater than about 40% of saturation versus air. The pH was maintained at about 5.0 to 8.5 by the addition of 5N caustic soda on pH control. Both a fatty acid feedstream (commercial oleic acid in this example) having a typical composition: 2.4% $C_{14}$; 0.7% $C_{14:1}$; 4.6% $C_{16}$; 5.7%

$C_{16:1}$; 5.7% $C_{17:1}$; 1.0% $C_{18}$; 69.9% $C_{18:1}$; 8.8% $C_{18:2}$; 0.30% $C_{18:3}$; 0.90% $C_{20:1}$ and a glucose co-substrate feed were added in a feedbatch mode beginning near the end of exponential growth. Caustic was added on pH control during the bioconversion of fatty acids to diacids to maintain the pH in the desired range. Typically, samples for gene induction studies were collected just prior to starting the fatty acid feed and over the first 10 hours of bioconversion. Determination of fatty acid and diacid content was determined by a standard methyl ester protocol using gas liquid chromatography (GLC). Gene induction was measured using the QC-RT-PCR protocol described in this application.

EXAMPLE 10

RNA Preparation

The first step of this protocol involves the isolation of total cellular RNA from cultures of C. tropicalis. The cellular RNA was isolated using the Qiagen RNeasy Mini Kit (Qiagen Inc., Chatsworth, Calif.) as follows: 2 ml samples of C. tropicalis cultures were collected from the fermentor in a standard 2 ml screw capped Eppendorf style tubes at various times before and after the addition of the fatty acid or alkane substrate. Cell samples were immediately frozen in liquid nitrogen or a dry-ice/alcohol bath after their harvesting from the fermentor. To isolate total RNA from the samples, the tubes were allowed to thaw on ice and the cells pelleted by centrifugation in a microfuge for 5 minutes (min) at 4° C. and the supernatant was discarded while keeping the pellet ice-cold. The microfuge tubes were filled ⅔ full with ice-cold Zirconia/Silica beads (0.5 mm diameter, Biospec Products, Bartlesville, Okla.) and the tube filled to the top with ice-cold RLT* lysis buffer (* buffer included with the Qiagen RNeasy Mini Kit). Cell rupture was achieved by placing the samples in a mini bead beater (Biospec Products, Bartlesville, Okla.) and immediately homogenized at full speed for 2.5 min. The samples were allowed to cool in a ice water bath for 1 minute and the homogenization/cool process repeated two more times for a total of 7.5 min homogenization time in the beadbeater. The homogenized cells samples were microfuged at full speed for 10 min and 700 µl of the RNA containing supernatant removed and transferred to a new eppendorf tube. 700 µl of 70% ethanol was added to each sample followed by mixing by inversion. This and all subsequent steps were performed at room temperature. Seven hundred microliters of each ethanol treated sample were transferred to a Qiagen RNeasy spin column, followed by centrifugation at 8,000×g for 15 sec. The flow through was discarded and the column reloaded with the remaining sample (700 µl) and re-centrifuged at 8,000×g for 15 sec. The column was washed once with 700 µl of buffer RW1*, and centrifuged at 8,000×g for 15 sec and the flow through discarded. The column was placed in a new 2 ml collection tube and washed with 500 µl of RPE* buffer and the flow through discarded. The RPE* wash was repeated with centrifugation at 8,000×g for 2 min and the flow through discarded. The spin column was transferred to a new 1.5 ml collection tube and 100 µl of RNase free water added to the column followed by centrifugation at 8.000×g for 15 seconds. An additional 75 µl of RNase free water was added to the column followed by centrifugation at 8,000×g for 2 min. RNA eluted in the water flow through was collected for further purification.

The RNA eluate was then treated to remove contaminating DNA. Twenty microliters of 10× DNase I buffer (0.5 M tris (pH 7.5), 50 mM $CaCl_2$, 100 mM $MgCl_2$), 10 µl of RNase-free DNase I (2 Units/µl, Ambion Inc., Austin, Tex.) and 40 units Rnasin (Promega Corporation, Madison, Wis.) were added to the RNA sample. The mixture was then incubated at 37° C. for 15 to 30 min. Samples were placed on ice and 250 µl Lysis buffer RLT* and 250 µl ethanol (200 proof) added. The samples were then mixed by inversion. The samples were transferred to Qiagen RNeasy spin columns and centrifuged at 8,000×g for 15 sec and the flow through discarded. Columns were placed in new 2 ml collection tubes and washed twice with 500 µl of RPE* wash buffer and the flow through discarded. Columns were transferred to new 1.5 ml eppendorf tubes and RNA was eluated by the addition of 100 µl of DEPC treated water followed by centrifugation at 8,000×g for 15 sec. Residual RNA was collected by adding an additional 50 µl of RNase free water to the spin column followed by centrifugation at full speed for 2 min. 10 µl of the RNA preparation was removed and quantified by the $(A_{260\ 230})$ method. RNA was stored at −70° C. Yields were found to be 30–100 µg total RNA per 2.0 ml of fermentation broth.

EXAMPLE 11

Quantitative Competitive Reverse Transcription Polymerase Chain Reaction (QC-RT-PCR) Protocol QC-RT-PCR is a technique used to quantitate the amount of a specific RNA in a RNA sample. This technique employs the synthesis of a specific DNA molecule that is complementary to an RNA molecule in the original sample by reverse transcription and its subsequent amplification by polymerase chain reaction. By the addition of various amounts of a competitor RNA molecule to the sample one can determine the concentration of the RNA molecule of interest (in this case the mRNA transcripts of the CYP and CPR genes). The levels of specific mRNA transcripts were assayed over time in response to the addition of fatty acid and/or alkane substrates to the growth medium of fermentation grown C. tropicalis cultures for the identification and characterization of the genes involved in the oxidation of these substrates. This approach can be used to identify the CYP and CPR genes involved in the oxidation of any given substrate based upon their transcriptional regulation.

A. Primer Design

The first requirement for QC-RT-PCR is the design of the primer pairs to be used in the reverse transcription and subsequent PCR reactions. These primers need to be unique and specific to the gene of interest. As there is a family of genetically similar CYP genes present in C. tropicalis 20336, care had to be taken to design primer pairs that would be discriminating and only amplify the gene of interest, in this example the CYP52A5 gene. In this manner, unique primers directed to substantially non-homologous (aka variable) regions within target members of a gene family are constructed. What constitutes substantially non-homologous regions is determined on a case by case basis. Such unique primers should be specific enough to anneal the non-homologous region of the target gene without annealing to other non-target members of the gene family. By comparing the known sequences of the members of a gene family, non-homologous regions are identified and unique primers are constructed which will anneal to those regions. It is contemplated that non-homologous regions herein would typically exhibit less than about 85% homology but can be more homologous depending on the positions which are conserved and stringency of the reaction. After conducting PCR, it may be helpful to check the reaction product to assure it represents the unique target gene product. If not, the reaction conditions can be altered in terms of stringency to focus the reaction to the desired target. Alternatively a new primer or new non-homologous region can be chosen. Due to the high level of homology between the genes of the CYP52A family, the most variable 5 prime region of the CYP52A5 coding sequence was targeted for the design of the primer pairs. In FIG. 3, a portion of the 5 prime coding region for the CYP52A5A (SEQ ID NO: 36) allele of *C. tropicalis* 20336 is shown. The boxed sequences in FIG. 3 are the sequences of the forward and backwards primers (SEQ ID NOS: 47 and 48) used to quantitate expression of both alleles of this gene. The actual reverse primer (SEQ ID NO: 48) contains one less adenine than that shown in FIG. 3. Primers used to measure the expression of specific *C. tropicalis* 20336 genes using the QC-RT-PCR protocol are listed in Table 5 (SEQ ID NOS: 37–58).

TABLE 5

Primer used to measure *C. tropicalis* gene expression in the QC-RT-PCR reactions.

| Primer Name | Direction | Target | Sequence |
|---|---|---|---|
| 3737-89F | F | CYP52A1A | CCGATGAAGTTTTCGACGAGTACCC (SEQ ID NO: 37) |
| 3737-89B | B | CYP52A1A | AAGGCTTTAACGTGTCCAATCTGGTC (SEQ ID NO: 38) |
| alk2aF1 | F | CYP52A2A | ATTATCGCCACATACTTCACCAAATGG (SEQ ID NO: 39) |
| alk2aB5 | B | CYP52A2A | CGAGATCGTGGATACGCTGGAGTG (SEQ ID NO: 40) |
| 7581-178-3 | F | CYP52A3A | GCCACTCGGTAACTITGTCAGGGAC (SEQ ID NO: 41) |
| 7581-178-4 | B | CYP52A3A | CATTGAACTGAGTAGCCAAAACAGCC (SEQ ID NO: 42) |
| 3737-50F | F | CYP52A3A & CYP52A3B | CCTACGTTTGGTATCGCTACTCCGTTG (SEQ ID NO: 43) |
| 3737-50B | B | CYP52A3A & CYP52A3B | TTTCCAGCCAGCACGGTCCAAG (SEQ ID NO: 44) |
| 3737-175F | F | CYP52D4A | GCAGAGCCGATGTATGTTTGCGTCC (SEQ ID NO: 45) |
| 3737-175B | B | CYP52D4A | TCATTGAATGCTTCCAGGAACCTCG (SEQ ID NO: 46) |
| 7581-97-F | F | CYP52A5A & CYP52A5B | AAGAGGGCAGGGCTCAAGAG (SEQ ID NO: 47) |
| 7581-97-M | B | CYP52A5A & CYP52A5B | TCCATGTGAAGATCCCATCAC (SEQ ID NO: 48) |
| 4P-2 | F | CYP52A8A | CTTGAAGGCCGTGTTGAACG (SEQ ID NO: 49) |
| 4M-1 | B | CYP52A8A | CAGGATTTGTCTGAGTTTGCCG (SEQ ID NO: 50) |
| 3737-52F | F | POX4A & POX4B | CCATTGCCTTGAGATACGCCATTGGTAG (SEQ ID NO: 51) |
| 3737-52B | B | POX4A & POX4B | AGCCTTGGTGTCGTTGTTTTCAACGG (SEQ ID NO: 52) |
| 3737-53F | F | POX5A | TTGGGTTTGTTTGTTTCCTGTGTCCG (SEQ ID NO: 53) |
| 3737-53B | B | POX5A | CCTTTGACCTTCAATCTGGCGTAGACG (SEQ ID NO: 54) |
| F33 | F | CPRA | GGTTTGCTGAATACCCTGAAGGTGATG (SEQ ID NO: 55) |
| B63 | B | CPRA | TGGAGCTGAACAACTCTTGTCGTCTCGG (SEQ ID NO: 56) |
| 3737-133F | F | CPRA & CPRB | TTCCTCAACACGGACAGCGG (SEQ ID NO: 57) |
| 3737-133B | B | CPRA & CPRB | AGTCAACCAGGTGTGGAACTTCGTC (SEQ ID NO: 58) |

F—Forward
B—Backward

B. Design and Synthesis of the Competitor DNA Template

The competitor RNA is synthesized in vitro from a competitor DNA template that has the T7 polymerase promoter and preferably carries a small deletion of e.g., about 10 to 25 nucleotides relative to the native target RNA sequence. The DNA template for the in-vitro synthesis of the competitor RNA is synthesized using PCR primers that are between 46 and 60 nucleotides in length. In this example, the primer pairs for the synthesis of the CYP52A5 competitor DNA are shown in Tables 6 and 7 (SEQ ID NOS: 59 AND 60).

TABLE 6

Forward and Reverse primers used to synthesize the competitor RNA template for the QC-RT-PCR measurement of CYP52A5A gene expression.

Forward Primer CYP52A5A GGATCGTAATACGACTCACTATAGGGA
GGAAGAGGGCAGGGGTCAAGAG
(SEQ ID NO: 59)

Reverse Primer CYP52A5A TCCATGTGAAGATCCCATCACGAGTGT
GCCTCTTGCCCAAAG
(SEQ ID NO: 60)

TABLE 7

Primers for the synthesis of the QC-RT-PCR competitor RNA templates

| Primer Name | Direction | Target | Sequence 5'–3' |
|---|---|---|---|
| 3737-89C | F | CYP52A1A | GGATCCTAATACGACTCACFATAGGGAGGCGGAT GAAGTTTTGGACGAGTACCC (SEQ ID NO: 61) |
| 3737-89D | B | CYP52A1A | AAGGCTTTAACGTGTCCAATCTGGTC AACATAGCTCTGGAGTGGTTCCAACC (SEQ ID NO: 62) |
| 7581-137-A | F | CYP52A2A | GGATCATACGACTCACTATAGGGAGGATTAT CGCCACATACTTCACCAAATGG (SEQ ID NO: 63) |
| 7581-137-B | B | CYP52A2A | CGAGATCGTGGATACGGTGGAGTGCGTCGCTCTT CTTCTTCAACAATTCAAG (SEQ ID NO: 64) |
| 7581-137-D | B | CYP52A3A | CATTGAACTGAGTAGCCAAAACAGCCCATGGTTT CAATCAATGGGAGGC (SEQ ID NO: 65) |
| 7581-137-C | F | CYP52A3A | GGATCCTAATACGACTCACTATAGGGAGGGCCAC TCGGTAACTTTGTCAGGGAC (SEQ ID NO: 66) |
| 3737-50-D | F | CYP52A3A & CYP52A3B | GGATCTAATACGACTCAGTATAGGGAGGCCTAC GTTTGGTATCGCTACTCCGTTG (SEQ ID NO: 67) |
| 3737-50-C | B | CYP52A3A & CYP52A3B | TTTCCAGCCAGCACCGTCGAAGCAACAAGGAGTA CAAGAAATCGTGTC (SEQ ID NO: 68) |
| 3737-175G | F | CYP52D4A | GGATCCTAATACGACTCACTATAGGGAGGGCAGA GCCGATCTATGTTGCGTCC (SEQ ID NO: 69) |
| 3737-175D | B | CYP52D4A | TCATTGAATGCTTCCAGGAACCTCGCCACATCCAT CGAGAACCGG (SEQ ID NO: 70) |
| 7581-97-A | F | CYP52A5A & CYP52A5B | GGATCCTAATACGACTCACTATAGGGAGGAAGAG GGCAGGGGTCAAGAG (SEQ ID NO: 59) |
| 7581-97-B | B | CYP52A5A & CYP52A3B | TCCATGTGAAGATCCCATCACGAGTGTGCCTCTT GCCCAAAG (SEQ ID NO: 60) |
| 4P-2/T7 | F | CYP52A8A | GGATCCTAATACGACTCACTATAGGGAGGCTTGA AGGCCGTGTTGAACG (SEQ ID NO: 71) |
| 4M-3/4M-1 | B | CYP52A8A | CAGGATTGTGTGAGTTGCGGCCTGATCAAGATA GGATCGTTGCCG (SEQ ID NO: 72) |
| 3737-26-D | F | CPRA | GGATCCTAATACGATTCACTATAGGGAGGGGTTT GCTGAATACGCTGAAGGTGATG (SEQ ID NO: 73) |
| 3737-26-C | B | CPRA | TGGAGCTGAACAACTCTCTCGTCTCGGGTGGTCG AATGGACCCTTGGTCAAG (SEQ ID NO: 74) |
| 3737-133C | F | CPRA & CPRB | GGATCTACGAGTCACTATAGGGAGGTTCCT CAACACGGACAGCGG (SEQ ID NO: 75) |
| 3737-133D | B | CPRA & GPRB | AGTCAACCAGGTGTGGAACTCGTCGGTGGCAACA ATGAAAAACACCAAG (SEQ ID NO: 76) |
| 3737-52-C | F | POX4A & POX4B | GGATCTACGACTCACTATAGGGAGGCCATT GCCTTGAGATACGCCATTGGTAG |

TABLE 7-continued

Primers for the synthesis of the QC-RT-PCR competitor RNA templates

| Primer Name | Direction | Target | Sequence 5'–3' |
|---|---|---|---|
| 3737-52-D | B | POX4A & POX4B | (SEQ ID NO: 77) AGCCTTGGTGTCGTTCTTTTCAACGGAAGGTGGT GTCGATGGTGTGTTTCAACC (SEQ ID NO: 78) |
| 3737-53-C | F | POX5A | GGATCCTAATACGAGTCATATAGGGAGGTTGGG TTTGTTTGTTTCGCTGTGTCCG (SEQ ID NO: 79) |
| 3737-53-D | B | POX5A | CCTTTGACCTTCAATCTGGCGTAGACGCAGCACC ACCGATCCACCACTTG (SEQ ID NO: 80) |

F—Forward
B—Backword

The forward primer (SEQ ID NO: 59) contains the T7 promoter consensus sequence "GGATCCTAATACGA CTCACTATAGGG AGG" (SEQ ID NO: 109) fused to the primer 7581-97-F sequence (SEQ ID NO: 47). The Reverse Primer (SEQ ID NO: 60) contains the sequence of primer 7581-97M (SEQ ID NO: 48) followed by the 20 bases of upstream sequence with a 18 base pair deletion between the two blocks of the CYP52A5 sequence. The forward primer was used with the corresponding reverse primer to synthesize the competitor DNA template. The primer pairs were combined in a standard Taq Gold polymerase PCR reaction according to the manufacturer's recommended conditions (Perkin-Elmer/Applied Biosystems, Foster City, Calif.). The PCR reaction mix contained a final concentration of 250 nM each primer and 10 ng C. tropicalis chromosomal DNA for template. The reaction mixture was placed in a thermocycler for 25 to 35 cycles using the highest annealing temperature possible during the PCR reactions to assure a homogeneous PCR product (in this case 62° C.). The PCR products were either gel purified or filtered purified to remove unincorporated nucleotides and primers. The competitor template DNA was then quantified using the ($A_{260/280}$) method. Primers used in QC-RT-PCR experiments for the synthesis of various competitive DNA templates are listed in Table 7 (SEQ ID NOS: 61–80).

C. Synthesis of the Competitor RNA

Competitor template DNA was transcribed In-Vitro to make the competitor RNA using the Megascript T7 kit from Ambion Biosciences (Ambion Inc., Austin, Tex.). 250 nanograms (ng) of competitor DNA template and the in-vitro transcription reagents are mixed according to the directions provided by the manufacturer. The reaction mixture was incubated for 4 hours at 37° C. The resulting RNA preparations were then checked by gel electrophoresis for the conditions giving the highest yields and quality of competitor RNA. This often required optimization according to the manufacturer's specifications. The DNA template was then removed using DNase I as described in the Ambion kit. The RNA competitor was then quantified by the ($A_{260\ 280}$) method. Serial dilution's of the RNA (1 ng/µl to 1 femtogram (fg)/µl) were made for use in the QC-RT-PCR reactions and the original stocks stored at −70° C.

D. QC-RT-PCR Reactions

QC-RT-PCR reactions were performed using rTth polymerase from Perkin-Elmer(Perkin-Elmer/Applied Biosystems, Foster City, Calif.) according to the manufacturer's recommended conditions. The reverse transcription reaction was performed in a 10 µl volume with a final concentrations of 200 µM for each dNTP, 1.25 units rTth polymerase, 1.0 mM $MnCl_2$, 1× of the 10× buffer supplied with the Enzyme from the manufacturer, 100 ng of total RNA isolated from a fermentor grown culture of C. tropicalis and 1.25 µM of the appropriate reverse primer. To quantitate CYP52A5 expression in C. tropicalis an appropriate reverse primer was 7581-97M (SEQ ID NO: 48). Several reaction mixes were prepared for each RNA sample characterized. To quantitate CYP52A5 expression a series of 8 to 12 of the previously described QC-RT-PCR reaction mixes were aliquoted to different reaction tubes. To each tube 1 µl of a serial dilution containing from 100 pg to 100 fg CYP52A5 competitor RNA per µl was added bringing the final reaction mixtures up to the final volume of 10 µl. The QC-RT-PCR reaction mixtures were mixed and incubated at 70° C. for 15 min according to the manufacturer's recommended times for reverse transcription to occur. At the completion of the 15 minute incubation, the sample temperature was reduced to 4° C. to stop the reaction and 40 µl of the PCR reaction mix added to the reaction to bring the total volume up to 50 µl. The PCR reaction mix consists of an aqueous solution containing 0.3125 µM of the forward primer 7581-97F (SEQ ID NO: 47), 3.125 mM MgCl. and 1× chelating buffer supplied with the enzyme from Perkin-Elmer. The reaction mixtures were placed in a thermocycler (Perkin-Elmer GeneAmp PCR System 2400, Perkin-Elmer/Applied Biosystems, Foster City, Calif.) and the following PCR cycle performed: 94° C. for 1 min. followed by 94° C. for 10 seconds followed by 58° C. for 40 seconds for 17 to 22 cycles. The PCR reaction was completed with a final incubation at 58° C. for 2 min followed by 4° C. In some reactions where no detectable PCR products were produced the samples were returned the thermocycler for additional cycles, this process was repeated until enough PCR products were produced to quantify using HPLC. The number of cycles necessary to produce enough PCR product is a function of the amount of the target mRNA in the 100 ng of total cellular RNA. In cultures where the CYP52A5 gene is highly expressed there is sufficient CYP52A5 mRNA message present and less PCR cycles (≦17) are required to produce quantifiable amount of PCR product. The lower the concentrations of the target mRNA present the more PCR cycles are required to produce a detectable amount of product. These QC-RT-PCR procedures were applied to all the target genes listed in Table 5 using the respective primers indicated therein.

E. HPLC Quantification

Upon completion of the QC-RT-PCR reactions the samples were analyzed and quantitated by HPLC. Five to fifteen microliters of the QC-RT-PCR reaction mix was injected into a Waters Bio-Compatible 625 HPLC with an attached Waters 484 tunable detector. The detector was set to measure a wave length of 254 nm. The HPLC contained a Sarasep brand DNASep™ column (Sarasep, Inc., San Jose, Calif.) which was placed within the oven and the temperature set for 52° C. The column was installed according to the manufacturer's recommendation of having 30 cm. of heated PEEK tubing installed between the injector and the column. The system was configured with a Sarasep brand Guard column positioned before the injector. In addition, there was a 0.22 μm filter disk just before the column, within the oven. Two Buffers were used to create an elution gradient to resolve and quantitate the PCR products from the QC-RT-PCR reactions. Buffer-A consists of 0.1 M tri-ethyl ammonium acetate (TEAA) and 5% acetonitrile (volume to volume). Buffer-B consists of 0.1 M TEAA and 25% acetonitrile (volume to volume). The QC-RT-PCR samples were injected into the HPLC and the linear gradient of 75% buffer-A/25% buffer-B to 45% buffer-A/55% B was run over 6 min at a flow rate of 0.85 ml per minute. The QC-RT-PCR product of the competitor RNA being 18 base pairs smaller is eluted from the HPLC column before the QC-RT-PCR product from the CYP52A5 mRNA(U). The amount of the QC-RT-PCR products are plotted and quantitated with an attached Waters Corporation 745 data module. The log ratios of the amount of CYP52A5A mRNA QC-RT-PCR product (U) to competitor QC-RT-PCR product (C), as measured by peak areas, was plotted and the amount of competitor RNA required to equal the amount of CYP52A5 mRNA product determined. In the case of each of the target genes listed in Table 5, the competitor RNA contained fewer base pairs as compared to the native target mRNA and eluted before the native mRNA in a manner similar to that demonstrated by CYP52A5. HPLC quantification of the genes was conducted as above.

EXAMPLE 12

Evaluation of New Strains in Shake Flasks

Figure 35:
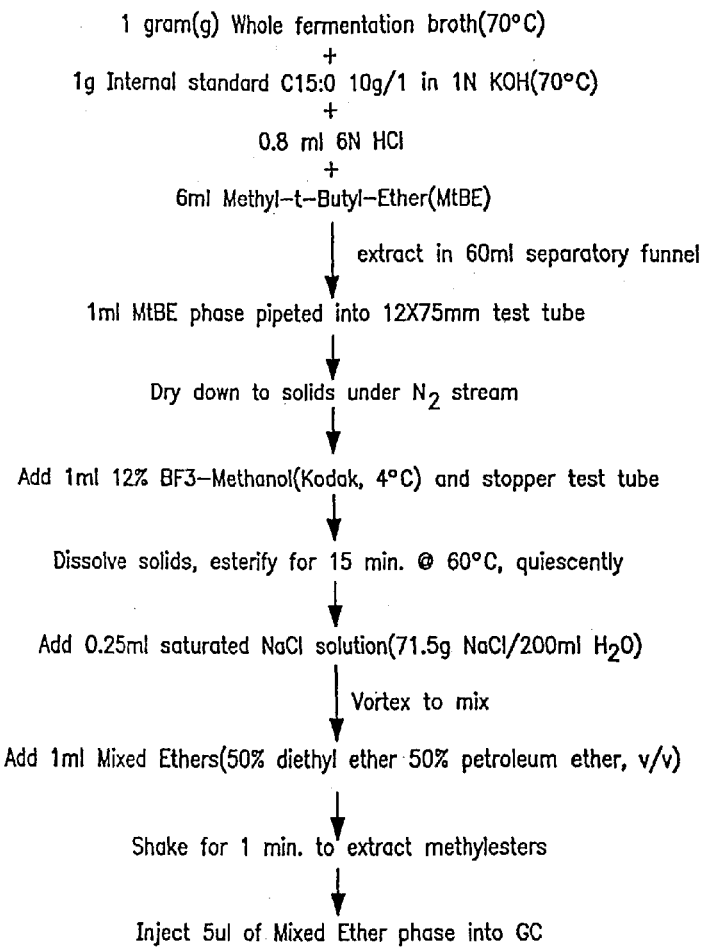
FIG. 35 depicts a scheme used for the extraction and analysis of diacids and monoacids from fermentation broths.

The CYP and CPR amplified strains such as strains HDC10, HDC15, HDC20 and HDC23 (Table 1) and H5343 were evaluated for diacid production in shake flasks. A single colony for each strain was transferred from a YPD agar plate into 5 ml of YPD broth and grown overnight at 30° C., 250 rpm. An inoculum was then transferred into 50 ml of DCA2 medium (Table 9) and grown for 24 h at 30° C., 300 rpm. The cells were centrifuged at 5000 rpm for 5 min and resuspended in 50 ml of DCA3 medium (Table 9) and grown for 24 h at 30° C., 300 rpm. 3% oleic acid w/v was added after 24 h growth in DCA3 medium and the cultures were allowed to bioconvert oleic acid for 48 h. Samples were harvested and the diacid and monoacid concentrations were analyzed as per the scheme given in FIG. 35. Each strain was tested in duplicate and the results shown in Table 8 represent the average value from two flasks.

TABLE 8

Bioconversion of oleic acid by different recombinant strains of *Candida tropicalis*

| Strain | Conversion to Oleic diacid (%) | Specific Conversion (g diacid/g biomass |
|---|---|---|
| H5343 | 41.9 | 0.53 |
| HDC 10-2 | 50.5 | 0.85 |
| HDC 15 | 54.4 | 0.85 |
| HDC 20-1 | 45.1 | 0.72 |
| HDC 20-2 | 45.3 | 0.58 |
| HDC 23-2 | 55.2 | 0.84 |
| HDC 23-3 | 58.8 | 0.89 |

EXAMPLE 13

Cloning and Characterization of *C. tropicalis* 20336 Cytochrome P450 Monooxygenase (CYP) and Cytochrome P450 NADPH Oxidoreductase (CPR) Genes To clone CYP and CPR genes several different strategies were employed. Available CYP amino acid sequences were aligned and regions of similarity were observed (FIG. 4). These regions corresponded to described conserved regions seen in other cytochrome P450 families (Goeptar et al., supra and Kalb et al. supra). Proteins from eight eukaryotic cytochrome P450 families share a segmented region of sequence similarity. One region corresponded to the HR2 domain containing the invariant cysteine residue near the carboxyl terminus which is required for heme binding while the other region corresponded to the central region of the I helix thought to be involved in substrate recognition (FIG. 4). Degenerate oligonucleotide primers corresponding to these highly conserved regions of the CYP52 gene family present in *Candida maltosa* and *Candida tropicalis* ATCC 750 were designed and used to amplify DNA fragments of CYP genes from *C. tropicalis* 20336 genomic DNA. These discrete PCR fragments were then used as probes to isolate full-length CYP genes from the *C. tropicalis* 20336 genomic libraries. In a few instances oligonucleotide primers corresponding to highly conserved regions were directly used as probes to isolate full-length CYP genes-from genomic libraries. In the case of CPR a heterologous probe based upon the known DNA sequence for the CPR gene from *C. tropicalis* 750 was used to isolate the *C. tropicalis* 20336 CPR gene.

A. Cloning of the CPR Gene from *C. tropicalis* 20336

1) Cloning of the CPRA Allele

Approximately 25,000 phage particles from the first genomic library of *C. tropicalis* 20336 were screened with a 1.9 kb BamHI-NdeI fragment from plasmid pCU3RED (See Picattagio et al., Bio/Technology 10:894–898 (1992), incorporated herein by reference) containing most of the *C. tropicalis* 750 CPR gene. Five clones that hybridized to the probe were isolated and the plasmid DNA from these lambda clones was rescued and characterized b restriction enzyme analysis. The restriction, enzyme analysis suggested that all five clones were identical but it was not clear that a complete CPR gene was present.

Figure 5:
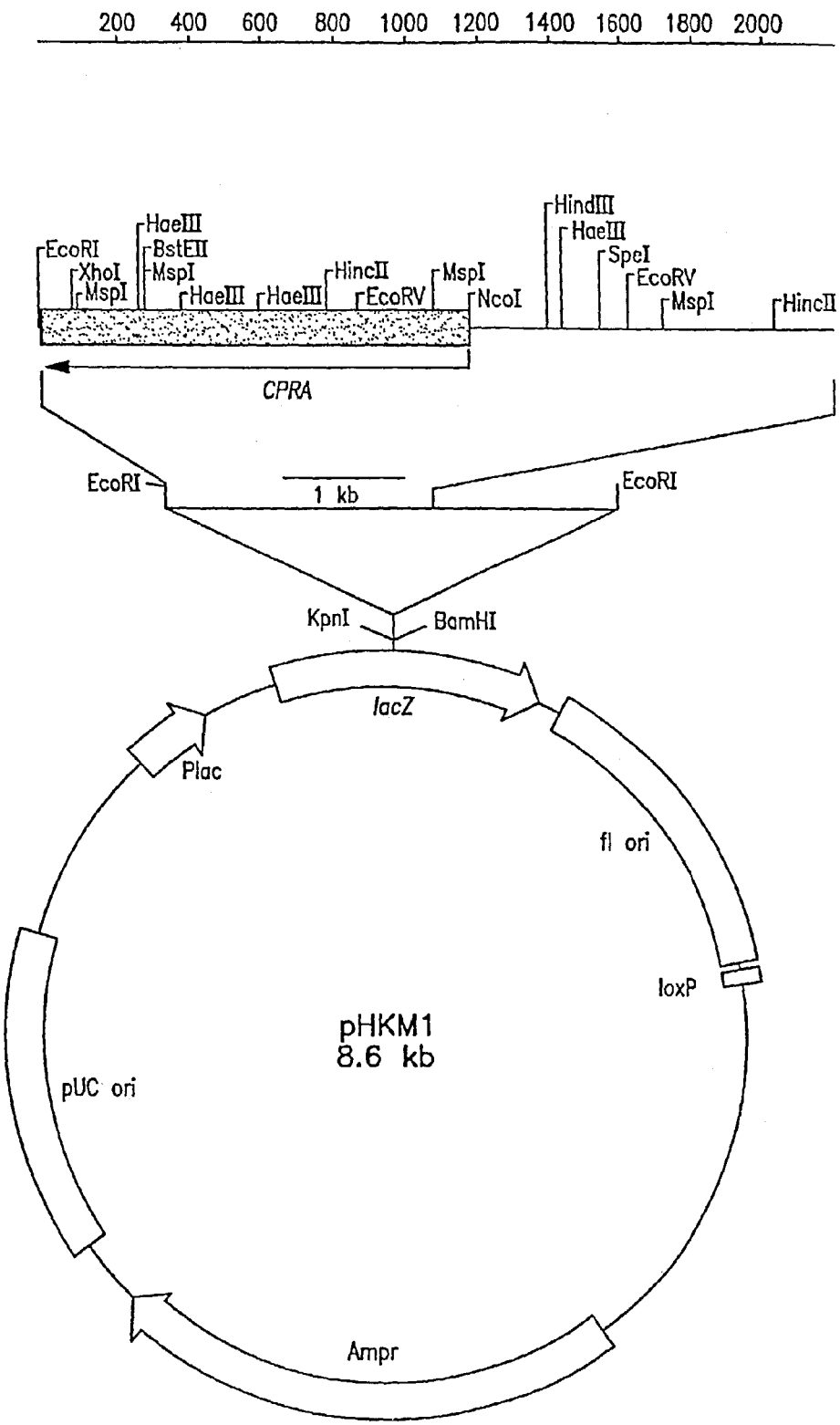
FIG. 5 is a diagrammatic representation of the plasmid pHKM1 containing the truncated CPRA gene present in the pTriplEx vector. A detailed restriction map of only the sequenced region is shown at the top. The bar indicates the open reading frame. The direction of transcription is indicated by an arrow under the open reading frame.

PCR analysis was used to determine if a complete CPR gene was present in any of the five clones. Degenerate primers were prepared for highly conserved regions of known CPR genes (See Sutter et al., *J. Biol. Chem.* 265: 16428–16436 (1990), incorporated herein by reference) (FIG. 4). Two Primers were synthesized for the FMN binding region (FMN1, SEQ ID NO: 16 and FMN2, SEQ ID NO: 17). One primer was synthesized for the FAD binding region (FAD, SEQ ID NO: 18), and one primer for the NADPH binding region (NADPH, SEQ ID NO: 19) (Table 4). These four primers were used in PCR amplification experiments using as a template plasmid DNA isolated from four of the five clones described above. The FMN (SEQ ID NOS: 16 and 17) and FAD (SEQ ID NO: 18) primers served as forward primers and the NADPH primer (SEQ ID NO: 19) as the reverse primer in the PCR reactions. When different combinations of forward and reverse primers were used, no PCR products were obtained from any of the plasmids. However, all primer combinations amplified expected size products with a plasmid containing the *C. tropicalis* 750 CPR gene (positive control). The most likely reason for the failure of the primer pairs to amplify a product, was that all four of clones contained a truncated CPR gene. One of the four clones (pHKM1) was sequenced using the Triplex 5' (SEQ ID NO: 30) and the Triplex 3' (SEQ ID NO: 31) primers (Table 4) which flank the insert and the multiple cloning site on the cloning vector, and with the degenerate primer based upon the NADPH binding site described above. The NADPH primer (SEQ ID NO: 19) failed to yield any sequence data and this is consistent with the PCR analysis. Sequences obtained with Triplex primers were compared with *C. tropicalis* 750 CPR sequence using the Mac Vector™ program (Oxford Molecular Group, Campbell, Calif.). Sequence obtained with the Triplex 3' primer (SEQ ID NO: 31) showed similarity to an internal sequence of the *C. tropicalis* 750 CPR gene confirming that pHKM1 contained a truncated version of a 20336 CPR gene. pHKM1 had a 3.8 kb insert which included a 1.2 kb coding region of the CPR gene accompanied by 2.5 kb of upstream DNA (FIG. 5). Approximately 0.85 kb of the 20336 CPR gene encoding the C-terminal portion of the CPR protein is missing from this clone.

Figure 6:
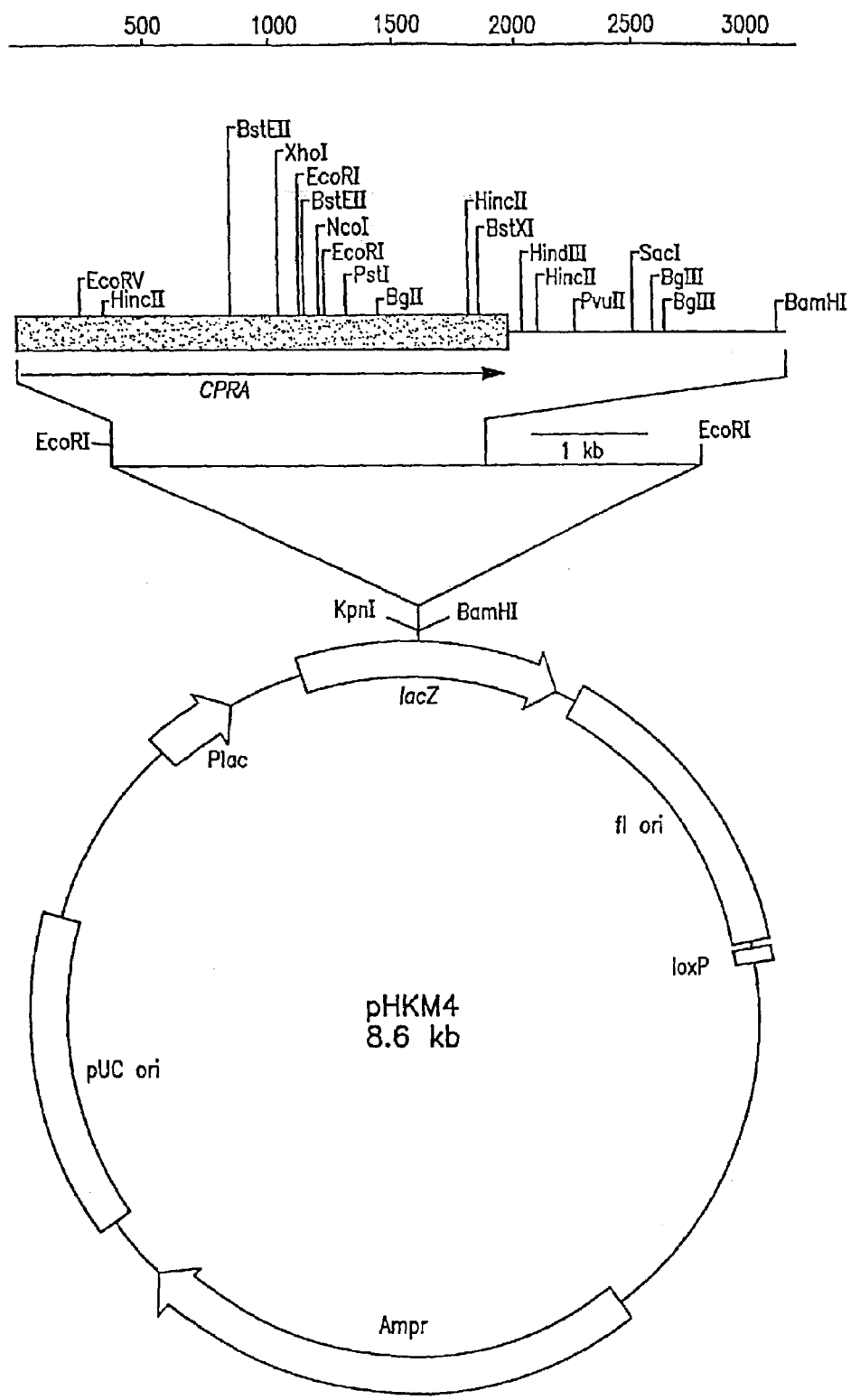
FIG. 6 is a diagrammatic representation of the plasmid pHKM4 containing the truncated CPRA gene present in the pTriplEx vector. A detailed restriction map of only the sequenced region is shown at the top. The bar indicates the open reading frame. The direction of transcription is indicated by an arrow under the open reading frame.

Since the first Clontech library yielded only a truncated CPR gene, the second library prepared by Clontech was screened to isolate a full-length CPR gene. Three putative CPR clones were obtained. The three clones, having inserts in the range of 5–7 kb, were designated pHKM2, pHKM3 and pHKM4. All three were characterized by PCR using the degenerate primers described above. Both pHKM2 and pHKM4 gave PCR products with two sets of internal primers. pHKM3 gave a PCR product only with the FAD (SEQ ID NO: 18) and NADPH (SEQ ID NO: 19) primers suggesting that this clone likely contained a truncated CPR gene. All three plasmids were partially sequenced using the two Triplex primers and a third primer whose sequence was selected from the DNA sequence near the truncated end of the CPR gene present in pHKM1. This analysis confirmed that both pHKM2 & 4 have sequences that overlap pHKM1 and that both contained the 3' region of CPR gene that is missing from pHKM1. Portions of inserts from pHKM1 and pHKM4 were sequenced and a full-length CPR gene was identified. Based on the DNA sequence and PCR analysis, it was concluded that pHKM1 contained the putative promoter region and 1.2 kb of sequence encoding a portion (5' end) of a CPR gene. pHKM4 had 1.1 kb of DNA that overlapped pHKM1 and contained the remainder (3' end) of a CPR gene along with a downstream untranslated region (FIG. 6). Together these two plasmids contained a complete CPRA gene with an upstream promoter region. CPRA is 4206 nucleotides in length (SEQ ID NO: 81) and includes a regulatory region and a protein coding region (defined by nucleotides 1006–3042) which is 2037 base pairs in length and codes for a putative protein of 679 amino acids (SEQ ID NO: 83) (FIGS. 13 and 14). In FIG. 13, the asterisks denote conserved nucleotides between CPRA and CPRB, bold denotes protein coding nucleotides, and the start and stop codons are underlined. The CPRA protein, when analyzed by the protein alignment program of the GeneWorks™ software package (Oxford Molecular Group, Campbell, Calif.), showed extensive homology to CPR proteins from *C. tropicalis* 750 and *C. maltosa*.

2) Cloning of the CPRB Allele

Figure 7:
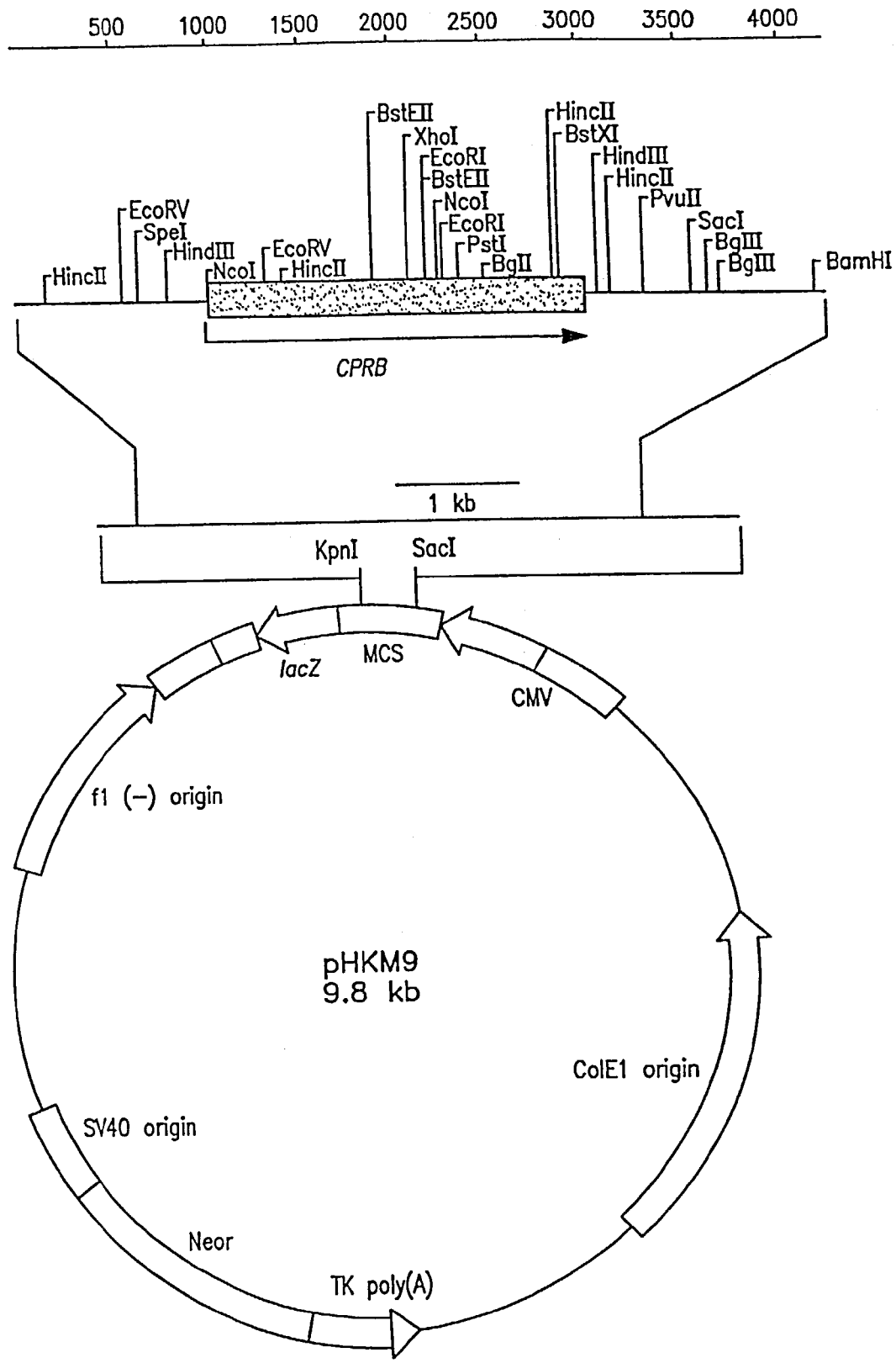
FIG. 7 is a diagrammatic representation of the plasmid pHKM9 containing the CPRB gene (SEQ ID NO: 82) present in the pBK-CMV vector. A detailed restriction map of only the sequenced region is shown at the top. The bar indicates the open reading frame. The direction of transcription is indicated by an arrow under the open reading frame.

To clone the second CPRB allele, the third genomic library, prepared by Henkel, was screened using DNA fragments from pBKM1 and pEKM4 as probes. Five clones were obtained and these were sequenced with the three internal primers used to sequence CPRA. These primers were designated PRK1.F3 (SEQ ID NO: 20), PRK1.F5 (SEQ ID NO: 21) and PRK4.R20 (SEQ ID NO: 22) (Table 4). and the two outside primers (M13-20 and T3 [Stratagene]) for the polylinker region present in the pBK-CMV cloning vector. Sequence analysis suggested that four of these clones, designated pHKM5 to 8, contained inserts which were identical to the CPRA allele isolated earlier. All four seemed to contain a full length CPR gene. The fifth clone was very similar to the CPRA allele, especially in the open reading frame region where the identity was very high. However, there were significant differences in the 5' and 3' untranslated regions. This suggested that the fifth clone was the allele to CPRA. The plasmid was designated pHKM9 (FIG. 7) and a 4.14 kb region of this plasmid was sequenced and the analysis of this sequence confirmed the presence of the CPRB allele (SEQ ID NO: 82), which includes a regulatory region and a protein coding region (defined by nucleotides 1033–3069) (FIG. 13). The amino acid sequence of the CPRB protein is set forth in SEQ ID NO: 84 (FIG. 14).

B. Cloning of *C. tropicalis* 20336 (CYP) Genes

1) Cloning of CYP52A2A, CYP52A3A & 3B and CYP52A5A & 5B

Figure 26:
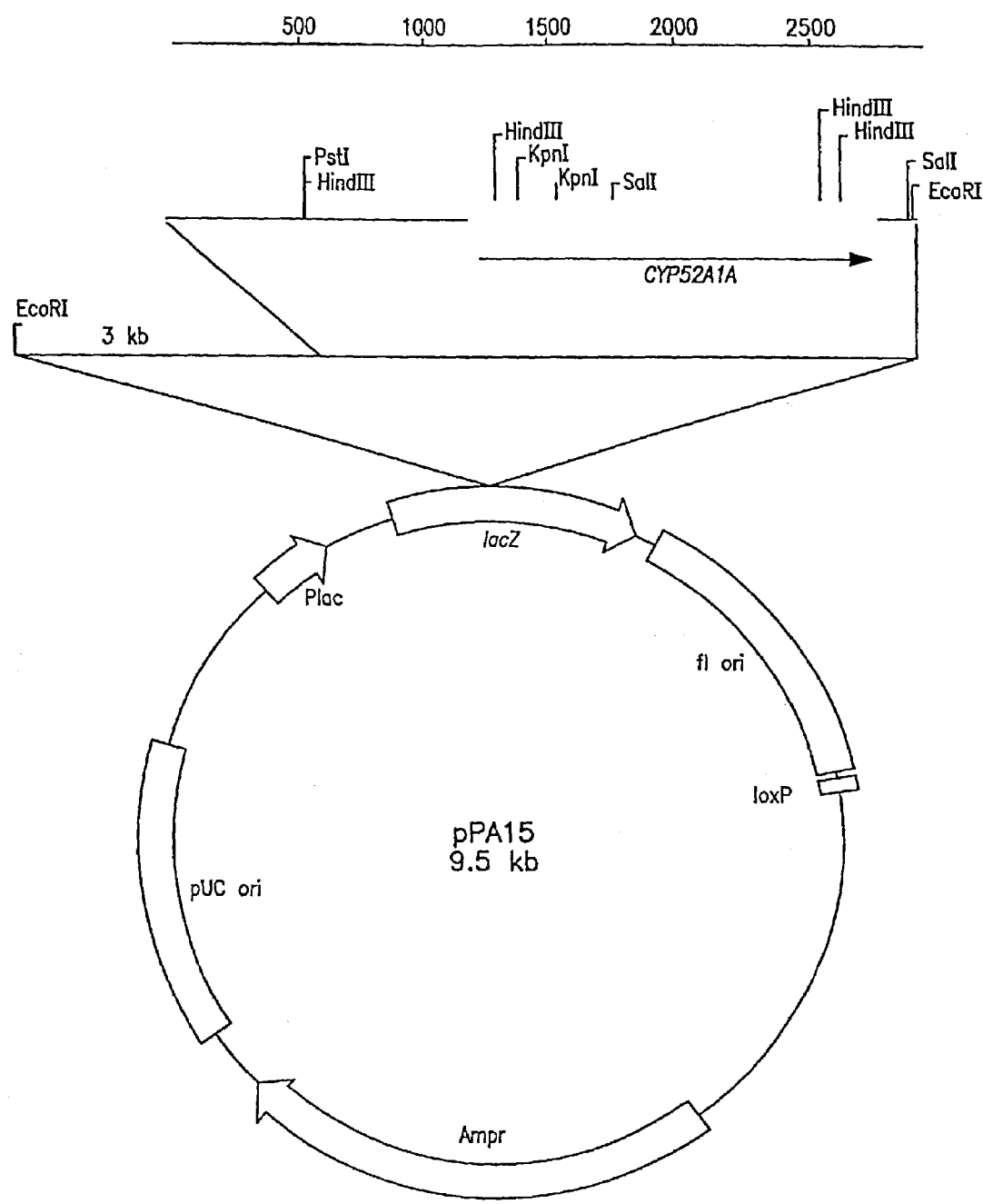
FIG. 26 is a diagrammatic representation of the plasmid pPA15 containing the truncated CYP52A2A gene present in the pTriplEx vector. A detailed restriction map of only the sequenced region is shown at the top. The bar indicates the open reading frame. The direction of transcription is indicated by an arrow under the open reading frame.
Figure 29:
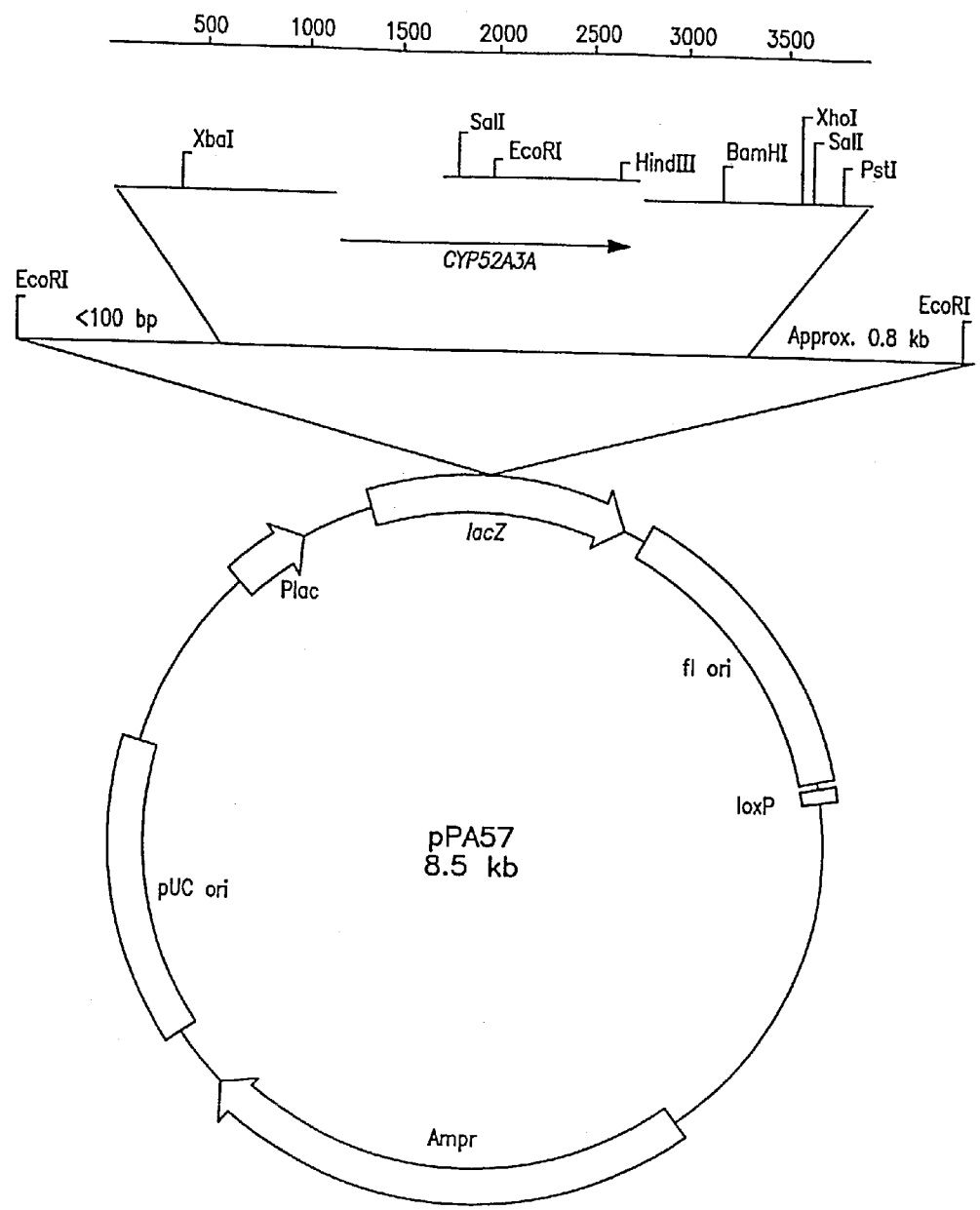
FIG. 29 is a diagrammatic representation of the plasmid pPA57 containing the truncated CYP52A3A gene present in the pTriplEx vector. A detailed restriction map of only the sequenced region is shown at the top. The bar indicates the open reading frame. The direction of transcription is indicated by an arrow under the open reading frame.
Figure 30:
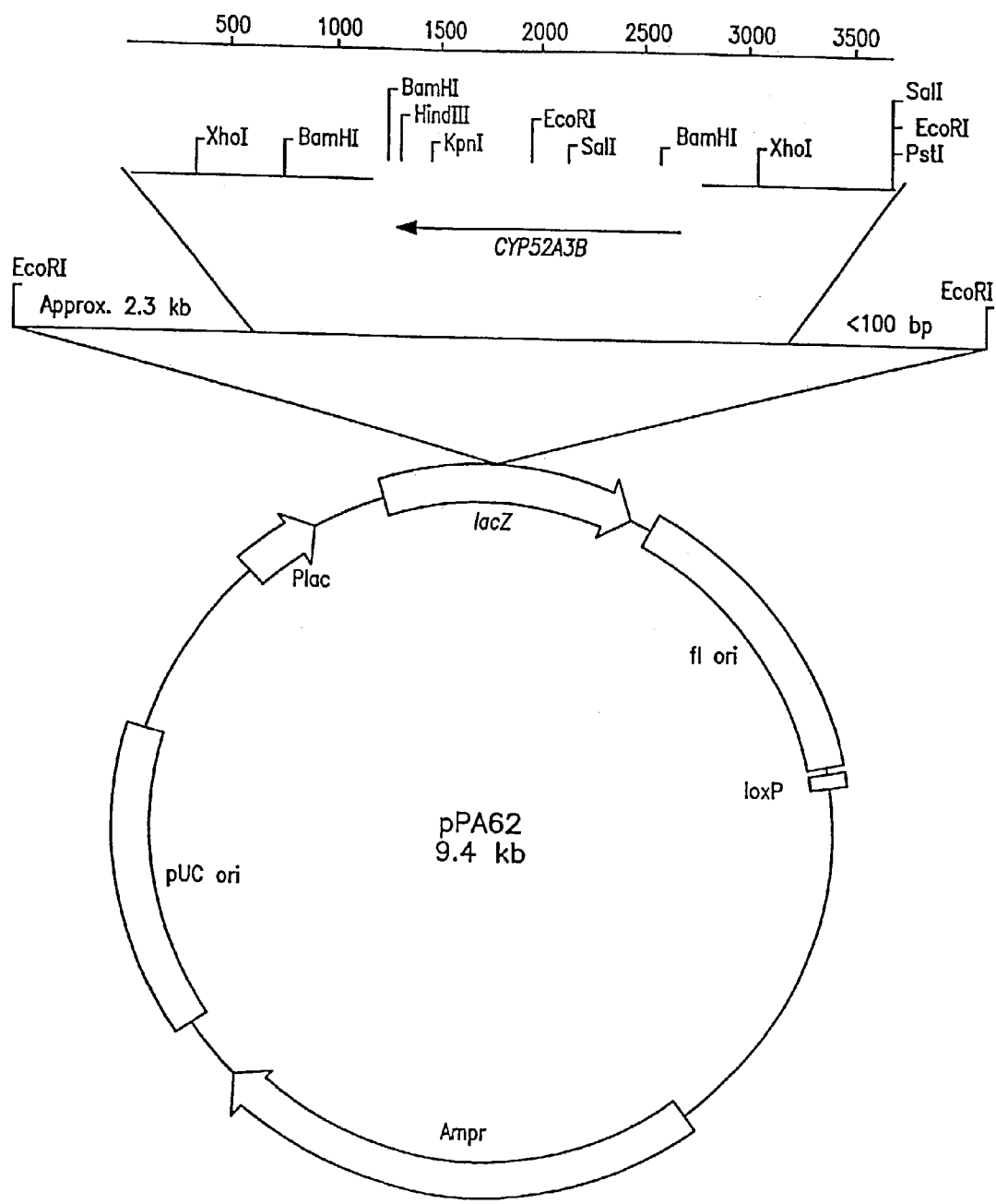
FIG. 30 is a diagrammatic representation of the plasmid pPA62 containing the truncated CYP52A3B gene present in the pTriplEx vector. A detailed restriction map of only the sequenced region is shown at the top. The bar indicates the open reading frame. The direction of transcription is indicated by an arrow under the open reading frame.
Figure 31:
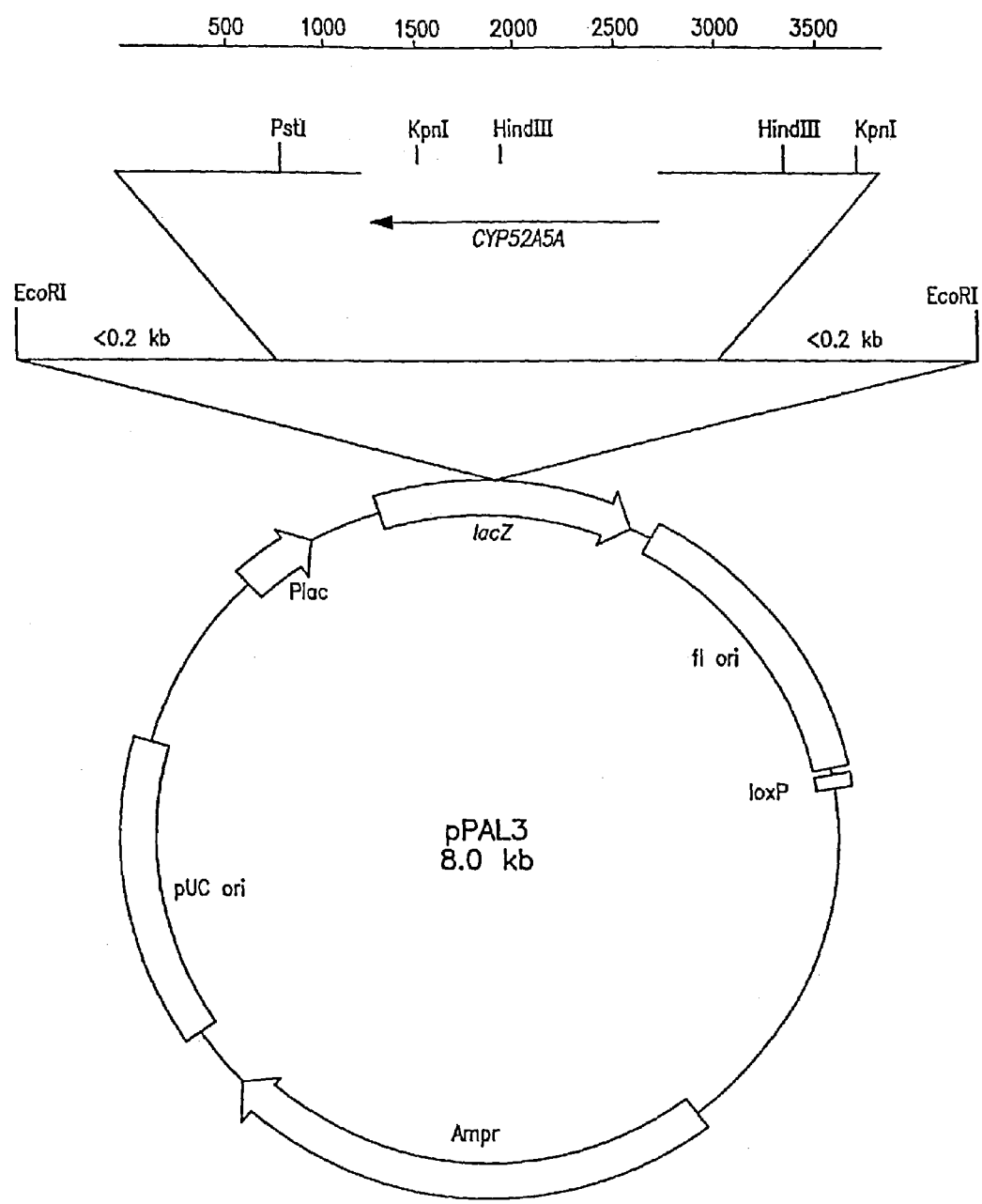
FIG. 31 is a diagrammatic representation of the plasmid pPAL3 containing the truncated CYP52A5A gene present in the pTriplEx vector. A detailed restriction map of only the sequenced region is shown at the top. The bar indicates the open reading frame. The direction of transcription is indicated by an arrow under the open reading frame.
Figure 32:
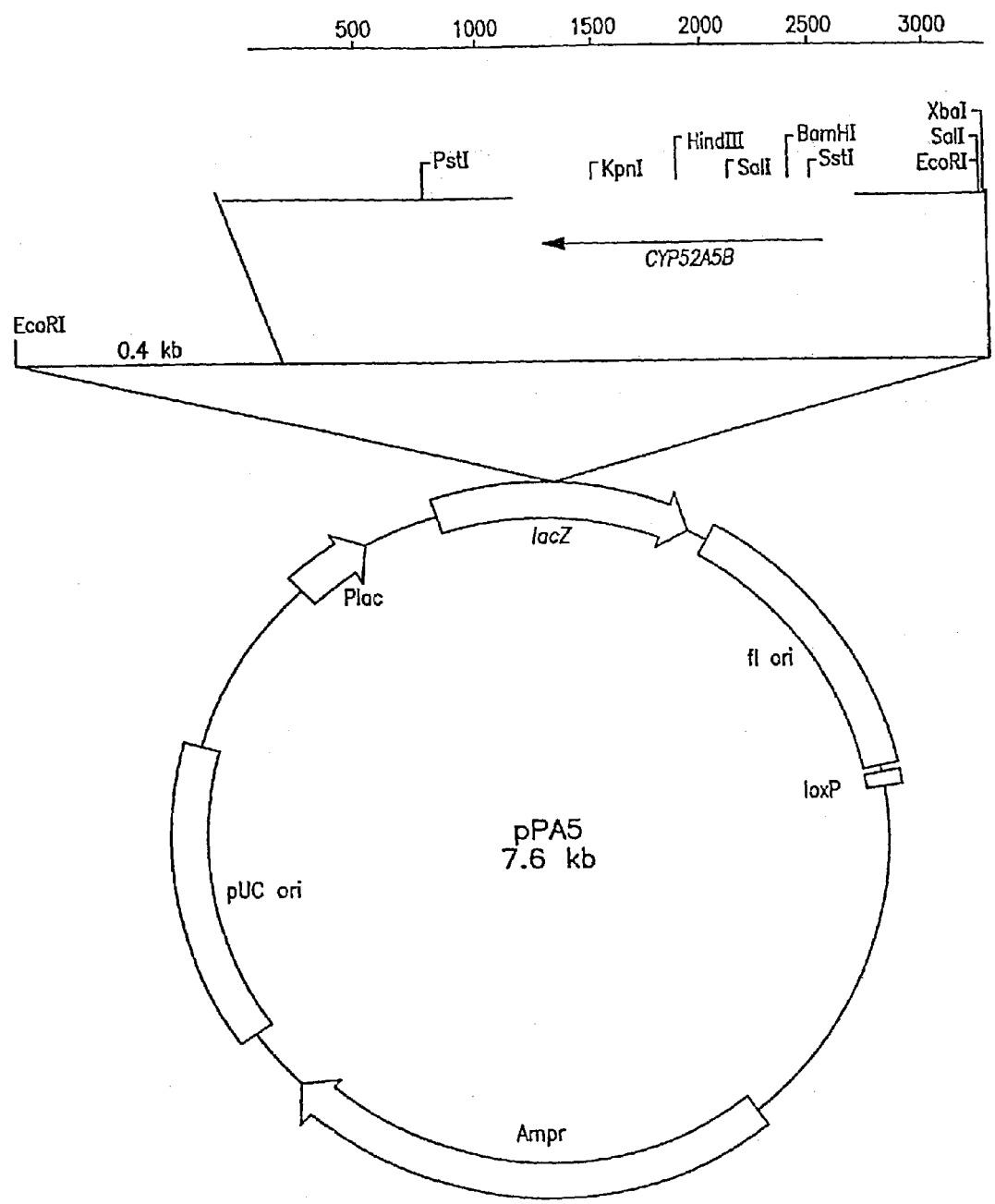
FIG. 32 is a diagrammatic representation of the plasmid pPA5 containing the truncated CYP52A5A gene present in the pTriplEx vector. A detailed restriction map of only the sequenced region is shown at the top. The bar indicates the open reading frame. The direction of transcription is indicated by an arrow under the open reading frame.

Clones carrying CYP52A2A, A3A, A3B, A5A and A5B genes were isolated from the first and second Clontech genomic libraries using an oligonucleotide probe (HemeB1, SEQ ID NO: 27) whose sequence was based upon the amino acid sequence for the highly conserved heme binding region present throughout the CYP52 family. The first and second libraries were converted to the plasmid form and screened by colony hybridizations using the HemeB1 probe (SEQ ID NO: 27) (Table 4). Several potential clones were isolated and the plasmid DNA was isolated from these clones and sequenced using the HemeB1 oligonucleotide (SEQ ID NO: 27) as a primer. This approach succeeded in identifying five CYP52 genes. Three of the CYP genes appeared unique, while the remaining two were classified as alleles. Based upon an arbitrary choice of homology to CYP52 genes from *Candida maltosa,* these five genes and corresponding plasmids were designated CYP52A2A (pPA15 [FIG. 26]), CYP52A3A (pPA57 [FIG. 29]), CYP52A3B (pPA62 [FIG. 30]), CYP52A5A (pPAL3 [FIG. 31]) and CYP52A5B (pPA5 [FIG. 32]). The complete DNA sequence including regulatory and protein coding regions of these five genes was obtained and confirmed that all five were CYP52 genes (FIG. 15). In FIG. 15, the asterisks denote conserved nucleotides among the CYP genes. Bold indicates the protein coding nucleotides of the CYP genes, and the start and stop codons are underlined. The CYP52A2A gene as represented by SEQ ID NO: 86 has a protein coding region defined by nucleotides 1199–2767 and the encoded protein has an amino acid sequence as set forth in SEQ ID NO: 96. The CYP52A3A gene as represented by SEQ ID NO: 88 has a protein encoding region defined by nucleotides 1126–2748 and the encoded protein has an amino acid sequence as set forth in SEQ ID NO: 98. The CYP52A3B gene as represented by SEQ ID NO: 89 has a protein coding defined by nucleotides 913–2535 and the encoded protein has an amino acid sequence as set forth in SEQ ID NO: 99. The CYP52A5A gene as represented by SEQ ID NO: 90 has a protein coding region defined by nucleotides 1103–2656 and the encoded protein has an amino acid sequence as set forth in SEQ ID NO: 100. The CYP52A5B gene as represented by SEQ ID NO: 91 has a protein coding region defined by nucleotides 1142–2695 and the encoded protein has an amino acid sequence as set forth in SEQ ID NO: 101.

2) Cloning of CYP52A1A and CYP52A8A

Figure 8:
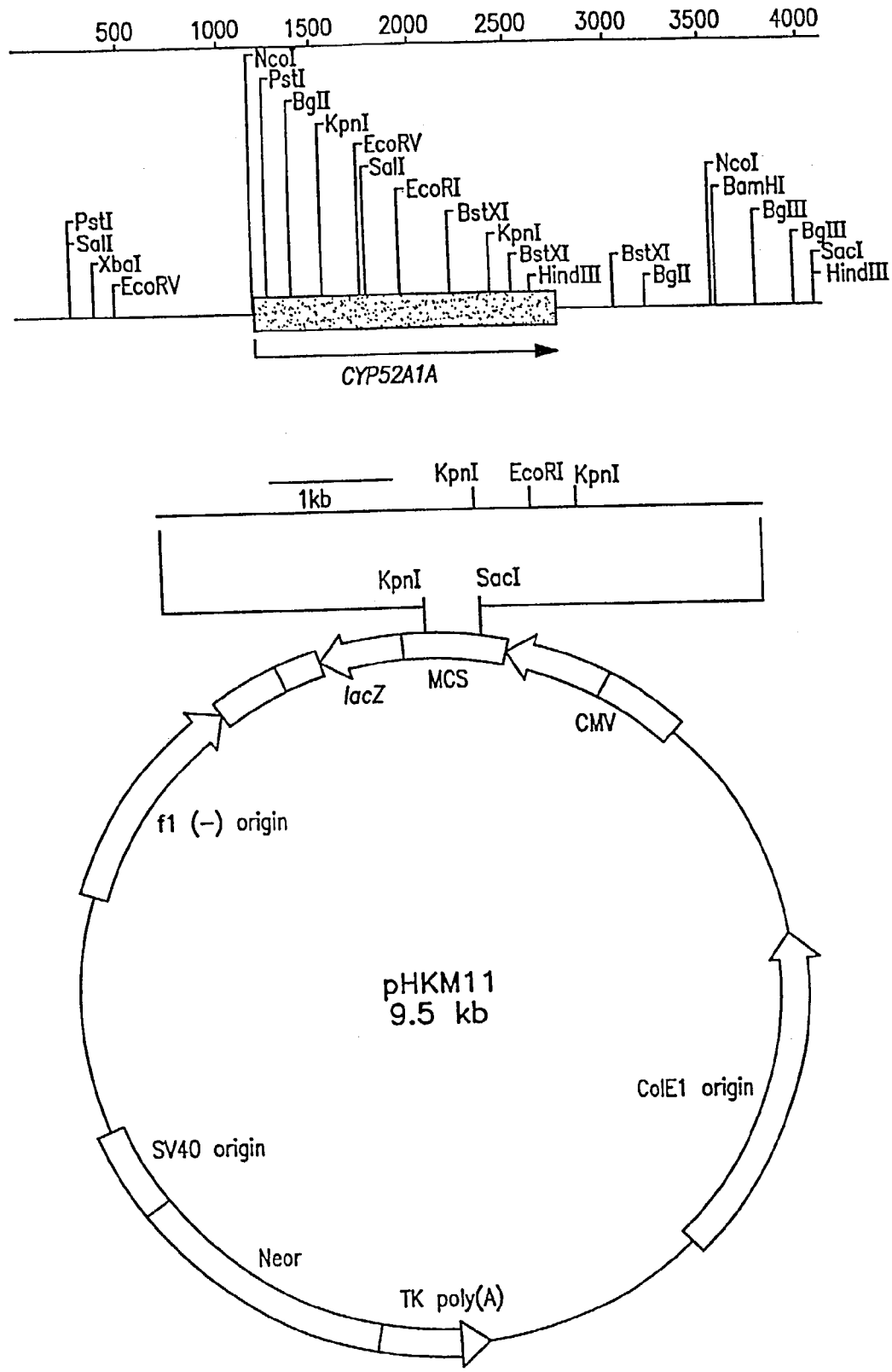
FIG. 8 is a diagrammatic representation of the plasmid pHKM11 containing the CYP52A1A gene (SEQ ID NO: 85) present in the pBK-CMV vector. A detailed restriction map of only the sequenced region is shown at the top. The bar indicates the open reading frame. The direction of transcription is indicated by an arrow under the open reading frame.
Figure 17:
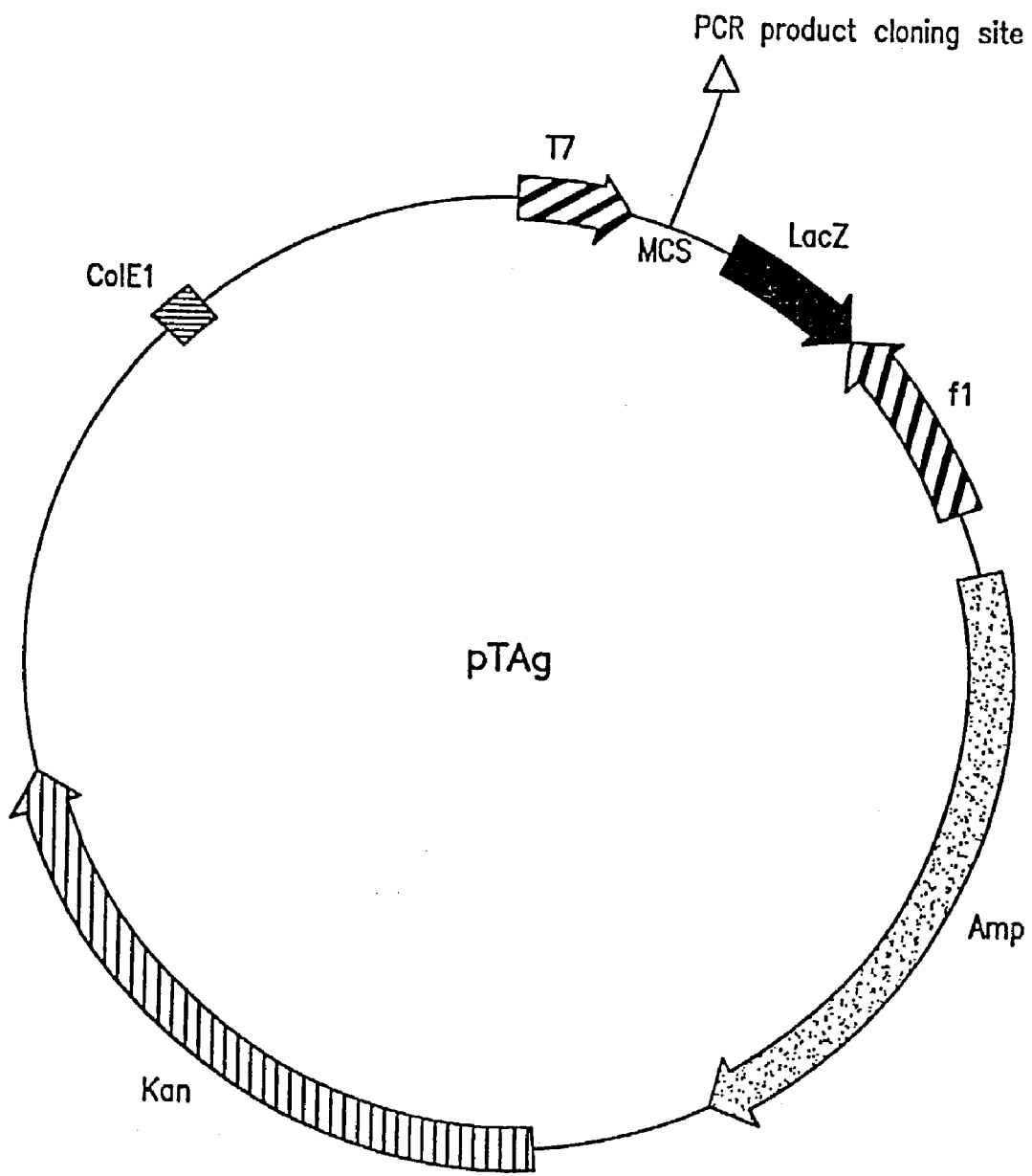
FIG. 17 is a diagrammatic representation of the pTAg PCR product cloning vector (commercially available from R&D Systems, Minneapolis, Minn.).

CYP52A1A and CYP52A8A genes were isolated from the third genomic library using PCR fragments as probes. The PCR fragment probe for CYP52A1 was generated after PCR amplification of 20336 genomic DNA with oligonucleotide primers that were designed to amplify a region from the Helix I region to the HR2 region using all available CYP52 genes from National Center for Biotechnology Information. Degenerate forward primers UCup1 (SEQ ID NO: 23) and UCup2 (SEQ ID NO: 24) were designed based upon an amino acid sequence (-RDTTAG-) from the Helix I region (Table 4). Degenerate primers UCdown1 (SEQ ID NO: 25) and UCdown2 (SEQ ID NO: 26) were designed based upon an amino acid sequence (-GQQFAL-) from the HR2 region (Table 4). For the reverse primers, the DNA sequence represents the reverse complement of the corresponding amino acid sequence. These primers were used in pairwise combinations in a PCR reaction with Stoffel Taq DNA polymerase (Perkin-Elmer Cetus, Foster City, Calif.) according to the manufacturer's recommended procedure. A PCR product of approximately 450 bp was obtained. This product was purified from agarose gel using Gene-clean™ (Bio 101, LaJolla, Calif.) and ligated to the pTAG™ vector (FIG. 17) (R&D systems, Minneapolis, Minn.) according to the recommendations of the manufacturer. No treatment was necessary to clone into pTAG because it employs the use of the TA cloning technique. Plasmids from several transformants were isolated and their inserts were characterized. One plasmid contained the PCR clone intact. The DNA sequence of the PCR fragment (designated 44CYP3, SEQ ID NO: 107) shared homology with the DNA sequences for the CYP52A1 gene of *C. maltosa* and the CYP52A3 gene of *C. tropicalis* 750. This fragment was used as a probe in isolating the *C. tropicalis* 20336 CYP52A1 homolog. The third genomic library was screened using the 44CYP3 PCR probe (SEQ ID NO: 107) and a clone (pHKM11) that contained a full-length CYP52 gene was obtained (FIG. 8). The clone contained a gene having regulatory and protein coding regions. An open reading frame of 1572 nucleotides encoded a CYP52 protein of 523 amino acids (FIGS. 15 and 16). This CYP52 gene was designated CYP52A1A (SEQ ID NO: 85) since its putative amino acid sequence (SEQ ID NO: 95) was most similar to the CYP52A1 protein of *C. maltosa*. The protein coding region of the CYP52A1A gene is defined by nucleotides 1177–2748 of SEQ ID NO: 85.

Figure 9:
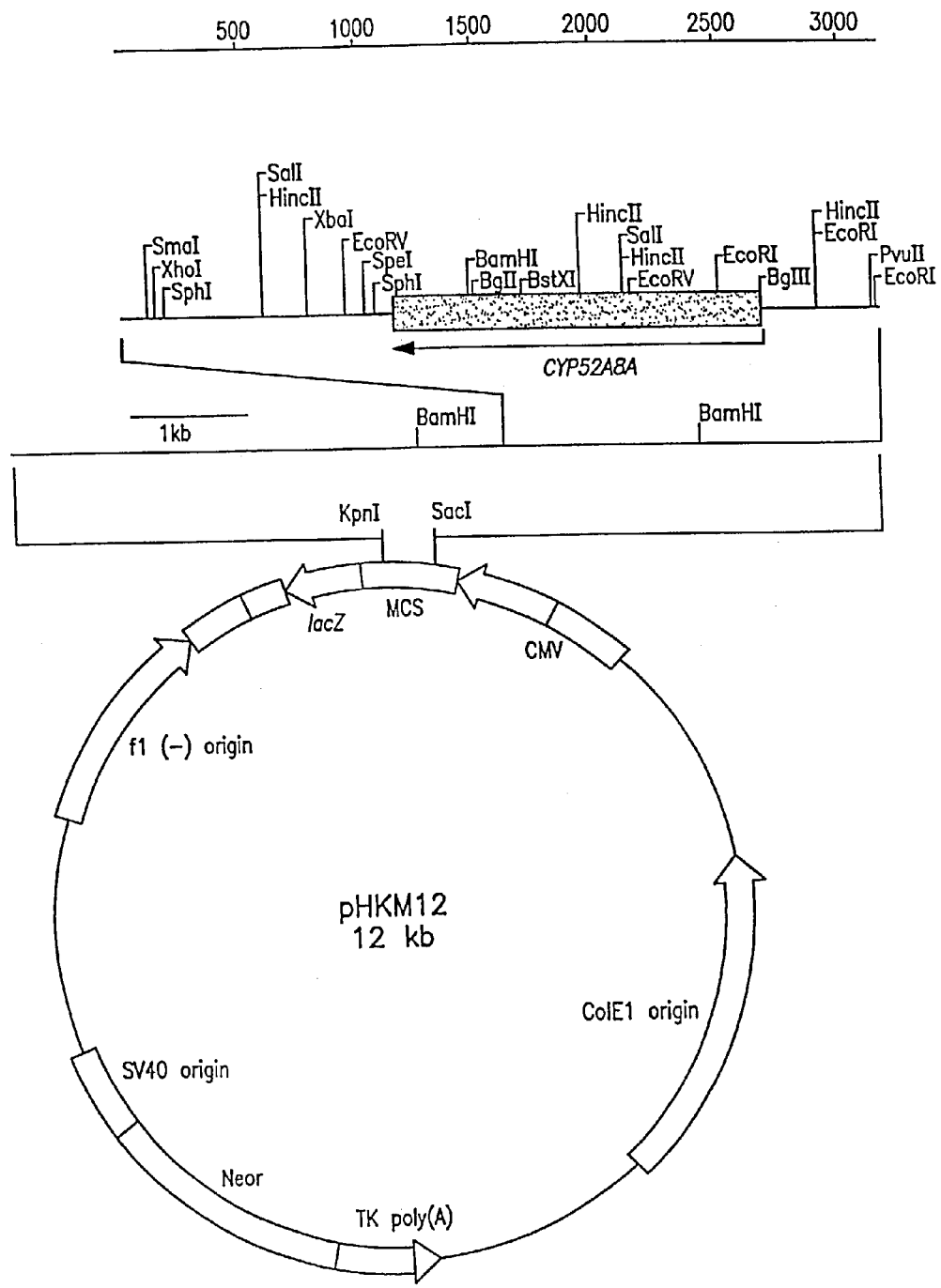
FIG. 9 is a diagrammatic representation of the plasmid pHKM12 containing the CYP52A8A gene (SEQ ID NO: 92) present in the pBK-CMV vector. A detailed restriction map of only the sequenced region is shown at the top. The bar indicates the open reading frame. The direction of transcription is indicated by an arrow under the open reading frame.

A similar approach was taken to clone CYP52A8A. A PCR fragment probe for CYP52A8 was generated using primers for highly conserved sequences of CYP52A3, CYP52A2 and CYP52A5 genes of *C. tropicalis* 750. The reverse primer (primer 2,3,5,M) (SEQ ID NO: 29) was designed based on the highly conserved heme binding region (Table 4). The design of the forward primer (primer 2,3,5,P) (SEQ ID NO: 28) was based upon a sequence conserved near the N-terminus of the CYP52A3, CYP52A2 and CYP52A5 genes from *C. tropicalis* 750 (Table 4). Amplification of 20336 genomic DNA with these two primers gave a mixed PCR product. One amplified PCR fragment was 1006 bp long (designated DCA1002). The DNA sequence for this fragment was determined and was found to have 85% identity to the DNA sequence for the CYP52D4 gene of *C. tropicalis* 750. When this PCR product was used to screen the third genomic library one clone (pHKM12) was identified that contained a full-length CYP52 gene along with 5' and 3' flanking sequences (FIG. 9). The CYP52 gene included regulatory and protein coding regions with an open reading frame of 1539 nucleotides long which encoded a putative CYP52 protein of 512 amino acids (FIGS. 15 and 16). This gene was designated as CYP52A8A (SEQ ID NO: 92) since its amino acid sequence (SEQ ID NO: 102) was most similar to the CYP52A8 protein of *C. maltosa*. The protein coding region of the CYP52A8A gene is defined by nucleotides 464–2002 of SEQ ID NO: 92. The amino acid sequence of the CYP52A8A protein is set forth in SEQ ID NO: 102.

3) Cloning of CYP52D4A

Figure 10:
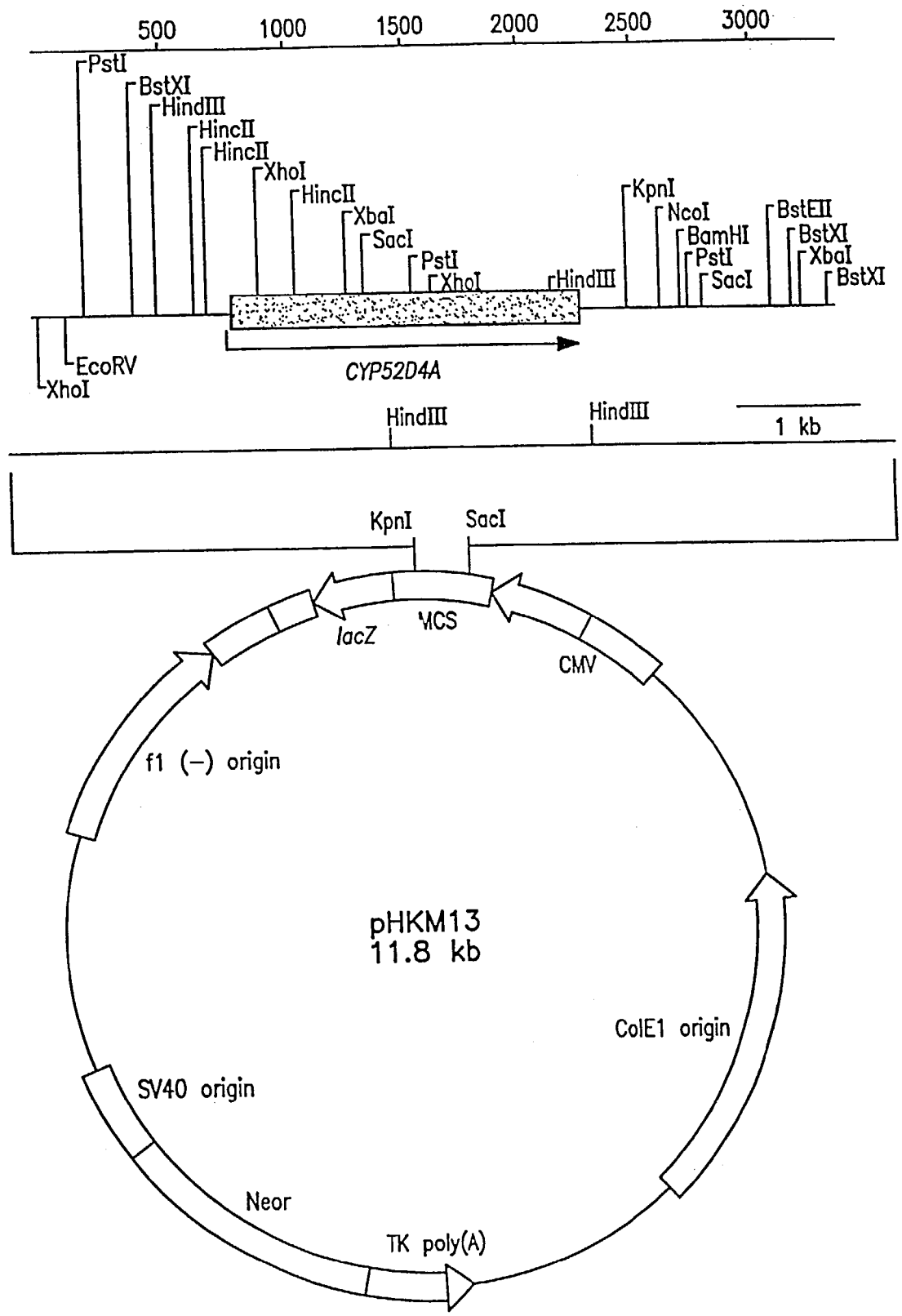
FIG. 10 is a diagrammatic representation of the plasmid pHKM13 containing the CYP52D4A gene (SEQ ID NO: 94) present in the pBK-CMV vector. A detailed restriction map of only the sequenced region is shown at the top. The bar indicates the open reading frame. The direction of transcription is indicated by an arrow under the open reading frame.
Figure 33:
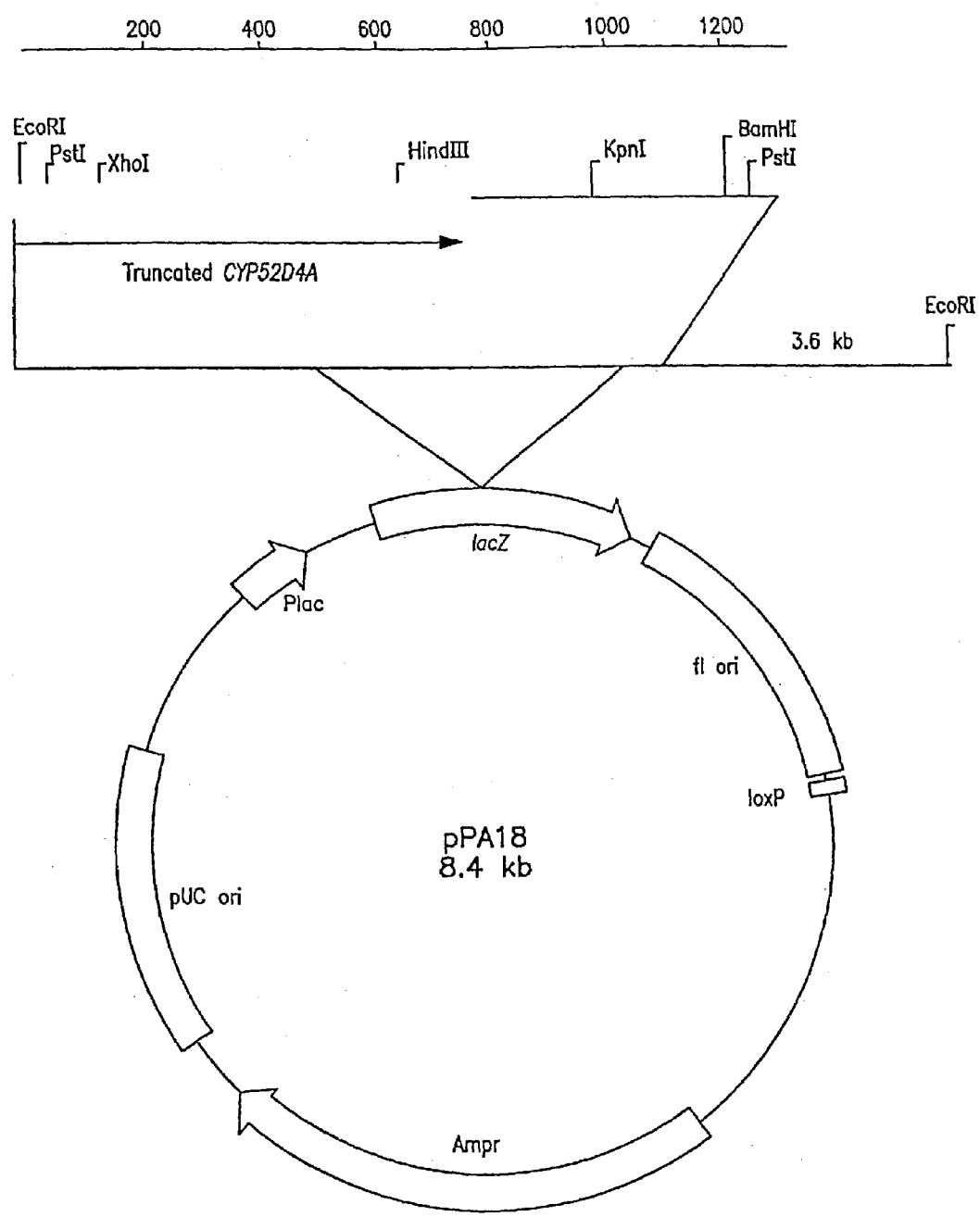
FIG. 33 is a diagrammatic representation of the plasmid pPA18 containing the truncated CYP52D4A gene present in the pTriplEx vector. A detailed restriction map of only the sequenced region is shorn at the top. The bar indicates the open reading frame. The direction of transcription is indicated by an arrow under the open reading frame.

The screening of the second genomic library with the HemeB1 (SEQ ID NO: 27) primer (Table 4) yielded a clone carrying a plasmid (pPA18) that contained a truncated gene having homology with the CYP52D4 gene of *C. maltosa* (FIG. 33). A 1.3 to 1.5-kb EcoRI-SstI fragment from pPA18 containing part of the truncated CYP gene was isolated and used as a probe to screen the third genomic library for a full length CYP52 gene. One clone (pHKM13) was isolated and found to contain a full-length CYP gene with extensive 5' and 3' flanking sequences (FIG. 10). This gene has been designated as CYP52D4A (SEQ ID NO: 94) and the complete DNA including regulatory and protein coding regions (coding region defined by nucleotides 767–2266) and putative amino acid sequence (SEQ ID NO: 104) of this gene is shown in FIGS. 15 and 16. CYP52D4A (SEQ ID NO: 94) shares the greatest homology with the CYP52D4 gene of *C. maltosa*.

4) Cloning of CYP52A2B and CYP52A8B

Figure 11:
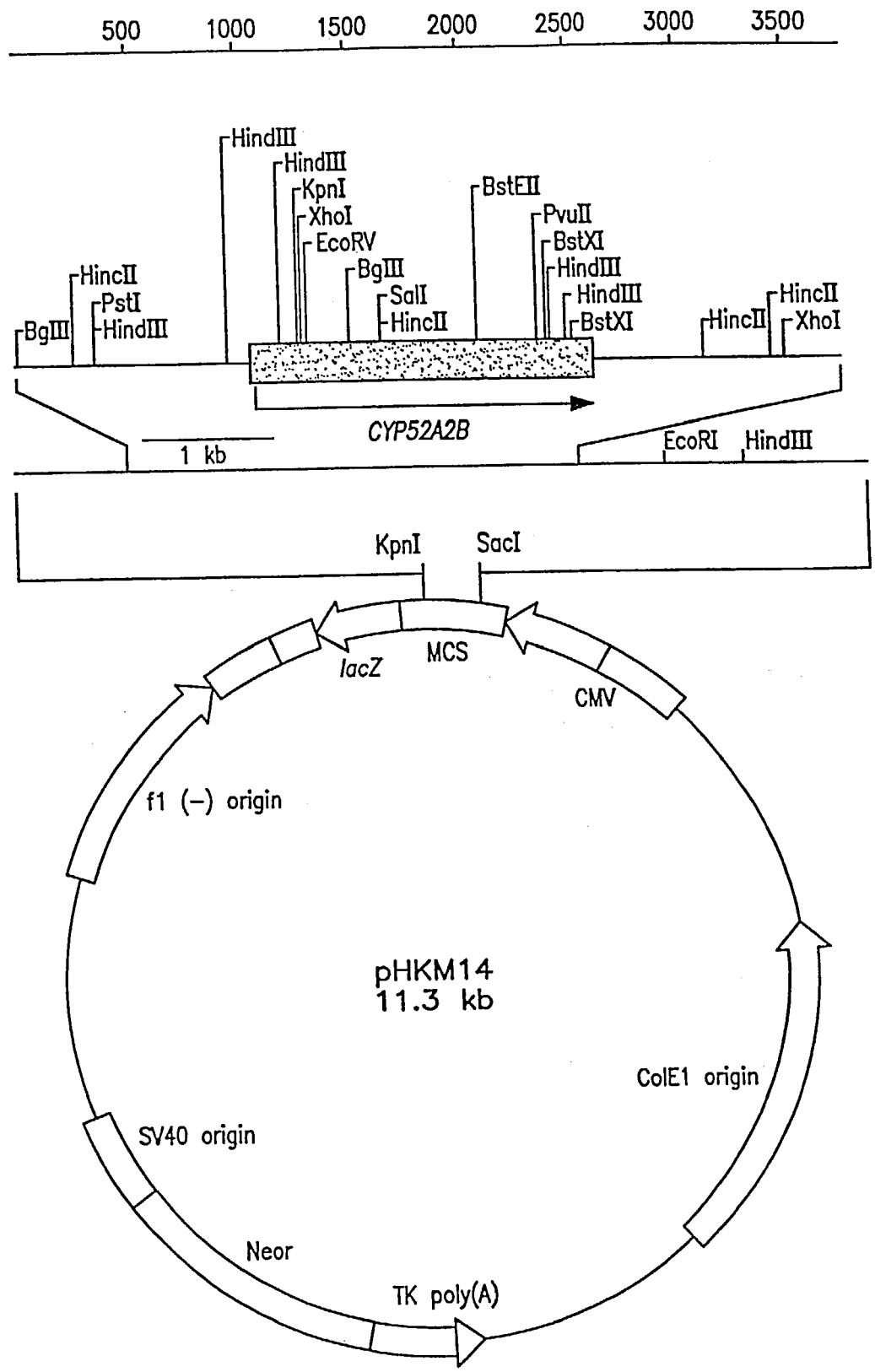
FIG. 11 is a diagrammatic representation of the plasmid pHKM14 containing the CYP52A2B gene (SEQ ID NO: 87) present in the pBK-CMV vector. A detailed restriction map of only the sequenced region is shown at the top. The bar indicates the open reading frame. The direction of transcription is indicated by an arrow under the open reading frame.
Figure 12:
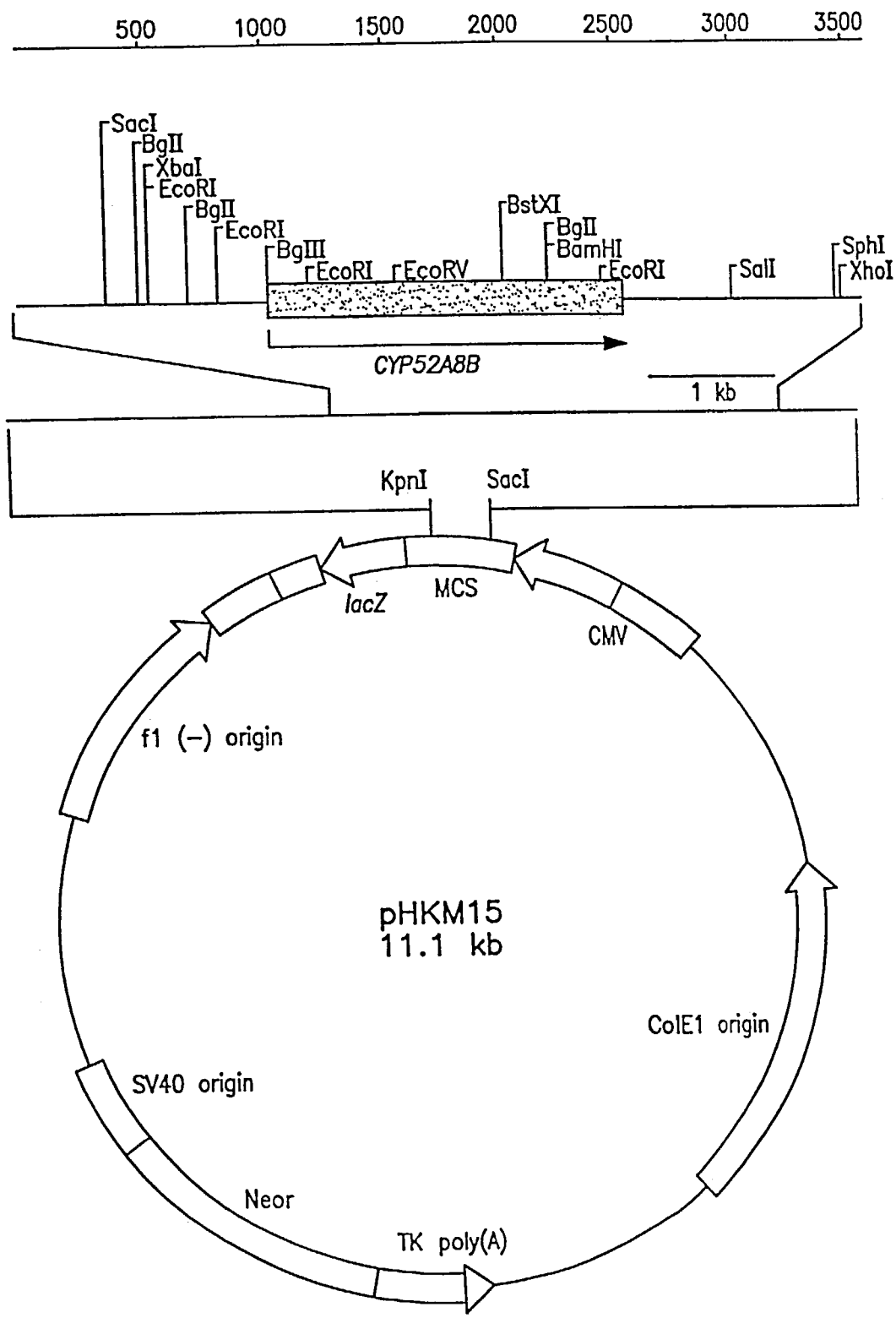
FIG. 12 is a diagrammatic representation of the plasmid pHKM15 containing the CYP52A8B gene (SEQ ID NO: 93) present in the pBK-CMV vector. A detailed restriction map of only the sequenced region is shown at the top. The bar indicates the open reading frame. The direction of transcription is indicated by an arrow under the open reading frame.

A mixed probe containing CYP52A1A, A2A, A3A, D4A, A5A and A8A genes was used to screen the third genomic library and several putative positive clones were identified. Seven of these were sequenced with the degenerate primers Cyp52a (SEQ ID NO: 32), Cyp52b (SEQ ID NO: 33), Cyp52c (SEQ ID NO: 34) and Cyp52d (SEQ ID NO: 35) shown in Table 4. These primers were designed from highly conserved regions of the four CYP52 subfamilies, namely CYP52A, B, C & D. Sequences from two clones, pHKM14 and pHKM15 (FIGS. 11 and 12), shared considerable homology with DNA sequence of the *C. tropicalis* 20336 CYP52A2 and CYP52A8 genes, respectively. The complete DNA (SEQ ID NO: 87) including regulatory and protein coding regions (coding region defined by nucleotides 1072–2640) and putative amino acid sequence (SEQ ID NO: 97) of the CYP52 gene present in pHKM14 suggested that it is CYP52A2B (FIGS. 15 and 16). The complete DNA (SEQ ID NO: 93) including regulatory and protein coding regions (coding region defined by nucleotides 1017–2555) and putative amino acid sequence (SEQ ID NO: 103) of the CYP52 gene present in pHKM15 suggested that it is CYP52A8B (FIGS. 15 and 16).

EXAMPLE 14

Figure 18:
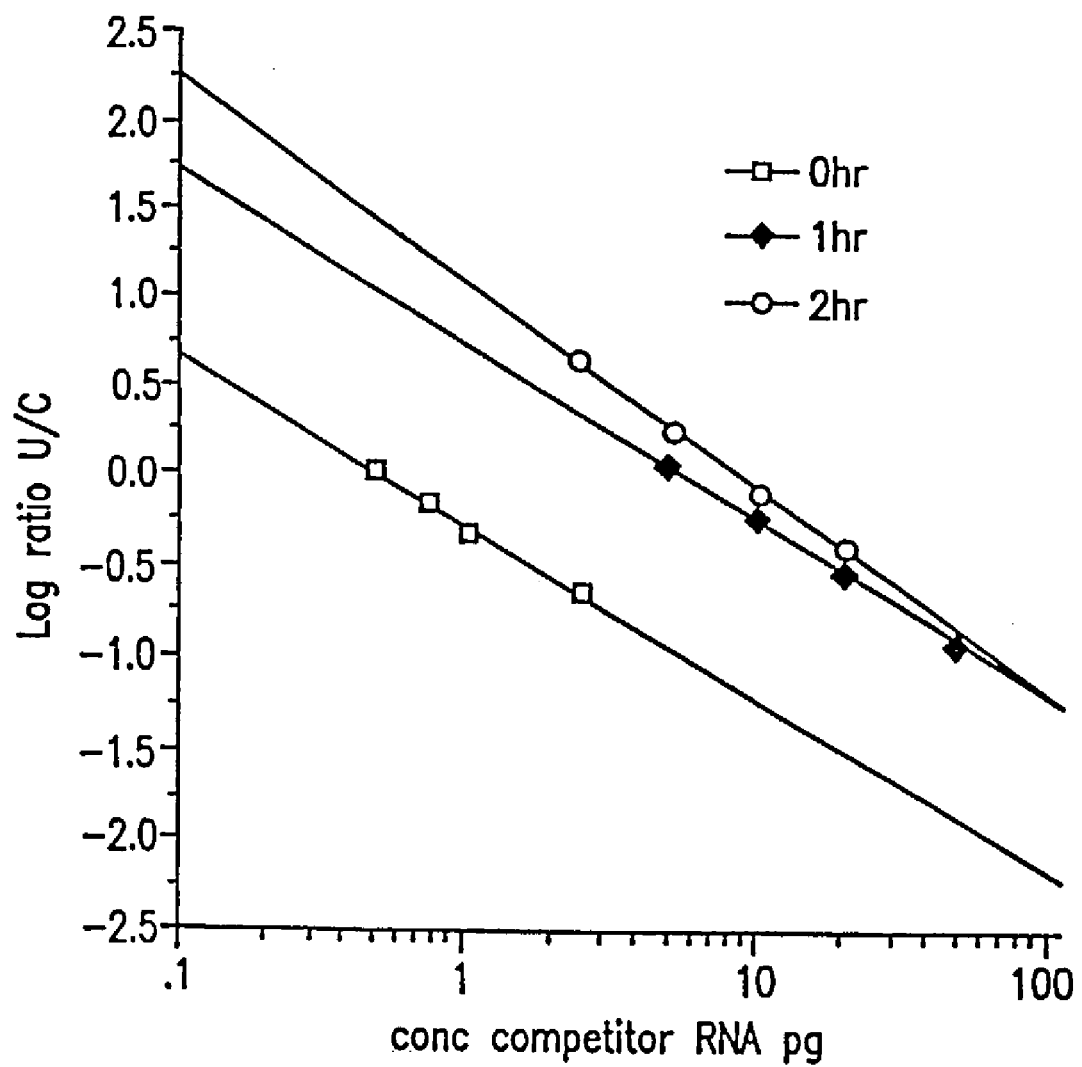
FIG. 18 is a plot of die log ratio (U/C) of unknown target DNA product to competitor DNA product versus the concentration of competitor mRNA. The plot is used to calculate the target messenger RNA concentration in a quantitative competitive reverse transcription polymerase chain reaction (QC-RT-PCR).
Figure 19:
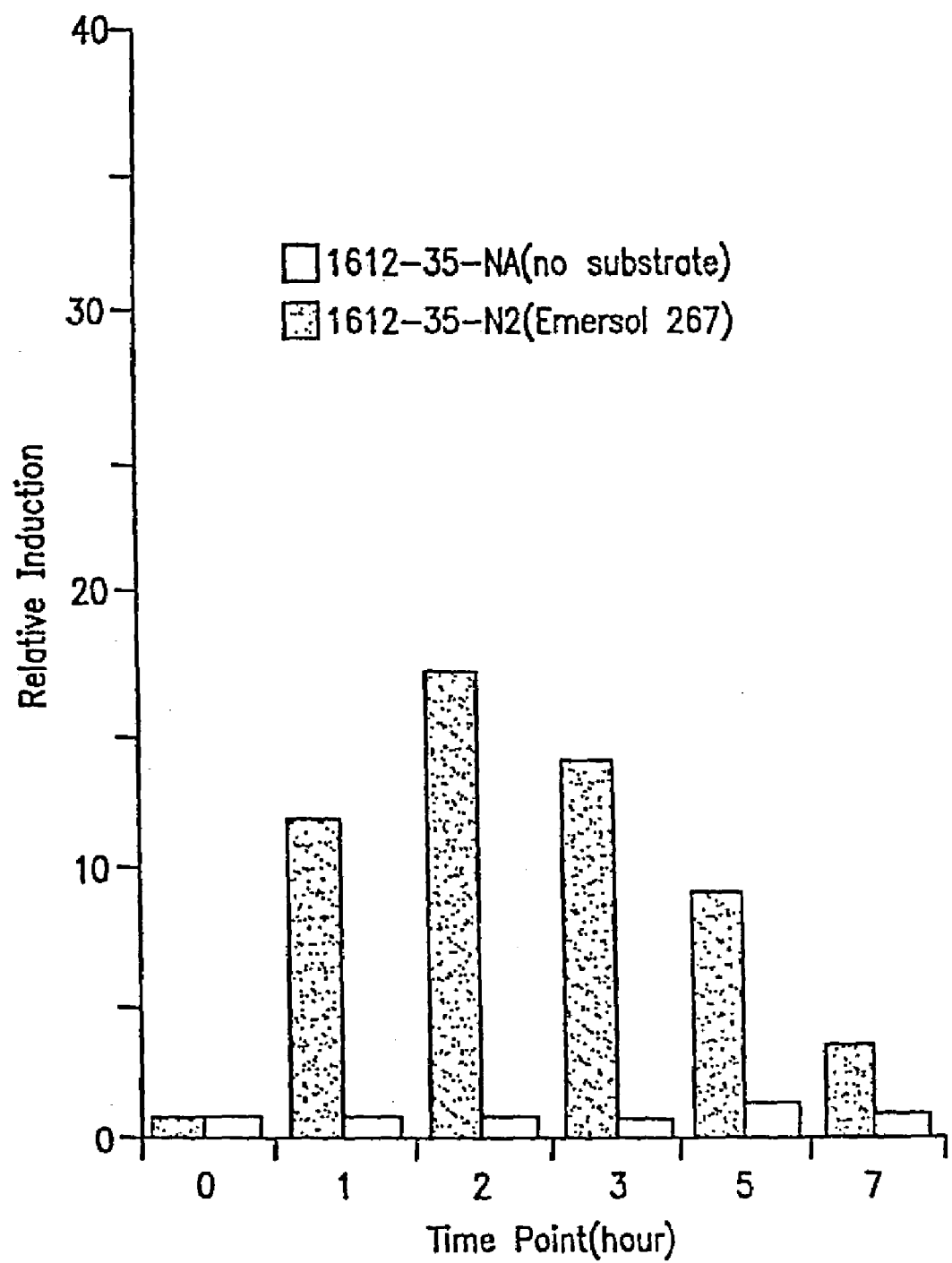
FIG. 19 is a graph showing the relative induction of C. tropicalis ATCC 20962 CYP52A5A (SEQ ID NO: 90) by the addition of the fatty acid substrate Emersol® 267 to the growth medium.

Identification of CYP and CPR Genes Induced by Selected Fatty Acid and Alkane Substrates Genes whose transcription is turned on by the presence of selected fatty acid or alkane substrates have been identified using the QC-RT-PCR assay. This assay was used to measure (CYP) and (CPR) gene expression in fermentor grown cultures C. tropicalis ATCC 20962. This method involves the isolation of total cellular RNA from cultures of C. tropicalis and the quantification of a specific mRNA within that sample through the design and use of sequence specific QC-RT-PCR primers and an RNA competitor. Quantification is achieved through the use of known concentrations of highly homologous competitor RNA in the QC-RT-PCR reactions. The resulting QC-RT-PCR amplified cDNA's are separated and quantitated through the use of ion pairing reverse phase HPLC. This assay was used to characterize the expression of CYP52 genes of C. tropicalis ATCC 20962 in response to various fatty acid and alkane substrates. Genes which were induced were identified by the calculation of their mRNA concentration at various times before and after induction. FIG. 18 provides an example of how the concentration of mRNA for CYP52A5 can be calculated using the QC-RT-PCR assay. The log ratio of unknown (U) to competitor product (C) is plotted versus the concentration of competitor RNA present in the QC-RT-PCR reactions. The concentration of competitor which results in a log ratio of U/C of zero, represents the point where the unknown messenger RNA concentration is equal to the concentration of the competitor. FIG. 18 allows for the calculation of the amount of CYP52A5 message present in 100 ng of total RNA isolated from cell samples taken at 0, 1, and 2 hours after the addition of Emersol® 267 in a fermentor run. From this analysis, it is possible to determine the concentration of the CYP52A5 mRNA present in 100 ng of total cellular RNA. In the plot contained in FIG. 18 it takes 0.46 pg of competitor to equal the number of mRNA's of CYP52A5 in 100 ng of RNA isolated from cells just prior (time 0) to the addition of the substrate, Emersol® 267. In cell samples taken at one and two hours after the addition of Emersol® 267 it takes 5.5 and 8.5 pg of competitor RNA, respectively. This result demonstrates that CYP52A5 (SEQ ID NOS: 90 and 91) is induced more than 18 fold within two hours after the addition of Emersol® 267. This type of analysis was used to demonstrate that CYP52A5 (SEQ ID NO: 90 and 91) is induced by Emersol® 267. FIG. 19 shows the relative amounts of CYP52A5 (SEQ ID NOS: 90 and 91) expression in fermentor runs with and without Emersol® 267 as a substrate. The differences in the CYP52A5 (SEQ. ID NOS: 90 and 91) expression patterns are due to the addition of Emersol® 267 to the fermentation medium.

Figure 20:
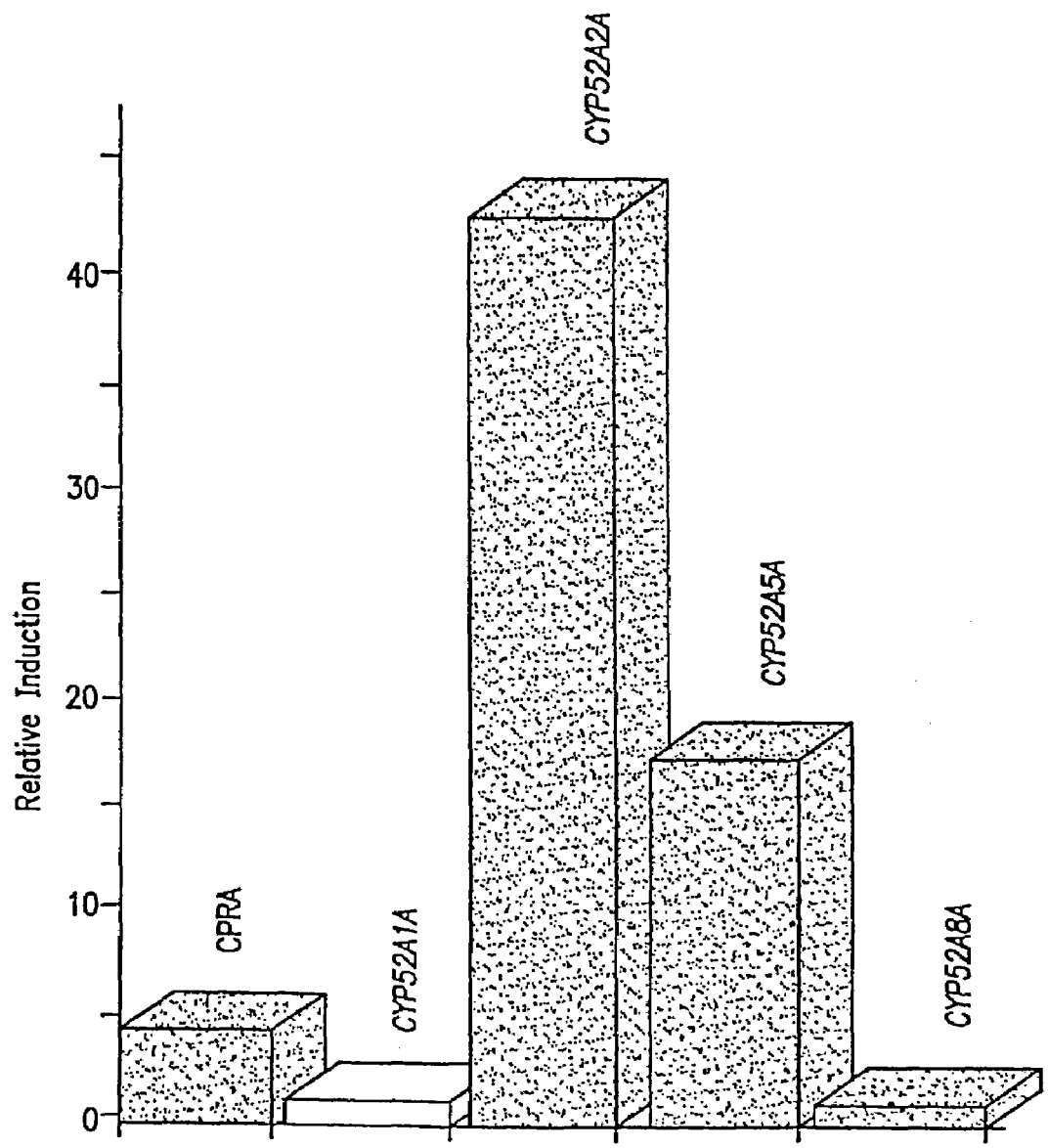
FIG. 20 is a graph showings the induction of C. tropicalis ATCC 20962 CYP52 and CPR genes by Emersol® 267. P450. genes CYP52A3A (SEQ ID NO: 88), CYP52A3B (SEQ ID NO: 89), and CYP52D4A (SEQ ID NO: 94) are expressed at levels below the detection level of the QC-RT-PCR assay.
Figure 34:
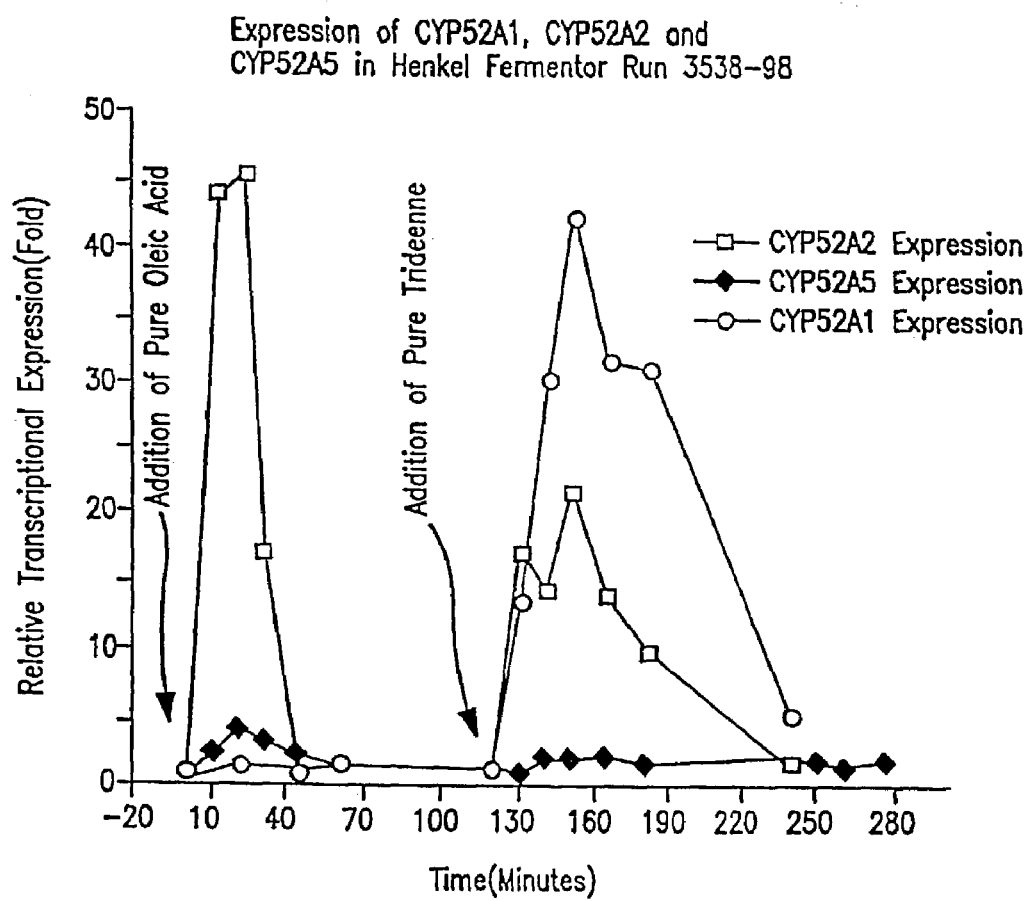
FIG. 34 is a graph showing the expression of CYP52A1 (SEQ ID NO: 85), CYP52A2 (SEQ ID NO: 86) and CYP52A5 genes (SEQ ID NOS: 90 and 91) from C. tropicalis 20962 in a fermentor run upon the addition of amounts of the substrate oleic acid or tridecane in a spiking experiment.
Figure 36:
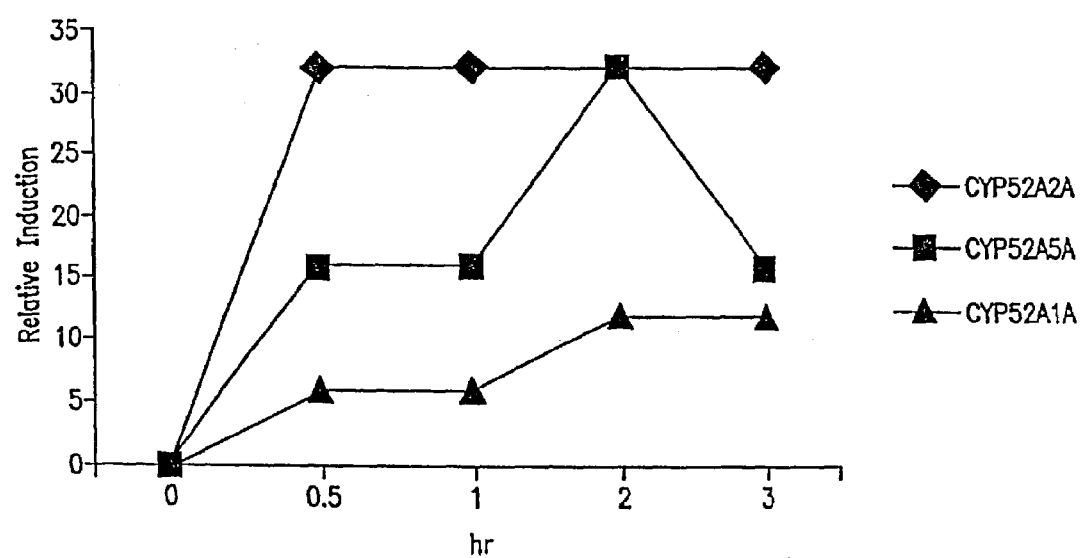
FIG. 36 is a graph showing the induction of expression of CYP52A1A, CYP52A2A and CYP52A5A in a fermentor run upon addition of the substrate octadecane. No induction of CYP52A3A or CYP52A3B was observed under these conditions.

This analysis clearly demonstrates that expression of CYP52A5 (SEQ ID NOS: 90 and 91) in C. tropicalis 20962 is inducible by the addition of Emersol® 267 to the growth medium. This analysis was performed to characterize the expression of CYP52A2A (SEQ ID NO: 86), CYP52A3AB (SEQ ID NOS: 88 and 89), CYP52A8A (SEQ ID NO: 92), CYP52A1A (SEQ ID NO: 85), CYP52D4A (SEQ ID NO: 94) and CPRB (SEQ ID NO: 82) in response to the presence of Emersol® 267 in the fermentation medium (FIG. 20). The results of these analysis+ indicate, that like the CYP52A5 gene (SEQ ID NOS: 90 and 91) of C. tropicalis 20962, the CYP52A2A gene (SEQ ID NO: 86) is inducible by Emersol® 267. A small induction is observed for CYP52A1A (SEQ ID NO: 85) and CYP52A8A (SEQ ID NO: 92). In contrast, any induction for CYP52D4A (SEQ ID NO: 94), CYP52A3A (SEQ ID NO: 88), CYP52A3B (SEQ ID NO: 89) is below the level of detection of the assay. CPRB (SEQ ID NO: 82) is moderately induced by Emersol® 267, four to five fold. The results of these analysis are summarized in FIG. 20. FIG. 34 provides an example of selective induction of CYP52A genes. When pure fatty acid or alkanes are spiked into a fermentor containing C. tropicalis 20962 or a derivative thereof, the transcriptional activation of CYP52A genes was detected using the QC-RT-PCR assay. FIG. 34 shows that pure oleic acid (C18:1) strongly induces CYP52A2A (SEQ ID NO: 86) while inducing CYP52A5 (SEQ ID NOS: 90 and 91). In the same fermentor addition of pure alkane (tridecane) shows strong induction of both CYP52A2A (SEQ ID NO: 86) and CYP52A1A (SEQ ID NO: 85). However, tridecane did not induce CYP52A5 (SEQ ID NOS: 90 and 91). In a separate fermentation using ATCC 20962, containing pure octadecane as the substrate, induction of CYP52A2A, CYP52A5A and CYP52A1A is detected (see FIG. 36). The foregoing demonstrates selective induction of particular CYP genes by specific substrates, thus providing techniques for selective metabolic engineering of cell strains. For example, if tridecane modification is desired, organisms engineered for high levels of CYP52A2A (SEQ ID NO: 86) and CYP52A1A (SEQ ID NO: 85) activity are indicated. If oleic acid modification is desired, organisms engineered for high levels of CYP52A2A (SEQ ID NO: 86) activity are indicated.

EXAMPLE 15

Figure 21:
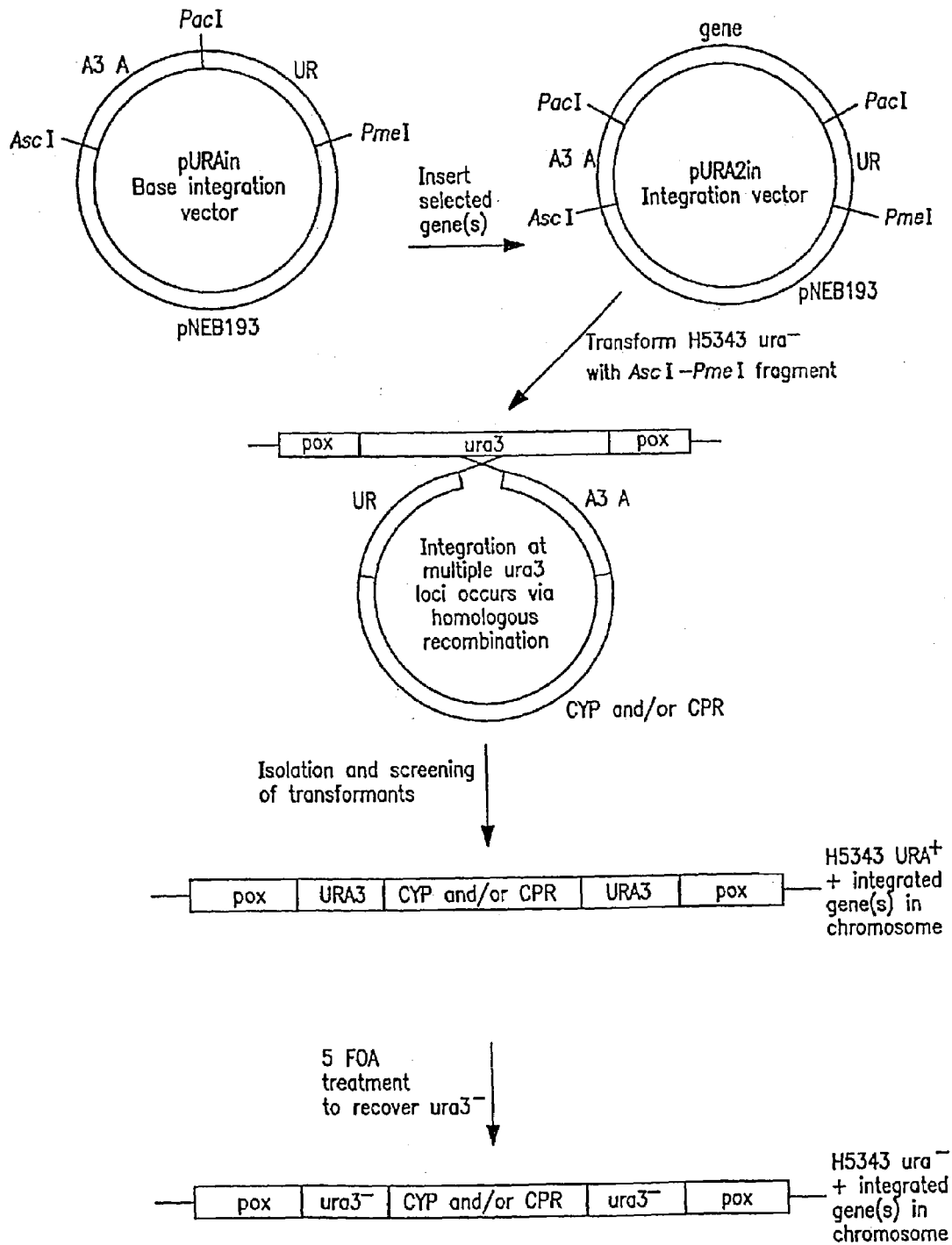
FIG. 21 is a scheme to integrate selected genes into the genome of Candida tropicalis strains and recovery of URA3A selectable marker.
Figure 22:
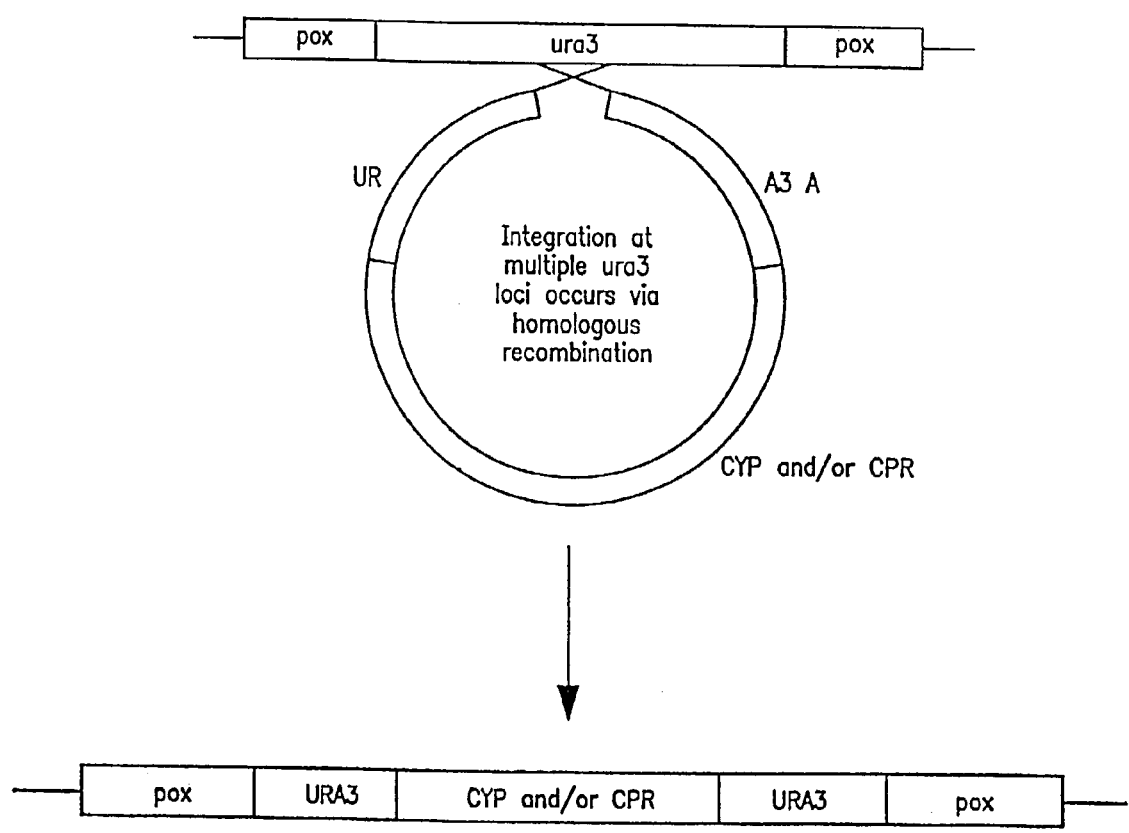
FIG. 22 is a schematic representation of the transformation of C. tropicalis H5343 ura3 with CYP and/or CPR genes. Only one URA3 locus needs to be functional. There are a total of 6 possible ura3 targets (5ura3A loci-2 pox4 disruptions, 2 pox 5 disruptions, 1 ura3A locus; and 1 ura3B locus).

Integration of Selected CYP and CPR Genes into the Genome of Candida tropicalis In order to integrate selected genes into the chromosome of C. tropicalis 20336 or its descendants, there has to be a target DNA sequence, which may or may not be an intact gene, into which the genes can be inserted. There must also be a method to select for the integration event. In some cases the target DNA sequence and the selectable marker are the same and, if so, then there must also be a method to regain use of the target gene as a selectable marker following the integration event. In C. tropicalis and its descendants, one gene which fits these criteria is URA3A, encoding orotidine-5'-phosphate decarboxylase. Using it as a target for integration, ura⁻ variants of C. tropicalis can be transformed in such a way as to regenerate a URA⁺ genotype via homologous recombination (FIG. 21). Depending upon the design of the integration vector, one or more genes can be integrated into the genome at the same time. Using a split URA3A gene oriented as shown in FIG. 22, homologous integration would yield at least one copy of the gene(s) of interest which are inserted between the split portions of the URA3A gene. Moreover, because of the high sequence similarity between URA3A and URA3B genes, integration of the construct can occur at both the URA3A and URA3B loci. Subsequently, an oligonucleotide designed with a deletion in a portion of the URA gene based on the identical sequence across both the URA3A and URA3B genes, can be utilized to yield C. tropicalis transformants which are once again ura⁻ but which still carry one or more newly integrated genes of choice (FIG. 21). ura⁻ variants of C. tropicalis can also be isolated via other methods such as classical mutagenesis or by spontaneous mutation. Using well established protocols, selection of ura⁻ strains can be facilitated by the use of 5-fluoroorotic acid (5-FOA) as described, e.g., in Boeke et al., Mol. Gen. Genet. 197:345–346, (1984), incorporated herein by reference. The utility of this approach for the manipulation of *C. tropicalis* has been well documented as described, e.g., in Picataggio et al., *Mol. and Cell. Biol.* 11:4333–4339 (1991); Rohrer et al., *Appl. Microbiol. Biotechnol.* 36:650–654 (1992); Picataggio et al., *Bio/Technology* 10:894–898 (1992); U.S. Pat. No. 5,648,247; U.S. Pat. No. 5,620,878; U.S. Pat. No. 5,204,252; U.S. Pat. No. 5,254,466, all of which are incorporated herein by reference.

A. Construction of a URA Integration Vector, pURAin.

Figure 24:
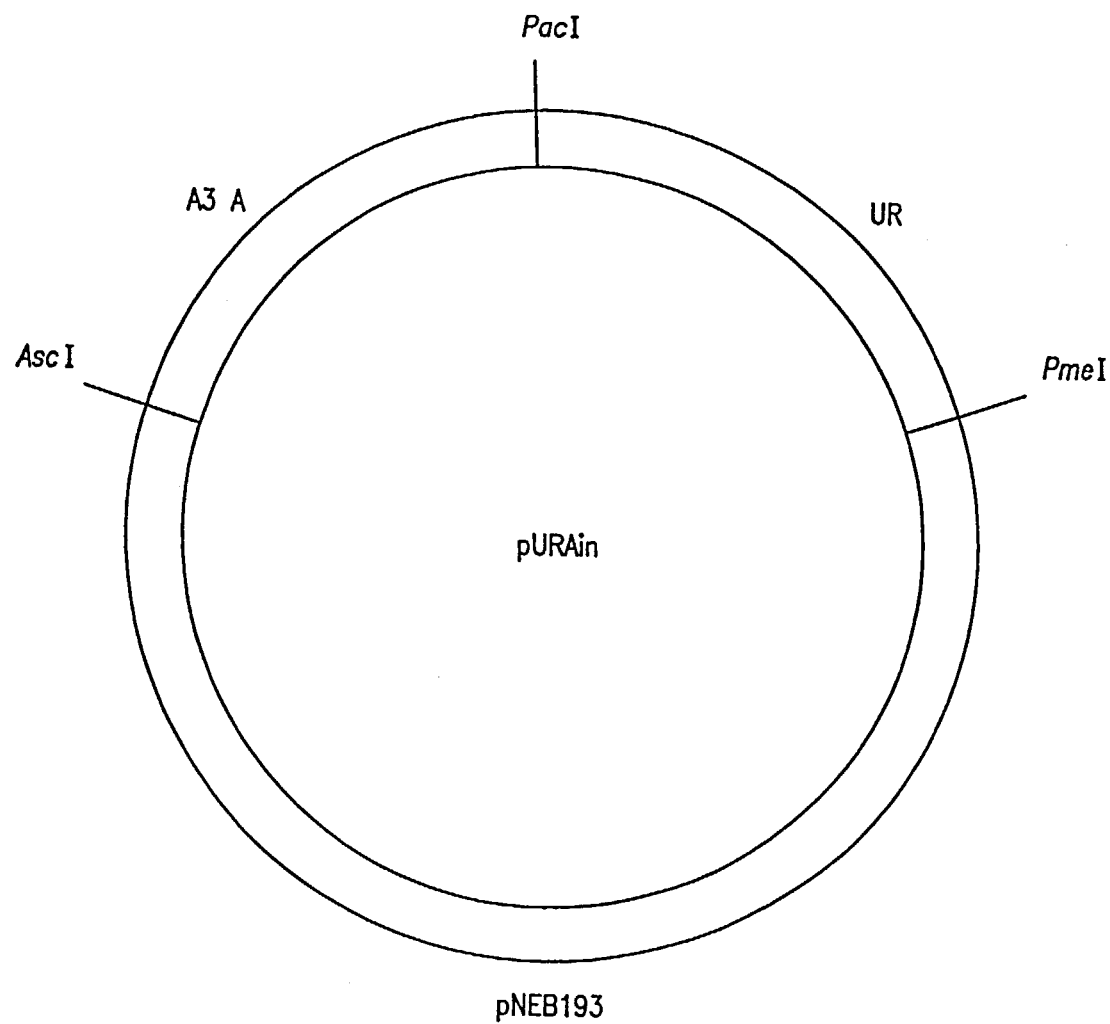
FIG. 24 is a schematic representation of the plasmid pURAin, the base vector for integrating selected genes into the genome of C. tropicalis. The detailed construction of pURAin is described in the text.
Figure 25:
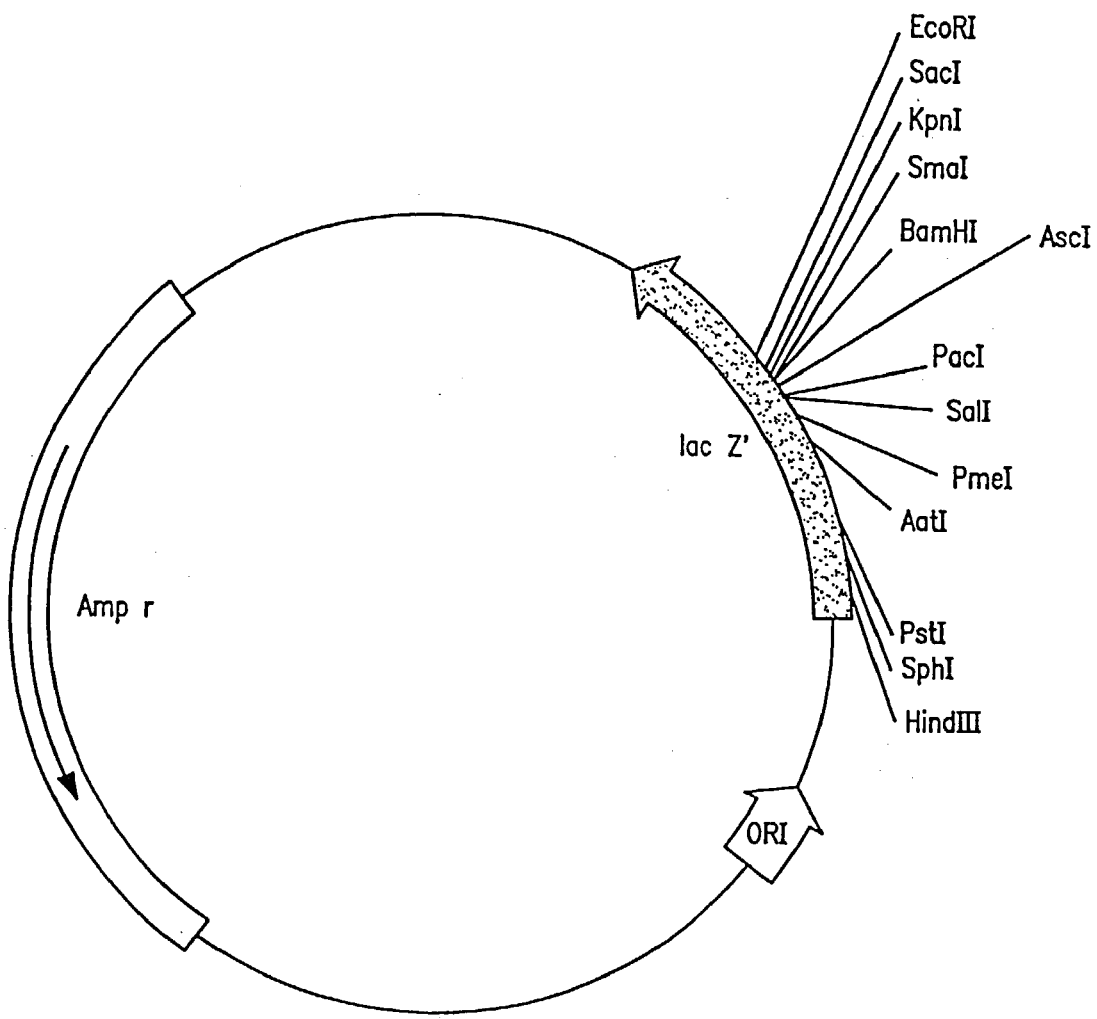
FIG. 25 is a schematic representation of the plasmid pNEB193 cloning vector (commercially available from New England Biolabs, Beverly, Mass.).

Primers were designed and synthesized based on the 1712 bp sequence of the URA3A gene of *C. tropicalis* 20336 (see FIG. 23). The nucleotide sequence of the URA3A gene of *C. tropicalis* 20336 is set forth in SEQ ID NO: 105 and the amino acid sequence of the encoded protein is set forth in SEQ ID NO: 106. URA3A Primer Set #1a (SEQ ID NO: 9) and #1b (SEQ ID NO: 10) (Table 4) was used in PCR with *C. tropicalis* 20336 genomic DNA to amplify URA3A sequences between nucleotide 733 and 1688 as shown in FIG. 23. The primers are designed to introduce unique 5' AscI and 3' PacI restriction sites into the resulting amplified URA3A fragment. AscI and PacI sites were chosen because these sites are not present within CYP or CPR genes identified to date. URA3A Primer Set #2 was used in PCR with *C. tropicalis* 20336 genomic DNA as a template, to amplify URA3A sequences between nucleotide 9 and 758 as shown in FIG. 23. URA3A Primer set #2a (SEQ ID NO: 11) and #2b (SEQ ID NO: 12) (Table 4) was designed to introduce unique 5' PacI and 3' PmeI restriction sites into the resulting amplified URA3A fragment. The PmeI site is also not present within CYP and CPR genes identified to date. PCR fragments of the URA3A gene were purified, restricted with AscI, PacI and PmeI restriction enzymes and ligated to a gel purified, QiaexII cleaned AscI-PmeI digest of plasmid pNEB193 (FIG. 25) purchased from New England Biolabs (Beverly, Mass.). The ligation was performed with an equimolar number of DNA termini at 16° C. for 16 hr using T4 DNA ligase (New England Biolabs). Ligations were transformed into *E. coli* XL1-Blue cells (Stratagene, LaJolla, Calif.) according to manufacturers recommendations. White colonies were isolated, grown, plasmid DNA isolated and digested with AscI-PmeI to confirm insertion of the modified URA3A into pNEB193. The resulting base integration vector was named pURAin (FIG. 24).

B. Amplification of CYP52A2A, CYP52A3A, CYP52A5A and CPRB from *C. tropicalis* 20336 Genomic DNA The genes encoding CYP52A2A, (SEQ ID NO: 86) and CYP52A3A (SEQ ID NO: 88) from *C. tropicalis* 20336 were amplified from genomic clones (pPA15 and pPA57, respectively) (FIGS. 26 and 29) via PCR using primers (Primer CYP2A#1, SEQ ID NO: 1 and Primer CYP2A#2, SEQ ID NO: 2 for CYP52A2A) (Primer CYP3A#1, SEQ ID NO: 3 and Primer CYP3A#2, SEQ ID NO: 4 for CYP52A3A) to introduce PacI cloning sites. These PCR primers were designed based upon the DNA sequence determined for CYP52A2A (SEQ ID NO: 86) (FIG. 15). The AmpliTaq Gold PCR kit (Perkin Elmer Cetus, Foster City, Calif.) was used according to manufacturers specifications. The CYP52A2A PCR amplification product was 2,230 base pairs in length, yielding 496 bp of DNA upstream of the CYP52A2A start codon and 168 bp downstream of the stop codon for the CYP52A2A ORF. The CYP52A3A PCR amplification product was 2154 base pairs in length, yielding 437 bp of DNA upstream of the CYP52A3A start codon and 97 bp downstream of the stop codon for the CYP52A3A ORF. The CYP52A3A PCR amplification product was 2154 base pairs in length, yielding 437 bp of DNA upstream of the CYP52A3A start codon and 97 bp downstream of the stop codon for the CYP52A3A ORF.

The gene encoding CYP52A5A (SEQ ID NO: 90) from *C. tropicalis* 20336 was amplified from genomic DNA via PCR using primers (Primer CYP 5A#1, SEQ ID NO: 5 and Primer CYP 5A#2, SEQ ID NO: 6) to introduce PacI cloning sites. These PCR primers were designed based upon the DNA sequence determined for CYP52A5A (SEQ ID NO: 90). The Expand Hi-Fi Taq PCR kit (Boehringer Mannheim, Indianapolis, Ind.) was used according to manufacturers specifications. The CYP52A5A PCR amplification product was 3,298 base pairs in length.

The gene encoding CPRB (SEQ ID NO: 82) from *C. tropicalis* 20336 was amplified from genomic DNA via PCR using primers (CPR B#1, SEQ ID NO: 7 and CPR B#2, SEQ ID NO: 8) based upon the DNA sequence determined for CPRB (SEQ ID NO: 82) (FIG. 13). These primers were designed to introduce unique PacI cloning sites. The Expand Hi-Fi Taq PCR kit (Boehringer Mannheim, Indianapolis, Ind.) was used according to manufacturers specifications. The CPRB PCR product was 3266 bp in length, yielding 747 bp pf DNA upstream of the CPRB start codon and 493 bp downstream of the stop codon for the CPRB ORF. The resulting PCR products were isolated via agarose gel electrophoresis, purified using QiaexII and digested with PacI. The PCR fragments were purified, desalted and concentrated using a Microcon 100 (Amicon, Beverly, Mass.).

The above described amplification procedures are applicable to the other genes listed in Table 5 using the respectively indicated primers.

C. Cloning of CYP and CPR Genes into pURAin.

The next step was to clone the selected CYP and CPR genes into the pURAin integration vector. In a preferred aspect of the present invention, no foreign DNA other than that specifically provided by synthetic restriction site sequences are incorporated into the DNA which was cloned into the genome of *C. tropicalis*, i.e., with the exception of restriction site DNA only native *C. tropicalis* DNA sequences are incorporated into the genome. pURAin was digested with PacI, Qiaex II cleaned, and dephosphorylated with Shrimp Alkaline Phosphatase (SAP) (United States Biochemical, Cleveland, Ohio) according the manufacturer's recommendations. Approximately 500 ng of PacI linearized pURAin was dephosphorylated for 1 hr at 37° C. using SAP at a concentration of 0.2 Units of enzyme per 1 pmol of DNA termini. The reaction was stopped by heat inactivation at 65° C. for 20 min.

Figure 27:
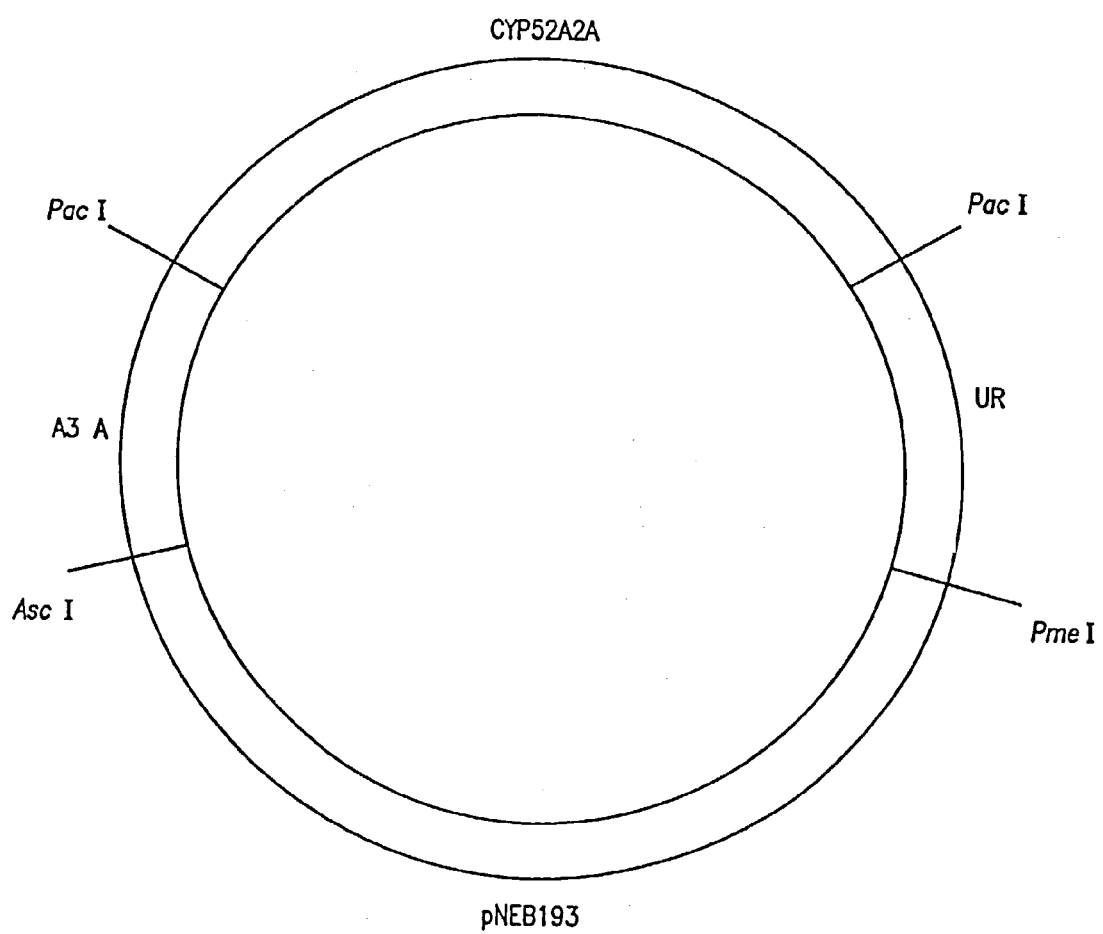
FIG. 27 is a schematic representation of pURA2in, the base vector is constructed in pNEB193 which contains the 8 bp recognition sequences for Asc I, Pac I and Pme I. URA3A (SEQ ID NO: 105) and CYP52A2A (SEQ ID NO: 86) do not contain these 8 bp recognition sites. URA3A is inverted so that the transforming fragment will attempt to recircularize prior to integration. An Asc I/Pme I fragment was used to transform H5343 ura⁻.

The CYP52A2A PacI fragment derived using the primer shown in Table 4 was ligated to plasmid pURAin which had also been digested with PacI. PacI digested pURAin was dephosphorylated, and ligated to the CYP52A2A ULTMA PCR product as described previously. The ligation mixture was transformed into *E. coli* XL1 Blue MRF' (Stratagene) and 2 resistant colonies were selected and screened for correct constructs which should contain vector sequence, the inverted URA3A gene, and the amplified CYP52A2A gene (SEQ ID NO: 86) of 20336. AscI-PmeI digestion identified one of the two constructs, plasmid pURA2in, as being correct (FIG. 27). This plasmid was sequenced and compared to CYP52A2A (SEQ ID NO: 86) to confirm that PCR did not introduce DNA base changes that would result in an amino acid change.

Prior to its use, the CPRB PacI fragment derived using the primers shown in Table 4 was sequenced and compared to CPRB (SEQ ID NO: 82) to confirm that PCR did not introduce DNA base pair changes that would result in an amino acid change. Following confirmation, CPRB (SEQ ID NO: 82) was ligated to plasmid pURAin which had also been digested with PacI. PacI digested pURAin was dephosphorylated, and ligated to the CPR Expand Hi-Fi PCR product as described previously. The ligation mixture was transformed into *E. coli* XL1 Blue MRF' (Stratagene) and several resistant colonies were selected and screened for correct constructs which should contain vector sequence, the inverted URA3A gene, and the amplified CPRB gene (SEQ ID NO: 82) of 20336. AscI-PmeI digestion confirmed a successful construct, pURAREDBin.

In a manner similar to the above, each of the other CYP and CPR genes disclosed herein are cloned into pURAin. PacI fragments of these genes, whose sequences are given in FIGS. 13 and 15, are derivable by methods known to those skilled in the art.

1) Construction of Vectors Used to Generate HDC 20 and HDC 23

A previously constructed integration vector containing CPRB (SEQ ID NO: 82), pURAREDBin, was chosen as the starting vector. This vector was partially digested with PacI and the linearized fragment was gel-isolated. The active PacI was destroyed by treatment with T4 DNA polymerase and the vector was re-ligated. Subsequent isolation and complete digestion of this new plasmid yielded a vector now containing only one active PacI site. This fragment was gel-isolated, dephosphorylated and ligated to the CYP52A2A PacI fragment. Vectors that contain the CYP52A2A (SEQ ID NO: 86) and CPRB (SEQ ID NO: 82) genes oriented in the same direction, pURAin CPR 2A S, as well as opposite directions (5' ends connected), pURAin CPR 2A O, were generated.

D. Confirmation of CYP Integration (FIG. 21 for Integration Scheme) into the Genome of *C. tropicalis*

Figure 28:
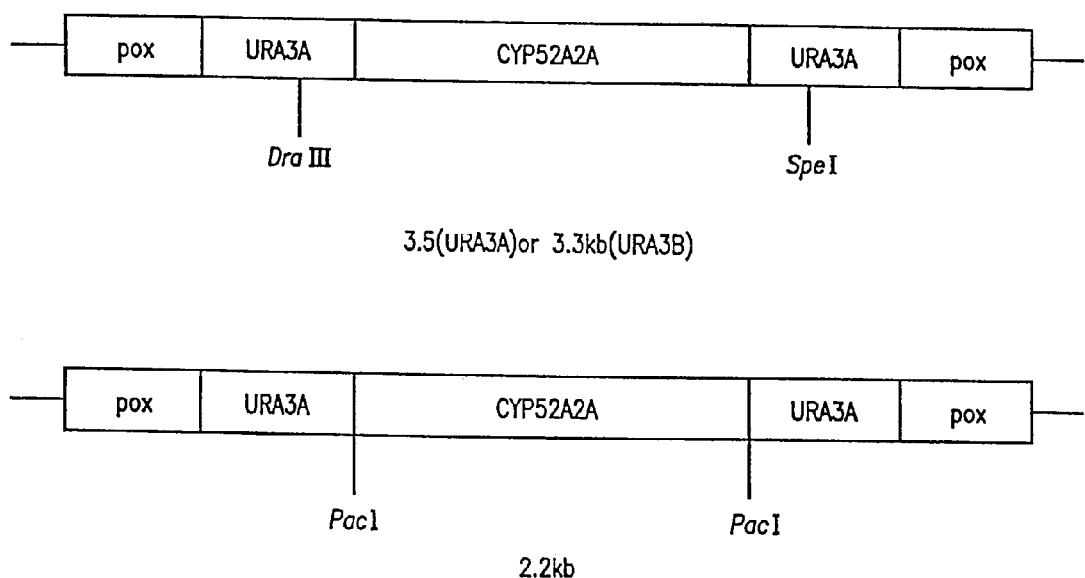
FIG. 28 shows a scheme to detect integration of CYP52A2A gene (SEQ ID NO: 86) into the genome of H5343 ura⁻. In all cases, hybridization band intensity could reflect the number of integrations.

Based on die construct, pURA2in, used to transform H5343 ura⁻, a scheme to detect integration was devised. Genomic DNA from transformants was digested with Dra III and Spe I which are enzymes that cut within the URA3A, and URA3B genes but not within the integrated CYP52A2A gene. Digestion of genomic DNA where an integration had occurred at the URA3A or URA3B loci would be expected to result in a 3.5 kb or a 3.3 kb fragment, respectively (FIG. 28). Moreover, digestion of the same genomic DNA with PacI would yield a 2.2 kb fragment characteristic for the integrated CYP52A2A gene (FIG. 28). Southern hybridizations of these digests with fragments of the CYP52A2A gene were used to screen for these integration events. Intensity of the band signal from the Southern using PacI digestion was used as a measure of the number of integration events, ((i.e. the more copies of the CYP52A2A gene (SEQ ID NO: 86) which are present, the stronger the hybridization signal)).

*C. tropicalis* H5343 transformed URA prototrophs were grown at 30° C., 170 rpm, in 10 ml SC-uracil media for preparation of genomic DNA. Genomic DNA was isolated by the method described previously. Genomic DNA was digested with SpeI and DraIII. A 0.95% agarose gel was used to prepare a Southern hybridization blot. The DNA from the gel was transferred to a MagnaCharge nylon filter membrane (MSI Technologies, Westboro, Mass.) according to the alkaline transfer method of Sambrook et al., supra. For the Southern hybridization, a 2.2 kb CYP52A2A DNA fragment was used as a hybridization probe. 300 ng of CYP52A2A DNA was labeled using a ECL Direct labeling and detection system (Amersham) and the Southern was processed according to the ECL kit specifications. The blot was processed in a volume of 30 ml of hybridization fluid corresponding to 0.125 ml/cm². Following a prehybridization at 42° C. for 1 hr, 300 ng of CYP52A2A probe was added and the hybridization continued for 16 hr at 42° C. Following hybridization, the blots were washed two times for 20 min each at 42° C. in primary wash containing urea. Two 5 min secondary washes at RT were conducted, followed by detection according to directions. The blots were exposed for 16 hours (hr) as recommended.

Integration was confirmed by the detection of a SpeI-DraIII 3.5 kb fragment from the genomic DNA of the transformants but not with the *C. tropicalis* 20336 control. Subsequently, a PacI digestion of the genomic DNA of the positive transformants, followed by a Southern hybridization using an CYP52A2A gene probe, confirmed integration by the detection of a 2.2 kb fragment. The resulting CYP52A2A integrated strain was named HDC1 (see Table 1).

In a manner similar to the above, each of the genes contained in the PacI fragments which are described in Section 3c above were confirmed for integration into the genome of *C. tropicalis*.

Transformants generated by transformation with the vectors, pURAin CPR 2A S or pURAin CPR 2A O, were analyzed by Southern hybridization for integration of both the CYP52A2A (SEQ ID NO: 86) and CPRB (SEQ ID NO: 82) genes tandemly. Three strains were generated in which the CYP52A2A (SEQ ID NO: 86) and CPRB (SEQ ID NO: 82) genes integrated are in the opposite orientation (HDC 20-1, HDC 20-2 and HDC 20-3) and three were generated with the CYP52A2A (SEQ ID NO: 86) and CPRB (SEQ ID NO: 82) genes integrated in the same orientation (HDC 23-1, HDC 23-2 and HDC 23-3), Table 1.

E. Confirmation of CPRB Integration into H5343 ura⁻

Seven transformants were screened by colony PCR using CPRB primer #2 (SEQ ID NO: 8) and a URA3A-specific primer. In five of the transformants, successful integration was detected by the presence of a 3899 bp PCR product. This 3899 bp PCR product represents the CPRB gene adjacent to the URA3A gene in the genome of H5343 thereby confirming integration. The resulting CPRB integrated strains were named HDC10-1 and HDC10-2 (see Table 1).

F. Strain Evaluation.

As determined by quantitative PCR, when compared to parent H5343, HDC10-1 contained three additional copies of the reductase gene and HDC10-2 contained four additional copies of the reductase gene. Evaluations of HDC20-1, HDC20-2 and HDC20-3 based on Southern hybridization data indicates that HDC20-1 contained multiple integrations, i.e., 2 to 3 times that of HDC20-2 or HDC20-3. Evaluations of HDC23-1, HDC23-2, and HDC23-3 base on Southern hybridization data indicates that HDC23-3 contained multiple integrations, i.e., 2 to 3 times that of HDC23-1 or HDC23-2. The data in Table 8 indicates that the integration of components of the ω-hydroxylase complex have a positive effect on the improvement of *Candida tropicalis* ATCC 20962 as a biocatalyst. The results indicate that CYP52A5A (SEQ ID NO: 90) is an important gene for the conversion of oleic acid to diacid. Surprisingly, tandem integrations of CYP and CPR genes oriented in the opposite direction (HDC 20 strains) seem to be less productive than tandem integrations oriented in the same direction (HDC 23 strains), Tables 1 and 8.

TABLE 9

| Media Composition | |
|---|---|
| LB Broth | |
| Bacto Tryptone | 10 g |
| Bacto Yeast Extract | 5 g |
| Sodium Chloride | 10 g |
| Distilled Water | 1,000 ml |
| LB Agar | |
| Bacto Tryptone | 10 g |
| Bacto Yeast Extract | 5 g |
| Sodium Chloride | 10 g |
| Agar | 15 g |
| Distilled Water | 1,000 ml |
| LB Top Agarose | |
| Bacto Tryptone | 10 g |
| Bacto Yeast Extract | 5 g |
| Sodium Chloride | 10 g |
| Agarose | 7 g |
| Distilled Water | 1,000 ml |
| NZCYM Broth | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Distilled Water | 1,000 ml |
| NZCYM Agar | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Agar | 15 g |
| Distilled Water | 1,000 ml |
| NZCYM Top Marose | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Agarose | 7 g |
| Distilled Water | 1,000 ml |
| YEPD Broth | |
| Bacto Yeast Extract | 10 g |
| Bacto Peptone | 20 g |
| Glucose | 20 g |
| Distilled Water | 1,000 ml |
| YEPD Agar* | |
| Bacto Yeast Extract | 10 g |
| Bacto Peptone | 20 g |
| Glucose | 20 g |
| Agar | 20 g |
| Distilled Water | 1,000 ml |
| SC-uracil* | |
| Bacto-yeast nitrogen base without amino acids | 6.7 g |
| Glucose | 20 g |
| Bacto-agar | 20 g |
| Drop-out mix | 2 g |
| Distilled water | 1,000 ml |
| DCA2 medium | |
| Peptone | 3.0 g/l |
| Yeast Extract | 6.0 g/l |
| Sodium Acetate | 3.0 g/l |
| Yeast Nitrogen Base (Difco) | 6.7 g/l |
| Glucose (anhydrous) | 50.0 g/l |
| Potassium Phosphate (dibasic, trihydrate) | 7.2 g/l |
| Potassium Phosphate (monobasic, anhydrous) | 9.3 g/l |
| DCA3 medium | |
| 0.3 M Phosphate buffer containing, pH 7.5 | |
| Glycerol | 50 g/l |
| Yeast Nitrogen base (Difco) | 6.7 g/l |
| Drop-out mix | |
| Adenine | 0.5 g |
| Arginine | 2 g |
| Aspartic acid | 2 g |
| Glutamine | 2 g |
| Glycine | 2 g |
| Inositol | 2 g |
| Leucine | 10 g |
| Methionine | 2 g |
| Phenylalanine | 2 g |
| Serine | 2 g |
| Tryptophan | 2 g |
| Valine | 2 g |
| Alanine | 2 g |
| Asparagine | 2 g |
| Cysteine | 2 g |
| Glutamic acid | 2 g |
| Histidine | 2 g |
| Isoleucine | 2 g |
| Lysine | 2 g |
| para-Aminobenzoic acid | 0.2 g |
| Proline | 2 g |
| Threonine | 2 g |
| Tyrosine | 2 g |

*See Kaiser et al., Methods in Yeast Genetics, Cold Spring Harbor Laboratory Press, USA (1994), incorporated herein by reference.

It will be understood that various modifications may be made to the embodiments and/or examples disclosed herein. Thus, the above description should not be construed as limiting, but merely as exemplifications of preferred embodiments. Those skilled in the art will envision other modifications within the scope and spirit of the claims appended hereto.

What is claimed is:

1. An isolated nucleic acid molecule comprising a regulatory region from a Cytochrome P450 monooxygenase 52A2A gene wherein the regulatory region consists of nucleotides 1–1198 of SEQ ID NO:86.

2. A vector comprising the isolated nucleic acid molecule of claim 1.

3. The vector of claim 2 wherein the vector is a plasmid, phagemid, phage, cosmid, or linear DNA vector.

4. An isolated host cell transformed or transfected with the vector of claim 2.

5. An isolated host cell transformed or transfected with the vector of claim 3.

* * * * *

SEQUENCE LISTING

<160> NUMBER OF SEQ ID NOS: 118

<210> SEQ ID NO 1
<211> LENGTH: 32
<212> TYPE: DNA
<213> ORGANISM: Artificial Sequence
<220> FEATURE:

-continued

<223> OTHER INFORMATION: Description of Artificial Sequence: Primer

<400> SEQUENCE: 1
ccttaattaa atgcacgaag cggagataaa ag        32

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
ccttaattaa gcataagctt gctcgagtct        30

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
ccttaattaa acgcaatggg aacatggagt g        31

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 4
ccttaattaa tcgcactacg gttattggta tcag        34

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 5
ccttaattaa tcaaagtacg ttcaggcgg        29

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 6
ccttaattaa ggcagacaac aacttggcaa agtc        34

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
ccttaattaa gaggtcgttg gttgagtttt c        31

```
<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
ccttaattaa ttgataatga cgttgcggg                               29

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 9
aggcgcgccg gagtccaaaa agaccaacct ctg                          33

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 10
ccttaattaa tacgtggata ccttcaagca agtg                         34

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 11
ccttaattaa gctcacgagt tttgggattt tcgag                        35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 12
gggtttaaac cgcagaggtt ggtcttttg gactc                         35

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 13
gggtttaaac                                                    10

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: Primer
```

```
<400> SEQUENCE: 14 aggcgcgcc                                                                9

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 15
ccttaattaa                                                              10

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: y=dCTP or dTTP
<220> FEATURE:
<221> NAME/KEY: misc_feature
<222> LOCATION: (9)..(10)
<223> OTHER INFORMATION: w=dATP or dTTP
<220> FEATURE:
<221> NAME/KEY: misc_feature
<222> LOCATION: (15)..(16)
<223> OTHER INFORMATION: w=dATP or dTTP
<220> FEATURE:
<221> NAME/KEY: misc_feature
<222> LOCATION: (18)..(19)
<223> OTHER INFORMATION: w=dATP or dTTP

<400> SEQUENCE: 16
tcycaaacwg gtacwgcwga a                                                 21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (12)..(13)
<223> OTHER INFORMATION: y=dCTP or dTTP
<220> FEATURE:
<221> NAME/KEY: misc_feature
<222> LOCATION: (15)..(16)
<223> OTHER INFORMATION: w=dATP or dTTP

<400> SEQUENCE: 17
ggtttgggta aytcwactta t                                                 21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
cgttattatc atttcttc                                                     18

<210> SEQ ID NO 19
<211> LENGTH: 20
```

```
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: m=dATP or dCTP
<220> FEATURE:
<221> NAME/KEY: misc_feature
<222> LOCATION: (9)..(10)
<223> OTHER INFORMATION: r=dATP or dGTP

<400> SEQUENCE: 19
gcmacaccrg tacctggacc                                            20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 20
atcccaatcg taatcagc                                              18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 21
acttgtcttc gtttagca                                              18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22
ctacgtctgt ggtgatgc                                              18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: n=dATP or dCTP or dGTP or dTTP
<220> FEATURE:
<221> NAME/KEY: misc_feature
<222> LOCATION: (6)..(7)
<223> OTHER INFORMATION: Y=dCTP or dTTP
<220> FEATURE:
<221> NAME/KEY: misc_feature
<222> LOCATION: (9)..(10)
<223> OTHER INFORMATION: n=dATP or dCTP or dGTP or dTTP
<220> FEATURE:
<221> NAME/KEY: misc_feature
<222> LOCATION: (12)..(13)
<223> OTHER INFORMATION: n=dATP or dCTP or dGTP or dTTP
<220> FEATURE:
<221> NAME/KEY: misc_feature
<222> LOCATION: (15)..(16)
```

```
<223> OTHER INFORMATION: n=dATP or dCTP or dGTP or dTTP

<400> SEQUENCE: 23
cgngayacna cngcngg                                                    17

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: r=dATP or dTTP
<220> FEATURE:
<221> NAME/KEY: misc_feature
<222> LOCATION: (6)..(7)
<223> OTHER INFORMATION: y=dCTP or dTTP
<220> FEATURE:
<221> NAME/KEY: misc_feature
<222> LOCATION: (9)..(10)
<223> OTHER INFORMATION: n=dATP or dCTP or dGTP or dTTP
<220> FEATURE:
<221> NAME/KEY: misc_feature
<222> LOCATION: (12)..(13)
<223> OTHER INFORMATION: n=dATP or dCTP or dGTP or dTTP
<220> FEATURE:
<221> NAME/KEY: misc_feature
<222> LOCATION: (15)..(16)
<223> OTHER INFORMATION: n=dATP or dCTP or dGTP or dTTP

<400> SEQUENCE: 24
agrgayacna cngcngg                                                    17

<210> SEQ ID NO 25
<211> LENGTH: 17
<212> TYPE: DNA
<213> ORGANISM: Artificial Sequence
<220> FEATURE:
<223> OTHER INFORMATION: Description of Artifiical Sequence: Primer
<220> FEATURE:
<221> NAME/KEY: misc_feature
<222> LOCATION: (3)..(4)
<223> OTHER INFORMATION: n=dATP or dCTP or dGTP or dTTP
<220> FEATURE:
<221> NAME/KEY: misc_feature
<222> LOCATION: (6)..(7)
<223> OTHER INFORMATION: r=dATP or dGTP
<220> FEATURE:
<221> NAME/KEY: misc_feature
<222> LOCATION: (9)..(10)
<223> OTHER INFORMATION: y=dCTP or dTTP
<220> FEATURE:
<221> NAME/KEY: misc_feature
<222> LOCATION: (12)..(13)
<223> OTHER INFORMATION: y=dCTP or dTTP
<220> FEATURE:
<221> NAME/KEY: misc_feature
<222> LOCATION: (15)..(16)
<223> OTHER INFORMATION: n=dATP or dCTP or dGTP or dTTP

<400> SEQUENCE: 25
agngcraayt gytgncc                                                    17

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
```

```
<222> LOCATION: (1)..(2)
<223> OTHER INFORMATION: y=dCTP or dTTP
<220> FEATURE:
<221> NAME/KEY: misc_feature
<222> LOCATION: (4)..(5)
<223> OTHER INFORMATION: n=dATP or dCTP or dGTP or dTTP
<220> FEATURE:
<221> NAME/KEY: misc_feature
<222> LOCATION: (7)..(8)
<223> OTHER INFORMATION: r=dATP or dGTP
<220> FEATURE:
<221> NAME/KEY: misc_feature
<222> LOCATION: (10)..(11)
<223> OTHER INFORMATION: y=dCTP or dTTP
<220> FEATURE:
<221> NAME/KEY: misc_feature
<222> LOCATION: (13)..(14)
<223> OTHER INFORMATION: y=dCTP or dTTP
<220> FEATURE:
<221> NAME/KEY: misc_feature
<222> LOCATION: (16)..(17)
<223> OTHER INFORMATION: n=dATP or dCTP or dGTP or dTTP

<400> SEQUENCE: 26
yaangcraay tgytgncc                                           18

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 27
attcaacggt ggtccaagaa tctgtttgg                               29

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 28
gagctatgtt gagaccacag tttgc                                   25

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 29
cttcagttaa agcaaattgt ttggcc                                  26

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
ctcgggaagc gcgccattgt gttgg                                   25

<210> SEQ ID NO 31
<211> LENGTH: 29
<212> TYPE: DNA
```

```
<213> ORGANISM: Artificial Sequence
<220> FEATURE:
<223> OTHER INFORMATION: Description of Artificial Sequence: Primer

<400> SEQUENCE: 31
taatacgact cactataggg cgaattggc                                29

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: r=dATP or dGTP
<220> FEATURE:
<221> NAME/KEY: misc_feature
<222> LOCATION: (4)..(5)
<223> OTHER INFORMATION: y=dCTP or dTTP
<220> FEATURE:
<221> NAME/KEY: misc_feature
<222> LOCATION: (16)..(17)
<223> OTHER INFORMATION: y=dCTP or dTTP

<400> SEQUENCE: 32
tgrytcaaac catctytctg g                                        21

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 33
ggaccggcgt taaaggg                                             17

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
catagtcgwa tyatgcttag acc                                      23

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 35
ggaccaccat tgaatgg                                             17

<210> SEQ ID NO 36
<211> LENGTH: 540
<212> TYPE: DNA
<213> ORGANISM: Candida tropicalis

<400> SEQUENCE: 36
atgattgaac aactcctaga atattggtat gtcgttgtgc cagtgttgta catcatcaaa      60
caactccttg catacacaaa gactcgcgtc ttgatgaaaa agttgggtgc tgctccagtc     120
```

```
acaaacaagt tgtacgacaa cgctttcggt atcgtcaatg gatggaaggc tctccagttc    180
aagaaagagg gcagggctca agagtacaac gattacaagt ttgaccactc caagaaccca    240
agcgtgggca cctacgtcag tattcttttc ggcaccagga tcgtcgtgac caaagatcca    300
gagaatatca aagctatttt ggcaacccag tttggtgatt tttctttggg caagaggcac    360
actcttttta agcctttgtt aggtgatggg atcttcacat tggacggcga aggctggaag    420
cacagcagag ccatgttgag accacagttt gccagagaac aagttgctca tgtgacgtcg    480
ttggaaccac acttccagtt gttgaagaag catattctta agcacaaggg tgaatacttt    540
```

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 37
ccgatgaagt tttcgacgag taccc    25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 38
aaggctttaa cgtgtccaat ctggtc    26

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 39
attatcgcca catacttcac caaatgg    27

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 40
cgagatcgtg gatacgctgg agtg    24

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 41
gccactcggt aactttgtca gggac    25

<210> SEQ ID NO 42
<211> LENGTH: 26
<212> TYPE: DNA

```
<213> ORGANISM: Artificial Sequence
<220> FEATURE:
<223> OTHER INFORMATION: Description of Artificial Sequence: Primer

<400> SEQUENCE: 42
cattgaactg agtagccaaa acagcc                                          26

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 43
cctacgtttg gtatcgctac tccgttg                                         27

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 44
tttccagcca gcaccgtcca ag                                              22

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 45
gcagagccga tctatgttgc gtcc                                            24

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 46
tcattgaatg cttccaggaa cctcg                                           25

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
aagagggcag ggctcaagag                                                 20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 48
tccatgtgaa gatcccatca c                                               21
```

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 49
cttgaaggcc gtgttgaacg                                                    20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 50
caggatttgt ctgagttgcc g                                                  21

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 51
ccattgcctt gagatacgcc attggtag                                           28

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 52
agccttggtg tcgttctttt caacgg                                             26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 53
ttgggtttgt ttgtttcctg tgtccg                                             26

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 54
cctttgacct tcaatctggc gtagacg                                            27

<210> SEQ ID NO 55
<211> LENGTH: 26
<212> TYPE: DNA
<213> ORGANISM: Artificial Sequence
<220> FEATURE:

<223> OTHER INFORMATION: Description of Artificial Sequence: Primer

<400> SEQUENCE: 55
gtttgctgaa tacgctgaag gtgatg             26

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 56
tggagctgaa caactctctc gtctcgg            27

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
ttcctcaaca cggacagcgg                    20

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 58
agtcaaccag gtgtggaact cgtc               24

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 59
ggatcctaat acgactcact atagggagga agagggcagg gctcaagag    49

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 60
tccatgtgaa gatcccatca cgagtgtgcc tcttgcccaa ag           42

<210> SEQ ID NO 61
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 61
ggatcctaat acgactcact atagggaggc cgatgaagtt ttcgacgagt accc    54

<210> SEQ ID NO 62
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 62
aaggctttaa cgtgtccaat ctggtcaaca tagctctgga gtgcttccaa cc                52

<210> SEQ ID NO 63
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 63
ggatcctaat acgactcact atagggagga ttatcgccac atacttcacc aaatgg            56

<210> SEQ ID NO 64
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 64
cgagatcgtg gatacgctgg agtgcgtcgc tcttcttctt caacaattca ag                52

<210> SEQ ID NO 65
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 65
cattgaactg agtagccaaa acagcccatg gtttcaatca atgggaggc                    49

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 66
ggatcctaat acgactcact atagggaggg ccactcggta actttgtcag ggac              54

<210> SEQ ID NO 67
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 67
ggatcctaat acgactcact atagggaggc ctacgtttgg tatcgctact ccgttg            56

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Primer

```
<400> SEQUENCE: 68
tttccagcca gcaccgtcca agcaacaagg agtacaagaa atcgtgtc          48

<210> SEQ ID NO 69
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 69
ggatcctaat acgactcact atagggaggg cagagccgat ctatgttgcg tcc     53

<210> SEQ ID NO 70
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 70
tcattgaatg cttccaggaa cctcgccaca tccatcgaga accgg               45

<210> SEQ ID NO 71
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 71
ggatcctaat acgactcact atagggaggc ttgaaggccg tgttgaacg           49

<210> SEQ ID NO 72
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 72
caggatttgt ctgagttgcc gcctgatcaa gataggatcc ttgccg              46

<210> SEQ ID NO 73
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 73
ggatcctaat acgactcact atagggaggg gtttgctgaa tacgctgaag gtgatg   56

<210> SEQ ID NO 74
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 74
tggagctgaa caactctctc gtctcgggtg gtcgaatgga cccttggtca ag       52

<210> SEQ ID NO 75
<211> LENGTH: 49
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 75
ggatcctaat acgactcact atagggaggt tcctcaacac ggacagcgg            49

<210> SEQ ID NO 76
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 76
agtcaaccag gtgtggaact cgtcggtggc aacaatgaaa acaccaag             49

<210> SEQ ID NO 77
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 77
ggatcctaat acgactcact atagggaggc cattgccttg agatacgcca ttggtag   57

<210> SEQ ID NO 78
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 78
agccttggtg tcgttctttt caacggaagg tggtctcgat ggtgtgttca acc       53

<210> SEQ ID NO 79
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 79
ggatcctaat acgactcact atagggaggt tgggtttgtt tgtttcctgt gtccg     55

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 80
cctttgacct tcaatctggc gtagacgcag caccaccgat ccaccacttg          50

<210> SEQ ID NO 81
<211> LENGTH: 4206
<212> TYPE: DNA
<213> ORGANISM: Candida tropicalis

<400> SEQUENCE: 81
catcaagatc atctatgggg ataattacga cagcaacatt gcagaaagag cgttggtcac    60
```

-continued

| | | | | | |
|---|---|---|---|---|---|
| aatcgaaaga | gcctatggcg | ttgccgtcgt | tgaggcaaat | gacagcacca | acaataacga | 120 |
| tggtcccagt | gaagagcctt | cagaacagtc | cattgttgac | gcttaaggca | cggataatta | 180 |
| cgtgggggcaa | aggaacgcgg | aattagttat | gggggggatca | aaagcggaag | atttgtgttg | 240 |
| cttgtgggtt | ttttccttta | tttttcatat | gatttctttg | cgcaagtaac | atgtgccaat | 300 |
| ttagtttgtg | attagcgtgc | cccacaattg | catcgtgga | cggcgtgtt | ttgtcatacc | 360 |
| ccaagtctta | actagctcca | cagtctcgac | ggtgtctcga | cgatgtcttc | ttccaccct | 420 |
| cccatgaatc | attcaaagtt | gttgggggat | ctccaccaag | gcaccggag | ttaatgctta | 480 |
| tgtttctccc | actttggttg | tgattgggt | agtctagtga | gttggagatt | ttctttttttt | 540 |
| cgcaggtgtc | tccgatatcg | aaatttgatg | aatatagaga | gaagccagat | cagcacagta | 600 |
| gattgccttt | gtagttagag | atgttgaaca | gcaactagtt | gaattacacg | ccaccacttg | 660 |
| acagcaagtg | cagtgagctg | taaacgatgc | agccagagtg | tcaccaccaa | ctgacgttgg | 720 |
| gtggagttgt | tgttgttgtt | gttggcaggg | ccatattgct | aaacgaagac | aagtagcaca | 780 |
| aaacccaagc | ttaagaacaa | aaataaaaaa | aattcatacg | acaattccaa | agccattgat | 840 |
| ttacataatc | aacagtaaga | cagaaaaaac | tttcaacatt | tcaaagttcc | ctttttccta | 900 |
| ttacttcttt | tttttcttct | ttccttcttt | ccttctgttt | ttcttacttt | atcagtcttt | 960 |
| tacttgtttt | tgcaattcct | catcctcctc | ctactcctcc | tcaccatggc | tttagacaag | 1020 |
| ttagatttgt | atgtcatcat | aacattggtg | gtcgctgtag | ccgcctattt | tgctaagaac | 1080 |
| cagttccttg | atcagcccca | ggacaccggg | ttcctcaaca | cggacagcgg | aagcaactcc | 1140 |
| agagacgtct | tgctgacatt | gaagaagaat | aataaaaaca | cgttgttgtt | gtttgggtcc | 1200 |
| cagacgggta | cggcagaaga | ttacgccaac | aaattgtcca | gagaattgca | ctccagattt | 1260 |
| ggcttgaaaa | cgatggttgc | agatttcgct | gattacgatt | gggataactt | cggagatatc | 1320 |
| accgaagaca | tcttggtgtt | tttcattgtt | gccacctatg | gtgagggtga | acctaccgat | 1380 |
| aatgccgacg | agttccacac | ctggttgact | gaagaagctg | acactttgag | taccttgaaa | 1440 |
| tacaccgtgt | tcgggttggg | taactccacg | tacgagttct | tcaatgccat | ggtagaaag | 1500 |
| tttgacagat | tgttgagcga | gaaaggtggt | gacaggtttg | ctgaatacgc | tgaaggtgat | 1560 |
| gacggtactg | gcaccttgga | cgaagatttc | atggcctgga | aggacaatgt | ctttgacgcc | 1620 |
| ttgaagaatg | atttgaactt | tgaagaaaag | gaattgaagt | acgaaccaaa | cgtgaaattg | 1680 |
| actgagagag | acgacttgtc | tgctgctgac | tcccaagttt | ccttgggtga | gccaaacaag | 1740 |
| aagtacatca | actccgaggg | catcgacttg | accaagggtc | cattcgacca | cacccaccca | 1800 |
| tacttggcca | gaatcaccga | gacgagagag | ttgttcagct | ccaaggacag | acactgtatc | 1860 |
| cacgttgaat | ttgacatttc | tgaatcgaac | ttgaaataca | ccaccggtga | ccatctagct | 1920 |
| atctggccat | ccaactccga | cgaaaacatt | aagcaatttg | ccaagtgttt | cggattggaa | 1980 |
| gataaactcg | acactgttat | tgaattgaag | gcgttggact | ccacttacac | catcccattc | 2040 |
| ccaacccca | ttacctacgg | tgctgtcatt | agacaccatt | tagaaatctc | cggtccagtc | 2100 |
| tcgagacaat | tcttttttgtc | aattgctggg | tttgctcctg | atgaagaaac | aaagaaggct | 2160 |
| tttaccagac | ttggtggtga | caagcaagaa | ttcgccgcca | aggtcacccg | cagaaagttc | 2220 |
| aacattgccg | atgccttgtt | atattcctcc | aacaacgctc | catggtccga | tgttcctttt | 2280 |
| gaattcctta | ttgaaaacgt | tccacacttg | actccacgtt | actactccat | ttcgtcttcg | 2340 |
| tcattgagtg | aaaagcaact | catcaacgtt | actgcagtt | ttgaagccga | agaagaagct | 2400 |
| gatggcagac | cagtcactgg | tgttgtcacc | aacttgttga | agaacgttga | aattgtgcaa | 2460 |

-continued

```
aacaagactg gcgaaaagcc acttgtccac tacgatttga gcggcccaag aggcaagttc      2520
aacaagttca agttgccagt gcatgtgaga agatccaact ttaagttgcc aaagaactcc      2580
accaccccag ttatcttgat tggtccaggt actggtgttg ccccattgag aggttttgtc      2640
agagaaagag ttcaacaagt caagaatggt gtcaatgttg gcaagacttt gttgttttat      2700
ggttgcagaa actccaacga ggactttttg tacaagcaag aatgggccga gtacgcttct      2760
gttttgggtg aaaactttga tgttcaat gccttctcca gacaagaccc atccaagaag       2820
gtttacgtcc aggataagat tttagaaaac agccaacttg tgcacgagtt gttgactgaa      2880
ggtgccatta tctacgtctg tggtgatgcc agtagaatgg ctagagacgt gcagaccaca      2940
atttccaaga ttgttgctaa agcagagaa attagtgaag acaaggctgc tgaattggtc       3000
aagtcctgga aggtccaaaa tagataccaa gaagatgttt ggtagactca acgaatctc       3060 tctttctccc aacgcattta tgaatcttta ttctcattga agctttacat atgttctaca      3120
ctttattttt ttttttttt ttattattat attacgaaac ataggtcaac tatatatact       3180
tgattaaatg ttatagaaac aataactatt atctactcgt ctacttcttt ggcattgaca      3240
tcaacattac cgttcccatt accgttgccg ttggcaatgc cgggatattt agtacagtat      3300
ctccaatccg gatttgagct attgtagatc agctgcaagt cattctccac cttcaaccag      3360
tacttatact tcatctttga cttcaagtcc aagtcataaa tattacaagt tagcaagaac      3420
ttctggccat ccacgatata gacgttattc acgttattat gcgacgtatg gatgtggtta      3480 tcctattga acttctcaaa cttcaaaaac aaccccacgt cccgcaacgt cattatcaac       3540
gacaagttct ggctcacgtc gtcggagctc gtcaagttct caattagatc gttcttgtta      3600
ttgatcttct ggtactttct caattgctgg aacacattg cctcgttgtt caaatagatc       3660
ttgaacaact ttttcaacgg gatcaacttc tcaatctggg ccaagatctc cgccgggatc      3720
ttcagaaaca agtcctgcaa cccctggtcg atggtctccg ggtacaacaa gtccaagggg      3780
cagaagtgtc taggcacgtg tttcaactgg ttcaacgaac atgttcgaca gtagttcgag      3840
ttatagttat cgtacaacca ttttggtttg atttcgaaaa tgacggagct gatgccatca      3900
ttctcctggt tcctctcata gtacaactgg cacttcttcg agaggctcaa ttcctcgtag      3960
ttcccgtcca agatattcgg caacaagagc ccgtaccgct cacggagcat caagtcgtgg      4020
ccctggttgt tcaacttgtt gatgaagtcc gaggtcaaga caatcaactg gatgtcgatg      4080
atctggtgcg ggaacaagtt cttgcatttt agctcgatga agtcgtacaa ctcacacgtc      4140
gagatatact cctgttcctc cttcaagagc cggatccgca agagcttgtg cttcaagtag      4200
tcgttg                                                                 4206
```

<210> SEQ ID NO 82
<211> LENGTH: 4145
<212> TYPE: DNA
<213> ORGANISM: Candida tropicalis

<400> SEQUENCE: 82

```
tatatgatat atgatatatc ttcctgtgta attattattc gtattcgtta atacttacta       60 cattttttt tctttatttta tgaagaaaag gagagttcgt aagttgagtt gagtagaata     120
ggctgttgtg catacgggga gcagaggaga gtatccgacg aggaggaact gggtgaaatt     180
tcatctatgc tgttgcgtcc tgtactgtac tgtaaatctt agatttccta gaggttgttc     240 tagcaaaataa agtgtttcaa gatacaattt tacaggcaag ggtaaaggat caactgatta     300
```

```
gcggaagatt ggtgttgcct gtggggttct tttattttc atatgatttc tttgcgcgag      360
taacatgtgc caatctagtt tatgattagc gtacctccac aattggcatc ttggacgggc      420
gtgttttgtc ttaccccaag ccttatttag ttccacagtc tcgacggtgt ctcgccgatg      480
tcttctccca cccctcgcag gaatcattcg aagttgttgg gggatctcct ccgcagttta      540
tgttcatgtc tttcccactt tggttgtgat tggggtagcg tagtgagttg gtgattttct      600
tttttcgcag gtgtctccga tatcgaagtt tgatgaatat aggagccaga tcagcatggt      660
atattgcctt tgtagataga gatgttgaac aacaactagc tgaattacac accaccgcta      720
aacgatgcgc acagggtgtc accgccaact gacgttgggt ggagttgttg ttggcagggc      780
catattgcta aacgaagaga agtagcacaa aacccaaggt taagaacaat taaaaaaatt      840
catacgacaa ttccacagcc atttacataa tcaacagcga caaatgagac agaaaaaact      900
ttcaacattt caaagttccc ttttttcctat tacttctttt tttctttcct tcctttcatt      960
tcctttcctt ctgcttttat tactttacca gtcttttgct tgtttttgca attcctcatc     1020
ctcctcctca ccatggcttt agacaagtta gatttgtatg tcatcataac attggtggtc     1080
gctgtggccg cctattttgc taagaaccag ttccttgatc agccccagga caccgggttc     1140
ctcaacacgg acagcggaag caactccaga gacgtcttgc tgacattgaa gaagaataat     1200
aaaaacacgt tgttgttgtt tgggtcccag accggtacgg cagaagatta cgccaacaaa     1260
ttgtcaagag aattgcactc cagatttggc ttgaaaacca tggttgcaga tttcgctgat     1320
tacgattggg ataacttcgg agatatcacc gaagatatct tggtgttttt catcgttgcc     1380
acctacggtg agggtgaacc taccgacaat gccgacgagt tccacacctg gttgactgaa     1440
gaagctgaca ctttgagtac tttgagatat accgtgttcg ggttgggtaa ctccacctac     1500
gagttcttca atgctattgg tagaaagttt gacagattgt tgagtgagaa aggtggtgac     1560
agatttgctg aatatgctga aggtgacgac ggcactggca ccttggacga agatttcatg     1620
gcctggaagg ataatgtctt tgacgccttg aagaatgact gaactttga agaaaaggaa     1680 ttgaagtacg aaccaaacgt gaaattgact gagagagatg acttgtctgc tgccgactcc     1740
caagtttcct tgggtgagcc aaacaagaag tacatcaact ccgagggcat cgacttgacc     1800
aagggtccat cgaccacac ccacccatac ttggccagga tcaccgagac cagagagttg     1860
ttcagctcca aggaaagaca ctgtattcac gttgaatttg acatttctga atcgaacttg     1920
aaatacacca ccggtgacca tctagccatc tggccatcca actccgacga aaacatcaag     1980
caatttgcca agtgtttcgg attggaagat aaactcgaca ctgttattga attgaaggca     2040
ttggactcca cttacaccat tccattccca actccaatta cttacggtgc tgtcattaga     2100
caccatttag aaatctccgg tccagtctcg agacaattct ttttgtcgat tgctgggttt     2160
gctcctgatg aagaaacaaa gaagactttc accagacttg gtggtgacaa acaagaattc     2220
gccaccaagg ttacccgcag aaagttcaac attgccgatg ccttgttata ttcctccaac     2280
aacactccat ggtccgatgt tcctttttgag ttccttattg aaaacatcca acacttgact     2340
ccacgttact actccattc ttcttcgtcg ttgagtgaaa acaactcat caatgttact     2400 gcagtcgttg aggccgaaga agaagccgat ggcagaccag tcactggtgt tgttaccaac     2460
ttgttgaaga acattgaaat tgcgcaaaac aagactggcg aaaagccact tgttcactac     2520
gatttgagcg gcccaagagg caagttcaac aagttcaagt tgccagtgca cgtgagaaga     2580
tccaacttta agttgccaaa gaactccacc accccagtta tcttgattgg tccaggtact     2640
ggtgttgccc cattgagagg tttcgttaga gaaagagttc aacaagtcaa gaatggtgtc     2700
```

```
aatgttggca agactttgtt gttttatggt tgcagaaact ccaacgagga cttttgtac      2760 aagcaagaat gggccgagta cgcttctgtt ttgggtgaaa actttgagat gttcaatgcc      2820
ttctctagac aagacccatc caagaaggtt tacgtccagg ataagatttt agaaaacagc      2880
caacttgtgc acgaattgtt gaccgaaggt gccattatct acgtctgtgg tgacgccagt      2940
agaatggcca gagacgtcca gaccacgatc tccaagattg ttgccaaaag cagagaaatc      3000
agtgaagaca aggccgctga attggtcaag tcctggaaag tccaaaatag ataccaagaa      3060
gatgtttggt agactcaaac gaatctctct ttctcccaac gcatttatga atattctcat      3120
tgaagtttta catatgttct atatttcatt tttttttat tatattacga aacataggtc       3180
aactatatat acttgattaa atgttataga acaataatt attatctact cgtctacttc       3240
tttggcattg gcattggcat tggcattggc attgccgttg ccgttggtaa tgccgggata      3300
tttagtacag tatctccaat ccggatttga gctattgtaa atcagctgca agtcattctc      3360
caccttcaac cagtacttat acttcatctt tgacttcaag tccaagtcat aaatattaca      3420
agttagcaag aacttctggc catccacaat atagacgtta ttcacgttat tatgcgacgt      3480
atggatatgg ttatccttat tgaacttctc aaacttcaaa acaaccca cgtcccgcaa       3540 cgtcattatc aacgacaagt tctgactcac gtcgtcggag ctcgtcaagt tctcaattag    3600
atcgttcttg ttattgatct tctggtactt tctcaactgc tggaacacat tgtcctcgtt     3660
gttcaaatag atcttgaaca acttcttcaa gggaatcaac ttttcgatct gggccaagat    3720
ttccgccggg atcttcagaa acaagtcctg caacccctgg tcgatggtct cggggtacaa    3780
caagtctaag gggcagaagt gtctaggcac gtgtttcaac tggttcaagg aacatgttcg    3840
acagtagttc gagttatagt tatcgtacaa ccactttggc ttgatttcga aaatgacgga    3900
gctgatccca tcattctcct ggttcctttc atagtacaac tggcatttct tcgagagact     3960
caactcctcg tagttcccgt ccaagatatt cggcaacaag agcccgtagc gctcacggag     4020
catcaagtcg tggccctggt tgttcaactt gttgatgaag tccgatgtca agacaatcaa    4080
ctggatgtcg atgatctggt gcggaaacaa gttcttgcac tttagctcga tgaagtcgta     4140
caact                                                                 4145
```

<210> SEQ ID NO 83
<211> LENGTH: 679
<212> TYPE: PRT
<213> ORGANISM: CANDIDATROPICALIS

<400> SEQUENCE: 83

```
Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
                20                  25                  30

Asp Thr Gly Phe Leu Asn Thr Asp Ser Gly Ser Asn Ser Arg Asp Val
            35                  40                  45

Leu Leu Thr Leu Lys Lys Asn Asn Lys Asn Thr Leu Leu Leu Phe Gly
        50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
                100                 105                 110
```

-continued

```
Phe Ile Val Ala Thr Tyr Gly Glu Gly Pro Thr Asp Asn Ala Asp
        115                 120                 125
Glu Phe His Thr Trp Leu Thr Glu Glu Ala Asp Thr Leu Ser Thr Leu
130                 135                 140
Lys Tyr Thr Val Phe Gly Leu Gly Asn Ser Thr Tyr Glu Phe Phe Asn
145                 150                 155                 160
Ala Ile Gly Arg Lys Phe Asp Arg Leu Leu Ser Glu Lys Gly Gly Asp
                165                 170                 175
Arg Phe Ala Glu Tyr Ala Glu Gly Asp Asp Gly Thr Gly Thr Leu Asp
                180                 185                 190
Glu Asp Phe Met Ala Trp Lys Asp Asn Val Phe Asp Ala Leu Lys Asn
        195                 200                 205
Asp Leu Asn Phe Glu Glu Lys Glu Leu Lys Tyr Glu Pro Asn Val Lys
        210                 215                 220
Leu Thr Glu Arg Asp Asp Leu Ser Ala Ala Asp Ser Gln Val Ser Leu
225                 230                 235                 240
Gly Glu Pro Asn Lys Lys Tyr Ile Asn Ser Glu Gly Ile Asp Leu Thr
                245                 250                 255
Lys Gly Pro Phe Asp His Thr His Pro Tyr Leu Ala Arg Ile Thr Glu
                260                 265                 270
Thr Arg Glu Leu Phe Ser Ser Lys Asp Arg His Cys Ile His Val Glu
        275                 280                 285
Phe Asp Ile Ser Glu Ser Asn Leu Lys Tyr Thr Thr Gly Asp His Leu
        290                 295                 300
Ala Ile Trp Pro Ser Asn Ser Asp Glu Asn Ile Lys Gln Phe Ala Lys
305                 310                 315                 320
Cys Phe Gly Leu Glu Asp Lys Leu Asp Thr Val Ile Glu Leu Lys Ala
                325                 330                 335
Leu Asp Ser Thr Tyr Thr Ile Pro Phe Pro Thr Pro Ile Thr Tyr Gly
                340                 345                 350
Ala Val Ile Arg His His Leu Glu Ile Ser Gly Pro Val Ser Arg Gln
        355                 360                 365
Phe Phe Leu Ser Ile Ala Gly Phe Ala Pro Asp Glu Glu Thr Lys Lys
        370                 375                 380
Ala Phe Thr Arg Leu Gly Gly Asp Lys Gln Glu Phe Ala Ala Lys Val
385                 390                 395                 400
Thr Arg Arg Lys Phe Asn Ile Ala Asp Ala Leu Leu Tyr Ser Ser Asn
                405                 410                 415
Asn Ala Pro Trp Ser Asp Val Pro Phe Glu Phe Leu Ile Glu Asn Val
                420                 425                 430
Pro His Leu Thr Pro Arg Tyr Tyr Ser Ile Ser Ser Ser Ser Leu Ser
        435                 440                 445
Glu Lys Gln Leu Ile Asn Val Thr Ala Val Val Glu Ala Glu Glu Glu
        450                 455                 460
Ala Asp Gly Arg Pro Val Thr Gly Val Val Thr Asn Leu Leu Lys Asn
465                 470                 475                 480
Val Glu Ile Val Gln Asn Lys Thr Gly Glu Lys Pro Leu Val His Tyr
                485                 490                 495
Asp Leu Ser Gly Pro Arg Gly Lys Phe Asn Lys Phe Lys Leu Pro Val
                500                 505                 510
His Val Arg Arg Ser Asn Phe Lys Leu Pro Lys Asn Ser Thr Thr Pro
        515                 520                 525
```

```
Val Ile Leu Ile Gly Pro Gly Thr Gly Val Ala Pro Leu Arg Gly Phe
    530             535             540

Val Arg Glu Arg Val Gln Gln Val Lys Asn Gly Val Asn Val Gly Lys
545             550             555             560

Thr Leu Leu Phe Tyr Gly Cys Arg Asn Ser Asn Glu Asp Phe Leu Tyr
            565             570             575

Lys Gln Glu Trp Ala Glu Tyr Ala Ser Val Leu Gly Glu Asn Phe Glu
            580             585             590

Met Phe Asn Ala Phe Ser Arg Gln Asp Pro Ser Lys Lys Val Tyr Val
            595             600             605

Gln Asp Lys Ile Leu Glu Asn Ser Gln Leu Val His Glu Leu Leu Thr
            610             615             620

Glu Gly Ala Ile Ile Tyr Val Cys Gly Asp Ala Ser Arg Met Ala Arg
625             630             635             640

Asp Val Gln Thr Thr Ile Ser Lys Ile Val Ala Lys Ser Arg Glu Ile
            645             650             655

Ser Glu Asp Lys Ala Ala Glu Leu Val Lys Ser Trp Lys Val Gln Asn
            660             665             670

Arg Tyr Gln Glu Asp Val Trp
            675

<210> SEQ ID NO 84
<211> LENGTH: 679
<212> TYPE: PRT
<213> ORGANISM: CANDIDATROPICALIS

<400> SEQUENCE: 84

Met Ala Leu Asp Lys Leu Asp Leu Tyr Val Ile Ile Thr Leu Val Val
1               5               10              15

Ala Val Ala Ala Tyr Phe Ala Lys Asn Gln Phe Leu Asp Gln Pro Gln
                20              25              30

Asp Thr Gly Phe Leu Asn Thr Asp Ser Gly Ser Asn Ser Arg Asp Val
            35              40              45

Leu Leu Thr Leu Lys Lys Asn Asn Lys Asn Thr Leu Leu Leu Phe Gly
    50              55              60

Ser Gln Thr Gly Thr Ala Glu Asp Tyr Ala Asn Lys Leu Ser Arg Glu
65              70              75              80

Leu His Ser Arg Phe Gly Leu Lys Thr Met Val Ala Asp Phe Ala Asp
                85              90              95

Tyr Asp Trp Asp Asn Phe Gly Asp Ile Thr Glu Asp Ile Leu Val Phe
            100             105             110

Phe Ile Val Ala Thr Tyr Gly Glu Gly Glu Pro Thr Asp Asn Ala Asp
            115             120             125

Glu Phe His Thr Trp Leu Thr Glu Glu Ala Asp Thr Leu Ser Thr Leu
    130             135             140

Arg Tyr Thr Val Phe Gly Leu Gly Asn Ser Thr Tyr Glu Phe Phe Asn
145             150             155             160

Ala Ile Gly Arg Lys Phe Asp Arg Leu Leu Ser Glu Lys Gly Gly Asp
                165             170             175

Arg Phe Ala Glu Tyr Ala Glu Gly Asp Asp Gly Thr Gly Thr Leu Asp
            180             185             190

Glu Asp Phe Met Ala Trp Lys Asp Asn Val Phe Asp Ala Leu Lys Asn
            195             200             205

Asp Leu Asn Phe Glu Glu Lys Glu Leu Lys Tyr Glu Pro Asn Val Lys
    210             215             220
```

```
Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
            245                 250                 255

Lys Gly Pro Phe Asp His Thr His Pro Tyr Leu Ala Arg Ile Thr Glu
            260                 265                 270

Thr Arg Glu Leu Phe Ser Ser Lys Glu Arg His Cys Ile His Val Glu
        275                 280                 285

Phe Asp Ile Ser Glu Ser Asn Leu Lys Tyr Thr Thr Gly Asp His Leu
    290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
                340                 345                 350

Ala Val Ile Arg His His Leu Glu Ile Ser Gly Pro Val Ser Arg Gln
                355                 360                 365

Phe Phe Leu Ser Ile Ala Gly Phe Ala Pro Asp Glu Glu Thr Lys Lys
        370                 375                 380

Thr Phe Thr Arg Leu Gly Gly Asp Lys Gln Glu Phe Ala Thr Lys Val
385                 390                 395                 400

Thr Arg Arg Lys Phe Asn Ile Ala Asp Ala Leu Leu Tyr Ser Ser Asn
                405                 410                 415

Asn Thr Pro Trp Ser Asp Val Pro Phe Glu Phe Leu Ile Glu Asn Ile
                420                 425                 430

Gln His Leu Thr Pro Arg Tyr Tyr Ser Ile Ser Ser Ser Leu Ser
                435                 440                 445

Glu Lys Gln Leu Ile Asn Val Thr Ala Val Glu Ala Glu Glu
    450                 455                 460

Ala Asp Gly Arg Pro Val Thr Gly Val Val Thr Asn Leu Leu Lys Asn
465                 470                 475                 480

Ile Glu Ile Ala Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
                500                 505                 510

His Val Arg Arg Ser Asn Phe Lys Leu Pro Lys Asn Ser Thr Thr Pro
                515                 520                 525

Val Ile Leu Ile Gly Pro Gly Thr Gly Val Ala Pro Leu Arg Gly Phe
                530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
                580                 585                 590

Met Phe Asn Ala Phe Ser Arg Gln Asp Pro Ser Lys Lys Val Tyr Val
                595                 600                 605

Gln Asp Lys Ile Leu Glu Asn Ser Gln Leu Val His Glu Leu Leu Thr
        610                 615                 620

Glu Gly Ala Ile Ile Tyr Val Cys Gly Asp Ala Ser Arg Met Ala Arg
625                 630                 635                 640
```

```
Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675

<210> SEQ ID NO 85
<211> LENGTH: 4115
<212> TYPE: DNA
<213> ORGANISM: Candida tropicalis

<400> SEQUENCE: 85
```

| | | | | | |
|---|---|---|---|---|---|
| catatgcgct | aatcttcttt | ttcttttat | cacaggagaa | actatcccac | ccccacttcg | 60 |
| aaacacaatg | acaactcctg | cgtaacttgc | aaattcttgt | ctgactaatt | gaaaactccg | 120 |
| gacgagtcag | acctccagtc | aaacggacag | acagacaaac | acttggtgcg | atgttcatac | 180 |
| ctacagacat | gtcaacgggt | gttagacgac | ggtttcttgc | aaagacaggt | gttggcatct | 240 |
| cgtacgatgg | caactgcagg | aggtgtcgac | ttctccttta | ggcaatagaa | aaagactaag | 300 |
| agaacagcgt | ttttacaggt | tgcattggtt | aatgtagtat | ttttttagtc | ccagcattct | 360 |
| gtgggttgct | ctgggtttct | agaataggaa | atcacaggag | aatgcaaatt | cagatggaag | 420 |
| aacaaagaga | taaaaaacaa | aaaaaaactg | agttttgcac | caatagaatg | tttgatgata | 480 |
| tcatccactc | gctaaacgaa | tcatgtgggt | gatcttctct | ttagttttgg | tctatcataa | 540 |
| aacacatgaa | agtgaaatcc | aaatacacta | cactccgggt | attgtccttc | gttttacaga | 600 |
| tgtctcattg | tcttactttt | gaggtcatag | gagttgcctg | tgagagatca | cagagattat | 660 |
| cacactcaca | tttatcgtag | tttcctatct | catgctgtgt | gtctctggtt | ggttcatgag | 720 |
| tttggattgt | tgtacattaa | aggaatcgct | ggaaagcaaa | gctaactaaa | ttttctttgt | 780 |
| cacaggtaca | ctaacctgta | aaacttcact | gccacgccag | tctttcctga | ttgggcaagt | 840 |
| gcacaaacta | caacctgcaa | aacagcactc | cgcttgtcac | aggttgtctc | ctctcaacca | 900 |
| acaaaaaaat | aagattaaac | tttctttgct | catgcatcaa | tcggagttat | ctctgaaaga | 960 |
| gttgcctttg | tgtaatgtgt | gccaaactca | aactgcaaaa | ctaaccacag | aatgatttcc | 1020 |
| ctcacaatta | tataaactca | cccacatttc | cacagaccgt | aatttcatgt | ctcactttct | 1080 |
| cttttgctct | tcttttactt | agtcaggttt | gataacttcc | tttttttatta | ccctatctta | 1140 |
| tttatttatt | tattcattta | taccaaccaa | ccaaccatgg | ccacacaaga | aatcatcgat | 1200 |
| tctgtacttc | cgtacttgac | caaatggtac | actgtgatta | ctgcagcagt | attagtcttc | 1260 |
| cttatctcca | caaacatcaa | gaactacgtc | aaggcaaaga | aattgaaatg | tgtcgatcca | 1320 |
| ccatacttga | aggatgccgg | tctcactggt | attctgtctt | tgatcgccgc | catcaaggcc | 1380 |
| aagaacgacg | gtagattggc | taactttgcc | gatgaagttt | tcgacgagta | cccaaaccac | 1440 |
| accttctact | gtctgttgc | cggtgctttg | aagattgtca | tgactgttga | cccagaaaac | 1500 |
| atcaaggctg | tcttggccac | ccaattcact | gacttctcct | tgggtaccag | acacgcccac | 1560 |
| tttgctcctt | tgttgggtga | cggtatcttc | accttggacg | gagaaggttg | gaagcactcc | 1620 |
| agagctatgt | tgagaccaca | gtttgctaga | gaccagattg | gacacgttaa | agccttggaa | 1680 |
| ccacacatcc | aaatcatggc | taagcagatc | aagttgaacc | agggaaagac | tttcgatatc | 1740 |
| caagaattgt | tctttagatt | taccgtcgac | accgctactg | agttcttgtt | tggtgaatcc | 1800 |
| gttcactcct | tgtacgatga | aaaattgggc | atcccaactc | aaacgaaat | cccaggaaga | 1860 |

```
gaaaactttg ccgctgcttt caacgtttcc caacactact tggccaccag aagttactcc    1920 cagactttt  actttttgac caaccctaag gaattcagag actgtaacgc caaggtccac    1980
cacttggcca agtactttgt caacaaggcc ttgaacttta ctcctgaaga actcgaagag    2040
aaatccaagt ccggttacgt tttcttgtac gaattggtta agcaaaccag agatccaaag    2100
gtcttgcaag atcaattgtt gaacattatg gttgccggaa gagacaccac tgccggtttg    2160
ttgtcctttg ctttgtttga attggctaga cacccagaga tgtggtccaa gttgagagaa    2220
gaaatcgaag ttaactttgg tgttggtgaa gactcccgcg ttgaagaaat taccttcgaa    2280
gccttgaaga gatgtgaata cttgaaggct atccttaacg aaaccttgcg tatgtaccca    2340
tctgttcctg tcaactttag aaccgccacc agagacacca ctttgccaag aggtggtggt    2400
gctaacggta ccgacccaat ctacattcct aaaggctcca ctgttgctta cgttgtctac    2460
aagacccacc gtttggaaga atactacggt aaggacgcta acgacttcag accagaaaga    2520
tggtttgaac catctactaa gaagttgggc tgggcttatg ttccattcaa cggtggtcca    2580
agagtctgct tgggtcaaca attcgccttg actgaagctt cttatgtgat cactagattg    2640
gcccagatgt ttgaaactgt ctcatctgat ccaggtctcg aataccctcc accaaagtgt    2700
attcacttga ccatgagtca caacgatggt gtctttgtca agatgtaaag tagtcgatgc    2760
tgggtattcg attacatgtg tataggaaga ttttggtttt ttattcgttc tttttttaa     2820 tttttgttaa attagtttag agatttcatt aatacataga tgggtgctat ttccgaaact    2880
ttacttctat ccctgtatc ccttattatc cctctcagtc acatgattgc tgtaattgtc      2940
gtgcaggaca caaactccct aacggactta aaccataaac aagctcagaa ccataagccg    3000
acatcactcc ttcttctctc ttctccaacc aatagcatgg acagaccac cctcctatcc      3060 gaatcgaaga cccttattga ctccataccc acctggaagc ccctcaagcc acacacgtca    3120
tccagcccac ccatcaccac atccctctac tcgacaacgt ccaaagacgg cgagttctgg    3180
tgtgcccgga aatcagccat cccggccaca tacaagcagc cgttgattgc gtgcatactc    3240
ggcgagccca caatgggagc cacgcattcg gaccatgaag caaagtacat tcacgagatc    3300
acgggtgttt cagtgtcgca gattgagaag ttcgacgatg gatggaagta cgatctcgtt    3360
gcggattacg acttcggtgg gttgttatct aaacgaagat tctatgagac gcagcatgtg    3420
tttcggttcg aggattgtgc gtacgtcatg agtgtgcctt tgatggacc caaggaggaa     3480 ggttacgtgg ttgggacgta cagatccatt gaaaggttga gctggggtaa agacggggac    3540
gtggagtgga ccatggcgac gacgtcggat cctggtgggt ttatcccgca atggataact    3600
cgattgagca tccctggagc aatcgcaaaa gatgtgccta gtgtattaaa ctacatacag    3660
aaataaaaac gtgtcttgat tcattggttt ggttcttgtt gggttccgag ccaatatttc    3720
acatcatctc ctaaattctc caagaatccc aacgtagcgt agtccagcac gccctctgag    3780
atcttattta atatcgactt ctcaaccacc ggtggaatcc cgttcagacc attgttacct    3840
gtagtgtgtt tgctcttgtt cttgatgaca atgatgtatt tgtcacgata cctgaaataa    3900 taaacatcc  agtcattgag cttattactc gtgaacttat gaaagaactc attcaagccg    3960
ttcccaaaaa acccagaatt gaagatcttg ctcaactggt catgcaagta gtagatcgcc    4020
atgatctgat actttaccaa gctatcctct ccaagttctc ccacgtacgg caagtacggc    4080
aacgagctct ggaagctttg ttgtttgggg tcata                               4115
```

<210> SEQ ID NO 86
<211> LENGTH: 3948

<212> TYPE: DNA
<213> ORGANISM: Candida tropicalis

<400> SEQUENCE: 86

| | | | | | |
|---|---|---|---|---|---|
| gacctgtgac | gcttccggtg | tcttgccacc | agtctccaag | ttgaccgacg | cccaagtcat | 60 |
| gtaccacttt | atttccggtt | acacttccaa | gatggctggt | actgaagaag | gtgtcacgga | 120 |
| accacaagct | actttctccg | cttgtttcgg | tcaaccattc | ttggtgttgc | acccaatgaa | 180 |
| gtacgctcaa | caattgtctg | acaagatctc | gcaacacaag | gctaacgcct | ggttgttgaa | 240 |
| caccggttgg | gttggttctt | ctgctgctag | aggtggtaag | agatgctcat | tgaagtacac | 300 |
| cagagccatt | ttggacgcta | tccactctgg | tgaattgtcc | aaggttgaat | acgaaacttt | 360 |
| cccagtcttc | aacttgaatg | tcccaacctc | ctgtccaggt | gtcccaagtg | aaatcttgaa | 420 |
| cccaaccaag | gcctggaccg | aaggtgttg | actccttcaa | caaggaaatc | aagtctttgg | 480 |
| ctggtaagtt | tgctgaaaac | ttcaagacct | atgctgacca | agctaccgct | gaagtgagag | 540 |
| ctgcaggtcc | agaagcttaa | agatatttat | tcattattta | gtttgcctat | ttatttctca | 600 |
| ttacccatca | tcattcaaca | ctatatataa | agttacttcg | gatatcattg | taatcgtgcg | 660 |
| tgtcgcaatt | ggatgatttg | gaactgcgct | tgaaacggat | tcatgcacga | agcggagata | 720 |
| aaagattacg | taatttatct | cctgagacaa | ttttagccgt | gttcacacgc | ccttctttgt | 780 |
| tctgagcgaa | ggataaataa | ttagacttcc | acagctcatt | ctaatttccg | tcacgcgaat | 840 |
| attgaagggg | ggtacatgtg | gccgctgaat | gtggggcag | taaacgcagt | ctctcctctc | 900 |
| ccaggaatag | tgcaacggag | gaaggataac | ggatagaaag | cggaatgcga | ggaaaatttt | 960 |
| gaacgcgcaa | gaaaagcaat | atccgggcta | ccagttttg | agccagggaa | cacactccta | 1020 |
| tttctgctca | atgactgaac | atagaaaaaa | caccaagacg | caatgaaacg | cacatggaca | 1080 |
| tttagaccctc | cccacatgtg | atagtttgtc | ttaacagaaa | agtataataa | gaacccatgc | 1140 |
| cgtcccttt | ctttcgccgc | ttcaactttt | tttttttat | cttacacaca | tcacgaccat | 1200 |
| gactgtacac | gatattatcg | ccacatactt | caccaaatgg | tacgtgatag | taccactcgc | 1260 |
| tttgattgct | tatagagtcc | tcgactactt | ctatggcaga | tacttgatgt | acaagcttgg | 1320 |
| tgctaaacca | tttttccaga | aacagacaga | cggctgtttc | ggattcaaag | ctccgcttga | 1380 |
| attgttgaag | aagaagagcg | acggtaccct | catagacttc | acactccagc | gtatccacga | 1440 |
| tctcgatcgt | cccgatatcc | caactttcac | attcccggtc | ttttccatca | accttgtcaa | 1500 |
| tacccttgag | ccggagaaca | tcaaggccat | cttggccact | cagttcaacg | atttctcctt | 1560 |
| gggtaccaga | cactcgcact | tgctcccttt | gttgggtgat | ggtatcttta | cgttggatgg | 1620 |
| cgccggctgg | aagcacagca | gatctatgtt | gagaccacag | tttgccagag | aacagatttc | 1680 |
| ccacgtcaag | ttgttggagc | cacacgttca | ggtgttcttc | aaacacgtca | gaaaggcaca | 1740 |
| gggcaagact | tttgacatcc | aggaattgtt | tttcagattg | accgtcgact | ccgccaccga | 1800 |
| gttttttgttt | ggtgaatccg | ttgagtcctt | gagagatgaa | tctatcggca | tgtccatcaa | 1860 |
| tgcgcttgac | tttgacggca | aggctggctt | tgctgatgct | tttaactatt | cgcagaatta | 1920 |
| tttggcttcg | agagcggtta | tgcaacaatt | gtactgggtg | ttgaacggga | aaagtttaa | 1980 |
| ggagtgcaac | gctaaagtgc | acaagtttgc | tgactactac | gtcaacaagg | ctttggactt | 2040 |
| gacgcctgaa | caattggaaa | agcaggatgg | ttatgtgttt | ttgtacgaat | tggtcaagca | 2100 |
| aaccagagac | aagcaagtgt | tgagagacca | attgttgaac | atcatggttg | ctggtagaga | 2160 |
| caccaccgcc | ggtttgttgt | cgtttgtttt | ctttgaattg | gccagaaacc | cagaagttac | 2220 |

-continued

```
caacaagttg agagaagaaa ttgaggacaa gtttggactc ggtgagaatg ctagtgttga      2280
agacatttcc tttgagtcgt tgaagtcctg tgaatacttg aaggctgttc tcaacgaaac      2340
cttgagattg tacccatccg tgccacagaa tttcagagtt gccaccaaga acactaccct      2400
cccaagaggt ggtggtaagg acgggttgtc tcctgttttg gtgagaaagg gtcagaccgt      2460
tatttacggt gtctacgcag cccacagaaa cccagctgtt tacggtaagg acgctcttga      2520
gtttagacca gagagatggt ttgagccaga gacaaagaag cttggctggg ccttcctccc      2580
attcaacggt ggtccaagaa tctgtttggg acagcagttt gccttgacag aagcttcgta      2640
tgtcactgtc aggttgctcc aggagtttgc acacttgtct atggacccag acaccgaata      2700
tccacctaag aaaatgtcgc atttgaccat gtcgcttttc gacggtgcca atattgagat      2760
gtattagagg gtcatgtgtt attttgattg tttagtttgt aattactgat taggttaatt      2820
catggattgt tatttattga taggggtttg cgcgtgttgc attcacttgg gatcgttcca      2880
ggttgatgtt tccttccatc ctgtcgagtc aaaaggagtt ttgttttgta actccggacg      2940
atgtttaaaa tagaaggtcg atctccatgt gattgtttg actgttactg tgattatgta       3000
atctgcggac gttatacaag catgtgattg tggttttgca gccttttgca cgacaaatga      3060
tcgtcagacg attacgtaat ctttgttaga ggggtaaaaa aaacaaaat ggcagccaga        3120
atttcaaaca ttctgcaaac aatgcaaaaa atgggaaact ccaacagaca aaaaaaaaa        3180
ctccgcagca ctccgaaccc acagaacaat ggggcgccag aattattgac tattgtgact      3240
tttttacgct aacgctcatt gcagtgtagt gcgtcttaca cggggtattg ctttctacaa      3300
tgcaagggca cagttgaagg tttgcaccta acgttgcccc gtgtcaactc aatttgacga      3360
gtaacttcct aagctcgaat tatgcagctc gtgcgtcaac ctatgtgcag aaagaaaaa       3420
atccaaaaaa atcgaaaatg cgactttcga ttttgaataa accaaaaaga aaaatgtcgc      3480
acttttttct cgctctcgct ctctcgaccc aaatcacaac aaatcctcgc gcgcagtatt      3540
tcgacgaaac cacaacaaat aaaaaaaaca aattctacac cacttctttt tcttcaccag      3600
tcaacaaaaa acaacaaatt atacaccatt tcaacgattt ttgctcttat aaatgctata      3660
taatggttta attcaactca ggtatgttta ttttactgtt ttcagctcaa gtatgttcaa      3720
atactaacta cttttgatgt ttgtcgcttt tctagaatca aaacaacgcc cacaacacgc      3780
cgagcttgtc gaatagacgg tttgtttact cattagatgg tcccagatta cttttcaagc      3840
caaagtctct cgagttttgt ttgctgtttc cccaattcct aactatgaag gttttttata      3900
aggtccaaag accccaaggc atagtttttt tggttccttc ttgtcgtg                   3948
```

<210> SEQ ID NO 87
<211> LENGTH: 3755
<212> TYPE: DNA
<213> ORGANISM: Candida tropicalis

<400> SEQUENCE: 87

```
gctcaacaat tgtctgacaa gatctcgcaa cacaaggcta acgcctggtt gttgaacact       60
ggttgggttg gttcttctgc tgctagaggt ggtaagagat gttcattgaa gtacaccaga      120
gccattttgg acgctatcca ctctggtgaa ttgtccaagg ttgaatacga gactttccca      180
gtcttcaact tgaatgtccc aacctcctgc ccaggtgtcc caagtgaaat cttgaaccca      240
accaaggcct ggaccgaagg tgttgactcc ttcaacaagg aaatcaagtc tttggctggt      300
aagtttgctg aaaacttcaa gacctatgct gaccaagcta ccgctgaagt tagagctgca      360
ggtccagaag cttaaagata tttattcact atttagtttg cctattttatt tctcatcacc    420
```

```
catcatcatt caacaatata tataaagtta tttcggaact catatatcat tgtaatcgtg    480
cgtgttgcaa ttgggtaatt tgaaactgta gttggaacgg attcatgcac gatgcggaga    540
taacacgaga ttatctccta agacaattt ggcctcattc acacgccctt cttctgagct     600
aaggataaat aattagactt cacaagttca ttaaaatatc cgtcacgcga aaactgcaac    660
aataaggaag gggggggtag acgtagccga tgaatgtggg gtgccagtaa acgcagtctc    720
tctctccccc ccccccccc cccctcagg aatagtacaa cggggaagg ataacggata       780 gcaagtggaa tgcgaggaaa attttgaatg cgcaaggaaa gcaatatccg ggctatcagg    840
ttttgagcca ggggacacac tcctcttctg cacaaaaact taacgtagac aaaaaaaaaa    900
aactccacca agacacaatg aatcgcacat ggacatttag acctcccac atgtgaaagc     960 ttctctggcg aaagcaaaaa agtataata aggacccatg ccttccctct tcctgggccg    1020
tttcaacttt ttcttttct ttgtctatca acacacacac acctcacgac catgactgca    1080
caggatatta tcgccacata catcaccaaa tggtacgtga tagtaccact cgctttgatt   1140
gcttataggg tcctcgacta cttttacggc agatacttga tgtacaagct tggtgctaaa   1200
ccgttttccc agaaacaaac agacggttat ttcggattca aagctccact tgaattgtta   1260
aaaaagaaga gtgacggtac cctcatagac ttcactctcg agcgtatcca agcgctcaat   1320
cgtccagata tcccaacttt tacattccca atctttccca tcaaccttat cagcaccctt   1380
gagccggaga acatcaaggc tatcttggcc acccagttca acgatttctc cttgggcacc   1440
agacactcgc actttgctcc tttgttgggc gatggtatct ttaccttgga cggtgccggc   1500
tggaagcaca gcagatctat gttgagacca cagtttgcca gagaacagat ttcccacgtc   1560
aagttgttgg agccacacat gcaggtgttc ttcaagcacg tcagaaaggc acagggcaag   1620
acttttgaca tccaagaatt gttttttcaga ttgaccgtcg actccgccac tgagttttg   1680 tttggtgaat ccgttgagtc cttgagagat gaatctattg ggatgtccat caatgcactt   1740
gactttgacg gcaaggctgg ctttgctgat gcttttaact actcgcagaa ctatttggct   1800
tcgagagcgg ttatgcaaca attgtactgg gtgttgaacg ggaaaaagtt taaggagtgc   1860
aacgctaaag tgcacaagtt tgctgactat tacgtcagca aggctttgga cttgacacct   1920
gaacaattgg aaaagcagga tggttatgtg ttccttgtacg agttggtcaa gcaaaccaga   1980
gacaggcaag tgttgagaga ccagttgttg aacatcatgg ttgccggtag agacaccacc   2040
gccggtttgt tgtcgtttgt tttctttgaa ttggccagaa acccagaggt gaccaacaag   2100
ttgagagaag aaatcgagga caagtttggt cttggtgaga atgctcgtgt tgaagacatt   2160
tcctttgagt cgttgaagtc atgtgaatac ttgaaggctg ttctcaacga aactttgaga   2220
ttgtacccat ccgtgccaca gaatttcaga gttgccacca aaaacactac ccttccaagg   2280
ggaggtggta aggacgggtt atctcctgtt ttggtcagaa agggtcaaac cgttatgtac   2340
ggtgtctacg ctgcccacag aaacccagct gtctacggta aggacgccct tgagtttaga   2400
ccagagaggt ggtttgagcc agagacaaag aagcttggct gggccttcct tccattcaac   2460
ggtggtccaa gaatttgctt gggacagcag tttgccttga cagaagcttc gtatgtcact   2520
gtcagattgc tccaagagtt tggacacttg tctatggacc ccaacaccga atatccacct   2580
aggaaaatgt cgcatttgac catgtccctt ttcgacggtg ccaacattga gatgtattag   2640
aggatcatgt gttatttttg attggtttag tctgtttgta gctattgatt aggttaattc   2700
acggattgtt atttattgat aggggtgcg tgtgtgtgtg tgtgttgcat tcacatggga   2760
```

-continued

```
tcgttccagg ttgttgtttc cttccatcct gttgagtcaa aaggagtttt gttttgtaac      2820
tccggacgat gtcttagata gaaggtcgat ctccatgtga ttgtttgact gctactctga      2880
ttatgtaatc tgtaaagcct agacgttatg caagcatgtg attgtggttt ttgcaacctg      2940
tttgcacgac aaatgatcga cagtcgatta cgtaatccat attatttaga ggggtaataa      3000
aaaataaatg gcagccagaa tttcaaacat tttgcaaaca atgcaaaaga tgagaaactc      3060
caacagaaaa aataaaaaaa ctccgcagca ctccgaacca acaaaacaat gggggcgcc      3120 agaattattg actattgtga ctttttttta tttttccgt taactttcat tgcagtgaag       3180
tgtgttacac ggggtggtga tggtgttggt ttctacaatg caagggcaca gttgaaggtt      3240
tccacataac gttgcaccat atcaactcaa tttatcctca ttcatgtgat aaagaagag       3300 ccaaaaggta attggcagac ccccaagggg gaacacggag tagaaagcaa tggaaacacg      3360
cccatgacag tgccatttag cccacaacac atctagtatt cttttttttt tttgtgcgca     3420
ggtgcacacc tggactttag ttattgcccc ataaagttaa caatctcacc tttggctctc      3480
ccagtgtctc cgcctccaga tgctcgtttt acaccctcga gctaacgaca acacaacacc      3540 catgaggga atgggcaaag ttaaacactt ttggtttcaa tgattcctat ttgctactct       3600
cttgttttgt gttttgattt gcaccatgtg aaataaacga caattatata tacctttttcg     3660 tctgtcctcc aatgtctctt tttgctgcca ttttgctttt tgcttttgc ttttgcactc      3720 tctcccactc ccacaatcag tgcagcaaca cacaa                                 3755
```

<210> SEQ ID NO 88
<211> LENGTH: 3900
<212> TYPE: DNA
<213> ORGANISM: Candida tropicalis

<400> SEQUENCE: 88

```
gacatcataa tgacccggtt atttcgccct caggttgctt atttgagccg taaagtgcag       60
tagaaacttt gccttgggtt caaactctag tataatggtg ataactggtt gcactcttgc      120
cataggcatg aaaataggcc gttatagtac tatatttaat aagcgtagga gtataggatg      180
catatgaccg gttttttctat attttttaaga taatctctag taaattttgt attctcagta    240
ggatttcatc aaatttcgca accaattctg gcgaaaaaat gattctttta cgtcaaaagc      300
tgaatagtgc agtttaaagc acctaaaatc acatatacag cctctagata cgacagagaa      360
gctctttatg atctgaagaa gcattagaat agctactatg agccactatt ggtgtatata      420
ttagggattg gtgcaattaa gtacgtacta ataaacagaa gaaaatactt aaccaatttc      480
tggtgtatac ttagtggtga gggaccttt ctgaacattc gggtcaaact ttttttttgga      540 gtgcgacatc gattttttcgt ttgtgtaata atagtgaacc tttgtgtaat aaatcttcat     600
gcaagacttg cataattcga gcttgggagt tcacgccaat ttgacctcgt tcatgtgata      660
aaagaaaagc caaaaggtaa ttagcagacg caatgggaac atggagtgga aagcaatgga     720
agcacgccca ggacggagta atttagtcca cactacatct gggggttttt ttttgtgcg       780 caagtacaca cctggactt agttttttgcc ccataaagtt aacaatctaa cctttggctc      840
tccaactctc tccgcccca atattcgtt tttacaccct caagctagcg acagcacaac        900
acccattaga ggaatgggc aaagttaaac acttttggct tcaatgattc ctattcgcta       960
ctacattctt ctcttgttttt gtgctttgaa ttgcaccatg tgaataaaac gacaattata    1020
tatacctttt catccctcct cctatatctc ttttttgctac attttgtttt ttacgttttct    1080 tgcttttgca ctctcccact cccacaaaga aaaaaaaact acactatgtc gtcttctcca    1140
```

-continued

```
tcgtttgccc aagaggttct cgctaccact agtccttaca tcgagtactt tcttgacaac    1200
tacaccagat ggtactactt catacctttg gtgcttcttt cgttgaactt tataagtttg    1260
ctccacacaa ggtacttgga acgcaggttc cacgccaagc cactcggtaa ctttgtcagg    1320
gaccctacgt ttggtatcgc tactccgttg cttttgatct acttgaagtc gaaaggtacg    1380
gtcatgaagt ttgcttgggg cctctggaac aacaagtaca tcgtcagaga cccaaagtac    1440
aagacaactg ggctcaggat tgttggcctc ccattgattg aaaccatgga cccagagaac    1500
atcaaggctg ttttggctac tcagttcaat gatttctctt tgggaaccag acacgatttc    1560
ttgtactcct tgttgggtga cggtattttc accttggacg gtgctggctg aaacatagt     1620
agaactatgt tgagaccaca gtttgctaga gaacaggttt ctcacgtcaa gttgttggag    1680
ccacacgttc aggtgttctt caagcacgtt agaaagcacc gcggtcaaac gttcgacatc    1740
caagaattgt tcttcaggtt gaccgtcgac tccgccaccg agttcttgtt tggtgagtct    1800
gctgaatcct gagggacga atctattgga ttgaccccaa ccaccaagga tttcgatggc     1860
agaagagatt tcgctgacgc tttcaactat tcgcagactt accaggccta cagatttttg    1920
ttgcaacaaa tgtactggat cttgaatggc tcggaattca gaaagtcgat tgctgtcgtg    1980
cacaagtttg ctgaccacta tgtgcaaaag gctttggagt tgaccgacga tgacttgcag    2040
aaacaagacg gctatgtgtt cttgtacgag ttggctaagc aaaccagaga cccaaaggtc    2100
ttgagagacc agttattgaa cattttggtt gccggtagag acacgaccgc cggtttgttg    2160
tcatttgttt tctacgagtt gtcaagaaac cctgaggtgt tgctaagtt gagagaggag     2220
gtggaaaaca gatttggact cggtgaagaa gctcgtgttg aagagatctc gtttgagtcc    2280
ttgaagtctt gtgagtactt gaaggctgtc atcaatgaaa ccttgagatt gtacccatcg    2340
gttccacaca actttagagt tgctaccaga aacactaccc tcccaagagg tggtggtgaa    2400
gatggatact cgccaattgt cgtcaagaag ggtcaagttg tcatgtacac tgttattgct    2460
acccacagag acccaagtat ctacggtgcc gacgctgacg tcttcagacc agaaagatgg    2520
tttgaaccag aaaactagaaa gttgggctgg gcatacgttc cattcaatgg tggtccaaga    2580
atctgtttgg gtcaacagtt tgccttgacc gaagcttcat acgtcactgt cagattgctc    2640
caggagtttg cacacttgtc tatggaccca gacaccgaat atccaccaaa attgcagaac    2700
accttgacct tgtcgctctt tgatggtgct gatgttagaa tgtactaagg ttgctttttcc    2760
ttgctaattt tcttctgtat agcttgtgta tttaaattga atcggcaatt gattttttctg    2820
ataccaataa ccgtagtgcg atttgaccaa aaccgttcaa acttttttgtt ctctcgttga    2880
cgtgctcgct catcagcact gtttgaagac gaaagagaaa attttttgta aacaacactg    2940
tccaaattta cccaacgtga accattatgc aaatgagcgg ccctttcaac tggtcgctgg    3000
aagcattcgg ggatatctac aacgccctta gtttgaaaac agacattgat ttagacacca    3060
tagatttcag cggcatcaag aatgaccttg cccacatttt gacgaccca acaccactgg     3120
aagaatcacg ccagaaacta ggcgatggat ccaagcctgt gaccttgccc aatggagacg    3180
aagtggagtt gaaccaagcg ttcctagaag ttaccacatt attgtcgaat gagtttgact    3240
tggaccaatt gaacgcggca gagttgttat actacgctgg cgacatatcc tacaagaagg    3300
gcacatcaat cgcagacagt gccagattgt cttattattt gagagcaaac tacatcttga    3360
acatacttgg gtatttgatt tcgaagcagc gattggattt gatagtcacg gacaacgacg    3420
cgttgtttga tagtatttttg aaaagttttg aaaagatcta caagttgata agcgtgttga    3480
```

```
acgatatgat tgacaagcaa aaggtgacaa gcgacatcaa cagtctagca ttcatcaatt   3540
gcatcaacta ctcgagaggt caactattct ccgcacacga acttttggga ctggttttgt   3600
ttggattggt cgacatctat ttcaaccagt ttggcacatt agacaactac aagaaggtat   3660
tggcattgat actgaagaac atcagcgatg aagcatctt gatcatacac ttcctcccat    3720
cgacactaca attgtttaag ctggtgttgg acaagaaaga cgacgctgca gttgaacagt   3780
tctacaagta catcacttca acagtgtcac gagactacaa ctccaacatc ggctccacag   3840
ccaaagatga tatcgatttg tccaaaacca aactcagtgg ctttgaggtg ttgacgagtt   3900

<210> SEQ ID NO 89
<211> LENGTH: 3668
<212> TYPE: DNA
<213> ORGANISM: Candida tropicalis

<400> SEQUENCE: 89
cctgcagaat tcgcggccgc gtcgacagag tagcagttat gcaagcatgt gattgtggtt     60 tttgcaaccct gtttgcacga caaatgatcg acagtcgatt acgtaatcca tattatttag   120
aggggtaata aaaataaat ggcagccaga atttcaaaca ttttgcaaac aatgcaaaag      180
atgagaaact ccaacagaaa aataaaaaa actccgcagc actccgaacc aacaaaacaa     240 tgggggggcgc cagaattatt gactattgtg acttttttt atttttttccg ttaacttttca   300 ttgcagtgaa gtgtgttaca cggggtggtg atggtgttgg tttctacaat gcaagggcac    360
agttgaaggt ttccacataa cgttgcacca tatcaactca atttatcctc attcatgtga    420
taaaagaaga gccaaaaggt aattggcaga ccccccaagg ggaacacgga gtagaaagca    480
atggaaacac gcccatgaca gtgccattta gcccacaaca catctagtat tctttttttt    540
ttttgtgcgc aggtgcacac ctggacttta gttattgccc cataaagtta acaatctcac    600 cttttggctct cccagtgtct ccgcctccag atgctcgttt tacacccctcg agctaacgac   660 aacacaacac ccatgagggg aatgggcaaa gttaaacact tttggtttca atgattccta    720
tttgctactc tcttgttttg tgttttgatt tgcaccatgt gaaataaacg acaattatat     780
ataccttttc gtctgtcctc caatgtctct ttttgctgcc attttgcttt ttgctttttg     840
cttttgcact ctctcccact cccacaatca gtgcagcaac acacaaagaa gaaaataaa     900 aaaacctaca ctatgtcgtc ttctccatcg tttgctcagg aggttctcgc taccactagt    960
ccttacatcg agtactttct tgacaactac accagatggt actacttcat cccctttggtg   1020 cttctttcgt tgaacttcat cagcttgctc cacacaaagt acttggaacg caggttccac    1080
gccaagccgc tcggtaacgt cgtgttggat cctacgtttg gtatcgctac tccgttgatc    1140
ttgatctact taaagtcgaa aggtacagtc atgaagtttt cctggagctt ctggaacaac    1200
aagtacattg tcaaagaccc aaagtacaag accactggcc ttagaattgt cggcctccca    1260
ttgattgaaa ccatagaccc agagaacatc aaagctgtgt tggctactca gttcaacgat    1320
ttctccttgg gaactagaca cgatttcttg tactccttgt tgggcgatgg tattttttacc   1380 ttggacggtg ctggctggaa acacagtaga actatgttga gaccacagtt tgctagagaa   1440
caggtttccc acgtcaagtt gttggaacca cacgttcagg tgttcttcaa gcacgttaga    1500
aaacaccgcg gtcagacttt tgacatccaa gaattgttct tcagattgac cgtcgactcc    1560
gccaccgagt tcttgtttgg tgagtctgct gaatccttga gagacgactc tgttggtttg    1620
accccaacca ccaaggattt cgaaggcaga ggagatttcg ctgacgcttt caactactcg    1680
cagacttacc aggcctacag attttttgttg caacaaatgt actggatttt gaatggcgcg   1740
```

-continued

```
gaattcagaa agtcgattgc catcgtgcac aagtttgctg accactatgt gcaaaaggct    1800
ttggagttga ccgacgatga cttgcagaaa caagacggct atgtgttctt gtacgagttg    1860
gctaagcaaa ctagagaccc aaaggtcttg agagaccagt tgttgaacat tttggttgcc    1920
ggtagagaca cgaccgccgg tttgttgtcg tttgtgttct acgagttgtc gagaaaccct    1980
gaagtgtttg ccaagttgag agaggaggtg gaaaacagat ttggactcgg cgaagaggct    2040
cgtgttgaag agatctcttt tgagtccttg aagtcctgtg agtacttgaa ggctgtcatc    2100
aatgaagcct tgagattgta cccatctgtt ccacacaact tcagagttgc caccagaaac    2160
actacccttc aagaggcggt ggtaaagac ggatgctcgc caattgttgt caagaagggt    2220
caagttgtca tgtacactgt cattggtacc cacagagacc caagtatcta cggtgccgac    2280
gccgacgtct tcagaccaga aagatggttc gagccagaaa ctagaaagtt gggctgggca    2340
tatgttccat tcaatggtgg tccaagaatc tgtttgggtc agcagtttgc cttgactgaa    2400
gcttcatacg tcactgtcag attgctccaa gagtttggaa acttgtccct ggatccaaac    2460
gctgagtacc caccaaaatt gcagaacacc ttgaccttgt cactctttga tggtgctgac    2520
gttagaatgt tctaaggttg cttatccttg ctagtgttat ttatagtttg tgtatttaaa    2580
ttgaatcggc gattgatttt tctggtacta ataactgtag tgggttttga ccaaaaccgt    2640
tcaaactttt tttttttttt tcttcccct accttcgttg ctcgctcatc agcactgttt    2700
gaaaacgaaa aaagaaaatt ttttgtaaac aacattgccc aaacttaccc aacgtgaacc    2760
attataacca aatgagcggc gctttcaact ggtcactgga ggcattcggg gatatctaca    2820
acacccttaa gtttgaggaa gacattgatt tagacaccat agatttcagc ggcatcaaga    2880
atgaccttgt ccacattttg acaaccccaa caccactgga agaatcgcgc cagaaactag    2940
gcgatggatc caagcctgtg gccttgccca atggagacga agtggagttg aaccaagcgt    3000
tcctagaagt taccacatta ttgtcgaacg agtttgactt ggaccaattg aacgcggccg    3060
agttgttata ctacgccggc gacatatcct acaagaaggg cacatcaatt gccgacagtg    3120
ccagattgtc ttactatttg agagcaaaact acatcttgaa catacttggg tactttattt    3180
cgaagcagcg attggatgtg atagtcaccg acaacaacgc gttgtttgat aatattttga    3240
aaagttttga aaagatctac aagttgataa gcgcgttgaa cgatatgatt gacaagcaaa    3300
aggtgacaag cgacatcaac agtctagcat ttatcaactg catcaactac tcgaggggtc    3360
aactattctc cgcacacgaa cttttgggac tggttttgtt tggattggtt gacaactatt    3420
tcaaccagtt tggctcatta gacaactaca agaaagtatt ggcattgata ctgaagaaca    3480
tcagtgatga agatatcttg atcgtacgct tcctcccatc gacactacaa ttgtttaagc    3540
tggtgttgga taagaaagac gacgccactg ttgaccagtt ctacaagtac atcacctcaa    3600
cagtgtcgca agactacaac tccaacatcg gagccacagc caaagatgat atcgatttgt    3660
ccaaagcc                                                             3668
```

```
<210> SEQ ID NO 90
<211> LENGTH: 3826
<212> TYPE: DNA
<213> ORGANISM: Candida tropicalis

<400> SEQUENCE: 90
tggagtcgcc agacttgctc acttttgact cccttcgaaa ctcaaagtac gttcaggcgg      60
tgctcaacga aacgctccgt atctacccgg gggtaccacg aaacatgaag acagctacgt     120
```

-continued

| | |
|---|---|
| gcaacacgac gttgccacgc ggaggaggca aagacggcaa ggaacctatc ttggtgcaga | 180 |
| agggacagtc cgttgggttg attactattg ccacgcagac ggacccagag tattttgggg | 240 |
| ccgacgctgg tgagtttaag ccggagagat ggtttgattc aagcatgaag aacttggggt | 300 |
| gtaaatactt gccgttcaat gctgggccac ggacttgctt ggggcagcag tacactttga | 360 |
| ttgaagcgag ctacttgcta gtccggttgg cccagaccta ccgggcaata gatttgcagc | 420 |
| caggatcggc gtacccacca agaaagaagt cgttgatcaa catgagtgct gccgacgggg | 480 |
| tgtttgtaaa gctttataag gatgtaacgg tagatggata gttgtgtagg aggagcggag | 540 |
| ataaattaga tttgattttg tgtaaggttt tggatgtcaa cctactccgc acttcatgca | 600 |
| gtgtgtgtga cacaagggtg tactacgtgt gcgtgtgcgc caagagacag cccaaggggg | 660 |
| tggtagtgtg tgttggcgga agtgcatgtg acacaacgcg tgggttctgg ccaatggtgg | 720 |
| actaagtgca ggtaagcagc gacctgaaac attcctcaac gcttaagaca ctggtggtag | 780 |
| agatgcggac caggctattc ttgtcgtgct acccggcgca tggaaaatca actgcgggaa | 840 |
| gaataaattt atccgtagaa tccacagagc ggataaattt gcccacctcc atcatcaacc | 900 |
| acgccgccac taactacatc actcccctat tttctctctc tctctttgtc ttactccgct | 960 |
| cccgtttcct tagccacaga tacacaccca ctgcaaacag cagcaacaat tataaagata | 1020 |
| cgccaggccc accttctttc ttttctttca cttttttgac tgcaactttc tacaatccac | 1080 |
| cacagccacc accacagccg ctatgattga caactcctag aatattggt atgtcgttgt | 1140 |
| gccagtgttg tacatcatca aacaactcct tgcatacaca aagactcgcg tcttgatgaa | 1200 |
| aaagttgggt gctgctccag tcacaaacaa gttgtacgac aacgctttcg gtatcgtcaa | 1260 |
| tggatggaag gctctccagt tcaagaaaga gggcagggct caagagtaca acgattacaa | 1320 |
| gtttgaccac tccaagaacc caagcgtggg cacctacgtc agtattcttt tcggcaccag | 1380 |
| gatcgtcgtg accaaagatc cagagaatat caaagctatt ttggcaaccc agtttggtga | 1440 |
| ttttttcttt ggcaagaggc acactctttt taagcctttg ttaggtgatg ggatcttcac | 1500 |
| attggacggc gaaggctgga agcacagcag agccatgttg agaccacagt ttgccagaga | 1560 |
| acaagttgct catgtgacgt cgttggaacc acacttccag ttgttgaaga agcatattct | 1620 |
| taagcacaag ggtgaatact ttgatatcca ggaattgttc tttagattta ccgttgattc | 1680 |
| ggccacggag ttcttatttg gtgagtccgt gcactcctta aaggacgaat ctattggtat | 1740 |
| caaccaagac gatatagatt ttgctggtag aaaggacttt gctgagtcgt tcaacaaagc | 1800 |
| ccaggaatac ttggctatta gaaccttggt gcagacgttc tactggttgg tcaacaacaa | 1860 |
| ggagtttaga gactgtacca agctggtgca caagttcacc aactactatg ttcagaaagc | 1920 |
| tttggatgct agcccagaag agcttgaaaa gcaaagtggg tatgtgttct tgtacgagct | 1980 |
| tgtcaagcag acaagagacc ccaatgtgtt gcgtgaccag tctttgaaca tcttgttggc | 2040 |
| cggaagagac accactgctg ggttgttgtc gtttgctgtc tttgagttgg ccagacaccc | 2100 |
| agagatctgg gccaagttga gagaggaaat tgaacaacag tttggtcttg gagaagactc | 2160 |
| tcgtgttgaa gagattacct tgagagcttg aagagatgt gagtacttga aagcgttcct | 2220 |
| taatgaaacc ttgcgtattt acccaagtgt cccaagaaac ttcagaatcg ccaccaagaa | 2280 |
| cacgacattg ccaaggggcg gtggttcaga cggtacctcg ccaatcttga tccaaaaggg | 2340 |
| agaagctgtg tcgtatggta tcaactctac tcatttggac cctgtctatt acggccctga | 2400 |
| tgctgctgag ttcagaccag agagatggtt tgagccatca accaaaaagc tcggctgggc | 2460 |
| ttacttgcca ttcaacggtg gtccaagaat ctgtttgggt cagcagtttg ccttgacgga | 2520 |

```
agctggctat gtgttggtta gattggtgca agagttctcc cacgttaggc tggacccaga    2580
cgaggtgtac ccgccaaaga ggttgaccaa cttgaccatg tgtttgcagg atggtgctat    2640
tgtcaagttt gactagcggc gtggtgaatg cgtttgattt tgtagtttct gtttgcagta    2700
atgagataac tattcagata aggcgagtgg atgtacgttt tgtaagagtt tccttacaac    2760
cttggtgggg tgtgtgaggt tgaggttgca tcttggggag attacacctt ttgcagctct    2820
ccgtatacac ttgtactctt tgtaacctct atcaatcatg tggggggggg ggttcattgt    2880
ttggccatgg tggtgcatgt taaatccgcc aactacccaa tctcacatga aactcaagca    2940
cactaaaaaa aaaaagatg ttgggggaaa actttggttt cccttcttag taattaaaca    3000
ctctcactct cactctcact ctctccactc agacaaacca accacctggg ctgcagacaa    3060
ccagaaaaaa aagaacaaa atccagatag aaaacaaag ggctggacaa ccataaataa    3120
acaatctagg gtctactcca tcttccactg tttcttcttc ttcagactta gctaacaaac    3180
aactcacttc accatggatt acgcaggcat cacgcgtggc tccatcagag gcgaggcctt    3240
gaagaaactc gcagaattga ccatccagaa ccagccatcc agcttgaaag aaatcaacac    3300
cggcatccag aaggacgact tgccaagtt gttgtctgcc accccgaaaa tccccaccaa    3360
gcacaagttg aacggcaacc acgaattgtc tgaggtcgcc attgccaaaa ggagtacga    3420 ggtgttgatt gccttgagcg acgccacaaa agacccaatc aaagtgacct cccagatcaa    3480
gatcttgatt gacaagttca aggtgtactt gtttgagttg cctgaccaga agttctccta    3540
ctccatcgtg tccaactccg tcaacatcgc cccctggacc ttgctcgggg agaagttgac    3600
cacgggcttg atcaacttgg ccttccagaa caacaagcag cacttggacg aggtcattga    3660
catcttcaac gagttcatcg acaagttctt tggcaacacg gagccgcaat tgaccaactt    3720
cttgaccttg tgcggtgtgt tggacgggtt gattgaccat gccaacttct tgagcgtgtc    3780
ctcgcggacc ttcaagatct tcttgaactt ggactcgtat gtggac                  3826
```

<210> SEQ ID NO 91
<211> LENGTH: 3910
<212> TYPE: DNA
<213> ORGANISM: Candida tropicalis

<400> SEQUENCE: 91

```
ttacaatcat ggagctcgct aggaacccag atgtctggga gaagctccgc gaagaggtca     60
acacgaactt tggcatggag tcgccagact tgctcacttt tgactctctt agaagctcaa    120
agtacgttca ggcggtgctc aacgaaacgc ttcgtatcta cccgggggtg ccacgaaaca    180
tgaagacagc tacgtgcaac acgacgttgc cgcgtgagg aggcaaagac ggtaaggaac    240
ctattttggt gcagaagggc cagtccgttg ggttgattac tattgccacg cagacggacc    300
cagagtattt tggggcagat gctggtgagt caaaccgga gagatggttt gattcaagca    360
tgaagaactt ggggtgtaag tacttgccgt tcaatgctgg gccccggact tgtttggggc    420
agcagtacac tttgattgaa gcgagctatt tgctagtcag gttggcgcag acctaccggg    480
taatcgattt gctgccaggg tcggcgtacc caccaagaaa gaagtcgttg atcaatatga    540
gtgctgccga tggggtggtt gtaaagtttc acaggatct agatggatat gtaaggtgtg    600
taggaggagc ggagataaat tagatttgat tttgtgtaag gtttagcacg tcaagctact    660
ccgcactttg tgtgtaggga gcacatactc cgtctcgcc tgtgccaaga gacggcccag    720
gggtagtgtg tggtggtgga agtgcatgtg acacaatacc ctggttctgg ccaattgggg    780
```

-continued

| | |
|---|---|
| atttagtgta ggtaagctgc gacctgaaac actcctcaac gcttgagaca ctggtgggta | 840 |
| gagatgcggg ccaggaggct attcttgtcg tgctacccgt gcacggaaaa tcgattgagg | 900 |
| gaagaacaaa tttatccgtg aaatccacag agcggataaa tttgtcacat tgctgcgttg | 960 |
| cccacccaca gcattctctt ttctctctct ttgtcttact ccgctcctgt ttccttatcc | 1020 |
| agaaatacac accaactcat ataaagatac gctagcccag ctgtctttct ttttcttcac | 1080 |
| ttttttggt gtgttgcttt tttggctgct actttctaca accaccacca ccaccaccac | 1140 |
| catgattgaa caaatcctag aatattggta tattgttgtg cctgtgttgt acatcatcaa | 1200 |
| acaactcatt gcctacagca agactcgcgt cttgatgaaa cagttgggtg ctgctccaat | 1260 |
| cacaaaccag ttgtacgaca acgttttcgg tatcgtcaac ggatggaagg ctctccagtt | 1320 |
| caagaaagag ggcagagctc aagagtacaa cgatcacaga tttgacagct ccaagaaccc | 1380 |
| aagcgtcggc acctatgtca gtattctttt tggcaccaag attgtcgtga ccaaggatcc | 1440 |
| agagaatatc aaagctattt ggcaaccca gtttggcgat ttttctttgg caagagaca | 1500 |
| cgctcttttt aaacctttgt taggtgatgg gatcttcacc ttggacggcg aaggctggaa | 1560 |
| gcatagcaga tccatgttaa gaccacagtt tgccagagaa caagttgctc atgtgacgtc | 1620 |
| gttggaacca cacttccagt tgttgaagaa gcatatcctt aaacacaagg gtgagtactt | 1680 |
| tgatatccag gaattgttct ttagatttac tgtcgactcg gccacggagt tcttatttgg | 1740 |
| tgagtccgtg cactccttaa aggacgaaac tatcggtatc aaccaagacg atatagattt | 1800 |
| tgctggtaga aaggactttg ctgagtcgtt caacaaagcc caggagtatt tgtctattag | 1860 |
| aattttggtg cagaccttct actggttgat caacaacaag gagtttagag actgtaccaa | 1920 |
| gctggtgcac aagtttacca actactatgt tcagaaaagct ttggatgcta ccccagagga | 1980 |
| acttgaaaag caaggcgggt atgtgttctt gtatgagctt gtcaagcaga cgagagaccc | 2040 |
| caaggtgttg cgtgaccagt cttttgaacat cttgttggca ggaagagaca ccactgctgg | 2100 |
| gttgttgtcc tttgctgtgt ttgagttggc cagaaaccca cacatctggg ccaagttgag | 2160 |
| agaggaaatt gaacagcagt ttggtcttgg agaagactct cgtgttgaag agattacctt | 2220 |
| tgagagcttg aagagatgtg agtacttgaa agcgttcctt aacgaaacct tgcgtgttta | 2280 |
| cccaagtgtc ccaagaaact tcagaatcgc caccaagaat acaacattgc caagggggtgg | 2340 |
| tggtccagac ggtacccagc caatcttgat ccaaaaggga gaaggtgtgt cgtatggtat | 2400 |
| caactctacc cacttagatc ctgtctatta tggccctgat gctgctgagt tcagaccaga | 2460 |
| gagatggttt gagccatcaa ccagaaagct cggctgggct tacttgccat tcaacggtgg | 2520 |
| gccacgaatc tgtttgggtc agcagtttgc cttgaccgaa gctggttacg ttttggtcag | 2580 |
| attggtgcaa gagttctccc acattaggct ggacccagat gaagtgtatc caccaaagag | 2640 |
| gttgaccaac ttgaccatgt gtttgcagga tggtgctatt gtcaagtttg actagtacgt | 2700 |
| atgagtgcgt ttgattttgt agtttctgtt tgcagtaatg agataactat tcagataagg | 2760 |
| cgggtggatg tacgttttgt aagagtttcc ttacaaccct ggtgggtgtg tgaggttgca | 2820 |
| tcttagggag agatagcacc ttttgcagct ctccgtatac agttttactc tttgtaacct | 2880 |
| atgccaatca tgtgggggatt cattgtttgc ccatggtggt gcatgcaaaa tcccccaac | 2940 |
| tacccaatct cacatgaaac tcaagcacac tagaaaaaaa agatgttgcg tgggttcttt | 3000 |
| tgatgttggg gaaaactttc gtttcctttc tcagtaatta acgttctca ctcagacaaa | 3060 |
| ccacctgggc tgcagacaac cagaaaaaac aaaatccaga tagaagaaga aagggctgga | 3120 |
| caaccataaa taaacaacct agggtccact ccatctttca cttcttcttc ttcagactta | 3180 |

-continued

```
tctaacaaac gactcacttc accatggatt acgcaggtat cacgcgtggg tccatcagag    3240
gcgaagcctt gaagaaactc gccgagttga ccatccagaa ccagccatcc agcttgaaag    3300
aaatcaacac cggcatccag aaggacgact ttgccaagtt gttgtcttcc accccgaaaa    3360
tccacaccaa gcacaagttg aatggcaacc acgaattgtc cgaagtcgcc attgccaaaa    3420
aggagtacga ggtgttgatt gccttgagcg acgccacgaa agaaccaatc aaagtcacct    3480
cccagatcaa gatcttgatt gacaagttca aggtgtactt gtttgagttg cccgaccaga    3540
agttctccta ctccatcgtg tccaactccg ttaacattgc ccctggacc ttgctcggtg     3600 agaagttgac cacgggcttg atcaacttgg cgttccagaa caacaagcag cacttggacg    3660
aagtcatcga catcttcaac gagttcatcg acaagttctt tggcaacaca gagccgcaat    3720
tgaccaactt cttgaccttg tccggtgtgt tggacgggtt gattgaccat gccaacttct    3780
tgagcgtgtc ctccaggacc ttcaagatct tcttgaactt ggactcgttt gtggacaact    3840
cggacttctt gaacgacgtg gagaactact ccgactttt gtacgacgag ccgaacgagt     3900
accagaactt                                                           3910
```

<210> SEQ ID NO 92
<211> LENGTH: 3150
<212> TYPE: DNA
<213> ORGANISM: Candida tropicalis

<400> SEQUENCE: 92

```
gaattctttg gatctaattc cagctgatct tgctaatcct tatcaacgta gttgtgatca      60
ttgtttgtct gaattataca caccagtgga agaatatggt ctaatttgca cgtcccactg     120
gcattgtgtg tttgtggggg gggggggtg cacacatttg tagtgccatt ctttgttgat     180 taccctccc ccctatcatt cattcccaca ggattagttt tttcctcact ggaattcgct     240
gtccacctgt caacccccc ccccccccc ccactgccc taccctgccc tgccctgcac       300
gtcctgtgtt ttgtgctgtg tcttcccac gctataaaag ccctggcgtc cggccaaggt     360
ttttccaccc agccaaaaaa acagtctaaa aaatttggtt gatcctttt ggttgcaagg     420 ttttccacca ccacttccac cacctcaact attcgaacaa aagatgctcg atcagatctt     480
acattactgg tacattgtct tgccattgtt ggccattatc aaccgatcg tggctcatgt     540 caggaccaat tatttgatga agaaattggg tgctaagcca ttcacacacg tccaacgtga    600
cgggtggttg ggcttcaaat tcggccgtga attcctcaaa gcaaaaagtg ctgggagact    660
ggttgattta atcatctccc gtttccacga taatgaggac actttctcca gctatgcttt    720 tgcaaccat gtggtgttca ccagggaccc cgagaatatc aaggcgcttt tggcaaccca     780
gtttggtgat ttttcattgg gcagcagggt caagttcttc aaaccattat tggggtacgg    840
tatcttcaca ttggacgccg aaggctggaa gcacagcaga gccatgttga gaccacagtt    900
tgccagagaa caagttgctc atgtgacgtc gttggaacca cacttccagt tgttgaagaa    960
gcatatcctt aaacacaagg gtgagtactt tgatatccag gaattgttct ttagatttac    1020
tgtcgactcg gccacggagt tcttatttgg tgagtccgtg cactccttaa aggacgagga    1080
aattggctac gacacgaaag acatgtctga agaagacgc agatttgccg acgcgttcaa    1140
caagtcgcaa gtctacgtgg ccaccagagt tgctttacag aacttgtact ggttggtcaa    1200
caacaaagag ttcaaggagt gcaatgcat tgtccacaag tttaccaact actatgttca    1260
gaaagccttg gatgctaccc cagaggaact tgaaaagcaa ggcggtatg tgttcttgta    1320
```

```
tgagcttgtc aagcagacga gagaccccaa ggtgttgcgt gaccagtctt tgaacatctt    1380
gttggcagga agagacacca ctgctgggtt gttgtccttt gctgtgtttg agttggccag    1440
aaacccacac atctgggcca agttgagaga ggaaattgaa cagcagtttg gtcttggaga    1500
agactctcgt gttgaagaga ttacctttga gagcttgaag agatgtgagt acttgaaggc    1560
cgtgttgaac gaaactttga gattacaccc aagtgtccca agaaacgcaa gatttgcgat    1620
taaagacacg actttaccaa gaggcggtgg ccccaacggc aaggatccta tcttgatcag    1680
gaaggatgag gtggtgcagt actccatctc ggcaactcag acaaatcctg cttattatgg    1740
cgccgatgct gctgatttta gaccggaaag atggtttgaa ccatcaacta gaaacttggg    1800
atgggctttc ttgccattca acggtggtcc aagaatctgt ttgggacaac agtttgcttt    1860
gactgaagcc ggttacgttt tggttagact tgttcaggag tttccaaact tgtcacaaga    1920
ccccgaaacc aagtacccac cacctagatt ggcacacttg acgatgtgct tgtttgacgg    1980
tgcacacgtc aagatgtcat aggtttcccc atacaagtag ttcagtaatt atacactgtt    2040
tttactttct cttcatacca aatggacaaa agttttaagc atgcctaaca acgtgaccgg    2100
acaattgtgt cgcactagta tgtaacaatt gtaaaaatag tgtacactaa tttgtggtgg    2160
ccggagataa attacagttt ggttttgtgt aaactcgcgg atatctctgg cagtttctct    2220
tctccgcagc agctttgcca cgggtttgct ctggggccaa caaattcaaa aggggggagaa    2280 acttaacacc ccttatctct ccactctagg ttgtagctct tgtggggatg caattgtcgt    2340 acgttttta tgttttgtct agactttgat gattacgttg gatttcttat gtctgaggcg    2400
tgcttgaaag aagtgtcaaa atgtgacagg cgacgctatt cgacatgaac gcgaaagggt    2460
tatttgcatc aatacgaggg gctgactcta gtctaggatg gcagtcctag gttgcaaaca    2520
tgttgcacca tatccctcct ggagttggtc gacctcgcct acgccaccct cagcgatcgg    2580
cactttccgt tgttcaatat ttctccttcc cattgttcca ggggttatca acaacgttgc    2640
cggcctcctc cccaaattac aagaaaaata aattgtcgca cggcaccgat ctgtcaaaga    2700
tacagataaa cctttaaatct gcaaaaacaa gaccccctccc catagcctag aagcaccagc    2760
aagatgatgg agcaactcct ccagtactgg tacatcgcac tctctgtatg gttcatcctt    2820
cgctacttgg cttcccacgc acgagccgtc tacttgcgcc acaagctcgg cgcggcgcca    2880
ttcacgcaca cccagtacga cggctggtat gggttcaagt ttgggcggga gtttctcaag    2940
gcgaagaaga tcgggcggca gacggacttg gtgcatgcgc ggttccgtgg cggcatggac    3000
accttctcga gctacacttt cggcatccat atcatcctta cccgggaccc ggagaacatc    3060
aaggcggtct tggcgacgca gttcgatgac ttctcgctcg gtggcaggat caggttcttg    3120
aagccgttgt tggggtatgg gatattcacg                                      3150
```

<210> SEQ ID NO 93
<211> LENGTH: 3579
<212> TYPE: DNA
<213> ORGANISM: Candida tropicalis

<400> SEQUENCE: 93

```
aaaaccgata caagaagaag acagtcaaca agaacgttaa tgtcaaccag gcgccaagaa      60
gacggtttgg cggacttgga agaatgtggc atttgcccat gatgtttatg ttctggagag     120 gttttttcaag gaatcgtcat cctccgccac cacaagaacc accagttaac gagatccata     180
ttcacaaccc accgcaaggt gacaatgctc aacaacaaca gcaacaacaa caaccccccac    240 aagaacagtg gaataatgcc agtcaacaaa gagtggtgac agacgaggga gaaaacgcaa    300
```

-continued

```
gcaacagtgg ttctgatgca agatcagcta caccgcttca tcaggaaaag caggagctcc    360
caccaccata tgcccatcac gagcaacacc agcaggttag tgtatagtag tctgtagtta    420
agtcaatgca atgtaccaat aagactatcc cttcttacaa ccaagttttc tgccgcgcct    480
gtctggcaac agatgctggc cgacacactt tcaactgagt ttggtctaga attcttgcac    540
atgcacgaca aggaaactct tacaaagaca cacttgtgc tctgatgcca cttgatcttg     600
ctaagcctta tcaacgtaat tgagatcatt gtttgtctga attatacaca ccagtggaag    660
aatctggtct aatctgcacg cctcatgggc attgtgtgtt ttggggggggg ggggggggggt  720
gcacacattt ttagtgcgaa tgtttgtttg ctggttcccc ctcccccctc cccctatca     780
tgcccacagg attagttttt tcctcactgg aattcgctgt ccacctgtca accccctcac    840
tgccctgccc tgcccctgcac gccctgtgtt ttgtgctgtg gcactcccac gctataaaag   900
ccctggcgta cggccaaggt ttttcctcac agccaaaaaa aaatttggct gatccttttg    960
ggctgcaagg ttttttcacca ccaccaccac caccacctca actattcaaa caaaggatgc  1020
tcgaccagat cttccattac tggtacattg tcttgccatt gttggtcatt atcaagcaga   1080
tcgtggctca tgccaggacc aattatttga tgaagaagtt gggcgctaag ccattcacac   1140
atgtccaact agacgggtgg tttggcttca aatttggccg tgaattcctc aaagctaaaa   1200
gtgctgggag gcaggttgat ttaatcatct cccgtttcca cgataatgag gacactttct   1260
ccagctatgc ttttggcaac catgtggtgt tcaccaggga ccccgagaat atcaaggcgc   1320
ttttggcaac ccagtttggt gattttttcat gggaagcag ggtcaaattc ttcaaaccat    1380
tgttggggta cggtatcttc accttggacg gcgaaggctg gaagcacagc agagccatgt   1440
tgagaccaca gtttgccaga gagcaagttg ctcatgtgac gtcgttggaa ccacatttcc   1500
agttgttgaa gaagcatatt cttaagcaca agggtgaata ctttgatatc caggaattgt   1560
tctttagatt taccgttgat tcagcgacgg agttcttatt tggtgagtcc gtgcactcct   1620
taagggacga ggaaattggc tacgatacga aggacatggc tgaagaaaga cgcaaatttg   1680
ccgacgcgtt caacaagtcg caagtctatt tgtccaccag agttgcttta cagacattgt   1740
actggttggt caacaacaaa gagttcaagg agtgcaacga cattgtccac aagttcacca   1800
actactatgt tcagaaagcc ttggatgcta ccccagagga acttgaaaaa caaggcgggt   1860
atgtgttctt gtacgagctt gccaagcaga cgaaagaccc caatgtgttg cgtgaccagt   1920
cttttgaacat cttgttggct ggaagggaca ccactgctgg gttgttgtcc tttgctgtgt   1980
ttgagttggc caggaaccca cacatctggg ccaagttgag agaggaaatt gaatcacact   2040
ttgggctggg tgaggactct cgtgttgaag agattacctt tgagagcttg aagagatgtg   2100
agtacttgaa agccgtgttg aacgaaacgt tgagattaca cccaagtgtc ccaagaaacg   2160
caagatttgc gattaaagac acgactttac caagaggcgg tggccccaac ggcaaggatc   2220
ctatcttgat cagaaagaat gaggtggtgc aatactccat ctcggcaact cagacaaatc   2280
ctgcttatta tggcgccgat gctgctgatt ttagaccgga aagatggttt gagccatcaa   2340
ctagaaactt gggatgggct tacttgccat tcaacggtgg tccaagaatc tgcttgggac   2400
aacagtttgc tttgaccgaa gccgttacg ttttggttag acttgttcag gaattcccta    2460
gcttgtcaca ggaccccgaa actgagtacc caccacctag attggcacac ttgacgatgt   2520
gcttgtttga cggggcatac gtcaagatgc aataggtttt ggtttgactt tgtttccata   2580
tgcaagtagt tcagtaatta cacactaatt tgtggtggcc ggcgataaat taccgtttgg   2640
```

-continued

| | |
|---|---|
| ttttgtgtaa aaattcggac atctctggtg gtttcccttc tccgcagcag ctttgccacg | 2700 |
| ggtttgctct gcggccaaca aattcgaaag ggggggggg ggggagaaa gttaacaccc | 2760 |
| cctgttccca ccgtaggctg tagctcttgt gggggatgt aattgtcgta cgttttcatg | 2820 |
| tttggcccag actttgatga ttacgtaggc tttcttatgt ctaaggcgtg cttgacacaa | 2880 |
| gtgtcaaaag gtgacaggcg acgttattcg acatgaacgc aaaagggtaa tttgcatcga | 2940 |
| tacgaggggt tgcctctggt ctaagaagga ccccccaggt tgcaaacatg ttgcactgca | 3000 |
| tcccactcag agttggtcga ccacgcctac gcttaccctc agcgatcggc actttccgtt | 3060 |
| gctcaatatt tctctccccc ctgcttcccc ccattgttcc agggattatc aacaacgttg | 3120 |
| ccggtctcct ctcccccccc tcccccagt tatgtacaag aaaattaaat tgtcgcacgg | 3180 |
| caccgatacg tcaaagatac agagaaacct taatccctcc catagcctag aagcatcaaa | 3240 |
| aagatgattg agcaactcct ccagtactgg tacattgcac tccctgtatg gttcattctc | 3300 |
| cgctacgtgg cttcccacgc acgaaccatc tacttgcgcc acaagctcgg cgcggcgccg | 3360 |
| ttcacgcaca cccagtacga cggatggtat gggttcaagt ttgggcggga gtttctcaag | 3420 |
| gcgaagaaga ttggaaggca gacggacttg gtgcatgcgc ggttccgtgg agggggcatg | 3480 |
| gatactttct cgagctatac tttcggcatc catatcattc ttactcggga cccggagaac | 3540 |
| atcaaggcgg tcttggcgac gcagttcgat gacttttcg | 3579 |

<210> SEQ ID NO 94
<211> LENGTH: 3348
<212> TYPE: DNA
<213> ORGANISM: Candida tropicalis

<400> SEQUENCE: 94

| | |
|---|---|
| gatgtggtgc ttgatttctc gagacacatc cttgtgaggt gccatgaatc tgtacctgtc | 60 |
| tgtaagcaca gggaactgct tcaacacctt attgcatatt ctgtctattg caagcgtgtg | 120 |
| ctgcaacgat atctgccaag gtatatagca gaacgtgctg atggttcctc cggtcatatt | 180 |
| ctgttggtag ttctgcaggt aaatttggat gtcaggtagt ggagggaggt ttgtatcggt | 240 |
| tgtgttttct tcttcctctc tctctgattc aacctccacg tctccttcgg gttctgtgtc | 300 |
| tgtgtctgag tcgtactgtt ggattaagtc catcgcatgt gtgaaaaaaa gtagcgctta | 360 |
| tttagacaac cagttcgttg ggcgggtatc agaaatagtc tgttgtgcac gaccatgagt | 420 |
| atgcaacttg acgagacgtc gttaggaatc cacagaatga tagcaggaag cttactacgt | 480 |
| gagagattct gcttagagga tgttctcttc ttgttgattc cattaggtgg gtatcatctc | 540 |
| cggtggtgac aacttgacac aagcagttcc gagaaccacc cacaacaatc accattccag | 600 |
| ctatcacttc tacatgtcaa cctacgatgt atctcatcac catctagttt cttggcaatc | 660 |
| gtttatttgt tatgggtcaa catccaatac aactccacca atgaagaaga aaaacggaaa | 720 |
| gcagaatacc agaatgacag tgtgagttcc tgaccattgc taatctatgg ctatatctag | 780 |
| tttgctatcg tgggatgtga tctgtgtcgt cttcatttgc gtttgtgttt atttcgggta | 840 |
| tgaatattgt tatactaaat acttgatgca caaacatggc gctcgagaaa tcgagaatgt | 900 |
| gatcaacgat gggttctttg ggttccgctt acctttgcta ctcatgcgag ccagcaatga | 960 |
| gggccgactt atcgagttca gtgtcaagag attcgagtcg cgccacatc cacagaacaa | 1020 |
| gacattggtc aaccgggcat tgagcgttcc tgtgatactc accaaggacc cagtgaatat | 1080 |
| caaagcgatg ctatcgaccc agtttgatga cttttccctt gggttgagac tacaccagtt | 1140 |
| tgcgccgttg ttggggaaag gcatctttac tttggacggc ccagagtgga agcagagccg | 1200 |

-continued

```
atctatgttg cgtccgcaat ttgccaaaga tcgggtttct catatcctgg atctagaacc    1260
gcattttgtg ttgcttcgga agcacattga tggccacaat ggagactact tcgacatcca    1320
ggagctctac ttccggttct cgatggatgt ggcgacgggg tttttgtttg gcgagtctgt    1380
ggggtcgttg aaagacgaag atgcgaggtt cctggaagca ttcaatgagt cgcagaagta    1440
tttggcaact agggcaacgt tgcacgagtt gtactttctt tgtgacgggt ttaggtttcg    1500
ccagtacaac aaggttgtgc gaaagttctg cagccagtgt gtccacaagg cgttagatgt    1560
tgcaccggaa gacaccagcg agtacgtgtt tctccgcgag ttggtcaaac acactcgaga    1620
tcccgttgtt ttacaagacc aagcgttgaa cgtcttgctt gctggacgcg acaccaccgc    1680
gtcgttatta tcgtttgcaa catttgagct agcccggaat gaccacatgt ggaggaagct    1740
acgagaggag gttatcctga cgatgggacc gtccagtgat gaaataaccg tggccgggtt    1800
gaagagttgc cgttacctca aagcaatcct aaacgaaact cttcgactat acccaagtgt    1860
gcctaggaac gcgagatttg ctacgaggaa tacgacgctt cctcgtggcg gaggtccaga    1920
tggatcgttt ccgattttga taagaaaggg ccagccagtg gggtattcca tttgtgctac    1980
acacttgaat gagaaggtat atgggaatga tagccatgtg tttcgaccgg agagatgggc    2040
tgcgttagag ggcaagagtt tgggctggtc gtatcttcca ttcaacgcg gcccgagaag     2100
ctgccttggt cagcagtttg caatccttga agcttcgtat gttttggctc gattgacaca    2160
gtgctacacg acgatacagc ttagaactac cgagtaccca ccaaagaaac tcgttcatct    2220
cacgatgagt cttctcaacg gggtgtacat ccgaactaga acttgattat gtgtttatgg    2280
ttaatcgggg caaagcactg caagtcattg atgtttgtgg aagcccagca ttggtgttcc    2340
ggagcatcaa taaccaatgt cttgaagggt ttgattttct tgaccttctt cttcctgagc    2400
ttctttccgt caaacttgta cagaatggcc atcatttcag gaacaaccac gtacgacggc    2460
cggtaccgca tctggagtat ctcgccgtcg ttcaagtagc acgaaaacag caacgacgtc    2520
accatctgct tcccaatctt gacacccaca gatacccctg cggcttcatg gatcaaaaac    2580
gtcggcaacc ccgcgtatat gtccatgtaa ttctccatgg ccacctccat caacacactg    2640
atggagcgac tgacggtgcc accactgccc tcggttgagt caaggcagta tgatgccggg    2700
atccagtact ccaatgggaa cctctgcacg gtgtcgctgc agttttgag gcgtatttcg      2760
atccatgatc gttctttggt gctgtagtat aacgagctct tggtgtcctt gaaatggaac    2820
aggttggatg tgttgttgag tttgtctgcg tgcttggttt gcaagtcttc gatcgagcgt    2880
agtgagtaga cagttggcgg gggtggtggc tcgggcttta ttctgtgttt gtgtttcctt    2940
cttagtcttg gaatgacgct gttatcgacg gttcgtagta aagtagcgc caatatgaga    3000
atgtatatcc gcatcaccca agactcttca gcctgttaca acgactgagg ctgttggccg    3060
tgtgaccaat tggtttcttt ggtgacctag attggtcccg cagggaaagc aagggctgct    3120
aggggggcat accaaacaag gtcgtgtaat cagtatctat ggtgctacca tgtgtgtggt    3180
tggggggaaa ttcccgcatt tttgtgtaac gaaagttcta gaaagttctc gtgggttctg    3240
agaatctgct ggaaccatcc acccgcattt ccgttgccaa agtgggaaga gcaatcaacc    3300
cacccctgct tgcccaatca gccattcccc tgggaatata aattcaac                3348
```

<210> SEQ ID NO 95
<211> LENGTH: 523
<212> TYPE: PRT
<213> ORGANISM: CANDIDATROPICALIS

<400> SEQUENCE: 95

```
Met Ala Thr Gln Glu Ile Ile Asp Ser Val Leu Pro Tyr Leu Thr Lys
1               5                   10                  15

Trp Tyr Thr Val Ile Thr Ala Val Leu Val Phe Leu Ile Ser Thr
            20                  25                  30

Asn Ile Lys Asn Tyr Val Lys Ala Lys Lys Leu Lys Cys Val Asp Pro
            35                  40                  45

Pro Tyr Leu Lys Asp Ala Gly Leu Thr Gly Ile Leu Ser Leu Ile Ala
        50                  55                  60

Ala Ile Lys Ala Lys Asn Asp Gly Arg Leu Ala Asn Phe Ala Asp Glu
65                  70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
            100                 105                 110

Leu Ala Thr Gln Phe Thr Asp Phe Ser Leu Gly Thr Arg His Ala His
            115                 120                 125

Phe Ala Pro Leu Leu Gly Asp Gly Ile Phe Thr Leu Asp Gly Glu Gly
130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
            195                 200                 205

Val His Ser Leu Tyr Asp Glu Lys Leu Gly Ile Pro Thr Pro Asn Glu
210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Glu Ile Thr Phe Glu
        355                 360                 365

Ala Leu Lys Arg Cys Glu Tyr Leu Lys Ala Ile Leu Asn Glu Thr Leu
    370                 375                 380

Arg Met Tyr Pro Ser Val Pro Val Asn Phe Arg Thr Ala Thr Arg Asp
385                 390                 395                 400

Thr Thr Leu Pro Arg Gly Gly Ala Asn Gly Thr Asp Pro Ile Tyr
                405                 410                 415
```

```
Ile Pro Lys Gly Ser Thr Val Ala Tyr Val Tyr Lys Thr His Arg
            420                 425                 430

Leu Glu Glu Tyr Tyr Gly Lys Asp Ala Asn Asp Phe Arg Pro Glu Arg
                435                 440                 445

Trp Phe Glu Pro Ser Thr Lys Lys Leu Gly Trp Ala Tyr Val Pro Phe
        450                 455                 460

Asn Gly Gly Pro Arg Val Cys Leu Gly Gln Gln Phe Ala Leu Thr Glu
465                 470                 475                 480

Ala Ser Tyr Val Ile Thr Arg Leu Ala Gln Met Phe Glu Thr Val Ser
                485                 490                 495

Ser Asp Pro Gly Leu Glu Tyr Pro Pro Lys Cys Ile His Leu Thr
                500                 505                 510

Met Ser His Asn Asp Gly Val Phe Val Lys Met
        515                 520

<210> SEQ ID NO 96
<211> LENGTH: 522
<212> TYPE: PRT
<213> ORGANISM: CANDIDATROPICALIS

<400> SEQUENCE: 96

Met Thr Val His Asp Ile Ile Ala Thr Tyr Phe Thr Lys Trp Tyr Val
1               5                   10                  15

Ile Val Pro Leu Ala Leu Ile Ala Tyr Arg Val Leu Asp Tyr Phe Tyr
                20                  25                  30

Gly Arg Tyr Leu Met Tyr Lys Leu Gly Ala Lys Pro Phe Phe Gln Lys
            35                  40                  45

Gln Thr Asp Gly Cys Phe Gly Phe Lys Ala Pro Leu Glu Leu Leu Lys
        50                  55                  60

Lys Lys Ser Asp Gly Thr Leu Ile Asp Phe Thr Leu Gln Arg Ile His
65                  70                  75                  80

Asp Leu Asp Arg Pro Asp Ile Pro Thr Phe Thr Phe Pro Val Phe Ser
                85                  90                  95

Ile Asn Leu Val Asn Thr Leu Glu Pro Glu Asn Ile Lys Ala Ile Leu
                100                 105                 110

Ala Thr Gln Phe Asn Asp Phe Ser Leu Gly Thr Arg His Ser His Phe
            115                 120                 125

Ala Pro Leu Leu Gly Asp Gly Ile Phe Thr Leu Asp Gly Ala Gly Trp
        130                 135                 140

Lys His Ser Arg Ser Met Leu Arg Pro Gln Phe Ala Arg Glu Gln Ile
145                 150                 155                 160

Ser His Val Lys Leu Leu Glu Pro His Val Gln Val Phe Phe Lys His
                165                 170                 175

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
                245                 250                 255

Gly Lys Lys Phe Lys Glu Cys Asn Ala Lys Val His Lys Phe Ala Asp
```

-continued

```
                260                 265                 270
Tyr Tyr Val Asn Lys Ala Leu Asp Leu Thr Pro Glu Gln Leu Glu Lys
            275                 280                 285

Gln Asp Gly Tyr Val Phe Leu Tyr Glu Leu Val Lys Gln Thr Arg Asp
            290                 295                 300

Lys Gln Val Leu Arg Asp Gln Leu Leu Asn Ile Met Val Ala Gly Arg
305                 310                 315                 320

Asp Thr Thr Ala Gly Leu Leu Ser Phe Val Phe Glu Leu Ala Arg
                325                 330                 335

Asn Pro Glu Val Thr Asn Lys Leu Arg Glu Glu Ile Glu Asp Lys Phe
            340                 345                 350

Gly Leu Gly Glu Asn Ala Ser Val Glu Asp Ile Ser Phe Glu Ser Leu
            355                 360                 365

Lys Ser Cys Glu Tyr Leu Lys Ala Val Leu Asn Glu Thr Leu Arg Leu
            370                 375                 380

Tyr Pro Ser Val Pro Gln Asn Phe Arg Val Ala Thr Lys Asn Thr Thr
385                 390                 395                 400

Leu Pro Arg Gly Gly Lys Asp Gly Leu Ser Pro Val Leu Val Arg
                405                 410                 415

Lys Gly Gln Thr Val Ile Tyr Gly Val Tyr Ala Ala His Arg Asn Pro
            420                 425                 430

Ala Val Tyr Gly Lys Asp Ala Leu Glu Phe Arg Pro Glu Arg Trp Phe
            435                 440                 445

Glu Pro Glu Thr Lys Lys Leu Gly Trp Ala Phe Leu Pro Phe Asn Gly
            450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ala His Leu Ser Met Asp
                485                 490                 495

Pro Asp Thr Glu Tyr Pro Pro Lys Lys Met Ser His Leu Thr Met Ser
            500                 505                 510

Leu Phe Asp Gly Ala Asn Ile Glu Met Tyr
            515                 520
```

<210> SEQ ID NO 97
<211> LENGTH: 522
<212> TYPE: PRT
<213> ORGANISM: CANDIDATROPICALIS

<400> SEQUENCE: 97

```
Met Thr Ala Gln Asp Ile Ile Ala Thr Tyr Ile Thr Lys Trp Tyr Val
1               5                   10                  15

Ile Val Pro Leu Ala Leu Ile Ala Tyr Arg Val Leu Asp Tyr Phe Tyr
                20                  25                  30

Gly Arg Tyr Leu Met Tyr Lys Leu Gly Ala Lys Pro Phe Phe Gln Lys
            35                  40                  45

Gln Thr Asp Gly Tyr Phe Gly Phe Lys Ala Pro Leu Glu Leu Leu Lys
        50                  55                  60

Lys Lys Ser Asp Gly Thr Leu Ile Asp Phe Thr Leu Glu Arg Ile Gln
65                  70                  75                  80

Ala Leu Asn Arg Pro Asp Ile Pro Thr Phe Thr Phe Pro Ile Phe Ser
                85                  90                  95

Ile Asn Leu Ile Ser Thr Leu Glu Pro Glu Asn Ile Lys Ala Ile Leu
            100                 105                 110
```

```
Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
        130                 135                 140

Lys His Ser Arg Ser Met Leu Arg Pro Gln Phe Ala Arg Glu Gln Ile
145                 150                 155                 160

Ser His Val Lys Leu Leu Glu Pro His Met Gln Val Phe Phe Lys His
                165                 170                 175

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
                245                 250                 255

Gly Lys Lys Phe Lys Glu Cys Asn Ala Lys Val His Lys Phe Ala Asp
            260                 265                 270

Tyr Tyr Val Ser Lys Ala Leu Asp Leu Thr Pro Glu Gln Leu Glu Lys
        275                 280                 285

Gln Asp Gly Tyr Val Phe Leu Tyr Glu Leu Val Lys Gln Thr Arg Asp
    290                 295                 300

Arg Gln Val Leu Arg Asp Gln Leu Leu Asn Ile Met Val Ala Gly Arg
305                 310                 315                 320

Asp Thr Thr Ala Gly Leu Leu Ser Phe Val Phe Phe Glu Leu Ala Arg
                325                 330                 335

Asn Pro Glu Val Thr Asn Lys Leu Arg Glu Glu Ile Glu Asp Lys Phe
            340                 345                 350

Gly Leu Gly Glu Asn Ala Arg Val Glu Asp Ile Ser Phe Glu Ser Leu
        355                 360                 365

Lys Ser Cys Glu Tyr Leu Lys Ala Val Leu Asn Glu Thr Leu Arg Leu
    370                 375                 380

Tyr Pro Ser Val Pro Gln Asn Phe Arg Val Ala Thr Lys Asn Thr Thr
385                 390                 395                 400

Leu Pro Arg Gly Gly Gly Lys Asp Gly Leu Ser Pro Val Leu Val Arg
                405                 410                 415

Lys Gly Gln Thr Val Met Tyr Gly Val Tyr Ala Ala His Arg Asn Pro
            420                 425                 430

Ala Val Tyr Gly Lys Asp Ala Leu Glu Phe Arg Pro Glu Arg Trp Phe
        435                 440                 445

Glu Pro Glu Thr Lys Lys Leu Gly Trp Ala Phe Leu Pro Phe Asn Gly
    450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Gly His Leu Ser Met Asp
                485                 490                 495

Pro Asn Thr Glu Tyr Pro Pro Arg Lys Met Ser His Leu Thr Met Ser
            500                 505                 510

Leu Phe Asp Gly Ala Asn Ile Glu Met Tyr
        515                 520
```

<210> SEQ ID NO 98
<211> LENGTH: 540
<212> TYPE: PRT
<213> ORGANISM: CANDIDATROPICALIS

<400> SEQUENCE: 98

```
Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
        35                  40                  45

Arg Tyr Leu Glu Arg Arg Phe His Ala Lys Pro Leu Gly Asn Phe Val
    50                  55                  60

Arg Asp Pro Thr Phe Gly Ile Ala Thr Pro Leu Leu Ile Tyr Leu
65                  70                  75                  80

Lys Ser Lys Gly Thr Val Met Lys Phe Ala Trp Gly Leu Trp Asn Asn
                85                  90                  95

Lys Tyr Ile Val Arg Asp Pro Lys Tyr Lys Thr Thr Gly Leu Arg Ile
            100                 105                 110

Val Gly Leu Pro Leu Ile Glu Thr Met Asp Pro Glu Asn Ile Lys Ala
        115                 120                 125

Val Leu Ala Thr Gln Phe Asn Asp Phe Ser Leu Gly Thr Arg His Asp
    130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
    210                 215                 220

Ser Ala Glu Ser Leu Arg Asp Glu Ser Ile Gly Leu Thr Pro Thr Thr
225                 230                 235                 240

Lys Asp Phe Asp Gly Arg Arg Asp Phe Ala Asp Ala Phe Asn Tyr Ser
                245                 250                 255

Gln Thr Tyr Gln Ala Tyr Arg Phe Leu Leu Gln Gln Met Tyr Trp Ile
            260                 265                 270

Leu Asn Gly Ser Glu Phe Arg Lys Ser Ile Ala Val Val His Lys Phe
        275                 280                 285

Ala Asp His Tyr Val Gln Lys Ala Leu Glu Leu Thr Asp Asp Asp Leu
    290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Phe Tyr Glu Leu
            340                 345                 350

Ser Arg Asn Pro Glu Val Phe Ala Lys Leu Arg Glu Glu Val Glu Asn
        355                 360                 365

Arg Phe Gly Leu Gly Glu Glu Ala Arg Val Glu Glu Ile Ser Phe Glu
    370                 375                 380
```

```
Ser Leu Lys Ser Cys Glu Tyr Leu Lys Ala Val Ile Asn Glu Thr Leu
385                 390                 395                 400

Arg Leu Tyr Pro Ser Val Pro His Asn Phe Arg Val Ala Thr Arg Asn
            405                 410                 415

Thr Thr Leu Pro Arg Gly Gly Glu Asp Gly Tyr Ser Pro Ile Val
        420                 425                 430

Val Lys Lys Gly Gln Val Val Met Tyr Thr Val Ile Ala Thr His Arg
            435                 440                 445

Asp Pro Ser Ile Tyr Gly Ala Asp Ala Asp Val Phe Arg Pro Glu Arg
        450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
            485                 490                 495

Ala Ser Tyr Val Thr Val Arg Leu Leu Gln Glu Phe Ala His Leu Ser
            500                 505                 510

Met Asp Pro Asp Thr Glu Tyr Pro Pro Lys Leu Gln Asn Thr Leu Thr
        515                 520                 525

Leu Ser Leu Phe Asp Gly Ala Asp Val Arg Met Tyr
530                 535                 540

<210> SEQ ID NO 99
<211> LENGTH: 540
<212> TYPE: PRT
<213> ORGANISM: CANDIDATROPICALIS

<400> SEQUENCE: 99

Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
        35                  40                  45

Lys Tyr Leu Glu Arg Arg Phe His Ala Lys Pro Leu Gly Asn Val Val
    50                  55                  60

Leu Asp Pro Thr Phe Gly Ile Ala Thr Pro Leu Ile Leu Ile Tyr Leu
65                  70                  75                  80

Lys Ser Lys Gly Thr Val Met Lys Phe Ala Trp Ser Phe Trp Asn Asn
            85                  90                  95

Lys Tyr Ile Val Lys Asp Pro Lys Tyr Lys Thr Thr Gly Leu Arg Ile
            100                 105                 110

Val Gly Leu Pro Leu Ile Glu Thr Ile Asp Pro Glu Asn Ile Lys Ala
        115                 120                 125

Val Leu Ala Thr Gln Phe Asn Asp Phe Ser Leu Gly Thr Arg His Asp
    130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
            165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
    210                 215                 220
```

-continued

Ser Ala Glu Ser Leu Arg Asp Asp Ser Val Gly Leu Thr Pro Thr Thr
225                 230                 235                 240

Lys Asp Phe Glu Gly Arg Gly Asp Phe Ala Asp Ala Phe Asn Tyr Ser
            245                 250                 255

Gln Thr Tyr Gln Ala Tyr Arg Phe Leu Leu Gln Gln Met Tyr Trp Ile
        260                 265                 270

Leu Asn Gly Ala Glu Phe Arg Lys Ser Ile Ala Ile Val His Lys Phe
    275                 280                 285

Ala Asp His Tyr Val Gln Lys Ala Leu Glu Leu Thr Asp Asp Asp Leu
290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
            325                 330                 335

Gly Arg Asp Thr Thr Ala Gly Leu Leu Ser Phe Val Phe Tyr Glu Leu
        340                 345                 350

Ser Arg Asn Pro Glu Val Phe Ala Lys Leu Arg Glu Glu Val Glu Asn
    355                 360                 365

Arg Phe Gly Leu Gly Glu Glu Ala Arg Val Glu Glu Ile Ser Phe Glu
370                 375                 380

Ser Leu Lys Ser Cys Glu Tyr Leu Lys Ala Val Ile Asn Glu Ala Leu
385                 390                 395                 400

Arg Leu Tyr Pro Ser Val Pro His Asn Phe Arg Val Ala Thr Arg Asn
            405                 410                 415

Thr Thr Leu Pro Arg Gly Gly Gly Lys Asp Gly Cys Ser Pro Ile Val
        420                 425                 430

Val Lys Lys Gly Gln Val Val Met Tyr Thr Val Ile Gly Thr His Arg
    435                 440                 445

Asp Pro Ser Ile Tyr Gly Ala Asp Ala Asp Val Phe Arg Pro Glu Arg
450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
            485                 490                 495

Ala Ser Tyr Val Thr Val Arg Leu Leu Gln Glu Phe Gly Asn Leu Ser
        500                 505                 510

Leu Asp Pro Asn Ala Glu Tyr Pro Pro Lys Leu Gln Asn Thr Leu Thr
    515                 520                 525

Leu Ser Leu Phe Asp Gly Ala Asp Val Arg Met Phe
530                 535                 540

<210> SEQ ID NO 100
<211> LENGTH: 517
<212> TYPE: PRT
<213> ORGANISM: CANDIDATROPICALIS

<400> SEQUENCE: 100

Met Ile Glu Gln Leu Leu Glu Tyr Trp Tyr Val Val Pro Val Leu
1               5                   10                  15

Tyr Ile Ile Lys Gln Leu Leu Ala Tyr Thr Lys Thr Arg Val Leu Met
            20                  25                  30

Lys Lys Leu Gly Ala Ala Pro Val Thr Asn Lys Leu Tyr Asp Asn Ala
        35                  40                  45

Phe Gly Ile Val Asn Gly Trp Lys Ala Leu Gln Phe Lys Lys Glu Gly

```
            50                  55                  60
Arg Ala Gln Glu Tyr Asn Asp Tyr Lys Phe Asp His Ser Lys Asn Pro
 65                  70                  75                  80

Ser Val Gly Thr Tyr Val Ser Ile Leu Phe Gly Thr Arg Ile Val Val
                     85                  90                  95

Thr Lys Asp Pro Glu Asn Ile Lys Ala Ile Leu Ala Thr Gln Phe Gly
                    100                 105                 110

Asp Phe Ser Leu Gly Lys Arg His Thr Leu Phe Lys Pro Leu Leu Gly
                    115                 120                 125

Asp Gly Ile Phe Thr Leu Asp Gly Glu Gly Trp Lys His Ser Arg Ala
                    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                    165                 170                 175

Gly Glu Tyr Phe Asp Ile Gln Glu Leu Phe Phe Arg Phe Thr Val Asp
                    180                 185                 190

Ser Ala Thr Glu Phe Leu Phe Gly Glu Ser Val His Ser Leu Lys Asp
                    195                 200                 205

Glu Ser Ile Gly Ile Asn Gln Asp Asp Ile Asp Phe Ala Gly Arg Lys
                    210                 215                 220

Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
                    245                 250                 255

Asp Cys Thr Lys Leu Val His Lys Phe Thr Asn Tyr Tyr Val Gln Lys
                    260                 265                 270

Ala Leu Asp Ala Ser Pro Glu Glu Leu Glu Lys Gln Ser Gly Tyr Val
                    275                 280                 285

Phe Leu Tyr Glu Leu Val Lys Gln Thr Arg Asp Pro Asn Val Leu Arg
                    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg His Pro Glu Ile Trp
                    325                 330                 335

Ala Lys Leu Arg Glu Glu Ile Glu Gln Gln Phe Gly Leu Gly Glu Asp
                    340                 345                 350

Ser Arg Val Glu Glu Ile Thr Phe Glu Ser Leu Lys Arg Cys Glu Tyr
                    355                 360                 365

Leu Lys Ala Phe Leu Asn Glu Thr Leu Arg Ile Tyr Pro Ser Val Pro
                    370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
                    405                 410                 415

Ser Tyr Gly Ile Asn Ser Thr His Leu Asp Pro Val Tyr Tyr Gly Pro
                    420                 425                 430

Asp Ala Ala Glu Phe Arg Pro Glu Arg Trp Phe Glu Pro Ser Thr Lys
                    435                 440                 445

Lys Leu Gly Trp Ala Tyr Leu Pro Phe Asn Gly Gly Pro Arg Ile Cys
                    450                 455                 460

Leu Gly Gln Gln Phe Ala Leu Thr Glu Ala Gly Tyr Val Leu Val Arg
465                 470                 475                 480
```

Leu Val Gln Glu Phe Ser His Val Arg Leu Asp Pro Asp Val Tyr
            485                 490                 495

Pro Pro Lys Arg Leu Thr Asn Leu Thr Met Cys Leu Gln Asp Gly Ala
            500                 505                 510

Ile Val Lys Phe Asp
        515

<210> SEQ ID NO 101
<211> LENGTH: 517
<212> TYPE: PRT
<213> ORGANISM: CANDIDATROPICALIS

<400> SEQUENCE: 101

Met Ile Glu Gln Ile Leu Glu Tyr Trp Tyr Ile Val Pro Val Leu
1               5                   10                  15

Tyr Ile Ile Lys Gln Leu Ile Ala Tyr Ser Lys Thr Arg Val Leu Met
            20                  25                  30

Lys Gln Leu Gly Ala Ala Pro Ile Thr Asn Gln Leu Tyr Asp Asn Val
        35                  40                  45

Phe Gly Ile Val Asn Gly Trp Lys Ala Leu Gln Phe Lys Lys Glu Gly
    50                  55                  60

Arg Ala Gln Glu Tyr Asn Asp His Lys Phe Asp Ser Ser Lys Asn Pro
65                  70                  75                  80

Ser Val Gly Thr Tyr Val Ser Ile Leu Phe Gly Thr Lys Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Ala Leu Phe Lys Pro Leu Leu Gly
        115                 120                 125

Asp Gly Ile Phe Thr Leu Asp Gly Glu Gly Trp Lys His Ser Arg Ser
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Thr Ile Gly Ile Asn Gln Asp Asp Ile Asp Phe Ala Gly Arg Lys
    210                 215                 220

Asp Phe Ala Glu Ser Phe Asn Lys Ala Gln Glu Tyr Leu Ser Ile Arg
225                 230                 235                 240

Ile Leu Val Gln Thr Phe Tyr Trp Leu Ile Asn Asn Lys Glu Phe Arg
                245                 250                 255

Asp Cys Thr Lys Leu Val His Lys Phe Thr Asn Tyr Tyr Val Gln Lys
            260                 265                 270

Ala Leu Asp Ala Thr Pro Glu Glu Leu Glu Lys Gln Gly Gly Tyr Val
        275                 280                 285

Phe Leu Tyr Glu Leu Val Lys Gln Thr Arg Asp Pro Lys Val Leu Arg
    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg Asn Pro His Ile Trp

```
                325                 330                 335
Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
            355                 360                 365

Leu Lys Ala Phe Leu Asn Glu Thr Leu Arg Val Tyr Pro Ser Val Pro
        370                 375                 380

Arg Asn Phe Arg Ile Ala Thr Lys Asn Thr Thr Leu Pro Arg Gly Gly
385                 390                 395                 400

Gly Pro Asp Gly Thr Gln Pro Ile Leu Ile Gln Lys Gly Glu Gly Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Arg
        435                 440                 445

Lys Leu Gly Trp Ala Tyr Leu Pro Phe Asn Gly Gly Pro Arg Ile Cys
    450                 455                 460

Leu Gly Gln Gln Phe Ala Leu Thr Glu Ala Gly Tyr Val Leu Val Arg
465                 470                 475                 480

Leu Val Gln Glu Phe Ser His Ile Arg Leu Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515

<210> SEQ ID NO 102
<211> LENGTH: 512
<212> TYPE: PRT
<213> ORGANISM: CANDIDATROPICALIS

<400> SEQUENCE: 102

Met Leu Asp Gln Ile Leu His Tyr Trp Tyr Ile Val Leu Pro Leu Leu
1               5                   10                  15

Ala Ile Ile Asn Gln Ile Val Ala His Val Arg Thr Asn Tyr Leu Met
            20                  25                  30

Lys Lys Leu Gly Ala Lys Pro Phe Thr His Val Gln Arg Asp Gly Trp
        35                  40                  45

Leu Gly Phe Lys Phe Gly Arg Glu Phe Leu Ala Lys Ser Ala Gly
    50                  55                  60

Arg Leu Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
        115                 120                 125

Thr Leu Asp Ala Glu Gly Trp Lys His Ser Arg Ala Met Leu Arg Pro
    130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175
```

```
Asp Ile Gln Glu Leu Phe Phe Arg Phe Thr Val Asp Ser Ala Thr Glu
            180                 185                 190

Phe Leu Phe Gly Glu Ser Val His Ser Leu Lys Asp Glu Ile Gly
        195                 200                 205

Tyr Asp Thr Lys Asp Met Ser Glu Glu Arg Arg Phe Ala Asp Ala
    210                 215                 220

Phe Asn Lys Ser Gln Val Tyr Val Ala Thr Arg Val Ala Leu Gln Asn
225                 230                 235                 240

Leu Tyr Trp Leu Val Asn Asn Lys Glu Phe Lys Glu Cys Asn Asp Ile
            245                 250                 255

Val His Lys Phe Thr Asn Tyr Val Gln Lys Ala Leu Asp Ala Thr
            260                 265                 270

Pro Glu Glu Leu Glu Lys Gln Gly Gly Tyr Val Phe Leu Tyr Glu Leu
        275                 280                 285

Val Lys Gln Thr Arg Asp Pro Lys Val Leu Arg Asp Gln Ser Leu Asn
    290                 295                 300

Ile Leu Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
            325                 330                 335

Glu Ile Glu Gln Gln Phe Gly Leu Gly Glu Asp Ser Arg Val Glu Glu
            340                 345                 350

Ile Thr Phe Glu Ser Leu Lys Arg Cys Glu Tyr Leu Lys Ala Val Leu
            355                 360                 365

Asn Glu Thr Leu Arg Leu His Pro Ser Val Pro Arg Asn Ala Arg Phe
            370                 375                 380

Ala Ile Lys Asp Thr Thr Leu Pro Arg Gly Gly Gly Pro Asn Gly Lys
385                 390                 395                 400

Asp Pro Ile Leu Ile Arg Lys Asp Glu Val Val Gln Tyr Ser Ile Ser
            405                 410                 415

Ala Thr Gln Thr Asn Pro Ala Tyr Tyr Gly Ala Asp Ala Ala Asp Phe
            420                 425                 430

Arg Pro Glu Arg Trp Phe Glu Pro Ser Thr Arg Asn Leu Gly Trp Ala
            435                 440                 445

Phe Leu Pro Phe Asn Gly Gly Pro Arg Ile Cys Leu Gly Gln Gln Phe
450                 455                 460

Ala Leu Thr Glu Ala Gly Tyr Val Leu Val Arg Leu Val Gln Glu Phe
465                 470                 475                 480

Pro Asn Leu Ser Gln Asp Pro Glu Thr Lys Tyr Pro Pro Arg Leu
            485                 490                 495

Ala His Leu Thr Met Cys Leu Phe Asp Gly Ala His Val Lys Met Ser
            500                 505                 510

<210> SEQ ID NO 103
<211> LENGTH: 512
<212> TYPE: PRT
<213> ORGANISM: CANDIDATROPICALIS

<400> SEQUENCE: 103

Met Leu Asp Gln Ile Phe His Tyr Trp Tyr Ile Val Leu Pro Leu Leu
1               5                   10                  15

Val Ile Ile Lys Gln Ile Val Ala His Ala Arg Thr Asn Tyr Leu Met
            20                  25                  30

Lys Lys Leu Gly Ala Lys Pro Phe Thr His Val Gln Leu Asp Gly Trp
        35                  40                  45
```

```
Phe Gly Phe Lys Phe Gly Arg Glu Phe Leu Lys Ala Lys Ser Ala Gly
     50                  55                  60

Arg Gln Val Asp Leu Ile Ile Ser Arg Phe His Asp Asn Glu Asp Thr
 65                  70                  75                  80

Phe Ser Ser Tyr Ala Phe Gly Asn His Val Phe Thr Arg Asp Pro
                 85                  90                  95

Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
            115                 120                 125

Thr Leu Asp Gly Glu Gly Trp Lys His Ser Arg Ala Met Leu Arg Pro
    130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175

Asp Ile Gln Glu Leu Phe Phe Arg Phe Thr Val Asp Ser Ala Thr Glu
            180                 185                 190

Phe Leu Phe Gly Glu Ser Val His Ser Leu Arg Asp Glu Glu Ile Gly
            195                 200                 205

Tyr Asp Thr Lys Asp Met Ala Glu Glu Arg Arg Lys Phe Ala Asp Ala
210                 215                 220

Phe Asn Lys Ser Gln Val Tyr Leu Ser Thr Arg Val Ala Leu Gln Thr
225                 230                 235                 240

Leu Tyr Trp Leu Val Asn Asn Lys Glu Phe Lys Glu Cys Asn Asp Ile
            245                 250                 255

Val His Lys Phe Thr Asn Tyr Val Gln Lys Ala Leu Asp Ala Thr
            260                 265                 270

Pro Glu Glu Leu Glu Lys Gln Gly Gly Tyr Val Phe Leu Tyr Glu Leu
    275                 280                 285

Ala Lys Gln Thr Lys Asp Pro Asn Val Leu Arg Asp Gln Ser Leu Asn
290                 295                 300

Ile Leu Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
            325                 330                 335

Glu Ile Glu Ser His Phe Gly Leu Gly Glu Asp Ser Arg Val Glu Glu
            340                 345                 350

Ile Thr Phe Glu Ser Leu Lys Arg Cys Glu Tyr Leu Lys Ala Val Leu
            355                 360                 365

Asn Glu Thr Leu Arg Leu His Pro Ser Val Pro Arg Asn Ala Arg Phe
    370                 375                 380

Ala Ile Lys Asp Thr Thr Leu Pro Arg Gly Gly Pro Asn Gly Lys
385                 390                 395                 400

Asp Pro Ile Leu Ile Arg Lys Asn Glu Val Val Gln Tyr Ser Ile Ser
                405                 410                 415

Ala Thr Gln Thr Asn Pro Ala Tyr Tyr Gly Ala Asp Ala Asp Phe
            420                 425                 430

Arg Pro Glu Arg Trp Phe Glu Pro Ser Thr Arg Asn Leu Gly Trp Ala
            435                 440                 445

Tyr Leu Pro Phe Asn Gly Gly Pro Arg Ile Cys Leu Gly Gln Gln Phe
    450                 455                 460
```

Ala Leu Thr Glu Ala Gly Tyr Val Leu Val Arg Leu Val Gln Glu Phe
465                 470                 475                 480

Pro Ser Leu Ser Gln Asp Pro Glu Thr Glu Tyr Pro Pro Arg Leu
                485                 490                 495

Ala His Leu Thr Met Cys Leu Phe Asp Gly Ala Tyr Val Lys Met Gln
            500                 505                 510

<210> SEQ ID NO 104
<211> LENGTH: 499
<212> TYPE: PRT
<213> ORGANISM: CANDIDATROPICALIS

<400> SEQUENCE: 104

Met Ala Ile Ser Ser Leu Leu Ser Trp Asp Val Ile Cys Val Val Phe
1               5                   10                  15

Ile Cys Val Cys Val Tyr Phe Gly Tyr Glu Tyr Cys Tyr Thr Lys Tyr
                20                  25                  30

Leu Met His Lys His Gly Ala Arg Glu Ile Glu Asn Val Ile Asn Asp
            35                  40                  45

Gly Phe Phe Gly Phe Arg Leu Pro Leu Leu Met Arg Ala Ser Asn
50                  55                  60

Glu Gly Arg Leu Ile Glu Phe Ser Val Lys Arg Phe Glu Ser Ala Pro
65                  70                  75                  80

His Pro Gln Asn Lys Thr Leu Val Asn Arg Ala Leu Ser Val Pro Val
                85                  90                  95

Ile Leu Thr Lys Asp Pro Val Asn Ile Lys Ala Met Leu Ser Thr Gln
            100                 105                 110

Phe Asp Asp Phe Ser Leu Gly Leu Arg Leu His Gln Phe Ala Pro Leu
        115                 120                 125

Leu Gly Lys Gly Ile Phe Thr Leu Asp Gly Pro Glu Trp Lys Gln Ser
130                 135                 140

Arg Ser Met Leu Arg Pro Gln Phe Ala Lys Asp Arg Val Ser His Ile
145                 150                 155                 160

Leu Asp Leu Glu Pro His Phe Val Leu Arg Lys His Ile Asp Gly
                165                 170                 175

His Asn Gly Asp Tyr Phe Asp Ile Gln Glu Leu Tyr Phe Arg Phe Ser
            180                 185                 190

Met Asp Val Ala Thr Gly Phe Leu Phe Gly Glu Ser Val Gly Ser Leu
        195                 200                 205

Lys Asp Glu Asp Ala Arg Phe Leu Glu Ala Phe Asn Glu Ser Gln Lys
210                 215                 220

Tyr Leu Ala Thr Arg Ala Thr Leu His Glu Leu Tyr Phe Leu Cys Asp
225                 230                 235                 240

Gly Phe Arg Phe Arg Gln Tyr Asn Lys Val Val Arg Lys Phe Cys Ser
                245                 250                 255

Gln Cys Val His Lys Ala Leu Asp Val Ala Pro Glu Asp Thr Ser Glu
            260                 265                 270

Tyr Val Phe Leu Arg Glu Leu Val Lys His Thr Arg Asp Pro Val Val
        275                 280                 285

Leu Gln Asp Gln Ala Leu Asn Val Leu Ala Gly Arg Asp Thr Thr
290                 295                 300

Ala Ser Leu Leu Ser Phe Ala Thr Phe Glu Leu Ala Arg Asn Asp His
305                 310                 315                 320

Met Trp Arg Lys Leu Arg Glu Glu Val Ile Leu Thr Met Gly Pro Ser
                325                 330                 335

| | | | | | | | | | | | |
|---|---|---|---|---|---|---|---|---|---|---|---|
|Ser|Asp|Glu|Ile|Thr|Val|Ala|Gly|Leu|Lys|Ser|Cys|Arg|Tyr|Leu|Lys|
| | | |340| | |345| | | |350| | | | | |

Ser Asp Glu Ile Thr Val Ala Gly Leu Lys Ser Cys Arg Tyr Leu Lys
          340                 345                350

Ala Ile Leu Asn Glu Thr Leu Arg Leu Tyr Pro Ser Val Pro Arg Asn
          355                 360                365

Ala Arg Phe Ala Thr Arg Asn Thr Thr Leu Pro Arg Gly Gly Gly Pro
          370                 375                380

Asp Gly Ser Phe Pro Ile Leu Ile Arg Lys Gly Gln Pro Val Gly Tyr
385                 390                 395                400

Phe Ile Cys Ala Thr His Leu Asn Glu Lys Val Tyr Gly Asn Asp Ser
                405                 410                415

His Val Phe Arg Pro Glu Arg Trp Ala Ala Leu Glu Gly Lys Ser Leu
                420                 425                430

Gly Trp Ser Tyr Leu Pro Phe Asn Gly Gly Pro Arg Ser Cys Leu Gly
                435                 440                445

Gln Gln Phe Ala Ile Leu Glu Ala Ser Tyr Val Leu Ala Arg Leu Thr
                450                 455                460

Gln Cys Tyr Thr Thr Ile Gln Leu Arg Thr Thr Glu Tyr Pro Pro Lys
465                 470                 475                480

Lys Leu Val His Leu Thr Met Ser Leu Leu Asn Gly Val Tyr Ile Arg
                485                 490                495

Thr Arg Thr

<210> SEQ ID NO 105
<211> LENGTH: 1712
<212> TYPE: DNA
<213> ORGANISM: Candida tropicalis

<400> SEQUENCE: 105

```
ggtaccgagc tcacgagttt tgggattttc gagtttggat tgtttccttt gttgattgaa      60
ttgacgaaac cagaggtttt caagacagat aagattgggt ttatcaaaac gcagtttgaa     120
atattccagt tggtttccaa gatatcttga agaagattga cgatttgaaa tttgaagaag     180
tggagaagat ctggtttgga ttgttggaga atttcaagaa tctcaagatt tactctaacg     240
acgggtacaa cgagaattgt attgaattga tcaagaacat gatcttggtg ttacagaaca     300
tcaagttctt ggaccagact gagaatgcca cagatataca aggcgtcatg tgataaaatg     360
gatgagattt atcccacaat tgaagaaaga gtttatggaa agtggtcaac cagaagctaa     420
acaggaagaa gcaaacgaag aggtgaaaca agaagaagaa ggtaaataag tattttgtat     480
tatataacaa acaaagtaag gaatacagat ttatacaata aattgccata ctagtcacgt     540
gagatatctc atccattccc caactcccaa gaaaaaaaaa aagtgaaaaa aaaaatcaaa     600
cccaaagatc aacctcccca tcatcatcgt catcaaaccc ccagctcaat tcgcaatggt     660
tagcacaaaa acatacacag aaagggcatc agcacacccc tccaaggttg cccaacgttt     720
attccgctta atggagtcca aaaagaccaa cctctgcgcc tcgatcgacg tgaccacaac     780
cgccgagttc ctttcgctca tcgacaagct cggtccccac atctgtctcg tgaagacgca     840
catcgatatc atctcagact tcagctacga gggcacgatt gagccgttgc ttgtgcttgc     900
agagcgccac gggttcttga tattcgagga caggaagttt gctgatatcg aaacaccgt      960
gatgttgcag tacacctcgg gggtataccg gatcgcggcg tggagtgaca tcacgaacgc    1020
gcacggagtg actgggaagg gcgtcgttga agggttgaaa cgcggtgcgg agggggtaga    1080
aaaggaaagg ggcgtgttga tgttggcgga gttgtcgagt aaaggctcgt tggcgcatgg    1140
```

-continued

```
tgaatatacc cgtgagacga tcgagattgc gaagagtgat cgggagttcg tgattgggtt    1200
catcgcgcag cgggacatgg ggggtagaga agaagggttt gattggatca tcatgacgcc    1260
tggtgtgggg ttggatgata aaggcgatgc gttgggccag cagtatagga ctgttgatga    1320
ggtggttctg actggtaccg atgtgattat tgtcgggaga gggttgtttg gaaaaggaag    1380
agaccctgag gtggagggaa agagatacag ggatgctgga tggaaggcat acttgaagag    1440
aactggtcag ttagaataaa tattgtaata aataggtcta tatacataca ctaagcttct    1500
aggacgtcat tgtagtcttc gaagttgtct gctagtttag ttctcatgat ttcgaaaacc    1560
aataacgcaa tggatgtagc agggatggtg gttagtgcgt tcctgacaaa cccagagtac    1620
gccgcctcaa accacgtcac attcgccctt tgcttcatcc gcatcacttg cttgaaggta    1680
tccacgtacg agttgtaata caccttgaag aa                                  1712
```

<210> SEQ ID NO 106
<211> LENGTH: 267
<212> TYPE: PRT
<213> ORGANISM: CANDIDATROPICALIS

<400> SEQUENCE: 106

```
Met Val Ser Thr Lys Thr Tyr Thr Glu Arg Ala Ser Ala His Pro Ser
1               5                   10                  15

Lys Val Ala Gln Arg Leu Phe Arg Leu Met Glu Ser Lys Lys Thr Asn
            20                  25                  30

Leu Cys Ala Ser Ile Asp Val Thr Thr Thr Ala Glu Phe Leu Ser Leu
        35                  40                  45

Ile Asp Lys Leu Gly Pro His Ile Cys Leu Val Lys Thr His Ile Asp
    50                  55                  60

Ile Ile Ser Asp Phe Ser Tyr Glu Gly Thr Ile Glu Pro Leu Leu Val
65                  70                  75                  80

Leu Ala Glu Arg His Gly Phe Leu Ile Phe Glu Asp Arg Lys Phe Ala
                85                  90                  95

Asp Ile Gly Asn Thr Val Met Leu Gln Tyr Thr Ser Gly Val Tyr Arg
            100                 105                 110

Ile Ala Ala Trp Ser Asp Ile Thr Asn Ala His Gly Val Thr Gly Lys
        115                 120                 125

Gly Val Val Glu Gly Leu Lys Arg Gly Ala Glu Gly Val Glu Lys Glu
    130                 135                 140

Arg Gly Val Leu Met Leu Ala Glu Leu Ser Ser Lys Gly Ser Leu Ala
145                 150                 155                 160

His Gly Glu Tyr Thr Arg Glu Thr Ile Glu Ile Ala Lys Ser Asp Arg
                165                 170                 175

Glu Phe Val Ile Gly Phe Ile Ala Gln Arg Asp Met Gly Gly Arg Glu
            180                 185                 190

Glu Gly Phe Asp Trp Ile Ile Met Thr Pro Gly Val Gly Leu Asp Asp
        195                 200                 205

Lys Gly Asp Ala Leu Gly Gln Gln Tyr Arg Thr Val Asp Glu Val Val
    210                 215                 220

Leu Thr Gly Thr Asp Val Ile Ile Val Gly Arg Gly Leu Phe Gly Lys
225                 230                 235                 240

Gly Arg Asp Pro Glu Val Glu Gly Lys Arg Tyr Arg Asp Ala Gly Trp
                245                 250                 255

Lys Ala Tyr Leu Lys Arg Thr Gly Gln Leu Glu
            260                 265
```

<210> SEQ ID NO 107
<211> LENGTH: 473
<212> TYPE: DNA
<213> ORGANISM: Artificial Sequence
<220> FEATURE:
<223> OTHER INFORMATION: Description of Artificial Sequence: Primer

<400> SEQUENCE: 107

```
gtcaaagcaa attgttggcc caagcagact cttggaccac cgttgaatgg aacataagcc      60
cagcccaact tcttagtaga tggttcaaac catctttctg gtctgaagtc gttagcgtcc     120
ttaccgtagt attcttccaa acggtgggtc ttgtagacaa cgtaagcaac agtggagcct     180
ttaggaatgt agattgggtc ggtaccgtta gcaccaccac ctcttggcaa agtggtgtct     240
ctggtggcgg ttctaaagtt gacaggaaca gatgggtaca tacgcaaggt ttcgttaagg     300
atagccttca gtattcaca tctcttcaag gcttcgaaag taatttcttc aacgcgggag      360
tcttcaccaa caccaaagtt aacttcgatt tcttctctca acttggacca catctctggg     420
tgtctagcca attcaaacaa agcaaggac aacaaacccg cggtggtgtc tct              473
```

<210> SEQ ID NO 108
<211> LENGTH: 540
<212> TYPE: DNA
<213> ORGANISM: Candida tropicalis

<400> SEQUENCE: 108

```
tactaacttg ttgaggatct tataaccata cagcaacacg gtcacaacat gtagtagttt      60
gttgaggaac gtatgtgttt ctgagcgcag aactactttt tcaacccacg acgaggtcag     120
tgtttgttca acatgctgtt gcgaaagcca tagcagttac ctaccttccg agaggtcaag     180
ttctttctcc cgtcccgagt tctcatgttg ctaatgttca aactggtgag gttcttgggt     240
tcgcacccgt ggatgcagtc ataagaaaag ccgtggtcct agcagcactg gtttctaggt     300
ctcttatagt ttcgataaaa ccgttgggtc aaaccactaa aaagaaaccc gttctccgtg     360
tgagaaaaat tcggaaacaa tccactaccc tagaagtgta acctgccgct tccgaccttc     420
gtgtcgtctc ggtacaactc tggtgtcaaa cggtctcttg ttcaacgagt acactgcagc     480
aaccttggtg tgaaggtcaa caacttcttc gtataagaat tcgtgttccc acttatgaaa     540
```

<210> SEQ ID NO 109
<211> LENGTH: 29
<212> TYPE: DNA
<213> ORGANISM: Bacteriophage T7

<400> SEQUENCE: 109

```
ggatcctaat acgactcact atagggagg                                       29
```

<210> SEQ ID NO 110
<211> LENGTH: 523
<212> TYPE: PRT
<213> ORGANISM: CANDIDATROPICALIS

<400> SEQUENCE: 110

Met Ala Thr Gln Glu Ile Ile Asp Ser Val Leu Pro Tyr Leu Thr Lys
1               5                   10                  15

Trp Tyr Thr Val Ile Thr Ala Ala Val Leu Val Phe Leu Ile Ser Thr
                20                  25                  30

Asn Ile Lys Asn Tyr Val Lys Ala Lys Lys Leu Lys Cys Val Asp Pro
            35                  40                  45

Pro Tyr Leu Lys Asp Ala Gly Leu Thr Gly Ile Ser Ser Leu Ile Ala
50              55                  60

Ala Ile Lys Ala Lys Asn Asp Gly Arg Leu Ala Asn Phe Ala Asp Glu
65              70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
                100                 105                 110

Leu Ala Thr Gln Phe Thr Asp Phe Ser Leu Gly Thr Arg His Ala His
            115                 120                 125

Phe Ala Pro Leu Leu Gly Asp Gly Ile Phe Thr Leu Asp Gly Glu Gly
        130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
        210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Glu Ile Thr Phe Glu
        355                 360                 365

Ala Leu Lys Arg Cys Glu Tyr Leu Lys Ala Ile Leu Asn Glu Thr Leu
370                 375                 380

Arg Met Tyr Pro Ser Val Pro Val Asn Phe Arg Thr Ala Thr Arg Asp
385                 390                 395                 400

Thr Thr Leu Pro Arg Gly Gly Ala Asn Gly Thr Asp Pro Ile Tyr
                405                 410                 415

Ile Pro Lys Gly Ser Thr Val Ala Tyr Val Tyr Lys Thr His Arg
            420                 425                 430

Leu Glu Glu Tyr Tyr Gly Lys Asp Ala Asn Asp Phe Arg Pro Glu Arg
        435                 440                 445

Trp Phe Glu Pro Ser Thr Lys Lys Leu Gly Trp Ala Tyr Val Pro Phe
450                 455                 460

Asn Gly Gly Pro Arg Val Cys Leu Gly Gln Gln Phe Ala Leu Thr Glu

```
                   465                 470                 475                 480
Ala Ser Tyr Val Ile Thr Arg Leu Ala Gln Met Phe Glu Thr Val Ser
                       485                 490                 495

Ser Asp Pro Gly Leu Glu Tyr Pro Pro Lys Cys Ile His Leu Thr
            500                 505                 510

Met Ser His Asn Asp Gly Val Phe Val Lys Met
            515                 520

<210> SEQ ID NO 111
<211> LENGTH: 540
<212> TYPE: PRT
<213> ORGANISM: CANDIDATROPICALIS

<400> SEQUENCE: 111

Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
                20                  25                  30

Ile Pro Leu Val Leu Leu Ser Leu Asn Phe Ile Ser Leu Leu His Thr
            35                  40                  45

Lys Tyr Leu Glu Arg Arg Phe His Ala Lys Pro Leu Gly Asn Val Val
    50                  55                  60

Leu Asp Pro Thr Phe Gly Ile Ala Thr Pro Leu Ile Leu Ile Tyr Leu
65                  70                  75                  80

Lys Ser Lys Gly Thr Val Met Lys Phe Ala Trp Ser Phe Trp Asn Asn
                85                  90                  95

Lys Tyr Ile Val Lys Asp Pro Lys Tyr Lys Thr Thr Gly Leu Arg Ile
                100                 105                 110

Val Gly Leu Pro Leu Ile Glu Thr Ile Asp Pro Glu Asn Ile Lys Ala
            115                 120                 125

Val Leu Ala Thr Gln Phe Asn Asp Phe Ser Leu Gly Thr Arg His Asp
    130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
                180                 185                 190

Lys His Val Arg Lys His Arg Gly Gln Thr Phe Asp Ile Gln Glu Leu
            195                 200                 205

Phe Phe Arg Leu Thr Val Asp Ser Ala Thr Glu Phe Leu Phe Gly Glu
    210                 215                 220

Ser Ala Glu Ser Leu Arg Asp Asp Ser Val Gly Leu Thr Pro Thr Thr
225                 230                 235                 240

Lys Asp Phe Glu Gly Arg Gly Asp Phe Ala Asp Ala Phe Asn Tyr Ser
                245                 250                 255

Gln Thr Tyr Gln Ala Tyr Arg Phe Leu Leu Gln Gln Met Tyr Trp Ile
                260                 265                 270

Leu Asn Gly Ala Glu Phe Arg Lys Ser Ile Ala Ile Val His Lys Phe
            275                 280                 285

Ala Asp His Tyr Val Gln Lys Ala Leu Glu Leu Thr Asp Asp Asp Leu
    290                 295                 300

Gln Lys Gln Asp Gly Tyr Val Phe Leu Tyr Glu Leu Ala Lys Gln Thr
305                 310                 315                 320
```

```
Arg Asp Pro Lys Val Leu Arg Asp Gln Leu Leu Asn Ile Leu Val Ala
            325                 330                 335
Gly Arg Asp Thr Thr Ala Gly Leu Leu Ser Phe Val Phe Tyr Glu Leu
            340                 345                 350
Ser Arg Asn Pro Glu Val Phe Ala Lys Leu Arg Glu Glu Val Glu Asn
            355                 360                 365
Arg Phe Gly Leu Gly Glu Glu Ala Arg Val Glu Glu Ile Ser Phe Glu
    370                 375                 380
Ser Leu Lys Ser Cys Glu Tyr Leu Lys Ala Val Ile Asn Glu Ala Leu
385                 390                 395                 400
Arg Leu Tyr Pro Ser Val Pro His Asn Phe Arg Val Ala Thr Arg Asn
                405                 410                 415
Thr Thr Leu Pro Arg Gly Gly Lys Asp Gly Cys Ser Pro Ile Val
                420                 425                 430
Val Lys Lys Gly Gln Val Val Met Tyr Thr Val Ile Gly Thr His Arg
                435                 440                 445
Asp Pro Ser Ile Tyr Gly Ala Asp Ala Asp Val Phe Arg Pro Glu Arg
            450                 455                 460
Trp Phe Glu Pro Glu Thr Arg Lys Leu Gly Trp Ala Tyr Val Pro Phe
465                 470                 475                 480
Asn Gly Gly Pro Arg Ile Cys Leu Gly Gln Gln Phe Ala Leu Thr Glu
                485                 490                 495
Ala Ser Tyr Val Thr Val Arg Leu Leu Gln Glu Phe Gly Asn Leu Ser
            500                 505                 510
Ser Asp Pro Asn Ala Glu Tyr Pro Pro Lys Leu Gln Asn Thr Leu Thr
        515                 520                 525
Leu Ser Leu Phe Asp Gly Ala Asp Val Arg Met Phe
    530                 535                 540

<210> SEQ ID NO 112
<211> LENGTH: 517
<212> TYPE: PRT
<213> ORGANISM: CANDIDATROPICALIS

<400> SEQUENCE: 112

Met Ile Glu Gln Leu Leu Glu Tyr Trp Tyr Val Val Pro Val Leu
1               5                   10                  15
Tyr Ile Ile Lys Gln Leu Leu Ala Tyr Thr Lys Thr Arg Val Leu Met
            20                  25                  30
Lys Lys Leu Gly Ala Ala Pro Val Thr Asn Lys Leu Tyr Asp Asn Ala
        35                  40                  45
Phe Gly Ile Val Asn Gly Trp Lys Ala Leu Gln Phe Lys Lys Glu Gly
    50                  55                  60
Arg Ala Gln Glu Tyr Asn Asp Tyr Lys Phe Asp His Ser Lys Asn Pro
65                  70                  75                  80
Ser Val Gly Thr Tyr Val Ser Ile Leu Phe Gly Thr Arg Ile Val Val
                85                  90                  95
Thr Lys Asp Pro Glu Asn Ile Lys Ala Ile Leu Ala Thr Gln Phe Gly
            100                 105                 110
Asp Phe Ser Leu Gly Lys Arg His Thr Leu Phe Lys Pro Leu Leu Gly
        115                 120                 125
Asp Gly Ile Phe Thr Leu Asp Gly Glu Gly Trp Lys His Ser Arg Ala
    130                 135                 140
Met Leu Arg Pro Gln Phe Ala Arg Glu Gln Val Ala His Val Thr Ser
145                 150                 155                 160
```

```
Leu Glu Pro His Phe Gln Leu Leu Lys Lys His Ile Leu Lys His Lys
            165                 170                 175
Gly Glu Tyr Phe Asp Ile Gln Glu Leu Phe Arg Phe Thr Val Asp
            180                 185                 190
Ser Ala Thr Glu Phe Leu Phe Gly Glu Ser Val His Ser Leu Lys Asp
            195                 200                 205
Glu Ser Ile Gly Ile Asn Gln Asp Asp Ile Asp Phe Ala Gly Arg Lys
    210                 215                 220
Asp Phe Ala Glu Ser Phe Asn Lys Ala Gln Glu Tyr Leu Ala Ile Arg
225                 230                 235                 240
Thr Leu Val Gln Thr Phe Tyr Trp Leu Val Asn Asn Lys Glu Phe Arg
                245                 250                 255
Asp Cys Thr Lys Ser Val His Lys Phe Thr Asn Tyr Tyr Val Gln Lys
                260                 265                 270
Ala Leu Asp Ala Ser Pro Glu Glu Leu Glu Lys Gln Ser Gly Tyr Val
            275                 280                 285
Phe Leu Tyr Glu Leu Val Lys Gln Thr Arg Asp Pro Asn Val Leu Arg
290                 295                 300
Asp Gln Ser Leu Asn Ile Leu Leu Ala Gly Arg Asp Thr Thr Ala Gly
305                 310                 315                 320
Leu Leu Ser Phe Ala Val Phe Glu Leu Ala Arg His Pro Glu Ile Trp
                325                 330                 335
Ala Lys Leu Arg Glu Glu Ile Glu Gln Gln Phe Gly Leu Gly Glu Asp
            340                 345                 350
Ser Arg Val Glu Glu Ile Thr Phe Glu Ser Leu Lys Arg Cys Glu Tyr
            355                 360                 365
Leu Lys Ala Phe Leu Asn Glu Thr Leu Arg Ile Tyr Pro Ser Val Pro
    370                 375                 380
Arg Asn Phe Arg Ile Ala Thr Lys Asn Thr Thr Leu Pro Arg Gly Gly
385                 390                 395                 400
Gly Ser Asp Gly Thr Ser Pro Ile Leu Ile Gln Lys Gly Glu Ala Val
                405                 410                 415
Ser Tyr Gly Ile Asn Ser Thr His Leu Asp Pro Val Tyr Tyr Gly Pro
            420                 425                 430
Asp Ala Ala Glu Phe Arg Pro Glu Arg Trp Phe Glu Pro Ser Thr Lys
            435                 440                 445
Lys Leu Gly Trp Ala Tyr Leu Pro Phe Asn Gly Gly Pro Arg Ile Cys
    450                 455                 460
Leu Gly Gln Gln Phe Ala Leu Thr Glu Ala Gly Tyr Val Leu Val Arg
465                 470                 475                 480
Leu Val Gln Glu Phe Ser His Val Arg Ser Asp Pro Asp Glu Val Tyr
                485                 490                 495
Pro Pro Lys Arg Leu Thr Asn Leu Thr Met Cys Leu Gln Asp Gly Ala
                500                 505                 510
Ile Val Lys Phe Asp
        515

<210> SEQ ID NO 113
<211> LENGTH: 517
<212> TYPE: PRT
<213> ORGANISM: CANDIDATROPICALIS

<400> SEQUENCE: 113

Met Ile Glu Gln Ile Leu Glu Tyr Trp Tyr Ile Val Val Pro Val Leu
```

```
1               5                   10                  15
Tyr Ile Ile Lys Gln Leu Ile Ala Tyr Ser Lys Thr Arg Val Leu Met
                20                  25                  30

Lys Gln Leu Gly Ala Ala Pro Ile Thr Asn Gln Leu Tyr Asp Asn Val
                35                  40                  45

Phe Gly Ile Val Asn Gly Trp Lys Ala Leu Gln Phe Lys Lys Glu Gly
                50                  55                  60

Arg Ala Gln Glu Tyr Asn Asp His Lys Phe Asp Ser Ser Lys Asn Pro
65                      70                  75                  80

Ser Val Gly Thr Tyr Val Ser Ile Leu Phe Gly Thr Lys Ile Val Val
                85                  90                  95

Thr Lys Asp Pro Glu Asn Ile Lys Ala Ile Leu Ala Thr Gln Phe Gly
                100                 105                 110

Asp Phe Ser Leu Gly Lys Arg His Ala Leu Phe Lys Pro Leu Leu Gly
                115                 120                 125

Asp Gly Ile Phe Thr Leu Asp Gly Glu Gly Trp Lys His Ser Arg Ser
                130                 135                 140

Met Leu Arg Pro Gln Phe Ala Arg Glu Gln Val Ala His Val Thr Ser
145                     150                 155                 160

Leu Glu Pro His Phe Gln Leu Lys Lys His Ile Leu Lys His Lys
                165                 170                 175

Gly Glu Tyr Phe Asp Ile Gln Glu Leu Phe Phe Arg Phe Thr Val Asp
                180                 185                 190

Ser Ala Thr Glu Phe Leu Phe Gly Glu Ser Val His Ser Leu Lys Asp
                195                 200                 205

Glu Thr Ile Gly Ile Asn Gln Asp Ile Asp Phe Ala Gly Arg Lys
                210                 215                 220

Asp Phe Ala Glu Ser Phe Asn Lys Ala Gln Glu Tyr Leu Ser Ile Arg
225                     230                 235                 240

Ile Leu Val Gln Thr Phe Tyr Trp Leu Ile Asn Asn Lys Glu Phe Arg
                245                 250                 255

Asp Cys Thr Lys Ser Val His Lys Phe Thr Asn Tyr Tyr Val Gln Lys
                260                 265                 270

Ala Leu Asp Ala Thr Pro Glu Glu Leu Glu Lys Gln Gly Gly Tyr Val
                275                 280                 285

Phe Leu Tyr Glu Leu Val Lys Gln Thr Arg Asp Pro Lys Val Leu Arg
                290                 295                 300

Asp Gln Ser Leu Asn Ile Leu Leu Ala Gly Arg Asp Thr Thr Ala Gly
305                     310                 315                 320

Leu Leu Ser Phe Ala Val Phe Glu Leu Ala Arg Asn Pro His Ile Trp
                325                 330                 335

Ala Lys Leu Arg Glu Glu Ile Glu Gln Gln Phe Gly Leu Gly Glu Asp
                340                 345                 350

Ser Arg Val Glu Glu Ile Thr Phe Glu Ser Leu Lys Arg Cys Glu Tyr
                355                 360                 365

Leu Lys Ala Phe Leu Asn Glu Thr Leu Arg Val Tyr Pro Ser Val Pro
                370                 375                 380

Arg Asn Phe Arg Ile Ala Thr Lys Asn Thr Thr Leu Pro Arg Gly Gly
385                     390                 395                 400

Gly Pro Asp Gly Thr Gln Pro Ile Leu Ile Gln Lys Gly Glu Gly Val
                405                 410                 415

Ser Tyr Gly Ile Asn Ser Thr His Leu Asp Pro Val Tyr Tyr Gly Pro
                420                 425                 430
```

```
Asp Ala Ala Glu Phe Arg Pro Glu Arg Trp Phe Glu Pro Ser Thr Arg
            435                 440                 445

Lys Leu Gly Trp Ala Tyr Leu Pro Phe Asn Gly Pro Arg Ile Cys
    450                 455                 460

Leu Gly Gln Gln Phe Ala Leu Thr Glu Ala Gly Tyr Val Leu Val Arg
465                 470                 475                 480

Leu Val Gln Glu Phe Ser His Ile Arg Ser Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
            515

<210> SEQ ID NO 114
<211> LENGTH: 512
<212> TYPE: PRT
<213> ORGANISM: CANDIDATROPICALIS

<400> SEQUENCE: 114

Met Leu Asp Gln Ile Leu His Tyr Trp Tyr Ile Val Leu Pro Leu Leu
1               5                   10                  15

Ala Ile Ile Asn Gln Ile Val Ala His Val Arg Thr Asn Tyr Leu Met
            20                  25                  30

Lys Lys Leu Gly Ala Lys Pro Phe Thr His Val Gln Arg Asp Gly Trp
        35                  40                  45

Leu Gly Phe Lys Phe Gly Arg Glu Phe Leu Lys Ala Lys Ser Ala Gly
    50                  55                  60

Arg Ser Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

Glu Asn Ile Lys Ala Leu Leu Ala Thr Gln Phe Gly Asp Phe Ser Leu
            100                 105                 110

Gly Ser Arg Val Lys Phe Lys Pro Leu Leu Gly Tyr Gly Ile Phe
        115                 120                 125

Thr Leu Asp Ala Glu Gly Trp Lys His Ser Arg Ala Met Leu Arg Pro
130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175

Asp Ile Gln Glu Leu Phe Phe Arg Phe Thr Val Asp Ser Ala Thr Glu
            180                 185                 190

Phe Leu Phe Gly Glu Ser Val His Ser Leu Lys Asp Glu Ile Gly
        195                 200                 205

Tyr Asp Thr Lys Asp Met Ser Glu Glu Arg Arg Phe Ala Asp Ala
    210                 215                 220

Phe Asn Lys Ser Gln Val Tyr Val Ala Thr Arg Val Ala Leu Gln Asn
225                 230                 235                 240

Leu Tyr Trp Leu Val Asn Asn Lys Glu Phe Lys Glu Cys Asn Asp Ile
                245                 250                 255

Val His Lys Phe Thr Asn Tyr Tyr Val Gln Lys Ala Leu Asp Ala Thr
            260                 265                 270

Pro Glu Glu Leu Glu Lys Gln Gly Gly Tyr Val Phe Leu Tyr Glu Leu
```

```
                    275                280                285
Val Lys Gln Thr Arg Asp Pro Lys Val Leu Arg Asp Gln Ser Leu Asn
290                     295                 300

Ile Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
                325                 330                 335

Glu Ile Glu Gln Gln Phe Gly Leu Gly Glu Asp Ser Arg Val Glu Glu
                340                 345                 350

Ile Thr Phe Glu Ser Leu Lys Arg Cys Glu Tyr Leu Lys Ala Val Leu
                355                 360                 365

Asn Glu Thr Leu Arg Leu His Pro Ser Val Pro Arg Asn Ala Arg Phe
370                     375                 380

Ala Ile Lys Asp Thr Thr Leu Pro Arg Gly Gly Pro Asn Gly Lys
385                 390                 395                 400

Asp Pro Ile Leu Ile Arg Lys Asp Glu Val Val Gln Tyr Ser Ile Ser
                405                 410                 415

Ala Thr Gln Thr Asn Pro Ala Tyr Tyr Gly Ala Asp Ala Asp Phe
                420                 425                 430

Arg Pro Glu Arg Trp Phe Glu Pro Ser Thr Arg Asn Leu Gly Trp Ala
                435                 440                 445

Phe Leu Pro Phe Asn Gly Gly Pro Arg Ile Cys Leu Gly Gln Gln Phe
450                     455                 460

Ala Leu Thr Glu Ala Gly Tyr Val Leu Val Arg Leu Val Gln Glu Phe
465                 470                 475                 480

Pro Asn Leu Ser Gln Asp Pro Glu Thr Lys Tyr Pro Pro Arg Leu
                485                 490                 495

Ala His Leu Thr Met Cys Leu Phe Asp Gly Ala His Val Lys Met Ser
                500                 505                 510

<210> SEQ ID NO 115
<211> LENGTH: 512
<212> TYPE: PRT
<213> ORGANISM: CANDIDATROPICALIS

<400> SEQUENCE: 115

Met Leu Asp Gln Ile Phe His Tyr Trp Tyr Ile Val Leu Pro Leu Leu
1               5                   10                  15

Val Ile Ile Lys Gln Ile Val Ala His Ala Arg Thr Asn Tyr Leu Met
                20                  25                  30

Lys Lys Leu Gly Ala Lys Pro Phe Thr His Val Gln Leu Asp Gly Trp
            35                  40                  45

Phe Gly Phe Lys Phe Gly Arg Glu Phe Leu Lys Ala Lys Ser Ala Gly
        50                  55                  60

Arg Gln Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

Glu Asn Ile Lys Ala Leu Leu Ala Thr Gln Phe Gly Asp Phe Ser Leu
                100                 105                 110

Gly Ser Arg Val Lys Phe Phe Lys Pro Leu Leu Gly Tyr Gly Ile Phe
            115                 120                 125

Thr Leu Asp Gly Glu Gly Trp Lys His Ser Arg Ala Met Leu Arg Pro
        130                 135                 140
```

```
Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
            165                 170                 175

Asp Ile Gln Glu Leu Phe Phe Arg Phe Thr Val Asp Ser Ala Thr Glu
        180                 185                 190

Phe Leu Phe Gly Glu Ser Val His Ser Leu Arg Asp Glu Ile Gly
    195                 200                 205

Tyr Asp Thr Lys Asp Met Ala Glu Glu Arg Arg Lys Phe Ala Asp Ala
210                 215                 220

Phe Asn Lys Ser Gln Val Tyr Leu Ser Thr Arg Val Ala Leu Gln Thr
225                 230                 235                 240

Leu Tyr Trp Leu Val Asn Asn Lys Glu Phe Lys Glu Cys Asn Asp Ile
                245                 250                 255

Val His Lys Phe Thr Asn Tyr Tyr Val Gln Lys Ala Leu Asp Ala Thr
            260                 265                 270

Pro Glu Glu Leu Glu Lys Gln Gly Gly Tyr Val Phe Leu Tyr Glu Leu
        275                 280                 285

Ala Lys Gln Thr Lys Asp Pro Asn Val Leu Arg Asp Gln Ser Leu Asn
    290                 295                 300

Ile Leu Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
                325                 330                 335

Glu Ile Glu Ser His Phe Gly Ser Gly Glu Asp Ser Arg Val Glu Glu
            340                 345                 350

Ile Thr Phe Glu Ser Leu Lys Arg Cys Glu Tyr Leu Lys Ala Val Leu
        355                 360                 365

Asn Glu Thr Leu Arg Leu His Pro Ser Val Pro Arg Asn Ala Arg Phe
    370                 375                 380

Ala Ile Lys Asp Thr Thr Leu Pro Arg Gly Gly Gly Pro Asn Gly Lys
385                 390                 395                 400

Asp Pro Ile Leu Ile Arg Lys Asn Glu Val Val Gln Tyr Ser Ile Ser
                405                 410                 415

Ala Thr Gln Thr Asn Pro Ala Tyr Tyr Gly Ala Asp Ala Ala Asp Phe
            420                 425                 430

Arg Pro Glu Arg Trp Phe Glu Pro Ser Thr Arg Asn Leu Gly Trp Ala
        435                 440                 445

Tyr Leu Pro Phe Asn Gly Gly Pro Arg Ile Cys Leu Gly Gln Gln Phe
    450                 455                 460

Ala Leu Thr Glu Ala Gly Tyr Val Leu Val Arg Leu Val Gln Glu Phe
465                 470                 475                 480

Pro Ser Leu Ser Gln Asp Pro Glu Thr Glu Tyr Pro Pro Arg Leu
                485                 490                 495

Ala His Leu Thr Met Cys Leu Phe Asp Gly Ala Tyr Val Lys Met Gln
            500                 505                 510

<210> SEQ ID NO 116
<211> LENGTH: 499
<212> TYPE: PRT
<213> ORGANISM: CANDIDATROPICALIS

<400> SEQUENCE: 116

Met Ala Ile Ser Ser Leu Leu Ser Trp Asp Val Ile Cys Val Val Phe
1               5                   10                  15
```

```
Ile Cys Val Cys Val Tyr Phe Gly Tyr Glu Tyr Cys Tyr Thr Lys Tyr
            20                  25                  30

Leu Met His Lys His Gly Ala Arg Glu Ile Glu Asn Val Ile Asn Asp
            35                  40                  45

Gly Phe Phe Gly Phe Arg Leu Pro Leu Leu Met Arg Ala Ser Asn
            50                  55                  60

Glu Gly Arg Leu Ile Glu Phe Ser Val Lys Arg Phe Glu Ser Ala Pro
 65                  70                  75                  80

His Pro Gln Asn Lys Thr Leu Val Asn Arg Ala Leu Ser Val Pro Val
                85                  90                  95

Ile Leu Thr Lys Asp Pro Val Asn Ile Lys Ala Met Leu Ser Thr Gln
                100                 105                 110

Phe Asp Asp Phe Ser Leu Gly Leu Arg Leu His Gln Phe Ala Pro Leu
                115                 120                 125

Leu Gly Lys Gly Ile Phe Thr Leu Asp Gly Pro Glu Trp Lys Gln Ser
        130                 135                 140

Arg Ser Met Leu Arg Pro Gln Phe Ala Lys Asp Arg Val Ser His Ile
145                 150                 155                 160

Ser Asp Leu Glu Pro His Phe Val Leu Leu Arg Lys His Ile Asp Gly
                165                 170                 175

His Asn Gly Asp Tyr Phe Asp Ile Gln Glu Leu Tyr Phe Arg Phe Ser
        180                 185                 190

Met Asp Val Ala Thr Gly Phe Leu Phe Gly Glu Ser Val Gly Ser Leu
        195                 200                 205

Lys Asp Glu Asp Ala Arg Phe Ser Glu Ala Phe Asn Glu Ser Gln Lys
210                 215                 220

Tyr Leu Ala Thr Arg Ala Thr Leu His Glu Leu Tyr Phe Leu Cys Asp
225                 230                 235                 240

Gly Phe Arg Phe Arg Gln Tyr Asn Lys Val Val Arg Lys Phe Cys Ser
                245                 250                 255

Gln Cys Val His Lys Ala Leu Asp Val Ala Pro Glu Asp Thr Ser Glu
            260                 265                 270

Tyr Val Phe Leu Arg Glu Leu Val Lys His Thr Arg Asp Pro Val Val
        275                 280                 285

Leu Gln Asp Gln Ala Leu Asn Val Leu Leu Ala Gly Arg Asp Thr Thr
    290                 295                 300

Ala Ser Leu Leu Ser Phe Ala Thr Phe Glu Leu Ala Arg Asn Asp His
305                 310                 315                 320

Met Trp Arg Lys Leu Arg Glu Glu Val Ile Ser Thr Met Gly Pro Ser
                325                 330                 335

Ser Asp Glu Ile Thr Val Ala Gly Leu Lys Ser Cys Arg Tyr Leu Lys
            340                 345                 350

Ala Ile Leu Asn Glu Thr Leu Arg Leu Tyr Pro Ser Val Pro Arg Asn
            355                 360                 365

Ala Arg Phe Ala Thr Arg Asn Thr Thr Leu Pro Arg Gly Gly Pro
    370                 375                 380

Asp Gly Ser Phe Pro Ile Leu Ile Arg Lys Gly Gln Pro Val Gly Tyr
385                 390                 395                 400

Phe Ile Cys Ala Thr His Leu Asn Glu Lys Val Tyr Gly Asn Asp Ser
                405                 410                 415

His Val Phe Arg Pro Glu Arg Trp Ala Ala Leu Glu Gly Lys Ser Leu
                420                 425                 430
```

```
Gly Trp Ser Tyr Leu Pro Phe Asn Gly Gly Pro Arg Ser Cys Leu Gly
        435                 440                 445

Gln Gln Phe Ala Ile Leu Glu Ala Ser Tyr Val Leu Ala Arg Leu Thr
    450                 455                 460

Gln Cys Tyr Thr Thr Ile Gln Leu Arg Thr Thr Glu Tyr Pro Pro Lys
465                 470                 475                 480

Lys Leu Val His Leu Thr Met Ser Leu Leu Asn Gly Val Tyr Ile Arg
            485                 490                 495

Thr Arg Thr

<210> SEQ ID NO 117
<211> LENGTH: 679
<212> TYPE: PRT
<213> ORGANISM: CANDIDATROPICALIS

<400> SEQUENCE: 117

Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
                20                  25                  30

Asp Thr Gly Phe Leu Asn Thr Asp Ser Gly Ser Asn Ser Arg Asp Val
            35                  40                  45

Leu Ser Thr Leu Lys Lys Asn Asn Lys Asn Thr Leu Leu Leu Phe Gly
50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
                100                 105                 110

Phe Ile Val Ala Thr Tyr Gly Glu Gly Glu Pro Thr Asp Asn Ala Asp
            115                 120                 125

Glu Phe His Thr Trp Leu Thr Glu Glu Ala Asp Thr Leu Ser Thr Leu
130                 135                 140

Lys Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Asp Arg His Cys Ile His Val Glu
        275                 280                 285

Phe Asp Ile Ser Glu Ser Asn Leu Lys Tyr Thr Thr Gly Asp His Leu
    290                 295                 300
```

```
Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
            325                 330                 335

Leu Asp Ser Thr Tyr Thr Ile Pro Phe Pro Thr Pro Ile Thr Tyr Gly
        340                 345                 350

Ala Val Ile Arg His His Leu Glu Ile Ser Gly Pro Val Ser Arg Gln
            355                 360                 365

Phe Phe Leu Ser Ile Ala Gly Phe Ala Pro Asp Glu Thr Lys Lys
        370                 375                 380

Ala Phe Thr Arg Leu Gly Gly Asp Lys Gln Glu Phe Ala Ala Lys Val
385                 390                 395                 400

Thr Arg Arg Lys Phe Asn Ile Ala Asp Ala Leu Leu Tyr Ser Ser Asn
                405                 410                 415

Asn Ala Pro Trp Ser Asp Val Pro Phe Glu Phe Leu Ile Glu Asn Val
            420                 425                 430

Pro His Leu Thr Pro Arg Tyr Tyr Ser Ile Ser Ser Ser Ser Leu Ser
        435                 440                 445

Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Val Glu Ile Val Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675

<210> SEQ ID NO 118
<211> LENGTH: 679
<212> TYPE: PRT
<213> ORGANISM: CANDIDATROPICALIS

<400> SEQUENCE: 118
```

```
Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu Ser Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
                100                 105                 110

Phe Ile Val Ala Thr Tyr Gly Glu Gly Glu Pro Thr Asp Asn Ala Asp
            115                 120                 125

Glu Phe His Thr Trp Leu Thr Glu Glu Ala Asp Thr Leu Ser Thr Leu
130                 135                 140

Arg Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
            195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Glu Arg His Cys Ile His Val Glu
            275                 280                 285

Phe Asp Ile Ser Glu Ser Asn Leu Lys Tyr Thr Thr Gly Asp His Leu
            290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
            355                 360                 365

Phe Phe Leu Ser Ile Ala Gly Phe Ala Pro Asp Glu Glu Thr Lys Lys
            370                 375                 380

Thr Phe Thr Arg Leu Gly Gly Asp Lys Gln Glu Phe Ala Thr Lys Val
385                 390                 395                 400

Thr Arg Arg Lys Phe Asn Ile Ala Asp Ala Leu Leu Tyr Ser Ser Asn
                405                 410                 415
```

```
Asn Thr Pro Trp Ser Asp Val Pro Phe Glu Phe Leu Ile Glu Asn Ile
            420                 425                 430

Gln His Leu Thr Pro Arg Tyr Tyr Ser Ile Ser Ser Ser Ser Leu Ser
            435                 440                 445

Glu Lys Gln Leu Ile Asn Val Thr Ala Val Glu Ala Glu Glu Glu
    450                 455                 460

Ala Asp Gly Arg Pro Val Thr Gly Val Val Thr Asn Leu Leu Lys Asn
465                 470                 475                 480

Ile Glu Ile Ala Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
            515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
            595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
            645                 650                 655

Ser Glu Asp Lys Ala Ala Glu Leu Val Lys Ser Trp Lys Val Gln Asn
            660                 665                 670

Arg Tyr Gln Glu Asp Val Trp
            675
```